(12) United States Patent
Spector et al.

(10) Patent No.: US 9,555,100 B2
(45) Date of Patent: Jan. 31, 2017

(54) HERPES VIRUS VACCINE AND METHODS OF USE

(71) Applicant: The Regents of the University of California, Oakland, CA (US)

(72) Inventors: Deborah H. Spector, La Jolla, CA (US); Christopher S. Morello, Carlsbad, CA (US); Kimberly A. Kraynyak, Encinitas, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/141,251

(22) Filed: Dec. 26, 2013

(65) Prior Publication Data

US 2014/0193460 A1 Jul. 10, 2014

Related U.S. Application Data

(63) Continuation of application No. PCT/US2012/045290, filed on Jul. 2, 2012.

(60) Provisional application No. 61/503,945, filed on Jul. 1, 2011.

(51) Int. Cl.
| | |
|---|---|
| *A61K 39/245* | (2006.01) |
| *A61K 39/12* | (2006.01) |
| *A61K 39/00* | (2006.01) |
| *A61K 39/39* | (2006.01) |
| *A61K 33/06* | (2006.01) |

(52) U.S. Cl.
CPC ............ *A61K 39/245* (2013.01); *A61K 39/12* (2013.01); *A61K 33/06* (2013.01); *A61K 2039/5252* (2013.01); *A61K 2039/53* (2013.01); *A61K 2039/54* (2013.01); *A61K 2039/545* (2013.01); *A61K 2039/55505* (2013.01); *A61K 2039/55572* (2013.01); *C12N 2710/16634* (2013.01)

(58) Field of Classification Search
CPC A61K 2300/00; A61K 39/12; A61K 2039/53; A61K 39/39; A61K 2039/55505; A61K 39/00; A61K 2039/545; A61K 2039/5252; A61K 2039/54; A61K 2039/55572; A61K 2039/5258; A61K 2039/55511; A61K 2039/57; A61K 39/245; A61K 33/06; C12N 7/00; C12N 2710/16634; C12N 15/869; C12N 15/8695; C07K 14/005

See application file for complete search history.

(56) References Cited

U.S. PATENT DOCUMENTS

| | | | |
|---|---|---|---|
| 4,861,760 A | 8/1989 | Mazuel et al. | |
| 4,911,920 A | 3/1990 | Jani et al. | |
| 5,034,506 A | 7/1991 | Summerton et al. | |
| 5,212,162 A | 5/1993 | Missel et al. | |
| 5,235,033 A | 8/1993 | Summerton et al. | |
| 5,403,841 A | 4/1995 | Lang et al. | |
| 6,146,632 A | 11/2000 | Momin et al. | |
| 6,451,320 B1 | 9/2002 | Stephenne et al. | |
| 7,357,936 B1 | 4/2008 | Garcon | |
| 2010/0272752 A1* | 10/2010 | Spector et al. | ............ 424/207.1 |

FOREIGN PATENT DOCUMENTS

| | | |
|---|---|---|
| WO | WO-94/21292 A1 | 9/1994 |
| WO | WO-00/03744 A2 | 1/2000 |
| WO | WO-00/03744 A3 | 1/2000 |
| WO | WO-00/15255 A1 | 3/2000 |
| WO | WO-01/17551 A2 | 3/2001 |
| WO | WO-01/17551 A3 | 3/2001 |
| WO | WO 2007/106404 A2 | 9/2007 |
| WO | WO 2007106404 A2 * | 9/2007 |
| WO | WO 2010062757 A1 * | 6/2010 |

OTHER PUBLICATIONS

Oram RJ, Marcellino D, Strauss D, Gustafson E, Talarico CL, Root AK, Sharma PL, Thompson K, Fingeroth JD, Crumpacker C, Herold BC. Characterization of an acyclovir-resistant herpes simplex virus type 2 strain isolated from a premature neonate. J Infect Dis. Apr. 2000;181(4):1458-61. Epub Apr. 13, 2000.*

Yang K, Baines JD. Selection of HSV capsids for envelopment involves interaction between capsid surface components pUL31, pUL17, and pUL25. Proc Natl Acad Sci U S A. Aug 23, 2011;108(34):14276-81. Epub Aug. 5, 2011.*

Belshe et al., "Efficacy results of a trial of a herpes simplex vaccine." *The New England Journal of Medicine* (2012), 366(1):34-43.

Bernstein et al., "Effects of DNA immunization formulated with bupivacaine in murine and guinea pig models of genital herpes simplex virus infection", *Vaccine* (1999), 17:1964-1969.

Bernstein et al., "Herpes simplex virus vaccines", *Vaccine* (1999), 17(13-14):1681-1689.

Bourne et al., "DNA Immunization against Experimental Genital Herpes Simplex Virus Infection", *The Journal of Infectious Diseases* (1996), 173:800-807.

Bourne et al., "DNA immunization confers protective immunity on mice challenged intravaginally with herpes simplex virus type 2", *Vaccine* (1996), 14(13):1230-1234.

Corey et al., "Recombinant glycoprotein vaccine for the prevention of genital HSV-2 infection: two randomized controlled trials." *JAMA Network* (1999), 282(4):331-340.

Da Costa et al., "Immunization against genital herpes with a vaccine virus that has defects in productive and latent infection." *Proc Natl Aced Sci USA* (1999), 96(12):6994-8.

Didierlaurent et al., "AS04, an Aluminum Salt- and TLR4 Agonist-Based Adjuvant System, Induces a Transient Localized Innate Immune Response Leading to Enhanced Adaptive Immunity." *The Journal of Immunology* (2009), 183:6186-6197.

Flo, J., "Co-immunization with plasmids coding the full length and a soluble form of glycoprotein D of HSV-2 induces protective cellular and humoral immune response in mice." *Vaccine* (2003), 21:1239-1245.

(Continued)

*Primary Examiner* — Rachel B Gill
(74) *Attorney, Agent, or Firm* — Zachary L. Terranova; Mintz, Levin, Cohn, Ferris, Glovsky and Popeo, P.C.

(57) ABSTRACT

Provided herein are, for example, immunogenic compositions and methods of using the same for the treatment or prevention of Herpesvirus infections.

5 Claims, 29 Drawing Sheets

(56) References Cited

OTHER PUBLICATIONS

Fotouhi et al., "Enhancement of protective humoral immune responses against Herpes simplex virus-2 in DNA-immunized guinea-pigs using protein boosting." *FEMS Immunol. Med. Microbiol.* (2008), 54:18-26.

Hem et al., "Imject Alum is not aluminum hydroxide adjuvant or aluminum phosphate adjuvant." *Vaccine* (2007), 25:4985-4986.

Higgins et al., "Plasmid DNA-Expressed Secreted and Nonsecreted Forms of Herpes Simplex Virus Glycoprotein D2 Induce Different Types of Immune Responses." *Journal of Infectious Diseases* (2000), 182(5):1311-1320.

Hoshino et al., "Comparative efficacy and immunogenicity of replication-defective, recombinant glycoprotein, and DNA vaccines for herpes simplex virus 2 infections in mice and guinea pigs." *Journal of Virology* (2005), 79(1):410-418.

Hoshino et al., "Protection from herpes simplex virus (HSV)-2 infection with replication-defective HSV-2 or glycoprotein D2 vaccines in HSV-1-seropositive and HSV-1-seronegative guinea pigs." *Journal of Infectious Diseases* (2009), 200(7):1088-1095.

Hoshino et al., "Comparison of immunogenicity and protective efficacy of genital herpes vaccine candidates herpes simplex virus 2 dl5-29 and dl5-29-41L in mice and guinea pigs." *Vaccine* (2008), 26(32):4034-4040.

Johnson et al., "Herpes simplex virus (HSV)-specific T cells activated in the absence of IFN-gamma express alternative effector functions but are not protective against genital HSV-2 infection." *Journal of Reproductive Immunology* (2010), 84:8-15.

Koelle, D.M., & Corey, L., "Herpes simplex: insights on pathogenesis and possible vaccines." *Annu. Rev. Med.* (2008), 59:381-395.

Morello et al., "Immunization with Herpes Simplex Virus 2 (HSV-2) genes plus inactivated HSV-2 Is highly protective against acute and recurrent HSV-2 disease." *Journal of Virology* (2011), 85(7):3461-3472.

Morello et al., "Systemic Priming-Boosting Immunization with a Trivalent Plasmid DNA and Inactivated Murine Cytomegalovirus (MCMV) Vaccine Provides Long-Term Protection against Viral Replication following Systemic or Mucosal MCMV Challenge." *Journal of Virology* (2005), 79(1):159-175.

Morello et al., "DNA Immunization Using Highly Conserved Murine Cytomegalovirus Genes Encoding Homologs of Human Cytomegalovirus UL54 (DNA Polymerase) and UL105 (Helicase) Elicits Strong CD8 T-Cell Responses and IS Protective against Systematic Challenge." *Journal of Virology* (2007), 81(14):7766-7775.

Morello et al., "Development of a Vaccine against Murine Cytomegalovirus (MCMV), Consisting of Plasmid DNA and Formalin-Inactivated MCMV, That Provides Long-Term, Complete Protection against Viral Replication." *Journal of Virology* (2002), 76(10):4822-4835.

Murata et al., "Excretion of herpes simplex virus type 2 glycoprotein D into the culture medium." *Journal of General Virology* (2002), 83:2791-2795.

Stanberry et al., "Glycoprotein-D-adjuvant vaccine to prevent genital herpes." *The New England Journal of Medicine* (2002), 347(21):1652-1661.

Strasser et al., "Herpes Simplex Virus DNA Vaccine Efficacy: Effect of Glycoprotein D Plasmid Constructs" *The Journal of Infectious Diseases* (2000), 182:1304-1310.

Straus et al., "Immunotherapy of Recurrent Genital Herpes with Recombinant Herpes Simplex Virus Type 2 Glycoproteins D and B: Results of a Placebo-Controlled Vaccine Trial." *The Journal of Infectious Diseases* (1997), 176:1129-1134.

Ye et al., "Strong CD8 T-Cell Responses following Coimmunization with Plasmids Expressing the Dominant pp89 and Subdominant M84 Antigens of Murine Cytomegalovirus Correlate with Long-Term Protection against Subsequent Viral Challenge." *Journal of Virology* (2002), 76(5):2100-2112.

International Preliminary Report on Patentability and Written Opinion dated Jan. 7, 2014 for International Application No. PCT/US2012/045290, 7 pages.

International Search Report dated Jan. 30, 2013 for International Application No. PCT/US2012/045290, 7 pages.

Bernstein, D.I. et al. (May 1, 2005, e-published Mar. 24, 2005). "Safety and immunogenicity of glycoprotein D-adjuvant genital herpes vaccine," *Clin Infect Dis* 40(9):1271-1281.

Garcon, N. et al. (Jun. 2011, e-published Apr. 27, 2011). "The safety evaluation of adjuvants during vaccine development: the AS04 experience," *Vaccine* 29(27):4453-4459.

* cited by examiner

Fig. 2A

Experiment 1

| HSV-2 Gene | Survivors (n=8) | |
|---|---|---|
| | -gD2t | +gD2t |
| pVAX | 1 | 7 |
| UL5 | 1 | 6 |
| UL30 | 0 | 8 |

Fig. 2B

Experiment 2

| HSV-2 Gene(s) | Survivors (n=8) | |
|---|---|---|
| | -gD2t | +gD2t |
| pVAX | 0 | 7 |
| UL5 + UL30 | 1 | 7 |

Immunization

Fig. 4A.
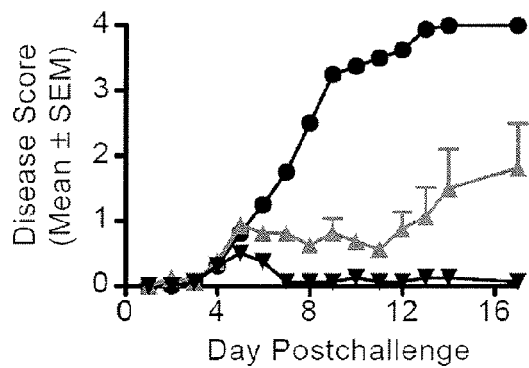
Fig. 4B.
Fig. 4C.
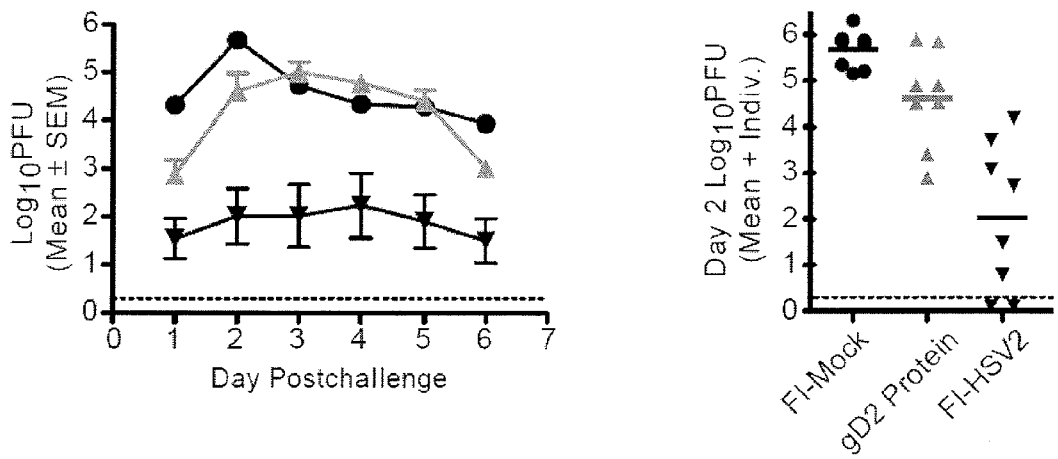

| DNA Prime | No. of Survivors (n=8) | | |
|---|---|---|---|
| | Boost + MPL/Alum | | |
| | FI-Mock | gD2t Protein | FI-HSV2 |
| pVAX | 0 | 8 | 7 |
| gD2t DNA | 5 | 8 | 8 |
| UL5, UL30, gD2t DNAs | 3 | 6* | 7 |

*n = 7

Day Postchallenge

HERPES VIRUS VACCINE AND METHODS OF USE

CROSS-REFERENCES TO RELATED APPLICATIONS

This application is a continuation of International Patent Application No. PCT/US2012/045290, filed Jul. 2, 2012, which claims the benefit of U.S. Provisional Patent Application No. 61/503,945, filed Jul. 1, 2011, each of which is incorporated herein by reference in its entirety and for all purposes.

STATEMENT AS TO RIGHTS TO INVENTIONS MADE UNDER FEDERALLY SPONSORED RESEARCH AND DEVELOPMENT

This invention was made with government support under 1R21AI073585 awarded by the National Institutes of Health. The Government has certain rights in the invention.

REFERENCE TO A "SEQUENCE LISTING," A TABLE, OR A COMPUTER PROGRAM LISTING APPENDIX SUBMITTED ON A COMPACT DISK

The Sequence Listing written in file 88654-006710PC-844147_ST25.TXT, created on Jul. 2, 2012, 4,077 bytes, machine format IBM-PC, MS-Windows operating system, is hereby incorporated by reference in its entirety for all purposes.

BACKGROUND OF THE INVENTION

In the United States, Herpes Simplex Virus type 2 (HSV-2) is one of the most common sexually transmitted infections, affecting 16.2% of adults (Xu, F. et al., *Seroprevalence of Herpes Simplex Virus Type 2 Among Persons Aged 14-49 Years—United States*, 2005-2008, Centers for Disease Control and Prevention (2010)). HSV-2 infection can cause significant morbidity and mortality in neonates (Kimberlin, D. W., *Herpes*, 14:11-16 (2007)) and immune compromised hosts (Dupuis, S. et al., *Nat. Genet.*, 33:388-391 (2003)). In addition, HSV-2 infection is the primary cause of genital lesions and has been linked to an increased risk of human immunodeficiency virus (HIV) acquisition (Freeman, E. E. et al., *AIDS*, 20:73-83 (2006); Wald, A., and K. Link, *J. Infect. Dis.*, 185:45-52 (2002)). HSV-2 replicates in the genital epithelium, followed by retrograde axonal transport to the dorsal root ganglia where virus can remain and establish a lifelong, latent infection with periodic reactivation. What is striking, however, is that most HSV-2 infections are asymptomatic, and yet these individuals shed virus with high frequency. As a result, HSV-2 is commonly transmitted from individuals who have no history of genital lesions (Mertz, G. J., *J. Infect. Dis.*, 198:1098-1100 (2008)). HSV-1 infection is also a significant cause of primary genital herpes disease and its incidence has been increasing in the U.S. and Europe (Wald, A. 2006. Genital HSV-1 infections. Sex Transm. Infect 82:189-190). Notably, in the negative control group of the Herpevac vaccine trial, HSV-1 had a higher attack rate for infection than did HSV-2 (3.2% vs. 1.5%, respectively) (Belshe, R. B., et al., Efficacy results of a trial of a herpes simplex vaccine. The New England Journal of Medicine, 2012. 366(1): p. 34-43.)

Without wishing to be bound by any theory, it is believed that the correlates of protective immunity against HSV-2 are unknown. Studies in HSV-2/HIV-1 co-infected individuals have shown that the loss of CD4+ T cells correlates with an increase in HSV-2 shedding (Schacker, T. et al., *J. Infect. Dis.*, 178:1616-1622 (1998)). In addition, a prophylactic vaccine eliciting neutralizing antibody responses did not result in sterilizing immunity (Corey, L. et al., *J. Amer. Med. Assoc.*, 282:331-340 (1999)). Human studies have also unveiled the role of CD8+ cytotoxic T cells in reducing HSV-2 replication and shedding. During primary infection, CD8+ T cells may prevent acute ganglion infection (Koelle, D. M., and L. Corey, *Annu. Rev. Med.*, 59:381-395 (2008)). In addition, CD8+ T cells have been found to infiltrate genital lesions, correlating with viral clearance (Koelle, D. M. et al., *J. Clin. Invest.*, 101:1500-1508 (1998)), and to accumulate at nerve endings in genital skin during HSV-2 reactivation (Zhu, J. et al., *J. Exp. Med.*, 204:595-603 (2007)). In the commonly utilized HSV-2 mouse and guinea pig models, the roles of cellular immunity have been less defined or the data have been ambiguous. T cell depletion studies in the mouse have suggested a role for both CD4+ and CD8+ T in protection against intravaginal (i.vag.) HSV-2 challenge (Milligan, G. N., and D. I. Bernstein, *Virology*, 229:259-268 (1997); Milligan, G. N., D. I. Bernstein, and N. Bourne, *J. Immunol.*, 160:6093-6100 (1998); Parr, M. B., and E. L. Parr, *J. Virol.*, 72:2677-2685 (1998)). The T-cell mediated clearance of virus from the mucosa is largely dependent upon IFN-γ (Milligan, G. N., and D. I. Bernstein, *Virology*, 229:259-268 (1997)), and T cells activated in the absence of IFN-γ are not protective against HSV-2 infection (Johnson, A. J. et al., *J. Reprod. Immunol.*, 84:8-15 (2010)).

Although many strategies have been tried, up to the present disclosure no successful HSV-2 vaccine has been developed (Koelle, D. M., and L. Corey, *Annu. Rev. Med.*, 59:381-395 (2008)). The glycoproteins gD and gB have been widely used as vaccine antigens in order to generate neutralizing antibodies (Corey, L. et al., *J. Amer. Med. Assoc.*, 282:331-340 (1999); Straus, S. E. et al., *J. Infect. Dis.*, 176:1129-1134 (1997)). Tested in two clinical trials in HSV-2 discordant couples, the most promising vaccine candidate, manufactured by GlaxoSmithKline (GSK), was composed of a secreted gD protein formulated with MPL and alum; however, it was efficacious only in HSV-1 and -2 seronegative women (Stanberry, L. R. et al., *N. Engl. J. Med.*, 347:1652-1661 (2002)). A subsequent Phase 3 study in 8,323 HSV-1 and -2 seronegative women (Herpevac trial) was not able to show significant protection against HSV-2 in this cohort. The secreted form of gD2 is truncated as a result of the deletion of the transmembrane domain (Higgins, T. J. et al., *J. Infect. Dis.*, 182:1311-1320 (2000)). A previous study by Strasser et al. showed that, when compared to the full-length or cytosolic portion of gD2, the secreted form provided the best protection from acute disease in both mice and guinea pigs (Strasser, J. E. et al., *J. Infect. Dis.*, 182:1304-1310 (2000)).

Replication-defective virus vaccines for HSV-2 are also in the clinical trial pipeline as they have been successful in animal models. UL5 (DNA helicase), UL29 (single-stranded DNA binding protein) are among the many proteins required for HSV-2 replication (Challberg, M. D., *Proc. Natl. Acad. Sci. USA*, 83:9094-9098 (1986); Knipe, D. M., *Virus Res.*, 37:85-123 (1989)). A mutant virus lacking UL5 and UL29 has exhibited promising immunogenicity and subsequent protection in the mouse (Da Costa, X. et al., *J. Virol.*, 74:7963-7971 (2000); Da Costa, X. J. et al., *Proc. Natl. Acad. Sci. USA*, 96:6994-6998 (1999)) and guinea pig models (Hoshino, Y. et al., *J. Virol.*, 79:410-418 (2005);

Hoshino, Y. et al., *J. Infect. Dis.*, 200:1088-1095 (2009); Hoshino, Y. et al., *Vaccine*, 26:4034-4040 (2008)). In the past, inactivated HSV-2 vaccines also were tested in humans, but subsequently dismissed due to a lack of controls required for accurate data interpretation (reviewed in (Whitley, R. J., *Herpes Simplex Viruses*, p. 2461-2509. In D. M. Knipe and P. M. Howley (ed.), Fields Virology, Fourth ed, vol. 2. Lippincott Williams & Wilkins, Philadelphia (2001))). Provided herein are solutions to these and other problems in the art.

BRIEF SUMMARY OF THE INVENTION

Provided in a first aspect is a Herpesvirus (HV) vaccine including inactivated HV, a lipopolysaccharide (LPS)-derived adjuvant and an aluminum-based mineral salt adjuvant.

Provided in a second aspect is a method of preparing a Herpesvirus (HV) vaccine, the method including: contacting an HV-cell mixture with a sulfated or sulfonated polysaccharide, wherein the HSV-cell mixture includes HV particles, cells and portions of cells; separating the HSV particles from the cells thereby forming isolated HV particles; inactivating the isolated HV particles thereby forming inactivated HV particles; combining the inactivated HV particles with a lipopolysaccharide-derived adjuvant and an aluminum-based mineral salt adjuvant thereby forming an HV vaccine.

Provided in a third aspect is a method of treating or preventing an HV infection in a patient in need of the treatment or prevention. The method including administering a therapeutically or prophylactically effective amount of an HV vaccine as described herein (including embodiments).

Provided in a fourth aspect is a method of treating or preventing a disease in a patient in need of the treatment or prevention. The method including administering a therapeutically or prophylactically effective amount of an HV vaccine as described herein (including embodiments).

Provided in a fifth aspect is a kit including an HV vaccine as described herein (including embodiments) and instructions for administering the HV vaccine to a patient.

BRIEF DESCRIPTION OF THE DRAWINGS

FIG. 1A. 293FT cells were transiently transfected with each HSV-2 ORF plasmid as shown or empty parent vector (pVAX) and cells were harvested at 48 h post transfection for SDS-PAGE and Western blot analysis using anti-FLAG M2 monoclonal antibody. FIG. 1B. 293FT cells were transfected with gD2t plasmid and cells and media were harvested on the days post transfection shown. Untransfected 293FT cells and media were harvested on day 2 of the experiment (293). Media were subjected to anti-FLAG M2 affinity chromatography and the bound material was solubilized in SDS-PAGE buffer and analyzed together with the corresponding cell lysates using the type common anti-gD monoclonal antibody DL6. FIG. 1C. The gD2t protein from media from pc3Δneo-gD2t transfected 293FT cells was purified by anti-FLAG M2 column and eluted with 3×FLAG peptide, the gD2t-containing fractions combined, and the volumes shown were analyzed by SDS-PAGE and Coomassie blue staining.

FIG. 2A to FIG. 2B. Protection of BALB/c mice against HSV-2 after immunization with UL5 and/or UL30 plasmids with or without gD2t plasmid co-immunization. FIG. 2A. Experiment 1. Twenty-one day survival of mice (n=8) that were immunized with the HSV-2 genes shown (25 µg DNA) together with either 25 µg of pVAX DNA (-gD2t) or gD2t DNA (+gD2t) and then given a lethal, i.vag. challenge of 10×LD$_{50}$ of HSV-2 strain G. FIG. 2B. Experiment 2: Mice (n=8) were coimmunized with UL5+UL30 with or without gD2t DNA. Mice received 20 µg each of UL5 and UL30 together with 20 µg of either pVAX or gD2t DNA. I.vag. challenge and survival for 21 days is shown as in FIG. 2A.

FIG. 3A. In two separate experiments, splenocytes were isolated from BALB/c mice that were either naïve (Naïve), HSV-2 infected in the footpad 7 days prior to harvest (HSV-2), or i.d. immunized with pVAX (pVAX). Splenocytes were stimulated with either ICP27 plasmid transfected BALB SV40 cells (ICP27 Cells; gray bars) or an ICP27 peptide of a known H-2$^d$ CD8+ T cell epitope (ICP27 Peptide, black bars) and CD8+ T cells producing IFN-γ were analyzed by intracellular cytokine staining FIG. 3B and FIG. 3C. Splenocytes from individual BALB/c mice (n=4) immunized with pVAX, UL5, or UL30 DNA plasmids either alone or in the combinations shown were stimulated with UL5 or UL30 plasmid transfected BALB SV40 cells in two separate experiments. One mouse that was infected with HSV-2 in the footpad 7 days prior to harvest was also analyzed (HSV-2). Plotted are the values from each mouse after subtraction of the background staining values from stimulation with pcDNA3-transfected SV40 BALB cells. Lines represent group means and closed symbols indicate values for individual mice.

FIG. 4A to FIG. 4C. Protection against HSV-2 after immunization with FI-HSV2 as compared with gD2t protein. Mice (n=8) were s.c. immunized twice with either 10$^7$ PFU equivalents of FI-HSV2, and equal volume of a FI-Mock virus preparation, or 5 µg of purified gD2t protein, with each immunization together with MPL and alum adjuvant as described in Materials and Methods. FIG. 4A. Twenty-one day postchallenge survival of each vaccine group. FIG. 4B. Disease severity following challenge as in FIG. 2A. FIG. 4C. Vaginal virus shedding following challenge as in FIG. 2A and Vaginal virus titers of each mouse on day 2 postchallenge. Each symbol represents the Log$_{10}$PFU titer of each mouse, horizontal lines represent the group means, and the dotted line shows the assay detection limit (equivalent to 2 PFU per swab). Legend: FI-Mock (circles); gD2t protein (triangle tip up); FI-HSV2 (triangle tip down).

FIG. 5A. Timeline of prime-boost immunization, challenge, and postchallenge outcome measurements. Mice were i.d. primed with either pVAX, gD2t DNA, or a cocktail of UL5, UL30, and gD2t DNAs on the weeks shown. Eight mice from each DNA prime group were s.c. boosted twice on the weeks shown with MPL/Alum together with either 10$^7$ PFU equivalents of FI-HSV2, an equal volume of FI-Mock virus preparation, or 5 µg gD2t protein subunit (gD2t SU). FIG. 5B. Postchallenge survival of mice given the prime-boost combinations. One mouse in the UL5, UL30, gD2t DNAs-gD2t protein group developed a severe ear infection and was sacrificed prior to the challenge day. FIG. 5C. Disease severity in the prime-boost immunized mice following i.vag. challenge as in FIG. 2B. Each panel shows the immunization groups given the same boost type, with either Mock (FI-Mock) (Left), gD2t protein (Middle), or FI-HSV2 (Right) boosts. FIG. 5D. Vaginal virus shedding following i.vag. challenge as in FIG. 2C, with immunization groups given the same boost type shown together and the pVAX–FI-Mock group shown in each panel for comparative purposes.

FIG. 6A and FIG. 6B. Groups of mice were immunized with $10^7$ PFU equivalents of FI-HSV2, 12.5 µg of MPL, and 54 µg of Adju-Phos (AdP). Some groups received 20 or 50 µg of each plasmid UL5, UL30, and gD2t. In addition, a negative control group received 60 µg of pVAX DNA mixed with MPL, Adju-Phos, and a volume of FI-Mock equal to the FI-HSV2 used in the other groups. Four weeks later, mice were given an additional immunization, rested for either 3 weeks (FIG. 6A) or 9 weeks (FIG. 6B), and then i.vag. challenged with HSV-2 as above. Mice were swabbed for vaginal HSV-2 shedding on day 2 and day 4 and data are shown similarly as in the FIG. 4C legend except that the limits of assay sensitivity were 4 PFU (FIG. 6A) and 2.22 PFU (FIG. 6B) per swab. FIG. 6C and FIG. 6D Virus specific antibody levels in immunized mice pre-challenge. Dashed lines represent the assay limits of sensitivity, and individual titers below the assay limit were assigned a value of one-half the assay limit for calculation and graphing purposes. (FIG. 6C) IgG titers measured by an ELISA against dextran sulfate-derived HSV-2 (2.35× $10^6$ PFU per well) before short-term (left panel) or long-term (right panel) challenge. The endpoint titer was defined as the highest, Fit Spline interpolated reciprocal dilution of serum at which the $A_{405}$ of the virion-coated well was equal to twice the $A_{405}$ of the same serum dilution in a well coated with an equal mass of Vero cell lysate. (FIG. 6D.) Virus neutralizing antibody titers prior to long-term challenge. Endpoint neutralization titers were calculated as the highest reciprocal serum dilution that resulted in a 50% reduction in the number of input PFU (50 PFU of dextran sulfate-derived HSV-2) using Fit Spline interpolation as above. Data points representing titers below the sensitivity limit were staggered for increased visibility. Significance scores of $(*)P<0.05$; $()P<0.01$; and $(*)P<0.001$ were determined by Kruskal-Wallis plus Dunn's Multiple Comparison Tests.

FIG. 7B and FIG. 7C. Mice surviving the HSV-2 challenge were medroxyprogesterone treated as before, and 17 weeks after challenge, these mice were re-challenged and a naïve group of mice was challenged i.vag. with $10 \times LD_{50}$ of HSV-2. Mice were swabbed for vaginal HSV-2 shedding on day 2 and day 4 as above. Vaginal HSV-2 titers for the naïve group are shown (FIG. 7B). Vaginal HSV-2 shedding in each mouse following challenge and re-challenge is plotted as the vaginal HSV-2 titer on day 2 following HSV-2 challenge on the x-axis and on day 2 following re-challenge on the y-axis (FIG. 7C). Each FI-HSV2 immunization group is shown in a separate panel for clarity, and the limit of detection for both assays was 10 PFU per swab. The numbers of overlapping data points on each graph are shown. Significance scores of $(*)P<0.05$; $()P<0.01$; and $(*)P<0.001$ were determined by Kruskal-Wallis plus Dunn's Multiple Comparison Tests.

FIG. 8A. Vaginal virus shedding on day 2 (left panel) or day 4 (right panel) postchallenge as in FIG. 6A and FIG. 6B except that the limit of assay sensitivity was 2.2 PFU per swab. FIG. 8B. Disease scores (using the scale described in FIG. 4A to FIG. 4C) from days 1-14 postchallenge were summed for individual mice (each symbol shows the value for one mouse). FIG. 8C. Protection against HSV-2 latent DNA load in the DRG. Four weeks postchallenge the lumbosacral DRG from each surviving mouse and 4 naïve mice were removed, pooled, frozen, and the DRG DNA from each pool was extracted and quantified by spectrophotometry. Cross-contamination safeguards, sample storage, DRG DNA extraction, and HSV-2 copy number determined by TaqMan quantitative PCR (Applied Biosystems, Inc.) using primers and a probe specific for gG2 were as previously described [19]. Each reaction contained 300 ng of DRG DNA and the DNA load for each mouse is expressed as HSV-2 DNA copy number per 300 ng of DRG DNA. The line represents the limit of detection for the assay (2 copies of HSV-2 DNA per 300 ng of DRG DNA). Uniformity of each template was ensured by TaqMan quantification of the mouse adipsin gene (GenBank accession no. X04673.1): sense primer (TGT GGC AAT GGC AAA AAG C) (SEQ ID NO:14), antisense primer (TGT TAC CAT TTG TGA TGT TTT CGA T) (SEQ ID NO:15), and probe (6-FAM-CGT CTA TAC-ZEN-CCG AGT GTC ATC CTA CCG GA-Iowa Black F Quencher) (SEQ ID NO:16).

FIG. 9A and FIG. 9B. Virus specific antibody levels in immunized mice. FIG. 9A. ELISA against HSV-2 virion was used to measure prechallenge, total IgG (left panel) or IgG1 and IgG2a isotypes (right panel) in the sera of immunized mice. The mean endpoint reciprocal titers and SD are shown for each immunization group as in FIG. 6C. FIG. 9B. Virus neutralizing antibody titers were measured against HSV-2 virion as in FIG. 6D. FIG. 9C. The means and standard errors of virus specific CD4+ T cells (left panel) and CD8+ T cells (right panel) producing IFN-γ were measured by intracellular cytokine staining Splenocytes from immunized and then in vivo restimulated mice (n=4) were collected and assayed 3 weeks following the second injection as described in Materials and Methods.

DETAILED DESCRIPTION OF THE INVENTION

I. Definitions

Figure 1A:
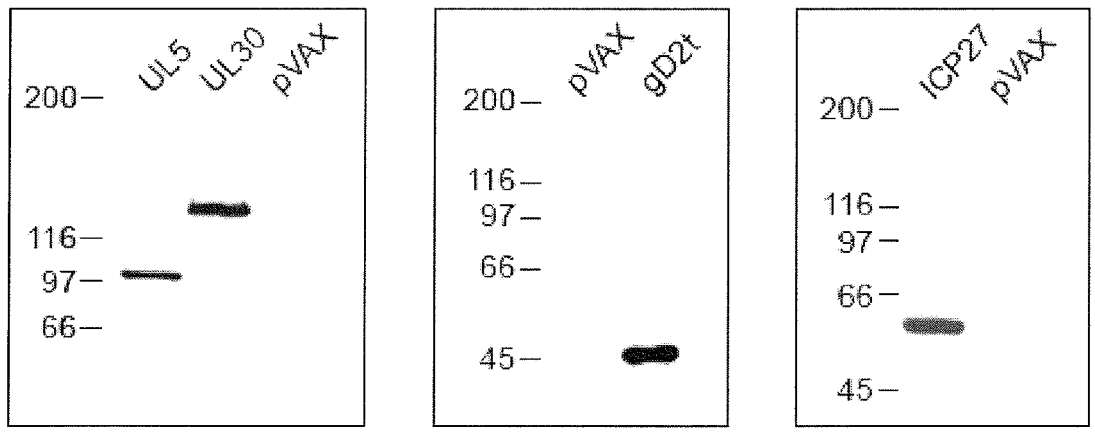
FIG. 1A to FIG. 1C. Expression of HSV-2 ORFs from plasmid vaccines and purification of gD2t protein.

The abbreviations used herein have their conventional meaning within the chemical and biological arts. The chemical structures and formulae set forth herein are constructed according to the standard rules of chemical valency known in the chemical arts.

The terms "a" or "an," as used in herein means one or more. In addition, the phrase "substituted with a[n]," as used herein, means the specified group may be substituted with one or more of any or all of the named substituents.

Description of compounds of the present invention is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the certain methods presented herein successfully treat HV (e.g. an HV selected from the group consisting of HHV-1, HHV-2, HHV-3, HHV-4, HHV-5, HHV-6, HHV-7, and HHV-8) infection by decreasing the incidence of HV (e.g. an HV selected from the group consisting of HHV-1, HHV-2, HHV-3, HHV-4, HHV-5, HHV-6, HHV-7, and HHV-8) infection, reducing one or more symptoms of HV (e.g. an HV selected from the group consisting of HHV-1, HHV-2, HHV-3, HHV-4, HHV-5, HHV-6, HHV-7, and HHV-8) infection, or preventing the spread of HV (e.g. an HV selected from the group consisting of HHV-1, HHV-2, HHV-3, HHV-4, HHV-5, HHV-6, HHV-7, and HHV-8). In some embodiments of the compositions or methods described herein, treating HV (e.g. an HV selected from the group consisting of HHV-1, HHV-2, HHV-3, HHV-4, HHV-5, HHV-6, HHV-7, and HHV-8) infection includes slowing the rate of growth or spread of HV (e.g. an HV selected from the group consisting of HHV-1, HHV-2, HHV-3, HHV-4, HHV-5, HHV-6, HHV-7, and HHV-8) or reducing the occurrence of lesions. The term "treating" and conjugations thereof, include prevention of an injury, pathology, condition, or disease. The term "preventing" or "prevention" refers to any indicia of success in protecting a subject or patient (e.g. a subject or patient at risk of developing a disease or condition) from developing, contracting, or having a disease or condition (e.g. HV (e.g. an HV selected from the group consisting of HHV-1, HHV-2, HHV-3, HHV-4, HHV-5, HHV-6, HHV-7, and HHV-8) infection), including preventing one or more symptoms of a disease or condition or diminishing the occurrence, severity, or duration of any symptoms of a disease or condition following administration of a prophylactic or preventative composition as described herein.

An "effective amount" is an amount sufficient for a compound to accomplish a stated purpose relative to the absence of the compound (e.g. achieve the effect for which it is administered, treat a disease, reduce spread of HV (e.g. an HV selected from the group consisting of HHV-1, HHV-2, HHV-3, HHV-4, HHV-5, HHV-6, HHV-7, and HHV-8), reduce one or more symptoms of a disease or condition (e.g. lesions, virus production, lytic cycle)). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a composition (vaccine) is an amount of a composition that, when administered to a subject, will have the intended prophylactic effect, e.g., preventing or delaying the onset (or reoccurrence) of an injury, disease (e.g. HV (e.g. an HV selected from the group consisting of HHV-1, HHV-2, HHV-3, HHV-4, HHV-5, HHV-6, HHV-7, and HHV-8) infection), pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses (e.g. prime-boost). Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of HV (e.g. an HV selected from the group consisting of HHV-1, HHV-2, HHV-3, HHV-4, HHV-5, HHV-6, HHV-7, and HHV-8) infection or one or more symptoms of HV (e.g. an HV selected from the group consisting of HHV-1, HHV-2, HHV-3, HHV-4, HHV-5, HHV-6, HHV-7, and HHV-8) infection in the absence of a composition (e.g. vaccine) as described herein (including embodiments).

"Contacting" is used in accordance with its plain ordinary meaning and refers to the process of allowing at least two distinct species (e.g. compositions, vaccines, virus, biomolecules, or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture. In some embodiments, contacting refers to allowing radiation (e.g. UV, gamma) to interact with matter (e.g. virus, virus component, virus protein, virus nucleic acid).

The term "contacting" may include allowing two species to react, interact, or physically touch, wherein the two species may be a composition (e.g. vaccine) as described herein and a cell, virus, virus particle, protein, enzyme, or patient. In some embodiments contacting includes allowing a composition described herein to interact with a protein or enzyme that is involved in a signaling pathway. In some embodiments contacting includes allowing a composition described herein to interact with an HV (e.g. an HV selected from the group consisting of HHV-1, HHV-2, HHV-3, HHV-4, HHV-5, HHV-6, HHV-7, and HHV-8). In some embodiments contacting includes allowing an agent described herein to interact with an HV (e.g. an HV selected from the group consisting of HHV-1, HHV-2, HHV-3, HHV-4, HHV-5, HHV-6, HHV-7, and HHV-8) and inactivate the HV (e.g. an HV selected from the group consisting of HHV-1, HHV-2, HHV-3, HHV-4, HHV-5, HHV-6, HHV-7, and HHV-8).

As defined herein, the term "inhibition", "inhibit", "inhibiting" and the like in reference to a protein-inhibitor or interaction means negatively affecting (e.g. decreasing) the activity or function of the protein. In some embodiments inhibition refers to reduction of a disease or symptoms of disease. In some embodiments inhibition refers to reduction of the growth, proliferation, or spread of a virus (e.g. HV (e.g. an HV selected from the group consisting of HHV-1, HHV-2, HHV-3, HHV-4, HHV-5, HHV-6, HHV-7, and HHV-8)). In some embodiments inhibition refers to preventing the infection of a subject by a virus (e.g. HV (e.g. an HV selected from the group consisting of HHV-1, HHV-2, HHV-3, HHV-4, HHV-5, HHV-6, HHV-7, and HHV-8)). In some embodiments, inhibition refers to a reduction in the activity of a signal transduction pathway or signaling pathway. Thus, inhibition includes, at least in part, partially or totally blocking stimulation, decreasing, preventing, or delaying activation, or inactivating, desensitizing, or down-regulating the signaling pathway or enzymatic activity or the amount of a protein.

The term "modulator" refers to a composition that increases or decreases the level of a target (e.g. molecule, cell, virus particle, protein) or the function of a target or the physical state of the target.

The term "modulate" is used in accordance with its plain ordinary meaning and refers to the act of changing or varying one or more properties. "Modulation" refers to the process of changing or varying one or more properties. For example, as applied to the effects of a modulator on a target, to modulate means to change by increasing or decreasing a property or function of the target or the amount of the target.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human. In some embodiments, a patient or subject in need thereof or a patient in need thereof, refers to a living organism (e.g. human) at risk of developing, contracting, or having a disease or condition (e.g. HV (e.g. an HV selected from the group consisting of HHV-1, HHV-2, HHV-3, HHV-4, HHV-5, HHV-6, HHV-7, and HHV-8) infection or disease associated with an HV (e.g. an HV selected from the group consisting of HHV-1, HHV-2, HHV-3, HHV-4, HHV-5, HHV-6, HHV-7, and HHV-8)).

"Disease" or "condition" refer to a state of being or health status of a patient or subject capable of being treated with the compositions (e.g. vaccines) or methods provided herein. In some embodiments, the disease is a disease related to (e.g. caused by) HV (e.g. an HV selected from the group consisting of HHV-1, HHV-2, HHV-3, HHV-4, HHV-5, HHV-6, HHV-7, and HHV-8). Examples of diseases, disorders, or conditions include, but are not limited to herpetic gingivostomatitis, herpes labialis, herpes genitalis, herpetic whitlow, herpes gladiatorum, herpesviral encephalitis, herpesviral meningitis, herpes esophagitis, herpes keratitis, Bell's palsy, Mollaret's meningitis, herpes rugbeiorum, eczema herpeticum, herpetic neuralgia, or post-herpetic neuralgia. In some instances, "disease" or "condition" refers to HV (e.g. an HV selected from the group consisting of HHV-1, HHV-2, HHV-3, HHV-4, HHV-5, HHV-6, HHV-7, and HHV-8) infection. In some instances, "disease" or "condition" refers to herpetic gingivostomatitis. In some instances, "disease" or "condition" refers to herpes labialis. In some instances, "disease" or "condition" refers to herpes genitalis. In some instances, "disease" or "condition" refers to herpetic whitlow. In some instances, "disease" or "condition" refers to herpes gladiatorum. In some instances, "disease" or "condition" refers to herpesviral encephalitis. In some instances, "disease" or "condition" refers to herpesviral meningitis. In some instances, "disease" or "condition" refers to herpes esophagitis. In some instances, "disease" or "condition" refers to herpes keratitis. In some instances, "disease" or "condition" refers to Bell's palsy. In some instances, "disease" or "condition" refers to Mollaret's meningitis. In some instances, "disease" or "condition" refers to herpes rugbeiorum. In some instances, "disease" or "condition" refers to eczema herpeticum. In some instances, "disease" or "condition" refers to herpetic neuralgia. In some instances, "disease" or "condition" refers to post-herpetic neuralgia. In some instances, "disease" or "condition" refers to HSV1 infection. In some instances, "disease" or "condition" refers to HSV2 infection. In some instances, "disease" or "condition" refers to HSV1 and HSV2 infection. In some instances, "disease" or "condition" refers to HHV-3 infection. In some instances, "disease" or "condition" refers to HHV-4 infection. In some instances, "disease" or "condition" refers to HHV-5 infection. In some instances, "disease" or "condition" refers to HHV-6 infection. In some instances, "disease" or "condition" refers to HHV-7 infection. In some instances, "disease" or "condition" refers to HHV-8 infection. In some instances, "disease" or "condition" refers to an HV (e.g. HHV-1, HHV-2, HHV-3, HHV-4, HHV-5, HHV-6, HHV-7, or HHV-8) infection.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, intraperitoneal, intramuscular, intralesional, intrathecal, intranasal, intradermal, mucosal, intrarectal, intravaginal, topical, transcutaneous (e.g. as in Combadie're, PLoS ONE 5(5): e10818), or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example HV (e.g. HHV-1, HHV-2, HHV-3, HHV-4, HHV-5, HHV-6, HHV-7, or HHV-8) infection therapies such as antiviral drugs (e.g. acyclovir, famciclovir, valacyclovir) or a different HV (e.g. HHV-1, HHV-2, HHV-3, HHV-4, HHV-5, HHV-6, HHV-7, or HHV-8) vaccine (e.g. DNA vaccine, DNA vaccine including different genes, isolated protein vaccine, different inactivated virus vaccine). The compositions (e.g. vaccines) of the invention can be administered alone or can be coadministered to the patient. Coadministration is meant to include simultaneous or sequential administration of the compounds individually or in combination (more than one composition) and includes vaccine administration in a prime-boost method. Thus, the preparations can also be combined, when desired, with other active substances (e.g. to reduce metabolic degradation, increase immune response (e.g. adjuvant)). The compositions of the present invention can be delivered by transdermally, by a topical route, transcutaneously, formulated as applicator sticks, solutions, suspensions, emulsions, gels, creams, ointments, pastes, jellies, paints, powders, and aerosols.

The term "administer (or administering) an HV vaccine" means administering a composition that prevents or treats an HV (e.g. HHV-1, HHV-2, HHV-3, HHV-4, HHV-5, HHV-6, HHV-7, or HHV-8) infection in a subject. Administration may include, without being limited by mechanism, allowing sufficient time for the HV (e.g. HHV-1, HHV-2, HHV-3, HHV-4, HHV-5, HHV-6, HHV-7, or HHV-8) vaccine to induce an immune response in the subject or to reduce one or more symptoms of a disease (e.g. HHV-1, HHV-2, HHV-3, HHV-4, HHV-5, HHV-6, HHV-7, or HHV-8 infection).

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

The terms "peptide," "polypeptide," and "protein" are used interchangeably herein to refer to a polymer of amino acid residues.

The term "peptidyl" and "peptidyl moiety" means a monovalent peptide.

The term "amino acid" refers to naturally occurring and synthetic amino acids, as well as amino acid analogs. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. An oligomer comprising amino acid mimetics is a peptidomimetic. A peptidomimetic moiety is a monovalent peptidomimetic.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

A "conservative substitution" as used with respect to amino acids, refers to the substitution of an amino acid with a chemically similar amino acid. Amino acid substitutions which often preserve the structural and/or functional properties of the polypeptide in which the substitution is made are known in the art and are described, for example, by H. Neurath and R. L. Hill, 1979, in "The Proteins," Academic Press, New York. The most commonly occurring exchanges are isoleucine/valine, tyrosine/phenylalanine, aspartic acid/glutamic acid, lysine/arginine, methionine/leucine, aspartic acid/asparagine, glutamic acid/glutamine, leucine/isoleucine, methionine/isoleucine, threonine/serine, tryptophan/phenylalanine, tyrosine/histidine, tyrosine/tryptophan, glutamine/arginine, histidine/asparagine, histidine/glutamine, lysine/asparagine, lysine/glutamine, lysine/glutamic acid, phenylalanine/leucine, phenylalanine/methionine, serine/alanine, serine/asparagine, valine/leucine, and valine/methionine. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)). In some embodiments, there may be at least 1, at least 2, at least 3, at least 4, at least 5, at least 6, at least 7, at least 8, at least 9, at least 10, at least 15, at least 20, at least 25, at least 30, at least 35, or at least 40 conservative substitutions. In some embodiments, there may be 1, 2, 3, 4, 5, 6, 7, 8, 9, 10, 15, 20, 25, 30, 35, or 40 conservative substitutions.

The term "amino acid substitution set" or "substitution set" refers to a group of amino acid substitutions. A substitution set can have 1, 2, 3, 4, 5, 6, 7, 8, 9, 10, 11, 12, 13, 14, 15, or more amino acid substitutions.

The term "isolated" refers to a nucleic acid, polynucleotide, polypeptide, protein, or other component that is partially or completely separated from components with which it is normally associated (other proteins, nucleic acids, cells, etc.). In some embodiments, an isolated polypeptide or protein is a recombinant polypeptide or protein.

A nucleic acid (such as a polynucleotide), a polypeptide, or a cell is "recombinant" when it is artificial or engineered, or derived from or contains an artificial or engineered protein or nucleic acid (e.g. non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"Nucleic acid" or "oligonucleotide" or "polynucleotide" or grammatical equivalents used herein means at least two nucleotides covalently linked together. The term "nucleic acid" includes single-, double-, or multiple-stranded DNA, RNA and analogs (derivatives) thereof. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. In certain embodiments, the nucleic acids herein contain phosphodiester bonds. In other embodiments, nucleic acid analogs are included that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

A particular nucleic acid sequence also encompasses "splice variants." Similarly, a particular protein encoded by a nucleic acid encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, then synthetic oligonucleotide adaptors or linkers are used in accordance with conventional practice.

"Identity" or "percent identity," in the context of two or more polypeptide sequences, refers to two or more sequences or subsequences that are the same or have a specified percentage of amino acid residues that are the same (e.g., share at least about 70%, at least about 75%, at least about 80%, at least about 85%, at least about 88% identity, at least about 89%, at least about 90%, at least about 91%, at least about 92%, at least about 93%, at least about 94%, at least about 95%, at least about 96%, at least about 97%, at least about 98%, or at least about 99% identity) over a specified region to a reference sequence, when compared and aligned for maximum correspondence over a comparison window, or designated region as measured using a sequence comparison algorithms or by manual alignment and visual inspection.

Optimal alignment of sequences for comparison and determination of sequence identity can be determined by a sequence comparison algorithm or by visual inspection (see, generally, Ausubel et al., infra). When optimally aligning sequences and determining sequence identity by visual inspection, percent sequence identity is calculated as the number of residues of the test sequence that are identical to the reference sequence divided by the number of non-gap positions and multiplied by 100. When using a sequence comparison algorithm, test and reference sequences are entered into a computer, subsequence coordinates and sequence algorithm program parameters are designated. The sequence comparison algorithm then calculates the percent sequence identities for the test sequences relative to the reference sequence, based on the program parameters as known in the art, for example BLAST or BLAST 2.0. For example, comparison can be conducted, e.g., by the local homology algorithm of Smith & Waterman, 1981, *Adv. Appl. Math.* 2:482, by the homology alignment algorithm of Needleman & Wunsch, 1970, *J. Mol. Biol.* 48:443, by the search for similarity method of Pearson & Lipman, 1988, *Proc. Nat'l. Acad. Sci. USA* 85:2444, or by computerized implementations of these algorithms (GAP, BESTFIT, FASTA, and TFASTA in the Wisconsin Genetics Software Package, Genetics Computer Group, 575 Science Dr., Madison, Wis.). Thus alignment can be carried out for sequences that have deletions and/or additions, as well as those that have substitutions, as well as naturally occurring, e.g., polymorphic or allelic variants, and man-made variants.

The phrase "substantial sequence identity" or "substantial identity," in the context of two polypeptide sequences, refers to a sequence that has at least 70% identity to a reference sequence. Percent identity can be any integer from 70% to 100%. Two polypeptide sequences that have 100% sequence identity are said to be "identical." A polypeptide sequence is said to have "substantial sequence identity" to a reference sequence when the sequences have at least about 70%, at least about 75%, at least 80%, at least 85%, at least 90%, at least 91%, at least 92%, at least 93%, at least 94%, at least 95%, at least 96%, at least 97%, at least 98%, or at least 99% or greater sequence identity as determined using the methods described herein, such as BLAST using standard parameters as described above.

The term "expression" includes any step involved in the production of the polypeptide including, but not limited to, transcription, post-transcriptional modification, translation, post-translational modification, and secretion.

An amino acid or peptide is "heterologous" to another sequence with which it is operably linked if the two sequences are not associated in nature.

The terms "dose" and "dosage" are used interchangeably herein. A dose refers to the amount of active ingredient given to an individual at each administration. For the present methods and compositions provided herein, the dose may generally refer to the amount of disease (e.g HV (e.g. HHV-1, HHV-2, HHV-3, HHV-4, HHV-5, HHV-6, HHV-7, or HHV-8) infection) treatment. The dose will vary depending on a number of factors, including the range of normal doses for a given therapy, frequency of administration; size and tolerance of the individual; severity of the condition; risk of side effects; and the route of administration. One of skill will recognize that the dose can be modified depending on the above factors or based on therapeutic progress. The term "dosage form" refers to the particular format of the pharmaceutical or pharmaceutical composition, and depends on the route of administration. For example, a dosage form can be in a liquid form for nebulization, e.g., for inhalants, in a tablet or liquid, e.g., for oral delivery, or a saline solution, e.g., for injection.

The term "herpesvirus" or "herpes virus" or "HV" refers to human herpesviruses and may be used, depending on the context, to refer to one, more, or all of the human herpesviruses, including Human Herpesvirus-1 (HHV-1, Herpes Simplex Virus-1, HSV1, HSV-1), HHV-2 (Herpes Simplex Virus-2, HSV2, HSV-2), HHV-3 (Varicella Zoster Virus, VZV), HHV-4 (Epstein-Barr Virus, EBV), HHV-5 (Cytomegalovirus, CMV, HCMV), HHV-6, HHV-7, HHV-8 (Kaposi's Sarcoma-associated Herpesvirus, KSHV). In some embodiments, a herpesvirus is HHV-1. In some embodiments, a herpesvirus is HHV-2. In some embodiments, a herpesvirus is HHV-3. In some embodiments, a herpesvirus is HHV-4. In some embodiments, a herpesvirus is HHV-5. In some embodiments, a herpesvirus is HHV-6. In some embodiments, a herpesvirus is HHV-7. In some embodiments, a herpesvirus is HHV-8. In some embodiments, each of the terms HHV-1, HHV-2, HHV-3, HHV-4, HHV-5, HHV-6, HHV-7, and HHV-8 may refer to all strains of each respective HHV. In some embodiments, each of the terms HHV-1, HHV-2, HHV-3, HHV-4, HHV-5, HHV-6, HHV-7, and HHV-8 may refer to a single strain of that HHV. In some embodiments, each of the terms HHV-1, HHV-2, HHV-3, HHV-4, HHV-5, HHV-6, HHV-7, and HHV-8 may include mutants of that particular HHV. In some embodiments HV is HSV (HHV-1 and/or HHV-2).

The terms "Herpes Simplex Virus" and "HSV" are used according to their common meaning and refer to the double stranded DNA viruses Herpes Simplex Virus 1 (HSV1, HSV-1, HHV-1) and Herpes Simplex Virus 2 (HSV2, HSV-2, HHV-2). In some embodiments, HSV includes all strains of HSV1 and HSV2. In some embodiments, HSV may refer to a single strain of HSV1 or HSV2. In some embodiments, HSV includes multiple strains of HSV1 and/or HSV2. In some embodiments, HSV includes mutants of HSV1 and/or HSV2. The terms "HSV1" and "HSV2" are used according to their plain ordinary meaning. In some embodiments, HSV1 includes all strains or HSV1. In some embodiments, HSV1 includes mutants of HSV1. In some embodiments, HSV2 includes all strains or HSV2. In some embodiments, HSV2 includes mutants of HSV2.

The terms "inactivate", "inactivating', and other verb forms thereof, when describing a virus or the process of modifying a virus, refer to a virus that is incapable of establishing a viable infection in a human, replicating, and generating virus particles capable of infecting a second human, and the process of generating such a virus. In some embodiments, an inactivated virus comprises a mutation that prevents the virus from replicating. In some embodiments, an inactivated virus comprises a mutation that prevents the virus from infecting a subject (e.g. human). In some embodiments, an inactivated virus comprises a mutation that prevents the virus from infecting a cell (e.g. human cell). In some embodiments, inactivating a virus includes contacting the virus with an agent that causes the virus to become incapable of establishing a viable infection in a human and generating virus particles capable of infecting a second human. In some embodiments, inactivating a virus includes contacting the virus with a cross-linking agent. In some embodiments, inactivating a virus includes contacting the virus with an oxidizing agent. In some embodiments, inactivating a virus includes contacting the virus with a reducing agent. In some embodiments, inactivating a virus includes contacting the virus with heat. In some embodiments, inactivating a virus includes contacting the virus with radiation. In some embodiments, inactivating a virus includes contacting the virus with a detergent. In some embodiments, inactivating a virus includes contacting the virus with a pH changing agent. In some embodiments, inactivating a virus includes contacting the virus with a chemical agent. In some embodiments, inactivating a virus includes contacting the virus with a furocoumarin. In some embodiments, inactivating a virus includes contacting the virus with aziridine. In some embodiments, inactivating a virus includes contacting the virus with ethylenimine. In some embodiments, inactivating a virus includes contacting the virus with a binary ethylenimine. In some embodiments, inactivating a virus includes contacting the virus with beta-propiolactone.

The terms "lipopolysaccharide-derived adjuvant" and "LPS-derived adjuvant" refer to lipopolysaccharides or molecules derived from lipopolysaccharides commonly employed as part of a vaccine formulation. The LPS-derived adjuvant may be designed to increase the immune response of a subject when administered to the subject as a component of a vaccine or method of vaccination relative to the absence of the lipopolysaccharide molecule. In some embodiments, an LPS-derived adjuvant includes a portion of an LPS. In some embodiments, an LPS-derived adjuvant includes an LPS. In some embodiments, an LPS-derived adjuvant includes a modified portion of an LPS. In some embodiments, an LPS-derived adjuvant includes a component that is a portion of an LPS and another component that is not a portion of an LPS. In some embodiments, an LPS-derived adjuvant includes a component that corresponds to a portion of an LPS, but which is chemically synthesized. The term "Lipopolysaccharides" and "LPS" are used according to their plain meaning in Biology, Biochemistry, and Immunology and refer to molecules comprising one or more lipids and one or more polysaccharides covalently bonded together. In some embodiments, LPS are components of the outer membrane of Gram-negative bacteria. In some embodiments, and LPS-derived adjuvant is a monophorphoryl lipid A (MPL) adjuvant.

The term "adjuvant" is used in accordance with its plain ordinary meaning within Immunology and refers to a substance that is commonly used as a component of a vaccine. Adjuvants may increase an antigen specific immune response in a subject when administered to the subject with one or more specific antigens as part of a vaccine. In some embodiments, an adjuvant accelerates an immune response to an antigen. In some embodiments, an adjuvant prolongs an immune response to an antigen. In some embodiments, an adjuvant enhances an immune response to an antigen. In some embodiments, an adjuvant is selected from the group consisting of aluminum-based mineral salt adjuvant, squalene, lipopolysaccharide-derived adjuvant, bacterial cell wall components, molecular cages, nucleic acid, oil, virosome, QS21, and MF59.

The term "aluminum-based mineral salt adjuvant" refers to an adjuvant including aluminum. In some embodiments, an aluminum-based mineral salt adjuvant includes aluminum hydroxide. In some embodiments, an aluminum-based mineral salt adjuvant is aluminum hydroxide. In some embodiments, an aluminum-based mineral salt adjuvant includes aluminum phosphate. In some embodiments, an aluminum-based mineral salt adjuvant is aluminum phosphate. In some embodiments, an aluminum-based mineral salt adjuvant includes potassium aluminum sulfate. In some embodiments, an aluminum-based mineral salt adjuvant is potassium aluminum sulfate. In some embodiments, an aluminum-based mineral salt adjuvant is aluminum hydroxide adjuvant. In some embodiments, an aluminum-based mineral salt adjuvant is aluminum phosphate adjuvant. In some embodiments, an aluminum-based mineral salt adjuvant is potassium aluminum sulfate adjuvant. In some embodiments, an aluminum-based mineral salt adjuvant is Alum. In some embodiments, an aluminum-based mineral salt adjuvant is CAS no. 21645-51-2. In some embodiments, an aluminum-based mineral salt adjuvant is aluminum hydroxide gel. In some embodiments, an aluminum-based mineral salt adjuvant is aluminum hydroxide gel in the form of a white gelatinous precipitate. In some embodiments, an aluminum-based mineral salt adjuvant is CAS no. 7784-30-7. In some embodiments, an aluminum-based mineral salt adjuvant is aluminum phosphate gel. In some embodiments, an aluminum-based mineral salt adjuvant is aluminum phosphate gel in the form of a white gelatinous precipitate. In some embodiments, an aluminum-based mineral salt adjuvant is not Imject Alum Adjuvant™. In some embodiments, an aluminum-based mineral salt adjuvant is aluminum hydroxide without magnesium hydroxide. In some embodiments, an aluminum-based mineral salt adjuvant is Alhydrogel™. In some embodiments, an aluminum-based mineral salt adjuvant is Adju-Phos™ In some embodiments, an aluminum-based mineral salt adjuvant is Adjuphos™. In some embodiments, an aluminum-based mineral salt adjuvant is amorphous aluminum hydroxide and not crystalline aluminum hydroxide. In some embodiments, an aluminum-based mineral salt adjuvant includes amorphous aluminum and not crystalline aluminum. In some embodiments, an aluminum-based mineral salt adjuvant is crystalline aluminum hydroxide and not amorphous aluminum hydroxide. In some embodiments, an aluminum-based mineral salt adjuvant includes crystalline aluminum and not amorphous aluminum. In some embodiments, an aluminum-based mineral salt adjuvant includes crystalline aluminum oxyhydroxide. In some embodiments, an aluminum-based mineral salt adjuvant is crystalline aluminum oxyhydroxide. In some embodiments, an aluminum-based mineral salt adjuvant includes amorphous aluminum hydroxyphosphate. In some embodiments, an aluminum-based mineral salt adjuvant is amorphous aluminum hydroxyphosphate. In some embodiments, an aluminum-based mineral salt adjuvant includes aluminum oxyhydroxide and not aluminum hydroxycarbonate. In some embodiments, an aluminum-based mineral salt adjuvant is aluminum oxyhydroxide and not aluminum hydroxycarbonate. In some embodiments, an aluminum-based mineral salt adjuvant includes aluminum oxyhydroxide and not magnesium hydroxide. In some embodiments, an aluminum-based mineral salt adjuvant is aluminum oxyhydroxide and not magnesium hydroxide. In some embodiments, an aluminum-based mineral salt adjuvant does not include amorphous aluminum hydroxide in which some hydroxyls are replaced by sulfate anions. In some embodiments, an aluminum-based mineral salt adjuvant includes aluminum oxyhydroxide in a Boehmite-like pattern. In some embodiments, an aluminum-based mineral salt adjuvant is aluminum oxyhydroxide in a Boehmite-like pattern. In some embodiments of an aluminum-based mineral salt adjuvant described above, the description is of the aluminum-based mineral salt adjuvant prior to inclusion in a vaccine. In some embodiments, an aluminum-based mineral salt adjuvant is an aluminum containing adjuvant approved by the FDA for administration to humans. In some embodiments, an aluminum-based mineral salt adjuvant is an aluminum hydroxide adjuvant approved for administration to humans by the FDA. In some embodiments, an aluminum-based mineral salt adjuvant is an aluminum phosphate adjuvant approved for administration to humans by the FDA.

The term "aluminum hydroxide adjuvant" as used herein refers to the aluminum hydroxide adjuvant that includes aluminum hydroxide and is currently used in licensed human vaccines. In some embodiments, "aluminum hydroxide adjuvant" as used herein refers to the aluminum hydroxide adjuvant that is currently used in licensed human vaccines and is used in accordance with the use of that term in Hem S. L., Vaccine 23 (2007) 4985-4986. In some embodiments, an aluminum hydroxide adjuvant includes CAS no. 21645-51-2. In some embodiments, an aluminum hydroxide adjuvant is aluminum hydroxide gel. In some embodiments, an aluminum hydroxide adjuvant is aluminum hydroxide gel in the form of a white gelatinous precipitate. In some embodiments, an aluminum hydroxide adjuvant includes aluminum hydroxide and does not include magnesium hydroxide. In some embodiments, an aluminum hydroxide adjuvant is Alhydrogel™. In some embodiments, an aluminum hydroxide adjuvant includes crystalline aluminum hydroxide and not amorphous aluminum hydroxide. In some embodiments, an aluminum hydroxide adjuvant includes crystalline aluminum and not amorphous aluminum. In some embodiments, an aluminum hydroxide adjuvant includes crystalline aluminum oxyhydroxide. In some embodiments, an aluminum hydroxide is crystalline aluminum oxyhydroxide. In some embodiments, an aluminum hydroxide adjuvant includes aluminum oxyhydroxide and not aluminum hydroxycarbonate. In some embodiments, an aluminum hydroxide adjuvant is aluminum oxyhydroxide and not aluminum hydroxycarbonate. In some embodiments, an aluminum hydroxide adjuvant does not include amorphous aluminum hydroxide in which some hydroxyls are replaced by sulfate anions. In some embodiments, aluminum hydroxide adjuvant includes aluminum oxyhydroxide in a Boehmite-like pattern. In some embodiments of an aluminum hydroxide adjuvant described above, the description is of the aluminum hydroxide adjuvant prior to inclusion in a vaccine.

The term "aluminum phosphate adjuvant" as used herein refers to the aluminum phosphate adjuvant that includes aluminum phosphate and is currently used in licensed human vaccines. In some embodiments, "aluminum phosphate adjuvant" as used herein refers to the aluminum phosphate adjuvant that is currently used in licensed human vaccines and is used in accordance with the use of that term in Hem S. L., Vaccine 23 (2007) 4985-4986. In some embodiments, an aluminum phosphate adjuvant includes CAS no. 7784-30-7. In some embodiments, an aluminum phosphate adjuvant is aluminum phosphate gel. In some embodiments, an aluminum phosphate adjuvant is aluminum phosphate gel in the form of a white gelatinous precipitate. In some embodiments, an aluminum phosphate adjuvant is Adju-Phos™. In some embodiments, an aluminum phosphate adjuvant is Adjuphos™. In some embodiments, an aluminum phosphate adjuvant includes amorphous aluminum hydroxyphosphate. In some embodiments of an aluminum phosphate adjuvant described above, the description is of the aluminum phosphate adjuvant prior to inclusion in a vaccine.

The term "lipid A adjuvant" refers to an adjuvant including the lipid A portion of lipopolysaccharide isolated from the remainder of a lipopolysaccharide molecule. A lipid A adjuvant is an example of an LPS-derived adjuvant. In some embodiments, lipid A includes two glucosamine molecules covalently bonded to fatty acid molecules and including one phosphate molecule covalently bonded to each glucosamine molecule. In some embodiments, lipid A includes six fatty acid molecules. In some embodiments, lipid A includes six fatty acid molecules each comprising 10 to 16 carbon atoms.

The terms "TLR4" and "Toll-like receptor 4" refer to the human gene, mRNA, and/or protein associated with UniProt O00206, Entrez 7099, RefSeq NM_003266.3, and/or NP_003257.1.

The terms "bind", "bound", "binding", and other verb forms thereof are used in accordance with their plain ordinary meaning within Enzymology and Biochemistry and refer to the formation of one or more interactions or contacts between two compositions that may optionally interact. Binding may be intermolecular or intramolecular.

The term "potassium aluminum sulfate adjuvant" refers to an adjuvant that includes potassium aluminum sulfate.

The term "vaccine" is used according to its plain ordinary meaning within medicine and Immunology and refers to a composition including an antigenic component for administration to a subject (e.g. human), which elicits an immune response to the antigenic component. In some embodiments a vaccine is a therapeutic. In some embodiments, a vaccine is prophylactic. In some embodiments a vaccine includes one or more adjuvants.

The term "replication decreasing DNA mutation" as applied to a virus, refers to a mutation of the viral genome resulting in a decrease in replication of the virus relative to the identical virus not including the replication decreasing DNA mutation. In some embodiments, a replication decreasing DNA mutation prevents viral replication.

The term "chemical inactivation" as applied to inactivation of a virus (e.g. HV, HSV, HHV-1, HHV-2, HHV-3, HHV-4, HHV-5, HHV-6, HHV-7, or HHV-8), refers to a method of inactivating (as defined herein) a virus including contacting the virus with a chemical agent, wherein the contacting causes the inactivation of the virus.

The term "cross-linking agent" is used in accordance with its plain meaning within Chemistry and Biochemistry and refers to an agent (e.g. chemical, biologic) capable of causing a covalent bond (e.g. irreversible, reversible) to form between two or more chemical species (e.g. proteins, nucleic acids, sugars, cells, compound, any combination thereof) and connecting two or more compositions. In some embodiments, the two or more compositions are directly connected through covalent bonds. In some embodiments, the two or more compositions are connected through covalent bonds to one or more cross-linker molecules or portions of one or more cross-linker molecules. In some embodiments, the compositions are connected through covalent bonds to intermediate molecules or atoms that are not crosslinkers or portions of the crosslinker.

The term "oxidizing agent" is used according to its plain ordinary meaning in Chemistry and refers to a substance that removes electrons from a second substance in a redox reaction.

The term "reducing agent" is used according to its plain ordinary meaning in Chemistry and refers to a substance that donates electrons to a second substance in a redox reaction.

The term "radiation" is used according to its plain ordinary meaning in physics and includes both ionizing and non-ionizing radiation. Some examples of radiation include, but are not limited to, UV, infrared, alpha, beta, gamma, X-ray, visible, microwave.

The term "aldehyde cross-linking agent" is used according to its plain ordinary meaning in Chemistry and refers to a cross-linking agent as defined herein, wherein one or more of the cross-linker moieties involved in forming covalent bonds is an aldehyde. In some embodiments, all (e.g. two) of the reactive moieties are aldehydes. In some embodiments, one reactive moiety is an aldehyde and one or more reactive moieties are not aldehydes.

The term "formalin" is used according to its plain ordinary meaning in Chemistry and refers to an aqueous solution including formaldehyde (e.g. 37% by mass). The components of formalin are typically designed to be in sufficient quantities to inactivate a virus. In some embodiments, formalin may include methanol. In some embodiments, formalin does not include methanol.

The term "viral shedding" is used according to its plain ordinary meaning in Medicine and Virology and refers to the production and release of virus from an infected cell. In some embodiments, the virus is released from a cell of a subject. In some embodiments virus is released into the environment from an infected subject. In some embodiments the virus is released from a cell within a subject.

The term "lesion" is used according to its plain ordinary meaning within medicine and refers to an abnormality or damage to the tissue of a subject.

The term "sulfated polysaccharide" is used according to its plain ordinary meaning in Biochemistry and Glycobiology and refers to two or more covalently bonded monosaccharides (including nitrogen containing monosaccharides), wherein one or more of the monosaccharides is sulfated. In some embodiments, a sulfated polysaccharide may be a synthetically made or modified sulfated polysaccharide or a synthetically sulfated polysaccharide. Examples include, but are not limited to, heparin, heparan sulfate, and dextran sulfate.

The term "sulfonated polysaccharide" is used according to its plain ordinary meaning in Biochemistry and Glycobiology and refers to two or more covalently bonded monosaccharides (including nitrogen containing monosaccharides), wherein one or more of the monosaccharides is sulfonated. In some embodiments, a sulfonated polysaccharide may be a synthetically made or modified sulfonated polysaccharide or a synthetically sulfonated polysaccharide.

The term "virus particle" is used according to its plain ordinary meaning within Virology and refers to a virion including the viral genome (e.g. DNA, RNA, single strand, double strand), viral capsid and associated proteins, and in the case of enveloped viruses (e.g. HV, HSV, HHV-1, HHV-2, HHV-3, HHV-4, HHV-5, HHV-6, HHV-7, or HHV-8), an envelope including lipids and optionally components of host cell membranes, and/or viral proteins.

The term "plaque forming units" is used according to its plain ordinary meaning in Virology and refers to a unit of measurement based on the number of plaques per unit volume of a sample. In some embodiments the units are based on the number of plaques that could form when infecting a monolayer of susceptible cells. Plaque forming unit equivalents are units of measure of inactivated virus. In some embodiments, plaque forming unit equivalents are derived from plaque forming units for a sample prior to inactivation.

The term "prime-boost" or "prime boost" as applied to a methodology of administering vaccines is used according to its plain ordinary meaning in Virology and Immunology and refers to a method of vaccine administration in which a first dose of a vaccine or vaccine component is administered to a subject or patient to begin the administration (prime) and at a later time (e.g. hours, days, weeks, months later) a second vaccine is administered to the same patient or subject (boost). The first and second vaccines may be the same or different but are intended to both elicit an immune response useful in treating or preventing the same disease or condition (e.g. infection by HV, HSV, HHV-1, HHV-2, HHV-3, HHV-4, HHV-5, HHV-6, HHV-7, or HHV-8). In some embodiments the prime is a DNA vaccine including one or more viral genes or portions thereof and the boost is a DNA vaccine including one or more viral genes or portions thereof, one or more viral proteins or portions thereof, or one or more inactivated or attenuated viruses. In some embodiments, the prime is one or more attenuated or inactivated viruses and the boost is a DNA vaccine including one or more viral genes or portions thereof, one or more viral proteins or portions thereof, or one or more inactivated or attenuated viruses. In some embodiments the prime is one or more viral proteins or portions thereof and the boost is a DNA vaccine including one or more viral genes or portions thereof, one or more viral proteins or portions thereof, or one or more inactivated or attenuated viruses. In some embodiments, the prime is a vaccine including an inactivated virus (e.g. HV, HSV, HHV-1, HHV-2, HHV-3, HHV-4, HHV-5, HHV-6, HHV-7, or HHV-8) and the boost is a second dose of the same vaccine as the prime.

The term "associated" or "associated with" as used herein to describe a disease (e.g. a virus associated disease, HV associated disease, HSV associated disease, HHV-1 associated disease, HHV-2 associated disease, HHV-3 associated disease, HHV-4 associated disease, HHV-5 associated disease, HHV-6 associated disease, HHV-7 associated disease, or HHV-8 associated disease) means that the disease is caused by, or a symptom of the disease is caused by, what is described as disease associated or what is described as associated with the disease. For example, a disease associated with HSV2 or HSV2 infection may be a disease that results (entirely or partially) from HSV2 or HSV2 infection. As used herein, what is described as being associated with a disease, if a causative agent, could be a target for treatment of the disease. For example, a disease associated with HSV2 or HSV2 infection, may be treated with an HSV2 vaccine as described herein (including embodiments). For example, a disease associated with HSV2 may be a disease that a subject with HSV2 or HSV2 infection is at higher risk of developing as compared to a subject without HSV2 or HSV2 infection.

The term "isolated nucleic acid sequence formulation" refers to a formulation having a nucleic acid in the absence of protein (e.g. viral protein). A person of ordinary skill in the art will understand that trace amounts of protein may be present in the isolated nucleic acid sequence formulation. In some embodiments, an isolated nucleic acid sequence formulation is a nucleic acid described in WO2007106404 (e.g pDNA). In some embodiments, the description above applies to the isolated nucleic acid sequence formation prior to incorporation into a vaccine.

The term "nucleic acid vaccine" refers to a vaccine in which the antigenic component is an isolated nucleic acid sequence formulation. The term "DNA vaccine" refers to a vaccine in which the antigenic component is a DNA sequence ("DNA antigenic component"). The isolated nucleic acid sequence formulation antigenic component (e.g. DNA antigenic component) may be an isolated nucleic acid sequence formulation (e.g. "DNA sequence") that encodes an antigenic protein such that when the isolated nucleic acid sequence formulation antigenic component (e.g. DNA antigenic component) is expressed, an antigenic protein is produced. The DNA antigenic component may be a DNA plasmid (e.g. pVAX), optionally including a DNA sequence capable of being translated to a corresponding protein (coding sequence), wherein the coding sequence is translated into a protein capable of causing an immune response specific to the protein, when administered to a subject (e.g. human). In some embodiments a DNA vaccine includes the vaccine DNA plasmid and DNA plasmids including coding sequences described in WO2007106404. In some embodiments, a DNA vaccine is the pVAX plasmid not ligated to a coding sequence. In some embodiments, a DNA vaccine is the pVAX plasmid ligated to a coding sequence. In some embodiments, a DNA vaccine is the pVAX plasmid ligated to a coding sequence from the HSV2 genome. In some embodiments, a DNA vaccine is the pVAX plasmid ligated to a coding sequence from the HCMV genome. In some embodiments, a DNA vaccine is the pVAX plasmid ligated to a coding sequence from the HSV1 genome. In some embodiments, a DNA vaccine is a plasmid capable of expressing an antigen in a human, wherein the antigen is a portion of an HSV2 protein. In some embodiments, a DNA vaccine is a plasmid capable of expressing an antigen in a human, wherein the antigen is a portion of an HSV1 protein. In some embodiments, a DNA vaccine is a plasmid capable of expressing an antigen in a human, wherein the antigen is a portion of an HSV protein. In some embodiments, a DNA vaccine is a plasmid capable of expressing an antigen in a human, wherein the antigen is a portion of an HV (e.g. HHV-1, HHV-2, HHV-3, HHV-4, HHV-5, HHV-6, HHV-7, or HHV-8) protein.

The term "vaccinate", or additional verb forms thereof, refers to administering a vaccine to a subject (e.g. human)

and eliciting an antigen specific immune response, wherein the antigen is included in the vaccine. The term "vaccinate" may also refer to eliciting an antigen specific immune response against an administered antigen. In some embodiments, vaccinate is to provide prophylaxis against a disease or infectious agent (e.g. HV, HSV, HHV-1, HHV-2, HHV-3, HHV-4, HHV-5, HHV-6, HHV-7, or HHV-8).

The term "portion" refers to a subset of a whole, which may also be the whole. In some embodiments, a portion is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%. In some embodiments, a portion is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%. Unless indicated otherwise, the term "about" in the context of a numeric value indicates the nominal value±10% of the nominal value. In some embodiments, "about" may be the nominal value.

II. Compositions

Provided in a first aspect is a Herpesvirus (HV) (e.g. HSV, HHV-1, HHV-2, HHV-3, HHV-4, HHV-5, HHV-6, HHV-7, or HHV-8)) vaccine including inactivated HV (e.g. HSV, HHV-1, HHV-2, HHV-3, HHV-4, HHV-5, HHV-6, HHV-7, or HHV-8), a lipopolysaccharide (LPS)-derived adjuvant and an aluminum-based mineral salt adjuvant.

In some embodiments of the HV (e.g. HSV, HHV-1, HHV-2, HHV-3, HHV-4, HHV-5, HHV-6, HHV-7, or HHV-8) vaccine, the LPS-derived adjuvant is MPL; the aluminum-based mineral salt adjuvant is aluminum hydroxide adjuvant or aluminum phosphate adjuvant; and the vaccine does not include an isolated nucleic acid sequence formulation. In some embodiments of the vaccine, the HV is a Herpes Simplex Virus (HSV). In some embodiments of the vaccine, the HSV is HSV1. In some embodiments of the vaccine, the HSV is HSV2. In some embodiments of the vaccine, the HSV is HSV1 and HSV2. In some embodiments of the vaccine, the HV is Human Cytomegalovirus (HCMV). In some embodiments of an HV vaccine, the HV is HHV-1. In some embodiments of an HV vaccine, the HV is HHV-2. In some embodiments of an HV vaccine, the HV is HHV-3. In some embodiments of an HV vaccine, the HV is HHV-4. In some embodiments of an HV vaccine, the HV is HHV-5. In some embodiments of an HV vaccine, the HV is HHV-6. In some embodiments of an HV vaccine, the HV is HHV-7. In some embodiments of an HV vaccine, the HV is HHV-8. In some embodiments of an HV (e.g. HSV, HHV-1, HHV-2, HHV-3, HHV-4, HHV-5, HHV-6, HHV-7, or HHV-8) vaccine, the lipopolysaccharide-derived adjuvant is derived from the *Salmonella minnesota* LPS. In some embodiments of an HV (e.g. HSV, HHV-1, HHV-2, HHV-3, HHV-4, HHV-5, HHV-6, HHV-7, or HHV-8) vaccine, the lipopolysaccharide-derived adjuvant is derived from the *Salmonella minnesota* Re595 LPS. In some embodiments of an HV (e.g. HSV, HHV-1, HHV-2, HHV-3, HHV-4, HHV-5, HHV-6, HHV-7, or HHV-8) vaccine, the lipopolysaccharide-derived adjuvant is derived from the R595 LPS. In some embodiments of an HV (e.g. HSV, HHV-1, HHV-2, HHV-3, HHV-4, HHV-5, HHV-6, HHV-7, or HHV-8) vaccine, the lipopolysaccharide-derived adjuvant is a lipid A adjuvant. In some embodiments of an HV (e.g. HSV, HHV-1, HHV-2, HHV-3, HHV-4, HHV-5, HHV-6, HHV-7, or HHV-8) vaccine, the lipopolysaccharide-derived adjuvant is a lipid A adjuvant without an (R)-3-hydroxytetradecanoyl moiety. In some embodiments of an HV (e.g. HSV, HHV-1, HHV-2, HHV-3, HHV-4, HHV-5, HHV-6, HHV-7, or HHV-8) vaccine, the lipopolysaccharide-derived adjuvant is a lipid A adjuvant without a 1-phosphate moiety. In some embodiments of an HV (e.g. HSV, HHV-1, HHV-2, HHV-3, HHV-4, HHV-5, HHV-6, HHV-7, or HHV-8) vaccine, the lipopolysaccharide-derived adjuvant is monophosphoryl lipid A. In some embodiments of an HV (e.g. HSV, HHV-1, HHV-2, HHV-3, HHV-4, HHV-5, HHV-6, HHV-7, or HHV-8) vaccine, the lipopolysaccharide-derived adjuvant is 3-O-desacyl-4'-monophosphoryl lipid A. In some embodiments of an HV (e.g. HSV, HHV-1, HHV-2, HHV-3, HHV-4, HHV-5, HHV-6, HHV-7, or HHV-8) vaccine, the lipopolysaccharide-derived adjuvant is capable of binding the TLR4 protein. In some embodiments of an HV (e.g. HSV, HHV-1, HHV-2, HHV-3, HHV-4, HHV-5, HHV-6, HHV-7, or HHV-8) vaccine, the lipopolysaccharide-derived adjuvant is a synthetic MPL analogue adjuvant. In some embodiments of an HV (e.g. HSV, HHV-1, HHV-2, HHV-3, HHV-4, HHV-5, HHV-6, HHV-7, or HHV-8) vaccine, the aluminum-based mineral salt adjuvant is aluminum hydroxide adjuvant. In some embodiments of an HV (e.g. HSV, HHV-1, HHV-2, HHV-3, HHV-4, HHV-5, HHV-6, HHV-7, or HHV-8) vaccine, the aluminum-based mineral salt adjuvant is aluminum phosphate adjuvant. In some embodiments of an HV (e.g. HSV, HHV-1, HHV-2, HHV-3, HHV-4, HHV-5, HHV-6, HHV-7, or HHV-8) vaccine, the aluminum-based mineral salt adjuvant is a potassium aluminum sulfate adjuvant. In some embodiments of an HV (e.g. HSV, HHV-1, HHV-2, HHV-3, HHV-4, HHV-5, HHV-6, HHV-7, or HHV-8) vaccine, the aluminum-based mineral salt adjuvant includes crystalline aluminum hydroxide and not amorphous aluminum hydroxide or aluminum hydroxycarbonate or magnesium hydroxide. In some embodiments of an HV (e.g. HSV, HHV-1, HHV-2, HHV-3, HHV-4, HHV-5, HHV-6, HHV-7, or HHV-8) vaccine, the aluminum-based mineral salt adjuvant includes aluminum phosphate gel in the form of a white gelatinous precipitate. In some embodiments of an HV (e.g. HSV, HHV-1, HHV-2, HHV-3, HHV-4, HHV-5, HHV-6, HHV-7, or HHV-8) vaccine, the aluminum-based mineral salt adjuvant includes aluminum hydroxide gel in the form of a white gelatinous precipitate. In some embodiments of an HV (e.g. HSV, HHV-1, HHV-2, HHV-3, HHV-4, HHV-5, HHV-6, HHV-7, or HHV-8) vaccine, the inactivated HV (e.g. HSV, HHV-1, HHV-2, HHV-3, HHV-4, HHV-5, HHV-6, HHV-7, or HHV-8) includes a replication decreasing DNA mutation. In some embodiments of an HV (e.g. HSV, HHV-1, HHV-2, HHV-3, HHV-4, HHV-5, HHV-6, HHV-7, or HHV-8) vaccine, the inactivated HV (e.g. HSV, HHV-1, HHV-2, HHV-3, HHV-4, HHV-5, HHV-6, HHV-7, or HHV-8) is formed by chemical inactivation. In some embodiments of an HV (e.g. HSV, HHV-1, HHV-2, HHV-3, HHV-4, HHV-5, HHV-6, HHV-7, or HHV-8) vaccine, the inactivated HV (e.g. HSV, HHV-1, HHV-2, HHV-3, HHV-4, HHV-5, HHV-6, HHV-7, or HHV-8) is formed by contacting the HV (e.g. HSV, HHV-1, HHV-2, HHV-3, HHV-4, HHV-5, HHV-6, HHV-7, or HHV-8), with one or more agents selected from a cross-linking agent, oxidizing agent, reducing agent, heat, radiation, detergent, a pH changing agent, and a chemical agent selected from a furocoumarin, aziridine, ethylenimine, binary ethylenimine, and beta-propiolactone.

In some embodiments, the chemical agent is aziridine. In some embodiments, the chemical agent is ethylenimine. In some embodiments, the chemical agent is binary ethylenimine. In some embodiments, the chemical agent is beta-propiolactone. In some embodiments, the radiation is UV radiation. In some embodiments, the radiation is electron beam radiation. In some embodiments, the radiation is infrared radiation. In some embodiments, the radiation is gamma radiation. In some embodiments, the cross-linking agent is an aldehyde cross-linking agent. In some embodiments, the cross-linking agent is formaldehyde. In some embodiments, the cross-linking agent is formalin. In some embodiments, the oxidizing agent is sodium periodate. In some embodiments, the oxidizing agent is hydrogen peroxide. In some embodiments, the reducing agent is aldrithiol-2. In some embodiments, the detergent is Triton-X-100. In some embodiments the detergent is NP-40. In some embodiments, the detergent is Tween-20. In some embodiments, the inactivated HV (e.g. HSV, HHV-1, HHV-2, HHV-3, HHV-4, HHV-5, HHV-6, HHV-7, or HHV-8) is formed by contacting the HV (e.g. HSV, HHV-1, HHV-2, HHV-3, HHV-4, HHV-5, HHV-6, HHV-7, or HHV-8) with one or more agents including UV radiation and a furocoumarin. In some embodiments, the furocoumarin is psoralen. In some embodiments, the furocoumarin is 4'-aminomethyl-4,5',8-trimethylpsoralen. In some embodiments, the furocoumarin is angelicin. In some embodiments, the furocoumarin is xanthotoxin. In some embodiments, the furocoumarin is bergapten. In some embodiments, the furocoumarin is nodakenetin. In some embodiments of an HV (e.g. HSV, HHV-1, HHV-2, HHV-3, HHV-4, HHV-5, HHV-6, HHV-7, or HHV-8) vaccine, the inactivated HV (e.g. HSV, HHV-1, HHV-2, HHV-3, HHV-4, HHV-5, HHV-6, HHV-7, or HHV-8) is an inactivated single strain of the HV (e.g. HSV, HHV-1, HHV-2, HHV-3, HHV-4, HHV-5, HHV-6, HHV-7, or HHV-8). In some embodiments of an HV (e.g. HSV, HHV-1, HHV-2, HHV-3, HHV-4, HHV-5, HHV-6, HHV-7, or HHV-8) vaccine, the inactivated HV (e.g. HSV, HHV-1, HHV-2, HHV-3, HHV-4, HHV-5, HHV-6, HHV-7, or HHV-8) is a combination of two or more inactivated strains of the HV (e.g. HSV, HHV-1, HHV-2, HHV-3, HHV-4, HHV-5, HHV-6, HHV-7, or HHV-8). In some embodiments, the inactivated HV is an inactivated single strain of HSV1. In some embodiments, the inactivated HV is an inactivated single strain of HSV2. In some embodiments, the inactivated HV is a combination of two or more inactivated strains of HSV1. In some embodiments, the inactivated HV is a combination of two or more inactivated strains of HSV2. In some embodiments, the inactivated HV is a combination of one or more inactivated strains or HSV1 and one or more inactivated strains of HSV2. In some embodiments of an HV (e.g. HSV, HHV-1, HHV-2, HHV-3, HHV-4, HHV-5, HHV-6, HHV-7, or HHV-8) vaccine, the HV (e.g. HSV, HHV-1, HHV-2, HHV-3, HHV-4, HHV-5, HHV-6, HHV-7, or HHV-8) vaccine is formulated for intramuscular administration. In some embodiments of an HV (e.g. HSV, HHV-1, HHV-2, HHV-3, HHV-4, HHV-5, HHV-6, HHV-7, or HHV-8) vaccine, the HV (e.g. HSV, HHV-1, HHV-2, HHV-3, HHV-4, HHV-5, HHV-6, HHV-7, or HHV-8) vaccine is formulated for intradermal administration. In some embodiments of an HV (e.g. HSV, HHV-1, HHV-2, HHV-3, HHV-4, HHV-5, HHV-6, HHV-7, or HHV-8) vaccine, the HV (e.g. HSV, HHV-1, HHV-2, HHV-3, HHV-4, HHV-5, HHV-6, HHV-7, or HHV-8) vaccine is formulated for mucosal administration. In some embodiments of an HV (e.g. HSV, HHV-1, HHV-2, HHV-3, HHV-4, HHV-5, HHV-6, HHV-7, or HHV-8) vaccine, the HV (e.g. HSV, HHV-1, HHV-2, HHV-3, HHV-4, HHV-5, HHV-6, HHV-7, or HHV-8) vaccine is formulated for intranasal administration. In some embodiments of an HV (e.g. HSV, HHV-1, HHV-2, HHV-3, HHV-4, HHV-5, HHV-6, HHV-7, or HHV-8) vaccine, the HV (e.g. HSV, HHV-1, HHV-2, HHV-3, HHV-4, HHV-5, HHV-6, HHV-7, or HHV-8) vaccine is formulated for intrarectal administration. In some embodiments of an HV (e.g. HSV, HHV-1, HHV-2, HHV-3, HHV-4, HHV-5, HHV-6, HHV-7, or HHV-8) vaccine, the HV (e.g. HSV, HHV-1, HHV-2, HHV-3, HHV-4, HHV-5, HHV-6, HHV-7, or HHV-8) vaccine is formulated for intravaginal administration. In some embodiments of an HV (e.g. HSV, HHV-1, HHV-2, HHV-3, HHV-4, HHV-5, HHV-6, HHV-7, or HHV-8) vaccine, the HV (e.g. HSV, HHV-1, HHV-2, HHV-3, HHV-4, HHV-5, HHV-6, HHV-7, or HHV-8) vaccine is formulated for topical administration. In some embodiments of an HV (e.g. HSV, HHV-1, HHV-2, HHV-3, HHV-4, HHV-5, HHV-6, HHV-7, or HHV-8) vaccine, the HV (e.g. HSV, HHV-1, HHV-2, HHV-3, HHV-4, HHV-5, HHV-6, HHV-7, or HHV-8) vaccine is formulated for subcutaneous administration. In some embodiments of an HV (e.g. HSV, HHV-1, HHV-2, HHV-3, HHV-4, HHV-5, HHV-6, HHV-7, or HHV-8) vaccine, the HV (e.g. HSV, HHV-1, HHV-2, HHV-3, HHV-4, HHV-5, HHV-6, HHV-7, or HHV-8) vaccine is formulated for transcutaneous administration. In some embodiments of an HV (e.g. HSV, HHV-1, HHV-2, HHV-3, HHV-4, HHV-5, HHV-6, HHV-7, or HHV-8) vaccine, the isolated nucleic acid sequence formulation is an antigenic isolated nucleic acid sequence formulation. In some embodiments of an HV (e.g. HSV, HHV-1, HHV-2, HHV-3, HHV-4, HHV-5, HHV-6, HHV-7, or HHV-8) vaccine, the isolated nucleic acid sequence formulation is a DNA vaccine. In some embodiments of an HV (e.g. HSV, HHV-1, HHV-2, HHV-3, HHV-4, HHV-5, HHV-6, HHV-7, or HHV-8) vaccine, the DNA vaccine is an antigenic isolated nucleic acid sequence formulation. In some embodiments of an HV (e.g. HSV, HHV-1, HHV-2, HHV-3, HHV-4, HHV-5, HHV-6, HHV-7, or HHV-8) vaccine, the vaccine vaccinates a recipient of the vaccine against HV (e.g. HSV, HHV-1, HHV-2, HHV-3, HHV-4, HHV-5, HHV-6, HHV-7, or HHV-8) infection for up to 1, 2, 3, 4, 5, 6, 7, 8, 9, 10, 11, 12, 13, 14, 15, 16, 17, 18, 19, 20, or more years. In some embodiments of an HV (e.g. HSV, HHV-1, HHV-2, HHV-3, HHV-4, HHV-5, HHV-6, HHV-7, or HHV-8) vaccine, the vaccine protects a patient administered the vaccine against one or more strains of the HV (e.g. HSV, HHV-1, HHV-2, HHV-3, HHV-4, HHV-5, HHV-6, HHV-7, or HHV-8). In some embodiments of an HV (e.g. HSV, HHV-1, HHV-2, HHV-3, HHV-4, HHV-5, HHV-6, HHV-7, or HHV-8) vaccine, the vaccine treats a patient administered the vaccine for one or more strains of the HV (e.g. HSV, HHV-1, HHV-2, HHV-3, HHV-4, HHV-5, HHV-6, HHV-7, or HHV-8). In some embodiments of an HV (e.g. HSV, HHV-1, HHV-2, HHV-3, HHV-4, HHV-5, HHV-6, HHV-7, or HHV-8) vaccine, the vaccine prevents a patient administered the vaccine from being infected by, contracting, getting, or having one or more strains of the HV (e.g. HSV, HHV-1, HHV-2, HHV-3, HHV-4, HHV-5, HHV-6, HHV-7, or HHV-8). In some embodiments of an HV (e.g. HSV, HHV-1, HHV-2, HHV-3, HHV-4, HHV-5, HHV-6, HHV-7, or HHV-8) vaccine, the vaccine prevents a patient administered the vaccine from being infected by, contracting, getting, or having more than one strain of the HV (e.g. HSV, HHV-1, HHV-2, HHV-3, HHV-4, HHV-5, HHV-6, HHV-7, or HHV-8). In some embodiments, the Herpesvirus (HV) (e.g. HSV, HHV-1, HHV-2, HHV-3, HHV-4, HHV-5, HHV-6, HHV-7, or HHV-8)) vaccine includes inactivated HV (e.g. HSV, HHV-1, HHV-2, HHV-3, HHV-4, HHV-5, HHV-6, HHV-7, or HHV- 8), a lipopolysaccharide (LPS)-derived adjuvant and an aluminum-based mineral salt adjuvant and the LPS-derived adjuvant is MPL; the aluminum-based mineral salt adjuvant is aluminum hydroxide adjuvant or aluminum phosphate adjuvant; and the vaccine does not include an isolated nucleic acid sequence formulation. In some embodiments of an HV (e.g. HSV, HHV-1, HHV-2, HHV-3, HHV-4, HHV-5, HHV-6, HHV-7, or HHV-8) vaccine, the isolated nucleic acid sequence formulation is an antigenic isolated nucleic acid sequence formulation. In some embodiments of an HV (e.g. HSV, HHV-1, HHV-2, HHV-3, HHV-4, HHV-5, HHV-6, HHV-7, or HHV-8) vaccine, the isolated nucleic acid sequence formulation is a DNA vaccine. In some embodiments of an HV (e.g. HSV, HHV-1, HHV-2, HHV-3, HHV-4, HHV-5, HHV-6, HHV-7, or HHV-8) vaccine, the DNA vaccine is an antigenic isolated nucleic acid sequence formulation.

Provided in another aspect is a Herpes Simplex Virus (HSV) vaccine including inactivated HSV, a lipopolysaccharide (LPS)-derived adjuvant and an aluminum-based mineral salt adjuvant.

In some embodiments of the HSV vaccine, the HSV is HSV1. In some embodiments of the HSV vaccine, the HSV is HSV2. In some embodiments of the HSV vaccine, the HSV is HSV1 and HSV2. In some embodiments of the HSV vaccine, the lipopolysaccharide-derived adjuvant is derived from the *Salmonella minnesota* LPS. In some embodiments of the HSV vaccine, the lipopolysaccharide-derived adjuvant is derived from the *Salmonella minnesota* Re595 LPS. In some embodiments of the HSV vaccine, the lipopolysaccharide-derived adjuvant is derived from the R595 LPS. In some embodiments of the HSV vaccine, the lipopolysaccharide-derived adjuvant is a lipid A adjuvant. In some embodiments of the HSV vaccine, the lipopolysaccharide-derived adjuvant is a lipid A adjuvant without an (R)-3-hydroxytetradecanoyl moiety. In some embodiments of the HSV vaccine, the lipopolysaccharide-derived adjuvant is a lipid A adjuvant that does not include an (R)-3-hydroxytetradecanoyl moiety. In some embodiments of the HSV vaccine, the lipopolysaccharide-derived adjuvant is a lipid A adjuvant without a 1-phosphate moiety. In some embodiments of the HSV vaccine, the lipopolysaccharide-derived adjuvant is a lipid A adjuvant that does not include a 1-phosphate moiety. In some embodiments of the HSV vaccine, the lipopolysaccharide-derived adjuvant is monophosphoryl lipid A (MPL). In some embodiments of the HSV vaccine, the lipopolysaccharide-derived adjuvant is 3-O-desacyl-4'-monophosphoryl lipid A. In some embodiments of the HSV vaccine, the lipopolysaccharide-derived adjuvant is capable of binding the TLR4 protein. In some embodiments of the HSV vaccine, the lipopolysaccharide-derived adjuvant is a synthetic MPL analogue adjuvant. In some embodiments of the HSV vaccine, the aluminum-based mineral salt adjuvant is an aluminum hydroxide adjuvant. In some embodiments of the HSV vaccine, the aluminum-based mineral salt adjuvant is an aluminum phosphate adjuvant. In some embodiments of the HSV vaccine, the aluminum-based mineral salt adjuvant is a potassium aluminum sulfate adjuvant. In some embodiments of the HSV vaccine, the inactivated HSV includes a replication decreasing DNA mutation. In some embodiments of the HSV vaccine, the inactivated HSV includes a replication decreasing DNA mutation that prevents viral replication. In some embodiments of the HSV vaccine, the inactivated HSV is formed by chemical inactivation. In some embodiments of the HSV vaccine, the inactivated HSV is formed by contacting the HSV with one or more agents selected from a cross-linking agent, oxidizing agent, reducing agent, heat, radiation, detergent, a pH changing agent, and a chemical agent selected from a furocoumarin, aziridine, ethylenimine, binary ethylenimine, and beta-propiolactone. In some embodiments of the HSV vaccine, the inactivated HSV is formed by contacting the HSV with aziridine. In some embodiments of the HSV vaccine, the inactivated HSV is formed by contacting the HSV with ethylenimine. In some embodiments of the HSV vaccine, the inactivated HSV is formed by contacting the HSV with binary ethylenimine. In some embodiments of the HSV vaccine, the inactivated HSV is formed by contacting the HSV with beta-propiolactone. In some embodiments of the HSV vaccine, the inactivated HSV is formed by contacting the HSV with UV radiation. In some embodiments of the HSV vaccine, the inactivated HSV is formed by contacting the HSV with electron beam radiation. In some embodiments of the HSV vaccine, the inactivated HSV is formed by contacting the HSV with infrared radiation. In some embodiments of the HSV vaccine, the inactivated HSV is formed by contacting the HSV with gamma radiation. In some embodiments of the HSV vaccine, the inactivated HSV is formed by contacting the HSV with an aldehyde cross-linking agent. In some embodiments of the HSV vaccine, the inactivated HSV is formed by contacting the HSV with formaldehyde. In some embodiments of the HSV vaccine, the inactivated HSV is formed by contacting the HSV with formalin. In some embodiments of the HSV vaccine, the inactivated HSV is formed by contacting the HSV with sodium periodate. In some embodiments of the HSV vaccine, the inactivated HSV is formed by contacting the HSV with hydrogen peroxide. In some embodiments of the HSV vaccine, the inactivated HSV is formed by contacting the HSV with aldrithiol-2. In some embodiments of the HSV vaccine, the inactivated HSV is formed by contacting the HSV with Triton-X-100. In some embodiments of the HSV vaccine, the inactivated HSV is formed by contacting the HSV with NP-40. In some embodiments of the HSV vaccine, the inactivated HSV is formed by contacting the HSV with Tween-20. In some embodiments of the HSV vaccine, the inactivated HSV is formed by contacting the HSV with two or more agents including UV radiation and a furocoumarin. In some embodiments of the HSV vaccine, the inactivated HSV is formed by contacting the HSV with UV radiation and psoralen. In some embodiments of the HSV vaccine, the inactivated HSV is formed by contacting the HSV with UV radiation and 4'-aminomethyl-4,5',8-trimethylpsoralen. In some embodiments of the HSV vaccine, the inactivated HSV is formed by contacting the HSV with UV radiation and angelicin. In some embodiments of the HSV vaccine, the inactivated HSV is formed by contacting the HSV with UV radiation and xanthotoxin. In some embodiments of the HSV vaccine, the inactivated HSV is formed by contacting the HSV with UV radiation and bergapten. In some embodiments of the HSV vaccine, the inactivated HSV is formed by contacting the HSV with UV radiation and nodakenetin. In some embodiments of the HSV vaccine, the inactivated HSV is an inactivated single strain of HSV1. In some embodiments of the HSV vaccine, the inactivated HSV is an inactivated single strain of HSV2. In some embodiments of the HSV vaccine, the inactivated HSV is a combination of two or more inactivated strains of HSV1. In some embodiments of the HSV vaccine, the inactivated HSV is a combination of two or more inactivated strains of HSV2. In some embodiments of the HSV vaccine, the inactivated HSV is a combination of one or more inactivated strains or HSV1 and one or more inactivated strains of HSV2. In some embodiments of the HSV vaccine, the vaccine is formulated for intramuscular administration. In some embodiments of the HSV vaccine, the vaccine is formulated for intradermal administration. In some embodiments of the HSV vaccine, the vaccine is formulated for mucosal administration. In some embodiments of the HSV vaccine, the vaccine is formulated for intranasal administration. In some embodiments of the HSV vaccine, the vaccine is formulated for intrarectal administration. In some embodiments of the HSV vaccine, the vaccine is formulated for intravaginal administration. In some embodiments of the HSV vaccine, the vaccine is formulated for topical administration. In some embodiments of the HSV vaccine, the vaccine is formulated for subcutaneous administration. In some embodiments of the HSV vaccine, the vaccine is formulated for parenteral administration. In some embodiments of the HSV vaccine, the vaccine is formulated for oral administration. In some embodiments of the HSV vaccine, the vaccine is formulated for transcutaneous administration.

In some embodiments, a chemical agent for inactivating HSV is aziridine. In some embodiments, a chemical agent for inactivating HSV is ethylenimine. In some embodiments, a chemical agent for inactivating HSV is binary ethylenimine. In some embodiments, a chemical agent for inactivating HSV is beta-propiolactone. In some embodiments, a radiation for inactivating HSV is UV radiation. In some embodiments, a radiation for inactivating HSV is electron beam radiation. In some embodiments, a radiation for inactivating HSV is infrared radiation. In some embodiments, a radiation for inactivating HSV is gamma radiation. In some embodiments, a cross-linking agent for inactivating HSV is an aldehyde cross-linking agent. In some embodiments, a cross-linking agent for inactivating HSV is formaldehyde. In some embodiments, a cross-linking agent for inactivating HSV is formalin. In some embodiments, a cross-linking agent for inactivating HSV is sodium periodate. In some embodiments, an oxidizing agent for inactivating HSV is hydrogen peroxide. In some embodiments, a reducing agent for inactivating HSV is aldrithiol-2. In some embodiments, a detergent for inactivating HSV is Triton-X-100. In some embodiments, a detergent for inactivating HSV is NP-40. In some embodiments, a detergent for inactivating HSV is Tween-20. In some embodiments, a furocoumarin for inactivating HSV is psoralen. In some embodiments, a furocoumarin for inactivating HSV is 4'-aminomethyl-4,5',8-trimethylpsoralen. In some embodiments, a furocoumarin for inactivating HSV is angelicin. In some embodiments, a furocoumarin for inactivating HSV is xanthotoxin. In some embodiments, a furocoumarin for inactivating HSV is bergapten. In some embodiments, a furocoumarin for inactivating HSV is nodakenetin.

In some embodiments of the HSV vaccine, the LPS-derived adjuvant is MPL; the aluminum-based mineral salt adjuvant is aluminum hydroxide adjuvant or aluminum phosphate adjuvant; and the vaccine does not include an isolated nucleic acid sequence formulation. In some embodiments of the HSV vaccine, the isolated nucleic acid sequence formulation is an antigenic isolated nucleic acid sequence formulation. In some embodiments of the HSV vaccine, the isolated nucleic acid sequence formulation is a DNA vaccine. In some embodiments of the HSV vaccine, the DNA vaccine is an antigenic isolated nucleic acid sequence formulation. In some embodiments of the HSV vaccine, the vaccine vaccinates a recipient of the vaccine against HSV infection for up to 1, 2, 3, 4, 5, 6, 7, 8, 9, 10, 11, 12, 13, 14, 15, 16, 17, 18, 19, 20, or more years. In some embodiments of the HSV1 vaccine, the LPS-derived adjuvant is MPL; the aluminum-based mineral salt adjuvant is aluminum hydroxide adjuvant or aluminum phosphate adjuvant; and the vaccine does not include an isolated nucleic acid sequence formulation. In some embodiments of the HSV1 vaccine, the isolated nucleic acid sequence formulation is an antigenic isolated nucleic acid sequence formulation. In some embodiments of the HSV1 vaccine, the isolated nucleic acid sequence formulation is a DNA vaccine. In some embodiments of the HSV1 vaccine, the DNA vaccine is an antigenic isolated nucleic acid sequence formulation. In some embodiments of the HSV1 vaccine, the vaccine vaccinates a recipient of the vaccine against HSV1 infection for up to 1, 2, 3, 4, 5, 6, 7, 8, 9, 10, 11, 12, 13, 14, 15, 16, 17, 18, 19, 20, or more years. In some embodiments of the HSV2 vaccine, the LPS-derived adjuvant is MPL; the aluminum-based mineral salt adjuvant is aluminum hydroxide adjuvant or aluminum phosphate adjuvant; and the vaccine does not include an isolated nucleic acid sequence formulation. In some embodiments of the HSV2 vaccine, the isolated nucleic acid sequence formulation is an antigenic isolated nucleic acid sequence formulation. In some embodiments of the HSV2 vaccine, the isolated nucleic acid sequence formulation is a DNA vaccine. In some embodiments of the HSV2 vaccine, the DNA vaccine is an antigenic isolated nucleic acid sequence formulation. In some embodiments of the HSV2 vaccine, the vaccine vaccinates a recipient of the vaccine against HSV2 infection for up to 1, 2, 3, 4, 5, 6, 7, 8, 9, 10, 11, 12, 13, 14, 15, 16, 17, 18, 19, 20, or more years.

III. Pharmaceutical Compositions and Methods

Provided in a second aspect is a method of preparing a Herpesvirus (HV (e.g. HSV, HHV-1, HHV-2, HHV-3, HHV-4, HHV-5, HHV-6, HHV-7, or HHV-8)) vaccine, the method including: contacting an HV (e.g. HSV, HHV-1, HHV-2, HHV-3, HHV-4, HHV-5, HHV-6, HHV-7, or HHV-8)-cell mixture with a sulfated or sulfonated polysaccharide, wherein the HV (e.g. HSV, HHV-1, HHV-2, HHV-3, HHV-4, HHV-5, HHV-6, HHV-7, or HHV-8)-cell mixture comprises HV particles, cells and portions of cells; separating the HV (e.g. HSV, HHV-1, HHV-2, HHV-3, HHV-4, HHV-5, HHV-6, HHV-7, or HHV-8) particles from the cells thereby forming isolated HV (e.g. HSV, HHV-1, HHV-2, HHV-3, HHV-4, HHV-5, HHV-6, HHV-7, or HHV-8) particles; inactivating the isolated HV particles thereby forming inactivated HV (e.g. HSV, HHV-1, HHV-2, HHV-3, HHV-4, HHV-5, HHV-6, HHV-7, or HHV-8) particles; combining the inactivated HV (e.g. HSV, HHV-1, HHV-2, HHV-3, HHV-4, HHV-5, HHV-6, HHV-7, or HHV-8) particles with a lipopolysaccharide-derived adjuvant and an aluminum-based mineral salt adjuvant thereby forming an HV (e.g. HSV, HHV-1, HHV-2, HHV-3, HHV-4, HHV-5, HHV-6, HHV-7, or HHV-8) vaccine.

In some embodiments of the method of preparing an HV vaccine, the HV is HSV. In some embodiments of the method of preparing an HV vaccine, the HSV is HSV1. In some embodiments of the method of preparing an HV vaccine, the HSV is HSV2. In some embodiments of the method of preparing an HV vaccine, the HSV is HSV1 and HSV2. In some embodiments of the method of preparing an HV vaccine, the HV is HHV-1. In some embodiments of the method of preparing an HV vaccine, the HV is HHV-2. In some embodiments of the method of preparing an HV vaccine, the HV is HHV-3. In some embodiments of the method of preparing an HV vaccine, the HV is HHV-4. In some embodiments of the method of preparing an HV vaccine, the HV is HHV-5. In some embodiments of the method of preparing an HV vaccine, the HV is HHV-6. In some embodiments of the method of preparing an HV vaccine, the HV is HHV-7. In some embodiments of the method of preparing an HV vaccine, the HV is HHV-8. In some embodiments of the method of preparing an HV (e.g. HSV, HHV-1, HHV-2, HHV-3, HHV-4, HHV-5, HHV-6, HHV-7, or HHV-8) vaccine, the sulfated or sulfonated polysaccharide is selected from dextran sulfate, heparin, and heparan sulfate. In some embodiments of the method of preparing an HV (e.g. HSV, HHV-1, HHV-2, HHV-3, HHV-4, HHV-5, HHV-6, HHV-7, or HHV-8) vaccine, the HV (e.g. HSV, HHV-1, HHV-2, HHV-3, HHV-4, HHV-5, HHV-6, HHV-7, or HHV-8) particles are isolated at a concentration of $10^7$ to $10^{10}$ (pfu/microgram protein). In some embodiments of the method of preparing an HV (e.g. HSV, HHV-1, HHV-2, HHV-3, HHV-4, HHV-5, HHV-6, HHV-7, or HHV-8) vaccine, the HV (e.g. HSV, HHV-1, HHV-2, HHV-3, HHV-4, HHV-5, HHV-6, HHV-7, or HHV-8) vaccine comprises $10^7$ to $10^{10}$ (pfu equivalents/microgram protein) of inactivated HV (e.g. HSV, HHV-1, HHV-2, HHV-3, HHV-4, HHV-5, HHV-6, HHV-7, or HHV-8). In some embodiments of the method of preparing an HV (e.g. HSV, HHV-1, HHV-2, HHV-3, HHV-4, HHV-5, HHV-6, HHV-7, or HHV-8) vaccine, the separating includes centrifugation, polyethylene glycol precipitation, filtration, gel filtration, ultra-filtration, tangential flow ultra-filtration, or affinity chromatography. In some embodiments of the method of preparing an HV (e.g. HSV, HHV-1, HHV-2, HHV-3, HHV-4, HHV-5, HHV-6, HHV-7, or HHV-8) vaccine, the lipopolysaccharide-derived adjuvant is derived from the *Salmonella minnesota* LPS. In some embodiments of the method of preparing an HV (e.g. HSV, HHV-1, HHV-2, HHV-3, HHV-4, HHV-5, HHV-6, HHV-7, or HHV-8) vaccine, the lipopolysaccharide-derived adjuvant is derived from the *Salmonella minnesota* Re595 LPS. In some embodiments of the method of preparing an HV (e.g. HSV, HHV-1, HHV-2, HHV-3, HHV-4, HHV-5, HHV-6, HHV-7, or HHV-8) vaccine, the lipopolysaccharide-derived adjuvant is derived from the R595 LPS. In some embodiments of the method of preparing an HV (e.g. HSV, HHV-1, HHV-2, HHV-3, HHV-4, HHV-5, HHV-6, HHV-7, or HHV-8) vaccine, the lipopolysaccharide-derived adjuvant is a lipid A adjuvant. In some embodiments of the method of preparing an HV (e.g. HSV, HHV-1, HHV-2, HHV-3, HHV-4, HHV-5, HHV-6, HHV-7, or HHV-8) vaccine, the lipopolysaccharide-derived adjuvant is a lipid A adjuvant without a (R)-3-hydroxytetradecanoyl moiety. In some embodiments of the method of preparing an HV (e.g. HSV, HHV-1, HHV-2, HHV-3, HHV-4, HHV-5, HHV-6, HHV-7, or HHV-8) vaccine, the lipopolysaccharide-derived adjuvant is a lipid A adjuvant without a 1-phosphate moiety (MPL). In some embodiments of the method of preparing an HV (e.g. HSV, HHV-1, HHV-2, HHV-3, HHV-4, HHV-5, HHV-6, HHV-7, or HHV-8) vaccine, the lipopolysaccharide-derived adjuvant is 3-O-desacyl-4'-monophosphoryl lipid A. In some embodiments of the method of preparing an HV (e.g. HSV, HHV-1, HHV-2, HHV-3, HHV-4, HHV-5, HHV-6, HHV-7, or HHV-8) vaccine, the lipopolysaccharide-derived adjuvant is monophosphoryl lipid A (MPL). In some embodiments of the method of preparing an HV (e.g. HSV, HHV-1, HHV-2, HHV-3, HHV-4, HHV-5, HHV-6, HHV-7, or HHV-8) vaccine, the lipopolysaccharide-derived adjuvant is a synthetic MPL analogue adjuvant. In some embodiments of the method of preparing an HV (e.g. HSV, HHV-1, HHV-2, HHV-3, HHV-4, HHV-5, HHV-6, HHV-7, or HHV-8) vaccine, the lipopolysaccharide-derived adjuvant is capable of binding the TLR4 protein. In some embodiments of the method of preparing an HV (e.g. HSV, HHV-1, HHV-2, HHV-3, HHV-4, HHV-5, HHV-6, HHV-7, or HHV-8) vaccine, the aluminum-based mineral salt adjuvant is an aluminum hydroxide adjuvant. In some embodiments of the method of preparing an HV (e.g. HSV, HHV-1, HHV-2, HHV-3, HHV-4, HHV-5, HHV-6, HHV-7, or HHV-8) vaccine, the aluminum-based mineral salt adjuvant is an aluminum phosphate adjuvant. In some embodiments of the method of preparing an HV (e.g. HSV, HHV-1, HHV-2, HHV-3, HHV-4, HHV-5, HHV-6, HHV-7, or HHV-8) vaccine, the aluminum-based mineral salt adjuvant is a potassium aluminum sulfate adjuvant. In some embodiments of the method of preparing an HV (e.g. HSV, HHV-1, HHV-2, HHV-3, HHV-4, HHV-5, HHV-6, HHV-7, or HHV-8) vaccine, the aluminum-based mineral salt adjuvant includes crystalline aluminum hydroxide and not amorphous aluminum hydroxide or aluminum hydroxycarbonate or magnesium hydroxide. In some embodiments of the method of preparing an HV (e.g. HSV, HHV-1, HHV-2, HHV-3, HHV-4, HHV-5, HHV-6, HHV-7, or HHV-8) vaccine, the aluminum-based mineral salt adjuvant includes aluminum phosphate gel in the form of a white gelatinous precipitate. In some embodiments of the method of preparing an HV (e.g. HSV, HHV-1, HHV-2, HHV-3, HHV-4, HHV-5, HHV-6, HHV-7, or HHV-8) vaccine, the aluminum-based mineral salt adjuvant includes aluminum hydroxide gel in the form of a white gelatinous precipitate. In some embodiments of the method of preparing an HV (e.g. HSV, HHV-1, HHV-2, HHV-3, HHV-4, HHV-5, HHV-6, HHV-7, or HHV-8) vaccine, the inactivating includes contacting the HV (e.g. HSV, HHV-1, HHV-2, HHV-3, HHV-4, HHV-5, HHV-6, HHV-7, or HHV-8) with one or more agents selected from a cross-linking agent, oxidizing agent, reducing agent, heat, radiation, detergent, a pH changing agent, and a chemical agent selected from a furocoumarin, aziridine, ethylenimine, binary ethylenimine, and beta-propiolactone. In some embodiments of the method, the chemical agent is aziridine. In some embodiments of the method, the chemical agent is ethylenimine. In some embodiments of the method, the chemical agent is binary ethylenimine. In some embodiments of the method, the chemical agent is beta-propiolactone. In some embodiments of the method, the radiation is UV radiation. In some embodiments of the method, the radiation is electron beam radiation. In some embodiments of the method, the radiation is infrared radiation. In some embodiments of the method, the radiation is gamma radiation. In some embodiments of the method, the cross-linking agent is an aldehyde cross-linking agent. In some embodiments of the method, the cross-linking agent is formaldehyde. In some embodiments of the method, the cross-linking agent is formalin. In some embodiments of the method, the oxidizing agent is sodium periodate. In some embodiments of the method, the oxidizing agent is hydrogen peroxide. In some embodiments of the method, the reducing agent is aldrithiol-2. In some embodiments of the method, the detergent is Triton-X-100. In some embodiments of the method, the detergent is NP-40. In some embodiments of the method, the detergent is Tween-20. In some embodiments of the method, the inactivating comprises contacting the HV (e.g. HSV, HHV-1, HHV-2, HHV-3, HHV-4, HHV-5, HHV-6, HHV-7, or HHV-8) with one or more agents including UV radiation and a furocoumarin. In some embodiments of the method, the furocoumarin is psoralen. In some embodiments of the method, the furocoumarin is 4'-aminomethyl-4,5',8-trimethylpsoralen. In some embodiments of the method, the furocoumarin is angelicin. In some embodiments of the method, the furocoumarin is xanthotoxin. In some embodiments of the method, the furocoumarin is bergapten. In some embodiments of the method, the furocoumarin is nodakenetin.

Provided in a third aspect is a method of treating or preventing an HV (e.g. HSV, HHV-1, HHV-2, HHV-3, HHV-4, HHV-5, HHV-6, HHV-7, or HHV-8) infection in a patient in need of the treatment or prevention, the method including administering a therapeutically or prophylactically effective amount of any one of the HV (e.g. HSV, HHV-1, HHV-2, HHV-3, HHV-4, HHV-5, HHV-6, HHV-7, or HHV-8) vaccines described herein (including embodiments).

In some embodiments of the method, the HV is HSV. In some embodiments of the method, the HSV is HSV1. In some embodiments of the method, the HSV is HSV2. In some embodiments of the method, the HSV is HSV1 and HSV2. In some embodiments of the method, the HV is HHV-1. In some embodiments of the method, the HV is HHV-2. In some embodiments of the method, the HV is HHV-3. In some embodiments of the method, the HV is HHV-4. In some embodiments of the method, the HV is HHV-5. In some embodiments of the method, the HV is HHV-6. In some embodiments of the method, the HV is HHV-7. In some embodiments of the method, the HV is HHV-8. In some embodiments of the method, the HV infection causes a disease selected from herpetic gingivostomatitis, herpes labialis, herpes genitalis, herpetic whitlow, herpes gladiatorum, herpesviral encephalitis, herpesviral meningitis, herpes esophagitis, herpes keratitis, Bell's palsy, Mollaret's meningitis, herpes rugbeiorum, eczema herpeticum, herpetic neuralgia, and post-herpetic neuralgia. In some embodiments of the method, the method is a method of treating. In some embodiments of the method, the method is a method of preventing. In some embodiments of the method, the method includes a reduction in viral shedding. In some embodiments of the method, the method includes a reduction in the frequency of lesion occurrence. In some embodiments of the method, the method includes a reduction in the duration of lesion occurrence. In some embodiments of the method, the method includes intramuscular administration. In some embodiments of the method, the method includes intradermal administration. In some embodiments of the method, the method includes mucosal administration. In some embodiments of the method, the method includes intranasal administration. In some embodiments of the method, the method includes intrarectal administration. In some embodiments of the method, the method includes intravaginal administration. In some embodiments of the method, the method includes topical administration. In some embodiments of the method, the method includes transcutaneous administration. In some embodiments of the method, the method includes subcutaneous administration. In some embodiments of the method, an isolated nucleic acid sequence formulation is not administered to the patient. In some embodiments of the method, the isolated nucleic acid sequence formulation is a DNA sequence. In some embodiments of the method, the isolated nucleic acid sequence formulation is a nucleic acid vaccine. In some embodiments of the method, the isolated nucleic acid sequence formulation is a DNA vaccine. In some embodiments of the method, the method does not include administration of a prime HV (e.g. HSV, HHV-1, HHV-2, HHV-3, HHV-4, HHV-5, HHV-6, HHV-7, or HHV-8) DNA vaccine. In some embodiments of the method, the method does not include administration of an HV (e.g. HSV, HHV-1, HHV-2, HHV-3, HHV-4, HHV-5, HHV-6, HHV-7, or HHV-8) DNA vaccine. In some embodiments of the method, the method does not include administration of a DNA vaccine including a gene selected from HSV UL30, UL5, gD2, gD2t, or portions thereof. In some embodiments of the method, the method administration consists of a single administration of the HV (e.g. HSV, HHV-1, HHV-2, HHV-3, HHV-4, HHV-5, HHV-6, HHV-7, or HHV-8) vaccine. In some embodiments of the method, the method administration consists of a prime-boost administration of the HV (e.g. HSV, HHV-1, HHV-2, HHV-3, HHV-4, HHV-5, HHV-6, HHV-7, or HHV-8) vaccine. In some embodiments of the method, the method administration consists of a prime-boost-boost administration of the HV (e.g. HSV, HHV-1, HHV-2, HHV-3, HHV-4, HHV-5, HHV-6, HHV-7, or HHV-8) vaccine. In some embodiments of the method of treating or preventing a disease, the method includes treating the disease. In some embodiments of the method of treating or preventing a disease, the method includes preventing the disease. In some embodiments of the method of treating or preventing a disease, the method is treating the disease. In some embodiments of the method of treating or preventing a disease, the method is preventing the disease. In some embodiments of the method of treating or preventing a disease, the method includes administering a therapeutically effective amount of an HV vaccine as described herein (including embodiments). In some embodiments of the method of treating or preventing a disease, the method includes administering a prophylactically effective amount of an HV vaccine as described herein (including embodiments).

Provided in a fourth aspect is a method of treating or preventing a disease in a patient in need of the treatment or prevention, the method including administering a therapeutically or prophylactically effective amount of any one of the HV (e.g. HSV, HHV-1, HHV-2, HHV-3, HHV-4, HHV-5, HHV-6, HHV-7, or HHV-8) vaccines described herein (including embodiments).

In some embodiments of the method, the disease is an HV (e.g. HSV, HHV-1, HHV-2, HHV-3, HHV-4, HHV-5, HHV-6, HHV-7, or HHV-8) associated disease. In some embodiments of the method, the HV is HSV. In some embodiments of the method, the HSV is HSV1. In some embodiments of the method, the HSV is HSV2. In some embodiments of the method, the HSV is HSV1 and HSV2. In some embodiments of the method, the HV is HHV-1. In some embodiments of the method, the HV is HHV-2. In some embodiments of the method, the HV is HHV-3. In some embodiments of the method, the HV is HHV-4. In some embodiments of the method, the HV is HHV-5. In some embodiments of the method, the HV is HHV-6. In some embodiments of the method, the HV is HHV-7. In some embodiments of the method, the HV is HHV-8. In some embodiments of the method, the disease is selected from the group consisting of herpetic gingivostomatitis, herpes labialis, herpes genitalis, herpetic whitlow, herpes gladiatorum, herpesviral encephalitis, herpesviral meningitis, herpes esophagitis, herpes keratitis, Bell's palsy, Mollaret's meningitis, herpes rugbeiorum, eczema herpeticum, herpetic neuralgia, and post-herpetic neuralgia. In some embodiments of the method, the disease is herpetic gingivostomatitis. In some embodiments of the method, the disease is herpes labialis. In some embodiments of the method, the disease is herpes genitalis. In some embodiments of the method, the disease is herpetic whitlow. In some embodiments of the method, the disease is herpes gladiatorum. In some embodiments of the method, the disease is herpesviral encephalitis. In some embodiments of the method, the disease is herpesviral meningitis. In some embodiments of the method, the disease is herpes esophagitis. In some embodiments of the method, the disease is herpes keratitis. In some embodiments of the method, the disease is Bell's palsy. In some embodiments of the method, the disease is Mollaret's meningitis. In some embodiments of the method, the disease is herpes rugbeiorum. In some embodiments of the method, the disease is eczema herpeticum. In some embodiments of the method, the disease is herpetic neuralgia. In some embodiments of the method, the disease is post-herpetic neuralgia. In some embodiments of the method, the disease is Alzheimer's disease. In some embodiments of the method, the method is a method of treating. In some embodiments of the method, the method is a method of preventing. In some embodiments of the method, the method includes a reduction in viral shedding. In some embodiments of the method, the method includes a reduction in the frequency of lesion occurrence. In some embodiments of the method, the method includes a reduction in the duration of lesion occurrence. In some embodiments of the method, the method includes intramuscular administration. In some embodiments of the method, the method includes intradermal administration. In some embodiments of the method, the method includes mucosal administration. In some embodiments of the method, the method includes intranasal administration. In some embodiments of the method, the method includes intrarectal administration. In some embodiments of the method, the method includes intravaginal administration. In some embodiments of the method, the method includes topical administration. In some embodiments of the method, the method includes transcutaneous administration. In some embodiments of the method, the method includes subcutaneous administration. In some embodiments of the method, an isolated nucleic acid sequence formulation is not administered to the patient. In some embodiments of the method, the isolated nucleic acid sequence formulation is a DNA sequence. In some embodiments of the method, the isolated nucleic acid sequence formulation is a nucleic acid vaccine. In some embodiments of the method, the isolated nucleic acid sequence formulation is a DNA vaccine. In some embodiments of the method, the method does not include administration of a prime HV (e.g. HSV, HHV-1, HHV-2, HHV-3, HHV-4, HHV-5, HHV-6, HHV-7, or HHV-8) DNA vaccine. In some embodiments of the method, the method does not include administration of an HV (e.g. HSV, HHV-1, HHV-2, HHV-3, HHV-4, HHV-5, HHV-6, HHV-7, or HHV-8) DNA vaccine. In some embodiments of the method, the method does not include administration of a DNA vaccine including a gene selected from HSV UL30, UL5, gD2, gD2t, or portions thereof. In some embodiments of the method, the method administration consists of a single administration of the HV (e.g. HSV, HHV-1, HHV-2, HHV-3, HHV-4, HHV-5, HHV-6, HHV-7, or HHV-8) vaccine. In some embodiments of the method, the method administration consists of a prime-boost administration of the HV (e.g. HSV, HHV-1, HHV-2, HHV-3, HHV-4, HHV-5, HHV-6, HHV-7, or HHV-8) vaccine. In some embodiments of the method, the method administration consists of a prime-boost-boost administration of the HV (e.g. HSV, HHV-1, HHV-2, HHV-3, HHV-4, HHV-5, HHV-6, HHV-7, or HHV-8) vaccine. In some embodiments of the method, a patient is protected against one or more strains of an HV (e.g. HSV, HHV-1, HHV-2, HHV-3, HHV-4, HHV-5, HHV-6, HHV-7, or HHV-8) following administration of the HV (e.g. HSV, HHV-1, HHV-2, HHV-3, HHV-4, HHV-5, HHV-6, HHV-7, or HHV-8) vaccine. In some embodiments of the method, a patient is prevented from being infected by, contracting, having, or getting one or more strains of an HV (e.g. HSV, HHV-1, HHV-2, HHV-3, HHV-4, HHV-5, HHV-6, HHV-7, or HHV-8) following administration of the HV (e.g. HSV, HHV-1, HHV-2, HHV-3, HHV-4, HHV-5, HHV-6, HHV-7, or HHV-8) vaccine. In some embodiments of the method, a patient is prevented from being infected by, contracting, having, or getting more than one strain of an HV (e.g. HSV, HHV-1, HHV-2, HHV-3, HHV-4, HHV-5, HHV-6, HHV-7, or HHV-8) following administration of the HV (e.g. HSV, HHV-1, HHV-2, HHV-3, HHV-4, HHV-5, HHV-6, HHV-7, or HHV-8) vaccine. In some embodiments of the method, a patient treated for one or more strains of an HV (e.g. HSV, HHV-1, HHV-2, HHV-3, HHV-4, HHV-5, HHV-6, HHV-7, or HHV-8) following administration of the HV (e.g. HSV, HHV-1, HHV-2, HHV-3, HHV-4, HHV-5, HHV-6, HHV-7, or HHV-8) vaccine. In some embodiments of the method of treating or preventing a disease, the method includes treating the disease. In some embodiments of the method of treating or preventing a disease, the method includes preventing the disease. In some embodiments of the method of treating or preventing a disease, the method is treating the disease. In some embodiments of the method of treating or preventing a disease, the method is preventing the disease. In some embodiments of the method of treating or preventing a disease, the method includes administering a therapeutically effective amount of an HV vaccine as described herein (including embodiments). In some embodiments of the method of treating or preventing a disease, the method includes administering a prophylactically effective amount of an HV vaccine as described herein (including embodiments).

Provided in a fifth aspect is a kit including any one of the HV (e.g. HSV, HHV-1, HHV-2, HHV-3, HHV-4, HHV-5, HHV-6, HHV-7, or HHV-8) vaccines as described herein (including embodiments) and instructions for administering the HV (e.g. HSV, HHV-1, HHV-2, HHV-3, HHV-4, HHV-5, HHV-6, HHV-7, or HHV-8) vaccine to a patient. In some embodiments of the kit, the HV (e.g. HSV, HHV-1, HHV-2, HHV-3, HHV-4, HHV-5, HHV-6, HHV-7, or HHV-8) vaccine is administered in a prime-boost administration. In some embodiments of the kit, the HV is HHV-1. In some embodiments of the kit, the HV is HHV-2. In some embodiments of the kit, the HV is HHV-3. In some embodiments of the kit, the HV is HHV-4. In some embodiments of the kit, the HV is HHV-5. In some embodiments of the kit, the HV is HHV-6. In some embodiments of the kit, the HV is HHV-7. In some embodiments of the kit, the HV is HHV-8. In some embodiments of the kit, the HV (e.g. HSV, HHV-1, HHV-2, HHV-3, HHV-4, HHV-5, HHV-6, HHV-7, or HHV-8) vaccine treats a patient for one or more strains of the HV (e.g. HSV, HHV-1, HHV-2, HHV-3, HHV-4, HHV-5, HHV-6, HHV-7, or HHV-8). HV (e.g. HSV, HHV-1, HHV-2, HHV-3, HHV-4, HHV-5, HHV-6, HHV-7, or HHV-8)

Provided in another aspect is a method of treating or preventing an HSV infection in a patient in need of the treatment or prevention. The method including administering a therapeutically or prophylactically effective amount of an HSV vaccine described herein (including embodiments).

In some embodiments of the method of treating or preventing an HSV infection, the HSV is HSV1. In some embodiments of the method of treating or preventing an HSV infection, the HSV is HSV2. In some embodiments of the method of treating or preventing an HSV infection, the HSV is HSV1 and HSV2. In some embodiments of the method of treating or preventing an HSV infection, the HSV infection causes a disease selected from the group consisting of herpetic gingivostomatitis, herpes labialis, herpes genitalis, herpetic whitlow, herpes gladiatorum, herpesviral encephalitis, herpesviral meningitis, herpes esophagitis, herpes keratitis, Bell's palsy, Mollaret's meningitis, herpes rugbeiorum, eczema herpeticum, herpetic neuralgia, and post-herpetic neuralgia. In some embodiments of the method of treating or preventing an HSV infection, the method includes treating the HSV infection. In some embodiments of the method of treating or preventing an HSV infection, the method includes preventing the HSV infection. In some embodiments of the method of treating or preventing an HSV infection, the method is treating the HSV infection. In some embodiments of the method of treating or preventing an HSV infection, the method is preventing the HSV infection. In some embodiments of the method of treating or preventing an HSV infection, the method includes administering a therapeutically effective amount of an HSV vaccine as described herein (including embodiments). In some embodiments of the method of treating or preventing an HSV infection, the method includes administering a prophylactically effective amount of an HSV vaccine as described herein (including embodiments). In some embodiments of the method of treating or preventing an HSV infection, the method includes a reduction in viral shedding. In some embodiments of the method of treating or preventing an HSV infection, the method includes a reduction in the frequency of lesion occurrence. In some embodiments of the method of treating or preventing an HSV infection, the method includes a reduction in the duration of lesion occurrence. In some embodiments of the method of treating or preventing an HSV infection, the method includes intramuscular administration of an HSV vaccine as described herein (including embodiments). In some embodiments of the method of treating or preventing an HSV infection, the method includes intradermal administration of an HSV vaccine as described herein (including embodiments). In some embodiments of the method of treating or preventing an HSV infection, the method includes mucosal administration of an HSV vaccine as described herein (including embodiments). In some embodiments of the method of treating or preventing an HSV infection, the method includes intranasal administration of an HSV vaccine as described herein (including embodiments). In some embodiments of the method of treating or preventing an HSV infection, the method includes intrarectal administration of an HSV vaccine as described herein (including embodiments). In some embodiments of the method of treating or preventing an HSV infection, the method includes intravaginal administration of an HSV vaccine as described herein (including embodiments). In some embodiments of the method of treating or preventing an HSV infection, the method includes topical administration of an HSV vaccine as described herein (including embodiments). In some embodiments of the method of treating or preventing an HSV infection, the method includes subcutaneous administration of an HSV vaccine as described herein (including embodiments). In some embodiments of the method of treating or preventing an HSV infection, the method includes transcutaneous administration of an HSV vaccine as described herein (including embodiments).

In some embodiments of the method of treating or preventing an HSV infection, the method does include administration of an HSV DNA vaccine (e.g. HSV1 DNA vaccine, HSV2 DNA vaccine, HSV1 and HSV2 DNA vaccine). In some embodiments of the method of treating or preventing an HSV infection, the method does include administration of prime HSV DNA vaccine (e.g. HSV1 DNA vaccine, HSV2 DNA vaccine, HSV1 and HSV2 DNA vaccine). In some embodiments of the method of treating or preventing an HSV infection, the method does include administration of an HSV DNA vaccine including a UL30 gene or portion of the gene. In some embodiments of the method of treating or preventing an HSV infection, the method does include administration of an HSV DNA vaccine including a UL5 gene or portion of the gene. In some embodiments of the method of treating or preventing an HSV infection, the method does include administration of an HSV DNA vaccine including a gD2 gene or portion of the gene. In some embodiments of the method of treating or preventing an HSV infection, the method does include administration of an HSV DNA vaccine including a gD2t gene or portion of the gene. In some embodiments of the method of treating or preventing an HSV infection, the method does include administration of an HSV protein vaccine (e.g. HSV1 protein vaccine, HSV2 protein vaccine, HSV1 and HSV2 protein vaccine). In some embodiments of the method of treating or preventing an HSV infection, the method does include administration of an HSV protein vaccine including a gD2t protein. In some embodiments of the method of treating or preventing an HSV infection, the method does not include administration of an HSV DNA vaccine (e.g. HSV1 DNA vaccine, HSV2 DNA vaccine, HSV1 and HSV2 DNA vaccine). In some embodiments of the method of treating or preventing an HSV infection, the method does not include administration of prime HSV DNA vaccine (e.g. HSV1 DNA vaccine, HSV2 DNA vaccine, HSV1 and HSV2 DNA vaccine). In some embodiments of the method of treating or preventing an HSV infection, the method does not include administration of an HSV DNA vaccine including a UL30 gene or portion of the gene. In some embodiments of the method of treating or preventing an HSV infection, the method does not include administration of an HSV DNA vaccine including a UL5 gene or portion of the gene. In some embodiments of the method of treating or preventing an HSV infection, the method does not include administration of an HSV DNA vaccine including a gD2 gene or portion of the gene. In some embodiments of the method of treating or preventing an HSV infection, the method does not include administration of an HSV DNA vaccine including a gD2t gene or portion of the gene. In some embodiments of the method of treating or preventing an HSV infection, the method does not include administration of an HSV protein vaccine (e.g. HSV1 protein vaccine, HSV2 protein vaccine, HSV1 and HSV2 protein vaccine). In some embodiments of the method of treating or preventing an HSV infection, the method does not include administration of an HSV protein vaccine including a gD2t protein. It will be understood by a person of ordinary skill in the art that when a composition or method that does not include a DNA vaccine or a nucleic acid sequence is recited, it is intended that such composition or method does not include the intentional addition of a composition comprising a nucleic acid composition (e.g. DNA vaccine, nucleic acid vaccine, antigenic nucleic acid, nucleic acid sequence, or other nucleic acid composition) described as being excluded or lacking. In some embodiments a composition or method that does not include a nucleic acid composition may include a nucleic acid composition in trace amounts or as included in another component of the composition, wherein a trace amount of a nucleic acid is an amount less than an amount necessary to elicit an antigen specific immune response to the nucleic acid or a protein expressed from or by the nucleic acid. In some embodiments, a trace amount of a nucleic acid is less than about 12.5, 10, 9, 8.5, 8, 7, 6, 5, 4, 3, 2, 1, 0.9, 0.8, 0.7, 0.6, 0.5, 0.4, 0.3, 0.2, 0.1, 0.009, 0.008, 0.007, 0.006, 0.005, 0.004, 0.003, 0.002, 0.001 micrograms of the nucleic acid. In some embodiments, a trace amount of nucleic acid is less than about 12.5, 10, 9, 8.5, 8, 7, 6, 5, 4, 3, 2, 1, 0.9, 0.8, 0.7, 0.6, 0.5, 0.4, 0.3, 0.2, 0.1, 0.009, 0.008, 0.007, 0.006, 0.005, 0.004, 0.003, 0.002, 0.001 micrograms of the nucleic acid per dose of vaccine. In some embodiments, a trace amount of nucleic acid is less than about 12.5, 10, 9, 8.5, 8, 7, 6, 5, 4, 3, 2, 1, 0.9, 0.8, 0.7, 0.6, 0.5, 0.4, 0.3, 0.2, 0.1, 0.009, 0.008, 0.007, 0.006, 0.005, 0.004, 0.003, 0.002, 0.001 micrograms of the nucleic acid per dose of vaccine administered i.m. In some embodiments, a trace amount of nucleic acid is less than 12.5, 10, 9, 8.5, 8, 7, 6, 5, 4, 3, 2, 1, 0.9, 0.8, 0.7, 0.6, 0.5, 0.4, 0.3, 0.2, 0.1, 0.009, 0.008, 0.007, 0.006, 0.005, 0.004, 0.003, 0.002, 0.001 micrograms of the nucleic acid. In some embodiments, a trace amount of nucleic acid is less than 12.5, 10, 9, 8.5, 8, 7, 6, 5, 4, 3, 2, 1, 0.9, 0.8, 0.7, 0.6, 0.5, 0.4, 0.3, 0.2, 0.1, 0.009, 0.008, 0.007, 0.006, 0.005, 0.004, 0.003, 0.002, 0.001 micrograms of the nucleic acid per dose of vaccine. In some embodiments, a trace amount of nucleic acid is less than 12.5, 10, 9, 8.5, 8, 7, 6, 5, 4, 3, 2, 1, 0.9, 0.8, 0.7, 0.6, 0.5, 0.4, 0.3, 0.2, 0.1, 0.009, 0.008, 0.007, 0.006, 0.005, 0.004, 0.003, 0.002, 0.001 micrograms of the nucleic acid per dose of vaccine administered i.m. In some embodiments, a trace amount of nucleic acid is 1 microgram. In some embodiments, a trace amount of nucleic acid is 0.5 micrograms. In some embodiments, a trace amount of nucleic acid is an amount less than an amount set forth in DNA vaccines in WO2007106404 or administered to elicit an immune response in WO2007106404. In some embodiments of the method, an isolated nucleic acid sequence formulation is not administered to the patient. In some embodiments of the method, the isolated nucleic acid sequence formulation is a DNA sequence. In some embodiments of the method, the isolated nucleic acid sequence formulation is a nucleic acid vaccine. In some embodiments of the method, the isolated nucleic acid sequence formulation is a DNA vaccine.

Provided in another aspect is a method of preparing a Herpes Simplex Virus (HSV) vaccine, the method including: contacting an HSV-cell mixture with a sulfated or sulfonated polysaccharide, wherein the HSV-cell mixture includes HSV particles, cells and portions of cells; separating the HSV particles from the cells thereby forming isolated HSV particles; inactivating the isolated HSV particles thereby forming inactivated HSV particles; combining the inactivated HSV particles with a lipopolysaccharide-derived adjuvant and an aluminum-based mineral salt adjuvant thereby forming an HSV vaccine.

In some embodiments of the method of preparing an HSV vaccine, the HSV is HSV1. In some embodiments of the method of preparing an HSV vaccine, the HSV is HSV2. In some embodiments of the method of preparing an HSV vaccine, the HSV is HSV1 and HSV2. In some embodiments of the method of preparing an HSV vaccine, the sulfated or sulfonated polysaccharide is selected from a group consisting of dextran sulfate, heparin, heparan sulfate. In some embodiments of the method of preparing an HSV vaccine, the HSV particles are isolated at a concentration of $10^7$ to $10^{10}$ (pfu/microgram protein). In some embodiments of the method of preparing an HSV vaccine, the HSV vaccine includes $10^7$ to $10^{10}$ (pfu equivalents/microgram protein) of inactivated HSV. In some embodiments of the method of preparing an HSV vaccine, the separating is selected from a group consisting of centrifugation, polyethylene glycol precipitation, filtration, gel filtration, ultra-filtration, tangential flow ultra-filtration, or affinity chromatography. In some embodiments of the method of preparing an HSV vaccine, the lipopolysaccharide-derived adjuvant is derived from the *Salmonella minnesota* LPS. In some embodiments of the method of preparing an HSV vaccine, the lipopolysaccharide-derived adjuvant is derived from the *Salmonella minnesota* Re595 LPS. In some embodiments of the method of preparing an HSV vaccine, the lipopolysaccharide-derived adjuvant is derived from the R595 LPS. In some embodiments of the method of preparing an HSV vaccine, the lipopolysaccharide-derived adjuvant is a lipid A adjuvant. In some embodiments of the method of preparing an HSV vaccine, the lipopolysaccharide-derived adjuvant is a lipid A adjuvant without a (R)-3-hydroxytetradecanoyl moiety. In some embodiments of the method of preparing an HSV vaccine, the lipopolysaccharide-derived adjuvant is a lipid A adjuvant without a 1-phosphate moiety. In some embodiments of the method of preparing an HSV vaccine, the lipopolysaccharide-derived adjuvant is a lipid A adjuvant that does not include a (R)-3-hydroxytetradecanoyl moiety. In some embodiments of the method of preparing an HSV vaccine, the lipopolysaccharide-derived adjuvant is a lipid A adjuvant that does not include a 1-phosphate moiety. In some embodiments of the method of preparing an HSV vaccine, the lipopolysaccharide-derived adjuvant is monophosphoryl lipid A (MPL). In some embodiments of the method of preparing an HSV vaccine, the lipopolysaccharide-derived adjuvant is 3-O-desacyl-4'-monophosphoryl lipid A. In some embodiments of the method of preparing an HSV vaccine, the lipopolysaccharide-derived adjuvant is a synthetic MPL analogue adjuvant. In some embodiments of the method of preparing an HSV vaccine, the lipopolysaccharide-derived adjuvant is capable of binding the TLR4 protein. In some embodiments of the method of preparing an HSV vaccine, the aluminum-based mineral salt adjuvant is an aluminum hydroxide adjuvant. In some embodiments of the method of preparing an HSV vaccine, the aluminum-based mineral salt adjuvant is an aluminum phosphate adjuvant. In some embodiments of the method of preparing an HSV vaccine, the aluminum-based mineral salt adjuvant is a potassium aluminum sulfate adjuvant. In some embodiments of the method of preparing an HSV vaccine, the aluminum-based mineral salt adjuvant includes an aluminum hydroxide adjuvant. In some embodiments of the method of preparing an HSV vaccine, the aluminum-based mineral salt adjuvant includes an aluminum phosphate adjuvant. In some embodiments of the method of preparing an HSV vaccine, the aluminum-based mineral salt adjuvant includes a potassium aluminum sulfate adjuvant. In some embodiments of the method of preparing an HSV vaccine, the aluminum-based mineral salt adjuvant is an aluminum hydroxide adjuvant. In some embodiments of the method of preparing an HSV vaccine, the aluminum-based mineral salt adjuvant is an aluminum phosphate adjuvant. In some embodiments of the method of preparing an HSV vaccine, the aluminum-based mineral salt adjuvant is a potassium aluminum sulfate adjuvant. In some embodiments of the method of preparing an HSV vaccine, the aluminum-based mineral salt adjuvant includes crystalline aluminum hydroxide and not amorphous aluminum hydroxide or aluminum hydroxycarbonate or magnesium hydroxide. In some embodiments of the method of preparing an HSV vaccine, the aluminum-based mineral salt adjuvant includes aluminum phosphate gel in the form of a white gelatinous precipitate. In some embodiments of the method of preparing an HSV vaccine, the aluminum-based mineral salt adjuvant includes aluminum hydroxide gel in the form of a white gelatinous precipitate. In some embodiments of the method of preparing an HSV vaccine, the inactivating including contacting the HSV with one or more agents selected from the group consisting of a cross-linking agent, oxidizing agent, reducing agent, heat, radiation, detergent, a pH changing agent, and a chemical agent selected from a furocoumarin, aziridine, ethylenimine, binary ethylenimine, and beta-propiolactone. In some embodiments of the method of preparing an HSV vaccine, the inactivating includes contacting the HSV with aziridine. In some embodiments of the method of preparing an HSV vaccine, the inactivating includes contacting the HSV with ethylenimine. In some embodiments of the method of preparing an HSV vaccine, the inactivating includes contacting the HSV with binary ethylenimine. In some embodiments of the method of preparing an HSV vaccine, the inactivating includes contacting the HSV with beta-propiolactone. In some embodiments of the method of preparing an HSV vaccine, the inactivating includes contacting the HSV with UV radiation. In some embodiments of the method of preparing an HSV vaccine, the inactivating includes contacting the HSV with electron beam radiation. In some embodiments of the method of preparing an HSV vaccine, the inactivating includes contacting the HSV with infrared radiation. In some embodiments of the method of preparing an HSV vaccine, the inactivating includes contacting the HSV with gamma radiation. In some embodiments of the method of preparing an HSV vaccine, the inactivating includes contacting the HSV with aldehyde cross-linking agent. In some embodiments of the method of preparing an HSV vaccine, the inactivating includes contacting the HSV with formaldehyde. In some embodiments of the method of preparing an HSV vaccine, the inactivating includes contacting the HSV with formalin. In some embodiments of the method of preparing an HSV vaccine, the inactivating includes contacting the HSV with sodium periodate. In some embodiments of the method of preparing an HSV vaccine, the inactivating includes contacting the HSV with hydrogen peroxide. In some embodiments of the method of preparing an HSV vaccine, the inactivating includes contacting the HSV with aldrithiol-2. In some embodiments of the method of preparing an HSV vaccine, the inactivating includes contacting the HSV with Triton-X-100. In some embodiments of the method of preparing an HSV vaccine, the inactivating includes contacting the HSV with NP-40. In some embodiments of the method of preparing an HSV vaccine, the inactivating includes contacting the HSV with Tween-20. In some embodiments of the method of preparing an HSV vaccine, the inactivating includes contacting the HSV with UV radiation and a furocoumarin. In some embodiments of the method of preparing an HSV vaccine, the inactivating includes contacting the HSV with UV radiation and psoralen. In some embodiments of the method of preparing an HSV vaccine, the inactivating includes contacting the HSV with UV radiation and 4'-aminomethyl-4,5',8-trimethylpsoralen. In some embodiments of the method of preparing an HSV vaccine, the inactivating includes contacting the HSV with UV radiation and angelicin. In some embodiments of the method of preparing an HSV vaccine, the inactivating includes contacting the HSV with UV radiation and xanthotoxin. In some embodiments of the method of preparing an HSV vaccine, the inactivating includes contacting the HSV with UV radiation and bergapten. In some embodiments of the method of preparing an HSV vaccine, the inactivating includes contacting the HSV with UV radiation and nodakenetin. In some embodiments of the method of preparing an HSV vaccine, the inactivating is contacting the HSV with aziridine. In some embodiments of the method of preparing an HSV vaccine, the inactivating is contacting the HSV with ethylenimine. In some embodiments of the method of preparing an HSV vaccine, the inactivating is contacting the HSV with binary ethylenimine. In some embodiments of the method of preparing an HSV vaccine, the inactivating is contacting the HSV with beta-propiolactone. In some embodiments of the method of preparing an HSV vaccine, the inactivating is contacting the HSV with UV radiation. In some embodiments of the method of preparing an HSV vaccine, the inactivating is contacting the HSV with electron beam radiation. In some embodiments of the method of preparing an HSV vaccine, the inactivating is contacting the HSV with infrared radiation. In some embodiments of the method of preparing an HSV vaccine, the inactivating is contacting the HSV with gamma radiation. In some embodiments of the method of preparing an HSV vaccine, the inactivating is contacting the HSV with aldehyde cross-linking agent. In some embodiments of the method of preparing an HSV vaccine, the inactivating is contacting the HSV with formaldehyde. In some embodiments of the method of preparing an HSV vaccine, the inactivating is contacting the HSV with formalin. In some embodiments of the method of preparing an HSV vaccine, the inactivating is contacting the HSV with sodium periodate. In some embodiments of the method of preparing an HSV vaccine, the inactivating is contacting the HSV with hydrogen peroxide. In some embodiments of the method of preparing an HSV vaccine, the inactivating is contacting the HSV with aldrithiol-2. In some embodiments of the method of preparing an HSV vaccine, the inactivating is contacting the HSV with Triton-X-100. In some embodiments of the method of preparing an HSV vaccine, the inactivating is contacting the HSV with NP-40. In some embodiments of the method of preparing an HSV vaccine, the inactivating is contacting the HSV with Tween-20. In some embodiments of the method of preparing an HSV vaccine, the inactivating is contacting the HSV with UV radiation and a furocoumarin. In some embodiments of the method of preparing an HSV vaccine, the inactivating is contacting the HSV with UV radiation and psoralen. In some embodiments of the method of preparing an HSV vaccine, the inactivating is contacting the HSV with UV radiation and 4'-aminomethyl-4,5',8-trimethylpsoralen. In some embodiments of the method of preparing an HSV vaccine, the inactivating is contacting the HSV with UV radiation and angelicin. In some embodiments of the method of preparing an HSV vaccine, the inactivating is contacting the HSV with UV radiation and xanthotoxin. In some embodiments of the method of preparing an HSV vaccine, the inactivating is contacting the HSV with UV radiation and bergapten. In some embodiments of the method of preparing an HSV vaccine, the inactivating is contacting the HSV with UV radiation and nodakenetin.

In some embodiments, a chemical agent for inactivating HSV is aziridine. In some embodiments, a chemical agent for inactivating HSV is ethylenimine. In some embodiments, a chemical agent for inactivating HSV is binary ethylenimine. In some embodiments, a chemical agent for inactivating HSV is beta-propiolactone. In some embodiments, a radiation for inactivating HSV is UV radiation. In some embodiments, a radiation for inactivating HSV is electron beam radiation. In some embodiments, a radiation for inactivating HSV is infrared radiation. In some embodiments, a radiation for inactivating HSV is gamma radiation. In some embodiments, a cross-linking agent for inactivating HSV is an aldehyde cross-linking agent. In some embodiments, a cross-linking agent for inactivating HSV is formaldehyde. In some embodiments, a cross-linking agent for inactivating HSV is formalin. In some embodiments, a cross-linking agent for inactivating HSV is sodium periodate. In some embodiments, an oxidizing agent for inactivating HSV is hydrogen peroxide. In some embodiments, a reducing agent for inactivating HSV is aldrithiol-2. In some embodiments, a detergent for inactivating HSV is Triton-X-100. In some embodiments, a detergent for inactivating HSV is NP-40. In some embodiments, a detergent for inactivating HSV is Tween-20. In some embodiments, a furocoumarin for inactivating HSV is psoralen. In some embodiments, a furocoumarin for inactivating HSV is 4'-aminomethyl-4,5',8-trimethylpsoralen. In some embodiments, a furocoumarin for inactivating HSV is angelicin. In some embodiments, a furocoumarin for inactivating HSV is xanthotoxin. In some embodiments, a furocoumarin for inactivating HSV is bergapten. In some embodiments, a furocoumarin for inactivating HSV is nodakenetin.

Provided in another aspect is a method of treating or preventing a disease in a patient in need of the treatment or prevention. The method including administering a therapeutically or prophylactically effective amount of an HSV vaccine as described herein (including embodiments). In some embodiments, a patient in need of preventing a disease is a patient at risk of developing, contracting, getting, or having the disease.

In some embodiments of the method of treating or preventing a disease, the disease is associated with HSV1. In some embodiments of the method of treating or preventing a disease, the disease is caused by HSV1. In some embodiments of the method of treating or preventing a disease, the disease is associated with HSV2. In some embodiments of the method of treating or preventing a disease, the disease is caused by HSV2. In some embodiments of the method of treating or preventing a disease, the disease is selected from the group consisting of herpetic gingivostomatitis, herpes labialis, herpes genitalis, herpetic whitlow, herpes gladiatorum, herpesviral encephalitis, herpesviral meningitis, herpes esophagitis, herpes keratitis, Bell's palsy, Mollaret's meningitis, herpes rugbeiorum, eczema herpeticum, herpetic neuralgia, and post-herpetic neuralgia. In some embodiments of the method of treating or preventing a disease, the disease is herpetic gingivostomatitis. In some embodiments of the method of treating or preventing a disease, the disease is herpes labialis. In some embodiments of the method of treating or preventing a disease, the disease is herpes genitalis. In some embodiments of the method of treating or preventing a disease, the disease is herpetic whitlow. In some embodiments of the method of treating or preventing a disease, the disease is herpes gladiatorum. In some embodiments of the method of treating or preventing a disease, the disease is herpesviral encephalitis. In some embodiments of the method of treating or preventing a disease, the disease is herpesviral meningitis. In some embodiments of the method of treating or preventing a disease, the disease is herpes esophagitis. In some embodiments of the method of treating or preventing a disease, the disease is herpes keratitis. In some embodiments of the method of treating or preventing a disease, the disease is Bell's palsy. In some embodiments of the method of treating or preventing a disease, the disease is Mollaret's meningitis. In some embodiments of the method of treating or preventing a disease, the disease is herpes rugbeiorum. In some embodiments of the method of treating or preventing a disease, the disease is eczema herpeticum. In some embodiments of the method of treating or preventing a disease, the disease is herpetic neuralgia. In some embodiments of the method of treating or preventing a disease, the disease is post-herpetic neuralgia. In some embodiments of the method of treating or preventing a disease, the disease is Alzheimer's disease. In some embodiments of the method of treating or preventing a disease, the method includes treating the disease. In some embodiments of the method of treating or preventing a disease, the method includes preventing the disease. In some embodiments of the method of treating or preventing a disease, the method is treating the disease. In some embodiments of the method of treating or preventing a disease, the method is preventing the disease. In some embodiments of the method of treating or preventing a disease, the method includes administering a therapeutically effective amount of an HSV vaccine as described herein (including embodiments). In some embodiments of the method of treating or preventing a disease, the method includes administering a prophylactically effective amount of an HSV vaccine as described herein (including embodiments). In some embodiments of the method of treating or preventing a disease, the method includes a reduction in viral shedding. In some embodiments of the method of treating or preventing a disease, the method includes a reduction in the frequency of lesion occurrence. In some embodiments of the method of treating or preventing a disease, the method includes a reduction in the duration of lesion occurrence. In some embodiments of the method of treating or preventing a disease, the method includes intramuscular administration of an HSV vaccine as described herein (including embodiments). In some embodiments of the method of treating or preventing a disease, the method includes intradermal administration of an HSV vaccine as described herein (including embodiments). In some embodiments of the method of treating or preventing a disease, the method includes mucosal administration of an HSV vaccine as described herein (including embodiments). In some embodiments of the method of treating or preventing a disease, the method includes intranasal administration of an HSV vaccine as described herein (including embodiments). In some embodiments of the method of treating or preventing a disease, the method includes intrarectal administration of an HSV vaccine as described herein (including embodiments). In some embodiments of the method of treating or preventing a disease, the method includes intravaginal administration of an HSV vaccine as described herein (including embodiments). In some embodiments of the method of treating or preventing a disease, the method includes topical administration of an HSV vaccine as described herein (including embodiments). In some embodiments of the method of treating or preventing a disease, the method includes subcutaneous administration of an HSV vaccine as described herein (including embodiments). In some embodiments of the method of treating or preventing a disease, the method includes transcutaneous administration of an HSV vaccine as described herein (including embodiments).

In some embodiments of the method of treating or preventing a disease, the method does include administration of an HSV DNA vaccine (e.g. HSV1 DNA vaccine, HSV2 DNA vaccine, HSV1 and HSV2 DNA vaccine). In some embodiments of the method of treating or preventing a disease, the method does include administration of prime HSV DNA vaccine (e.g. HSV1 DNA vaccine, HSV2 DNA vaccine, HSV1 and HSV2 DNA vaccine). In some embodiments of the method of treating or preventing a disease, the method does include administration of an HSV DNA vaccine including a UL30 gene or portion of the gene. In some embodiments of the method of treating or preventing a disease, the method does include administration of an HSV DNA vaccine including a UL5 gene or portion of the gene. In some embodiments of the method of treating or preventing a disease, the method does include administration of an HSV DNA vaccine including a gD2 gene or portion of the gene. In some embodiments of the method of treating or preventing a disease, the method does include administration of an HSV DNA vaccine including a gD2t gene or portion of the gene. In some embodiments of the method of treating or preventing a disease, the method does include administration of an HSV protein vaccine (e.g. HSV1 protein vaccine, HSV2 protein vaccine, HSV1 and HSV2 protein vaccine). In some embodiments of the method of treating or preventing a disease, the method does include administration of an HSV protein vaccine including a gD2t protein. In some embodiments of the method of treating or preventing a disease, the method does not include administration of an HSV DNA vaccine (e.g. HSV1 DNA vaccine, HSV2 DNA vaccine, HSV1 and HSV2 DNA vaccine). In some embodiments of the method of treating or preventing a disease, the method does not include administration of prime HSV DNA vaccine (e.g. HSV1 DNA vaccine, HSV2 DNA vaccine, HSV1 and HSV2 DNA vaccine). In some embodiments of the method of treating or preventing a disease, the method does not include administration of an HSV DNA vaccine including a UL30 gene or portion of the gene. In some embodiments of the method of treating or preventing a disease, the method does not include administration of an HSV DNA vaccine including a UL5 gene or portion of the gene. In some embodiments of the method of treating or preventing a disease, the method does not include administration of an HSV DNA vaccine including a gD2 gene or portion of the gene. In some embodiments of the method of treating or preventing a disease, the method does not include administration of an HSV DNA vaccine including a gD2t gene or portion of the gene. In some embodiments of the method of treating or preventing a disease, the method does not include administration of an HSV protein vaccine (e.g. HSV1 protein vaccine, HSV2 protein vaccine, HSV1 and HSV2 protein vaccine). In some embodiments of the method of treating or preventing a disease, the method does not include administration of an HSV protein vaccine including a gD2t protein. It will be understood by a person of ordinary skill in the art that when a composition or method that does not include a DNA vaccine or a nucleic acid sequence is recited, it is intended that such composition or method does not include the intentional addition of a composition comprising a nucleic acid composition (e.g. DNA vaccine, nucleic acid vaccine, antigenic nucleic acid, nucleic acid sequence, or other nucleic acid composition) described as being excluded or lacking. In some embodiments a composition or method that does not include a nucleic acid composition may include a nucleic acid composition in trace amounts or as included in another component of the composition, wherein a trace amount of a nucleic acid is an amount less than an amount necessary to elicit an antigen specific immune response to the nucleic acid or a protein expressed from or by the nucleic acid. In some embodiments, a trace amount of a nucleic acid is less than about 12.5, 10, 9, 8.5, 8, 7, 6, 5, 4, 3, 2, 1, 0.9, 0.8, 0.7, 0.6, 0.5, 0.4, 0.3, 0.2, 0.1, 0.009, 0.008, 0.007, 0.006, 0.005, 0.004, 0.003, 0.002, 0.001 micrograms of the nucleic acid. In some embodiments, a trace amount of nucleic acid is less than about 12.5, 10, 9, 8.5, 8, 7, 6, 5, 4, 3, 2, 1, 0.9, 0.8, 0.7, 0.6, 0.5, 0.4, 0.3, 0.2, 0.1, 0.009, 0.008, 0.007, 0.006, 0.005, 0.004, 0.003, 0.002, 0.001 micrograms of the nucleic acid per dose of vaccine. In some embodiments, a trace amount of nucleic acid is less than about 12.5, 10, 9, 8.5, 8, 7, 6, 5, 4, 3, 2, 1, 0.9, 0.8, 0.7, 0.6, 0.5, 0.4, 0.3, 0.2, 0.1, 0.009, 0.008, 0.007, 0.006, 0.005, 0.004, 0.003, 0.002, 0.001 micrograms of the nucleic acid per dose of vaccine administered i.m. In some embodiments, a trace amount of nucleic acid is less than 12.5, 10, 9, 8.5, 8, 7, 6, 5, 4, 3, 2, 1, 0.9, 0.8, 0.7, 0.6, 0.5, 0.4, 0.3, 0.2, 0.1, 0.009, 0.008, 0.007, 0.006, 0.005, 0.004, 0.003, 0.002, 0.001 micrograms of the nucleic acid. In some embodiments, a trace amount of nucleic acid is less than 12.5, 10, 9, 8.5, 8, 7, 6, 5, 4, 3, 2, 1, 0.9, 0.8, 0.7, 0.6, 0.5, 0.4, 0.3, 0.2, 0.1, 0.009, 0.008, 0.007, 0.006, 0.005, 0.004, 0.003, 0.002, 0.001 micrograms of the nucleic acid per dose of vaccine. In some embodiments, a trace amount of nucleic acid is less than 12.5, 10, 9, 8.5, 8, 7, 6, 5, 4, 3, 2, 1, 0.9, 0.8, 0.7, 0.6, 0.5, 0.4, 0.3, 0.2, 0.1, 0.009, 0.008, 0.007, 0.006, 0.005, 0.004, 0.003, 0.002, 0.001 micrograms of the nucleic acid per dose of vaccine administered i.m. In some embodiments, a trace amount of nucleic acid is 1 microgram. In some embodiments, a trace amount of nucleic acid is 0.5 micrograms. In some embodiments, a trace amount of nucleic acid is an amount less than an amount set forth in DNA vaccines in WO2007106404 or administered to elicit an immune response in WO2007106404. In some embodiments of the method, an isolated nucleic acid sequence formulation is not administered to the patient. In some embodiments of the method, the isolated nucleic acid sequence formulation is a DNA sequence. In some embodiments of the method, the isolated nucleic acid sequence formulation is a nucleic acid vaccine. In some embodiments of the method, the isolated nucleic acid sequence formulation is a DNA vaccine.

Provided in another aspect is a pharmaceutical composition including a pharmaceutically acceptable excipient and any of the compositions (e.g. vaccines) described herein (including embodiment).

The compositions described herein (including embodiments and examples) can be administered alone or can be coadministered to the patient. Coadministration is meant to include simultaneous or sequential administration of the compositions individually or in combination (more than one composition). Thus, the preparations can also be combined, when desired, with other active substances (e.g. to reduce metabolic degradation, increase immune response (e.g. adjuvants)). An example of coadministration of vaccine compositions is a prime-boost method of administration.

The compositions of the present invention can be prepared and administered in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compositions of the present invention can also be administered by injection, that is, intravenously, intramuscularly, intracutaneously, subcutaneously, intraduodenally, or intraperitoneally. Also, the compositions described herein can be administered by inhalation, for example, intranasally. Additionally, the compositions of the present invention can be administered transdermally. It is also envisioned that multiple routes of administration (e.g., intramuscular, oral, transdermal, mucosal, intranasal, intrarectal, intravaginal, subcutaneous, transcutaneous, topical, intradermal) can be used to administer the compositions of the invention. Accordingly, the present invention also provides pharmaceutical compositions including a pharmaceutically acceptable excipient and one or more compositions described herein (including embodiments).

For preparing pharmaceutical compositions from the compositions of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid in a mixture with the finely divided active component (e.g. a composition provided herein). In tablets, the active component is mixed with the carrier having the necessary binding properties in suitable proportions and compacted in the shape and size desired. The powders and tablets preferably contain from 5% to 70% of the active compound.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active composition (i.e., dosage). Pharmaceutical preparations of the invention can also be used orally using, for example, push-fit capsules made of gelatin, as well as soft, sealed capsules made of gelatin and a coating such as glycerol or sorbitol.

For preparing suppositories, a low melting wax, such as a mixture of fatty acid glycerides or cocoa butter, is first melted and the active composition is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampules are convenient unit dosages. The compositions of the invention can also be incorporated into liposomes or administered via transdermal pumps or patches. Pharmaceutical admixtures suitable for use in the present invention are well-known to those of skill in the art and are described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component (e.g. compositions described herein, including embodiments, examples) in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Some compositions may have limited solubility in water and therefore may require a surfactant or other appropriate co-solvent in the composition. Such co-solvents include: Polysorbate 20, 60 and 80; Pluronic F-68, F-84 and P-103; cyclodextrin; polyoxyl 35 castor oil; or other agents known to those skilled in the art. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, combinations of the foregoing, and other agents known to those skilled in the art. Such agents are typically employed at a level between about 0.01% and about 2% by weight. Determination of acceptable amounts of any of the above adjuvants is readily ascertained by one skilled in the art.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

Pharmaceutical compositions provided by the present invention include compositions wherein the active ingredient (e.g. compositions described herein, including embodiments) is contained in a therapeutically or prophylactically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., prevent HV (e.g. HSV, HHV-1, HHV-2, HHV-3, HHV-4, HHV-5, HHV-6, HHV-7, or HHV-8) infection, prevent HSV (e.g. HSV1 and/or HSV2) infection, and/or reducing, eliminating, or slowing the progression of disease symptoms (e.g. HV (e.g. HSV, HHV-1, HHV-2, HHV-3, HHV-4, HHV-5, HHV-6, HHV-7, or HHV-8) infection, HSV (e.g. HSV1 and/or HSV2) infection). Determination of a therapeutically or prophylactically effective amount of a composition of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. HV (e.g. HSV, HHV-1, HHV-2, HHV-3, HHV-4, HHV-5, HHV-6, HHV-7, or HHV-8) infection, HSV (e.g. HSV1 and/or HSV2) infection), kind of concurrent treatment, complications from the disease being treated or other health-related problems. Other therapeutic regimens or agents can be used in conjunction with the methods and compositions of Applicants' invention. Adjustment and manipulation of established dosages (e.g., frequency and duration) are well within the ability of those skilled in the art.

For any compositions described herein, the therapeutically effective amount can be initially determined from cell culture assays. Target concentrations will be those concentrations of active composition(s) that are capable of achieving the methods described herein, as measured using the methods described herein or known in the art.

As is well known in the art, therapeutically or prophylactically effective amounts for use in humans can also be determined from animal models. For example, a dose for humans can be formulated to achieve a concentration that has been found to be effective in animals. The dosage in humans can be adjusted by monitoring compositions effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the composition being employed. The dose administered to a patient, in the context of the present invention should be sufficient to effect a beneficial therapeutic or prophylactic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered composition effective for the particular clinical indication being treated or prevented. This will provide a therapeutic or prophylactic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active composition by considering factors such as composition potency, relative bioavailability, patient body weight, presence and severity of adverse side effects, preferred mode of administration and the toxicity profile of the selected agent.

The ratio between toxicity and therapeutic effect for a particular composition is its therapeutic index and can be expressed as the ratio between $LD_{50}$ (the amount of composition lethal in 50% of the population) and $ED_{50}$ (the amount of composition effective in 50% of the population). Compositions that exhibit high therapeutic indices are preferred. Therapeutic index data obtained from cell culture assays and/or animal studies can be used in formulating a range of dosages for use in humans. The dosage of such compositions preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration and dosage can be chosen by the individual physician in view of the patient's condition and the particular method in which the composition is used.

IV. Administration

The compositions of the present invention can be delivered by transdermally, by a topical route, transcutaneously, formulated as applicator sticks, solutions, suspensions, emulsions, gels, creams, ointments, pastes, jellies, paints, powders, and aerosols. The terms "compositions of the present invention", "compositions as described herein (including embodiments)", "compositions described herein (including embodiments)", "composition provided herein", and the like are used interchangeably.

The pharmaceutical compositions of the present invention can be provided as a salt and can be formed with many acids, including but not limited to hydrochloric, sulfuric, acetic, lactic, tartaric, malic, succinic, etc. Pharmaceutical compositions described herein may be salts of a compound or composition which are prepared with relatively nontoxic acids or bases, depending on the particular substituents found on the compositions described herein. When compositions of the present invention contain relatively acidic functionalities, base addition salts can be obtained by contacting the neutral form of such compositions with a sufficient amount of the desired base, either neat or in a suitable inert solvent. Examples of pharmaceutically acceptable base addition salts include sodium, potassium, calcium, ammonium, organic amino, or magnesium salt, or a similar salt. When compositions of the present invention contain relatively basic functionalities, acid addition salts can be obtained by contacting the neutral form of such compositions with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compositions of the present invention contain both basic and acidic functionalities that allow the compositions to be converted into either base or acid addition salts. Other pharmaceutically acceptable carriers known to those of skill in the art are suitable for the present invention. Salts tend to be more soluble in aqueous or other protonic solvents that are the corresponding free base forms.

The neutral forms of the compositions may be regenerated by contacting the salt with a base or acid and isolating the parent compositions in the conventional manner. The parent form of the compositions differs from the various salt forms in certain physical properties, such as solubility in polar solvents, but otherwise the salts are equivalent to the parent form of the compositions for the purposes of the present invention.

In another embodiment, the compositions of the present invention are useful for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents.

The compositions described herein can be used in combination with one another, with other active agents known to be useful in treating a disease associated with HV (e.g. HSV, HHV-1, HHV-2, HHV-3, HHV-4, HHV-5, HHV-6, HHV-7, or HHV-8) or HSV (e.g. HSV1 and/or HSV2) infection, or with adjunctive agents that may not be effective alone, but may contribute to the efficacy of the active agent (e.g. LPS-derived adjuvants, aluminum-based mineral salt adjuvants).

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, co-administration includes administering vaccines in a prime-boost method within 1, 2, 3, 4, 5, 6, 7, 8, 9, 10, 11, or 12 weeks of each other, or within 1, 2, 3, 4, 5, 6, 7, 8, 9, 10, 11, 12 months of each other. In some embodiments, the prime-boost administration is 4 weeks apart.

As a non-limiting example, the compositions described herein can be co-administered (e.g. prime-boost) with another HSV vaccine including, but not limited to, HSV DNA vaccines, HSV DNA vaccine comprising one or more portions of one or more of the HSV (e.g. HSV1 or HSV2) genes (e.g. UL1, UL2, UL3, UL4, UL5, UL6, UL7, UL8, UL9, UL10, UL11, UL12, UL13, UL14, UL15, UL16, UL17, UL18, UL19, UL20, UL21, UL22, UL23, UL24, UL25, UL26, UL27, UL28, UL29, UL30, UL31, UL32, UL33, UL34, UL35, UL36, UL37, UL38, UL39, UL40, UL41, UL42, UL43, UL44, UL45, UL46, UL47, UL48, UL49, UL50, UL51, UL52, UL53, UL54, UL55, UL56, US1, US2, US3, US4, US5, US6, US7, US8, US9, US10, US11, US12, RS1, ICP0, LRP1, LRP2, RL1, or LAT), HSV protein vaccine, HSV protein vaccine comprising one or more portions of one or more of the HSV (e.g. HSV1 or HSV2) proteins (e.g. protein expressed from the HSV gene UL1, UL2, UL3, UL4, UL5, UL6, UL7, UL8, UL9, UL10, UL11, UL12, UL13, UL14, UL15, UL16, UL17, UL18, UL19, UL20, UL21, UL22, UL23, UL24, UL25, UL26, UL27, UL28, UL29, UL30, UL31, UL32, UL33, UL34, UL35, UL36, UL37, UL38, UL39, UL40, UL41, UL42, UL43, UL44, UL45, UL46, UL47, UL48, UL49, UL50, UL51, UL52, UL53, UL54, UL55, UL56, US1, US2, US3, US4, US5, US6, US7, US8, US9, US10, US11, US12, RS1, ICP0, LRP1, LRP2, RL1, or LAT), an inactivated HSV, and the like. In some embodiments, the compositions described herein are not co-administered (e.g. prime-boost) with another HSV vaccine selected from the group consisting of HSV DNA vaccines, HSV DNA vaccine comprising one or more portions of one or more of the HSV (e.g. HSV1 or HSV2) genes (e.g. UL1, UL2, UL3, UL4, UL5, UL6, UL7, UL8, UL9, UL10, UL11, UL12, UL13, UL14, UL15, UL16, UL17, UL18, UL19, UL20, UL21, UL22, UL23, UL24, UL25, UL26, UL27, UL28, UL29, UL30, UL31, UL32, UL33, UL34, UL35, UL36, UL37, UL38, UL39, UL40, UL41, UL42, UL43, UL44, UL45, UL46, UL47, UL48, UL49, UL50, UL51, UL52, UL53, UL54, UL55, UL56, US1, US2, US3, US4, US5, US6, US7, US8, US9, US10, US11, US12, RS1, ICP0, LRP1, LRP2, RL1, or LAT), HSV protein vaccine, HSV protein vaccine comprising one or more portions of one or more of the HSV (e.g. HSV1 or HSV2) proteins (e.g. protein expressed from the HSV gene UL1, UL2, UL3, UL4, UL5, UL6, UL7, UL8, UL9, UL10, UL11, UL12, UL13, UL14, UL15, UL16, UL17, UL18, UL19, UL20, UL21, UL22, UL23, UL24, UL25, UL26, UL27, UL28, UL29, UL30, UL31, UL32, UL33, UL34, UL35, UL36, UL37, UL38, UL39, UL40, UL41, UL42, UL43, UL44, UL45, UL46, UL47, UL48, UL49, UL50, UL51, UL52, UL53, UL54, UL55, UL56, US1, US2, US3, US4, US5, US6, US7, US8, US9, US10, US11, US12, RS1, ICP0, LRP1, LRP2, RL1, or LAT), an inactivated HSV, and the like.

The pharmaceutical compositions of the present invention may be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate.

Formulations suitable for oral administration can comprise: (a) liquid solutions, such as an effective amount of a packaged compound or drug suspended in diluents, e.g., water, saline, or PEG 400; (b) capsules, sachets, or tablets, each containing a predetermined amount of an HSV (e.g. HSV1 and/or HSV2) vaccine composition, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise an HV (e.g. HSV, HHV-1, HHV-2, HHV-3, HHV-4, HHV-5, HHV-6, HHV-7, or HHV-8) vaccine composition or HSV (e.g. HSV1 and/or HSV2) vaccine composition in a flavor, e.g., sucrose, as well as pastilles comprising for example, an HV (e.g. HSV, HHV-1, HHV-2, HHV-3, HHV-4, HHV-5, HHV-6, HHV-7, or HHV-8) vaccine composition or HSV (e.g. HSV1 and/or HSV2) vaccine composition in an inert base, such as gelatin and glycerin or sucrose and acacia emulsions, gels, and the like, containing, in addition to for example, an HV (e.g. HSV, HHV-1, HHV-2, HHV-3, HHV-4, HHV-5, HHV-6, HHV-7, or HHV-8) vaccine composition or HSV (e.g. HSV1 and/or HSV2) vaccine composition, carriers known in the art.

The composition of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which comprises an effective amount of a packaged HV (e.g. HSV, HHV-1, HHV-2, HHV-3, HHV-4, HHV-5, HHV-6, HHV-7, or HHV-8) vaccine composition or HSV (e.g. HSV1 and/or HSV2) vaccine composition, with a suppository base. Suitable suppository bases include natural or synthetic triglycerides or paraffin hydrocarbons. In addition, it is also possible to use gelatin rectal capsules which contain a combination of for example, an HV (e.g. HSV, HHV-1, HHV-2, HHV-3, HHV-4, HHV-5, HHV-6, HHV-7, or HHV-8) vaccine composition or HSV (e.g. HSV1 and/or HSV2) vaccine composition of choice, with a base, including, for example, liquid triglycerides, polyethylene glycols, and paraffin hydrocarbons.

Formulations suitable for parenteral administration, such as, for example, by intraarticular (in the joints), intravaginal, intrarectal intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can also be prepared from sterile powders, granules, and tablets. In the practice of the present invention, compositions can be administered, for example, by intravenous infusion, orally, topically, intraperitoneally, intravesically, or intrathecally. Parenteral administration, nasal administration, oral administration, and intravenous administration are the preferred methods of administration. The formulations of compositions can be presented in unit-dose or multi-dose sealed containers, such as ampoules and vials.

The pharmaceutical preparation is preferably in unit dosage form. In such form the preparation is subdivided into unit doses containing appropriate quantities of the active component, e.g., an HV (e.g. HSV, HHV-1, HHV-2, HHV-3, HHV-4, HHV-5, HHV-6, HHV-7, or HHV-8) vaccine composition or HSV (e.g. HSV1 and/or HSV2) vaccine composition. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

In therapeutic use for the treatment of HV (e.g. HSV, HHV-1, HHV-2, HHV-3, HHV-4, HHV-5, HHV-6, HHV-7, or HHV-8) infection or a disease related to HV (e.g. HSV, HHV-1, HHV-2, HHV-3, HHV-4, HHV-5, HHV-6, HHV-7, or HHV-8) infection, the HV (e.g. HSV, HHV-1, HHV-2, HHV-3, HHV-4, HHV-5, HHV-6, HHV-7, or HHV-8) vaccine composition may be varied depending upon the requirements of the patient, the severity of the condition being treated, and the HV (e.g. HSV, HHV-1, HHV-2, HHV-3, HHV-4, HHV-5, HHV-6, HHV-7, or HHV-8) vaccine composition being employed. For example, dosages can be empirically determined considering the type and stage of HV (e.g. HSV, HHV-1, HHV-2, HHV-3, HHV-4, HHV-5, HHV-6, HHV-7, or HHV-8) related disease diagnosed in a particular patient. The dose administered to a patient, in the context of the present invention, should be sufficient to affect a beneficial therapeutic or prophylactic response in the patient over time. The size of the dose will also be determined by the existence, nature, and extent of any adverse side-effects that accompany the administration of a composition in a particular patient. Determination of the proper dosage for a particular situation is within the skill of the practitioner. Generally, treatment is initiated with smaller dosages which are less than the optimum dose of the composition. Thereafter, the dosage is increased by small increments until the optimum effect under circumstances is reached. For convenience, the total daily dosage may be divided and administered in portions during the day, if desired.

In some embodiments, there is provided a method of preventing or treating a Herpes Simplex Virus Type 2 (HSV-2) infection in a subject. The method includes administering to a subject in need thereof a DNA vaccine, wherein the DNA vaccine includes a DNA sequence encoding a portion of at least one conserved HSV-2 gene required for virus replication.

In some embodiments, the DNA vaccine further includes a monophosphoryl lipid A (MPL) adjuvant. In some embodiments, the DNA vaccine further includes an alum adjuvant. In some embodiments, the DNA vaccine includes whole, inactivated HSV-2. In some embodiments, the DNA vaccine includes formalin-inactivated HSV-2 (Fl-HSV-2). In some embodiments, the DNA sequence encodes at least a portion of a DNA polymerase from HSV-2. In some embodiments, the DNA polymerase is HSV-2 UL30 DNA polymerase. In some embodiments, the DNA vaccine includes a DNA molecule encoding at least a portion of HSV-2 secreted glycoprotein D2 (gD2t). In some embodiments, the DNA vaccine further includes a DNA molecule encoding at least a portion of HSV-2 secreted glycoprotein D2 (gD2t). In some embodiments, the DNA sequence encodes at least a portion of a helicase from HSV-2. In some embodiments, the helicase is HSV-2 UL5 helicase. In some embodiments, the administration step of the method is prime-boost immunization.

In another embodiment, there is provided a DNA vaccine which includes a DNA sequence encoding a portion of at least one conserved HSV-2 gene required for virus replication.

In some embodiments, the DNA vaccine further includes a monophosphoryl lipid A (MPL) adjuvant. In some embodiments, the DNA vaccine further includes an alum adjuvant. In some embodiments, the DNA vaccine includes whole, inactivated HSV-2. In some embodiments, the DNA vaccine includes formalin-inactivated HSV-2 (Fl-HSV-2). In some embodiments, the DNA sequence encodes at least a portion of a DNA polymerase from HSV-2. In some embodiments, the DNA polymers is HSV-2 UL30 DNA polymerase. In some embodiments, the DNA vaccine includes a DNA molecule encoding at least a portion of HSV-2 secreted glycoprotein D2 (gD2t). In some embodiments, the DNA vaccine further includes a DNA molecule encoding at least a portion of HSV-2 secreted glycoprotein D2 (gD2t). In some embodiments, the DNA sequence encodes at least a portion of a helicase from HSV-2. In some embodiments, the helicase is HSV-2 UL5 helicase.

Accordingly, in some embodiments of the method and vaccine described herein, there is provided formalin-inactivated herpesvirus mixed with an aluminum-based mineral salt adjuvant (alhydrogel or adju-phos) and monophosphoryl lipid A (MPL) as a vaccine to generate protective immune responses.

In some embodiments, dextran sulfate was employed to release high titers of herpesviruses from infected cells, greatly reducing the amount of cellular material in the preparation. The resulting virus is subsequently purified and inactivated with formaldehyde.

We have developed and tested several vaccine combinations against herpes simplex virus type 2 (HSV-2) in both mouse and guinea pig models of genital disease. Included in these vaccines were the adjuvant monophosphoryl lipid A (MPL) and various formulations of Alum. We asked whether a multivalent vaccine consisting of FI-HSV2 together with MPL/Alum could be more protective than gD2 protein subunit/MPL/Alum vaccination.

Accordingly, we have found that immunization with FI-HSV2/MPL/Alum provided significantly higher levels of protection against both disease and virus shedding compared with gD2t protein immunization in the mouse model of genital disease. In fact, in one experiment, 2 of the 8 mice that were immunized only with FI-HSV-2 did not shed any detectable virus on any day post challenge. All of the early experiments were done with Imject Alum from Pierce, which consists of both crystalline and amorphous aluminum phases and is not a well-defined form of alum suitable for clinical translation. Therefore we tested the protective efficacy of vaccines that were formulated with MPL and aluminum hydroxide (Alhydrogel) or aluminum phosphate (Adju-Phos) adjuvants, both of which have been licensed for use in clinical vaccines. We also tested various routes of immunization. The test immunization groups were: 1) FI-HSV2/MPL/Alhydrogel given subcutaneously; 2) FI-HSV2/MPL/Alhydrogel given intramuscularly; and 3) FI-HSV2/MPL/Adju-Phos given intramuscularly.

Following intravaginal challenge with HSV-2, the mean titers in the groups receiving FI-HSV2 were reduced by 3 Logs. In addition, half or more of the 8 mice in each FI-HSV2 groups had reductions in virus shedding to levels at or below the detection limit. Taken together, immunization with FI-HSV2 and MPL together with the aluminum containing adjuvants Alhydrogel or Adju-Phos resulted in protection against HSV-2 disease and shedding that was at least as robust as that afforded by Imject alum. In this experiment, several of the FI-HSV2 immunized mice in each group had no detectable shedding (<10 PFU) on either day tested.

Without wishing to be bound by any theory, it is believed important to question whether the high level protection against challenge that was provided by the FI-HSV2/MPL/Alum would also be effective against a long-term re-challenge. To this end, the FI-HSV2 immunized mice were re-challenged 17 weeks after the first challenge with the same $10\times LD_{50}$ dose of HSV-2). Strikingly, only 2 of the rechallenged mice in the FI-HSV2 groups had a detectable, low level of virus, with the mouse in the FI-HSV2/Alhydrogel s.c. group showing detectable virus on day 2 later dying on day 21. It is particularly notable that in the FI-HSV2/Alhydrogel i.m. group, 5 of the 8 mice had no detectable virus on day 2 postchallenge or post-rechallenge, and 2 additional mice in this group had very low level shedding postchallenge ($10^1$-$10^{1.5}$ PFU) and no detectable virus post-rechallenge.

Taken together, we found that immunization with FI-HSV2 that was formulated with MPL and aluminum containing adjuvants elicits nearly complete protection against HSV-2 disease. Moreover, these vaccines provide strong and durable protection against vaginal HSV-2 shedding, with some animals showing sterilizing immunity, following challenge or long-term rechallenge.

We have also evaluated the formalin-inactivated-HSV-2 (FI-HSV2)/MPL/Alhydrogel vaccine in the guinea pig model of acute and recurrent HSV-2 genital disease and compared it with the gD2t subunit protein vaccine in MPL/Alum. After challenge, both groups showed highly significant protection against acute viral disease and viral shedding compared to the mock-immunized animals. Only 1 of 10 guinea pigs immunized with FI-HSV2/MPL/Alhydrogel had an acute-phase lesion and virus shedding that persisted to day 9 postchallenge. Only this animal developed recurrent lesions over a 100 day period, whereas 3 out of 10 animals in the gD2t subunit protein/MPL/Alhydrogel developed recurrent lesions. To determine whether the protection against recurrent lesions or vaginal HSV-2 disease was associated with differences in the number of latent viral genomes in the DRG or in postreactivation immunity, the lumbosacral DRG from each surviving guinea pig were harvested. The levels of HSV-2 DNA were quantified by real-time quantitative PCR. Only the single guinea pig immunized with FI-HSV2/MPL/Alhydrogel that had both acute and recurrent lesions had detectable HSV-2 DNA (84 copies). In contrast, 4 of the 10 gD2t subunit MPL/Alhydrogel-immunized guinea pigs had detectable HSV-2 DNA levels. Taken together, these studies showed when the FI-HSV2/MPL alhydrogel vaccine was given to the guinea pigs, with the exception of one "nonresponder" animal in the group, there was complete protection against both acute and recurrent lesion development, undetectable levels of HSV-2 DNA in the DRG, lower cumulative acute disease scores, and lower numbers of recurrent disease days (Morello, C. S. et al., 2011, *Virol.*, 85:3461-3472).

V. Selected Embodiments

Embodiment 1

A Herpes Simplex Virus (HSV) vaccine comprising inactivated HSV, a lipopolysaccharide (LPS)-derived adjuvant and an aluminum-based mineral salt adjuvant.

Embodiment 2

The vaccine of Embodiment 1, wherein said LPS-derived adjuvant is MPL; said aluminum-based mineral salt adjuvant is aluminum hydroxide adjuvant or aluminum phosphate adjuvant; and said vaccine does not comprise an isolated nucleic acid sequence formulation.

Embodiment 3

The vaccine of any one of Embodiments 1 to 2, wherein said HSV is HSV1.

Embodiment 4

The vaccine of any one of Embodiments 1 to 2, wherein said HSV is HSV2.

Embodiment 5

The vaccine of any one of Embodiments 1 to 2, wherein said HSV is HSV1 and HSV2.

Embodiment 6

The vaccine of any one of Embodiments 1 to 2, wherein said lipopolysaccharide-derived adjuvant is derived from the *Salmonella Minnesota* LPS.

Embodiment 7

The vaccine of any one of Embodiments 1 to 2, wherein said lipopolysaccharide-derived adjuvant is derived from the *Salmonella Minnesota* Re595 LPS.

Embodiment 8

The vaccine of any one of Embodiments 1 to 8, wherein said lipopolysaccharide-derived adjuvant is derived from the R595 LPS.

Embodiment 9

The vaccine of any one of Embodiments 1 to 8, wherein said lipopolysaccharide-derived adjuvant is a lipid A adjuvant.

Embodiment 10

The vaccine of any one of Embodiments 1 to 8, wherein said lipopolysaccharide-derived adjuvant is a lipid A adjuvant without an (R)-3-hydroxytetradecanoyl moiety.

Embodiment 11

The vaccine of any one of Embodiments 1 to 8 and 10, wherein said lipopolysaccharide-derived adjuvant is a lipid A adjuvant without a 1-phosphate moiety.

Embodiment 12

The vaccine of any one of Embodiments 1 to 8 and 10 to 11, wherein said lipopolysaccharide-derived adjuvant is monophosphoryl lipid A (MPL).

Embodiment 13

The vaccine of any one of Embodiments 1 to 8 and 10 to 11, wherein said lipopolysaccharide-derived adjuvant is 3-O-desacyl-4'-monophosphoryl lipid A.

Embodiment 14

The vaccine of any one of Embodiments 1 to 13, wherein said lipopolysaccharide-derived adjuvant is capable of binding the TLR4 protein.

Embodiment 15

The vaccine of any one of Embodiments 1 to 14, wherein said lipopolysaccharide-derived adjuvant is a synthetic MPL analogue adjuvant.

Embodiment 16

The vaccine of any one of Embodiments 1 to 15, wherein said aluminum-based mineral salt adjuvant is an aluminum hydroxide adjuvant.

Embodiment 17

The vaccine of any one of Embodiments 1 to 15, wherein said aluminum-based mineral salt adjuvant is an aluminum phosphate adjuvant.

Embodiment 18

The vaccine of any one of Embodiments 1 to 15, wherein said aluminum-based mineral salt adjuvant includes crystalline aluminum hydroxide and not amorphous aluminum hydroxide or aluminum hydroxycarbonate or magnesium hydroxide.

Embodiment 19

The vaccine of any one of Embodiments 1 to 15, wherein said aluminum-based mineral salt adjuvant includes aluminum phosphate gel in the form of a white gelatinous precipitate.

Embodiment 20

The vaccine of any one of Embodiments 1 to 15, wherein said aluminum-based mineral salt adjuvant includes aluminum hydroxide gel in the form of a white gelatinous precipitate.

Embodiment 21

The vaccine of any one of Embodiments 1 to 15, wherein said aluminum-based mineral salt adjuvant is a potassium aluminum sulfate adjuvant.

Embodiment 22

The vaccine of any one of Embodiments 1 to 21, wherein said inactivated HSV comprises a replication decreasing DNA mutation.

Embodiment 23

The vaccine of any one of Embodiments 1 to 21, wherein said inactivated HSV is formed by chemical inactivation.

Embodiment 24

The vaccine of any one of Embodiments 1 to 21, wherein said inactivated HSV is formed by contacting said HSV with one or more agents selected from a cross-linking agent, oxidizing agent, reducing agent, heat, radiation, detergent, a pH changing agent, and a chemical agent selected from a furocoumarin, aziridine, ethylenimine, binary ethylenimine, and beta-propiolactone.

Embodiment 25

The vaccine of Embodiment 24, wherein said chemical agent is aziridine.

Embodiment 26

The vaccine of Embodiment 24, wherein said chemical agent is ethylenimine.

Embodiment 27

The vaccine of Embodiment 24, wherein said chemical agent is binary ethylenimine.

Embodiment 28

The vaccine of Embodiment 24, wherein said chemical agent is beta-propiolactone.

Embodiment 29

The vaccine of any one of Embodiments 24 to 28, wherein said radiation is UV radiation.

Embodiment 30

The vaccine of any one of Embodiments 24 to 28, wherein said radiation is electron beam radiation.

Embodiment 31

The vaccine of any one of Embodiments 24 to 28, wherein said radiation is infrared radiation.

Embodiment 32

The vaccine of any one of Embodiments 24 to 28, wherein said radiation is gamma radiation.

Embodiment 33

The vaccine of any one of Embodiments 24 to 32, wherein said cross-linking agent is an aldehyde cross-linking agent.

Embodiment 34

The vaccine of any one of Embodiments 24 to 32, wherein said cross-linking agent is formaldehyde.

Embodiment 35

The vaccine of any one of Embodiments 24 to 32, wherein said cross-linking agent is formalin.

Embodiment 36

The vaccine of any one of Embodiments 24 to 35, wherein said oxidizing agent is sodium periodate.

Embodiment 37

The vaccine of any one of Embodiments 24 to 35, wherein said oxidizing agent is hydrogen peroxide.

Embodiment 38

The vaccine of any one of Embodiments 24 to 37, wherein said reducing agent is aldrithiol-2.

Embodiment 39

The vaccine of any one of Embodiments 24 to 38, wherein said detergent is Triton-X-100.

Embodiment 40

The vaccine of any one of Embodiments 24 to 38, wherein said detergent is NP-40.

Embodiment 41

The vaccine of any one of Embodiments 24 to 38, wherein said detergent is Tween-20.

Embodiment 42

The vaccine of any one of Embodiments 1 to 41, wherein said inactivated HSV is formed by contacting said HSV with one or more agents comprising UV radiation and a furocoumarin.

Embodiment 43

The vaccine of any one of Embodiments 1 to 42, wherein said furocoumarin is psoralen.

Embodiment 44

The vaccine of any one of Embodiments 1 to 42, wherein said furocoumarin is 4'-aminomethyl-4,5',8-trimethylpsoralen.

Embodiment 45

The vaccine of any one of Embodiments 1 to 42, wherein said furocoumarin is angelicin.

Embodiment 46

The vaccine of any one of Embodiments 1 to 42, wherein said furocoumarin is xanthotoxin.

Embodiment 47

The vaccine of any one of Embodiments 1 to 42, wherein said furocoumarin is bergapten.

Embodiment 48

The vaccine of any one of Embodiments 1 to 42, wherein said furocoumarin is nodakenetin.

Embodiment 49

The vaccine of any one of Embodiments 1 to 48, wherein said inactivated HSV is an inactivated single strain of HSV1.

Embodiment 50

The vaccine of any one of Embodiments 1 to 48, wherein said inactivated HSV is an inactivated single strain of HSV2.

Embodiment 51

The vaccine of any one of Embodiments 1 to 48, wherein said inactivated HSV is a combination of two or more inactivated strains of HSV1.

Embodiment 52

The vaccine of any one of Embodiments 1 to 48, wherein said inactivated HSV is a combination of two or more inactivated strains of HSV2.

Embodiment 53

The vaccine of any one of Embodiments 1 to 48, wherein said inactivated HSV is a combination of one or more inactivated strains or HSV1 and one or more inactivated strains of HSV2.

Embodiment 54

The vaccine of any one of Embodiments 1 to 53, formulated for intramuscular administration.

Embodiment 55

The vaccine of any one of Embodiments 1 to 53, formulated for intradermal administration.

Embodiment 56

The vaccine of any one of Embodiments 1 to 53, formulated for mucosal administration.

Embodiment 57

The vaccine of any one of Embodiments 1 to 53, formulated for intranasal administration.

Embodiment 58

The vaccine of any one of Embodiments 1 to 53, formulated for intrarectal administration.

Embodiment 59

The vaccine of any one of Embodiments 1 to 53, formulated for intravaginal administration.

Embodiment 60

The vaccine of any one of Embodiments 1 to 53, formulated for topical administration.

Embodiment 61

The vaccine of any one of Embodiments 1 to 53, formulated for transcutaneous administration.

Embodiment 62

The vaccine of any one of Embodiments 1 to 53, formulated for subcutaneous administration.

Embodiment 63

The vaccine of any one of Embodiments 2 to 62, wherein said isolated nucleic acid sequence formulation is an antigenic isolated nucleic acid sequence formulation.

Embodiment 64

The HSV vaccine of any one of Embodiments 2 to 62, wherein said isolated nucleic acid sequence formulation is a DNA vaccine.

Embodiment 65

The HSV vaccine of Embodiment 64, wherein said DNA vaccine is an antigenic isolated nucleic acid sequence formulation.

Embodiment 66

The HSV vaccine of any one of Embodiments 1 to 65, wherein said vaccine vaccinates a recipient of said vaccine against HSV infection for up to 1, 2, 3, 4, 5, 6, 7, 8, 9, 10, 11, 12, 13, 14, 15, 16, 17, 18, 19, 20, or more years.

Embodiment 67

A method of treating or preventing HSV infection in a patient in need of such treatment or prevention, said method comprising administering a therapeutically or prophylactically effective amount of the HSV vaccine of any one of Embodiments 1 to 66.

Embodiment 68

The method of Embodiment 67, wherein said HSV is HSV1.

Embodiment 69

The method of Embodiment 67, wherein said HSV is HSV2.

Embodiment 70

The method of Embodiment 67, wherein said HSV is HSV1 and HSV2.

Embodiment 71

The method of any one of Embodiments 67 to 70, wherein said HSV infection causes a disease selected from herpetic gingivostomatitis, herpes labialis, herpes genitalis, herpetic whitlow, herpes gladiatorum, herpesviral encephalitis, herpesviral meningitis, herpes esophagitis, herpes keratitis, Bell's palsy, Mollaret's meningitis, herpes rugbeiorum, eczema herpeticum, herpetic neuralgia, and post-herpetic neuralgia.

Embodiment 72

The method of any one of Embodiments 67 to 71, comprising a therapeutically effective amount.

Embodiment 73

The method of any one of Embodiments 67 to 71, comprising a prophylactically effective amount.

Embodiment 74

The method of any one of Embodiments 67 to 73, comprising treating said disease.

Embodiment 75

The method of any one of Embodiments 67 to 73, comprising preventing said disease.

Embodiment 76

The method of any one of Embodiments 67 to 75, comprising a reduction in viral shedding.

Embodiment 77

The method of any one of Embodiments 67 to 76, comprising a reduction in the frequency of lesion occurrence.

Embodiment 78

The method of any one of Embodiments 67 to 77, comprising a reduction in the duration of lesion occurrence.

Embodiment 79

The method of any one of Embodiments 67 to 78, comprising intramuscular administration.

Embodiment 80

The method of any one of Embodiments 67 to 78, comprising intradermal administration.

Embodiment 81

The method of any one of Embodiments 67 to 78, comprising mucosal administration.

Embodiment 82

The method of any one of Embodiments 67 to 78, comprising intranasal administration.

Embodiment 83

The method of any one of Embodiments 67 to 78, comprising intrarectal administration.

Embodiment 84

The method of any one of Embodiments 67 to 78, comprising intravaginal administration.

Embodiment 85

The method of any one of Embodiments 67 to 78, comprising topical administration.

Embodiment 86

The method of any one of Embodiments 67 to 78, comprising transcutaneous administration.

Embodiment 87

The method of any one of Embodiments 67 to 78, comprising subcutaneous administration.

Embodiment 88

A method of preparing a Herpes Simplex Virus (HSV) vaccine, said method comprising:

contacting an HSV-cell mixture with a sulfated or sulfonated polysaccharide, wherein said HSV-cell mixture comprises HSV particles, cells and portions of cells;

separating said HSV particles from said cells thereby forming isolated HSV particles;

inactivating said isolated HSV particles thereby forming inactivated HSV particles;

Embodiment 89

The method of Embodiment 88, wherein said HSV is HSV1.

Embodiment 90

The method of Embodiment 88, wherein said HSV is HSV2.

Embodiment 91

The method of Embodiment 88, wherein said HSV is HSV1 and HSV2.

Embodiment 92

The method of any one of Embodiments 88 to 91, wherein said sulfated or sulfonated polysaccharide is selected from dextran sulfate, heparin, and heparan sulfate.

Embodiment 93

The method of any one of Embodiments 88 to 92, wherein said HSV particles are isolated at a concentration of $10^7$ to $10^{10}$ (pfu/microgram protein).

Embodiment 94

The method of any one of Embodiments 88 to 93, wherein said HSV vaccine comprises $10^7$ to $10^{10}$ (pfu equivalents/microgram protein) of inactivated HSV.

Embodiment 95

The method of any one of Embodiments 88 to 94, wherein said separating comprises centrifugation, polyethylene glycol precipitation, filtration, gel filtration, ultra-filtration, tangential flow ultra-filtration, or affinity chromatography.

Embodiment 96

The method of any one of Embodiments 88 to 95, wherein said lipopolysaccharide-derived adjuvant is derived from the *Salmonella Minnesota* LPS.

Embodiment 97

The method of any one of Embodiments 88 to 95, wherein said lipopolysaccharide-derived adjuvant is derived from the *Salmonella Minnesota* Re595 LPS.

Embodiment 98

The method of any one of Embodiments 88 to 95, wherein said lipopolysaccharide-derived adjuvant is derived from the R595 LPS.

Embodiment 99

The method of any one of Embodiments 88 to 98, wherein said lipopolysaccharide-derived adjuvant is a lipid A adjuvant.

combining said inactivated HSV particles with a lipopolysaccharide-derived adjuvant and an aluminum-based mineral salt adjuvant thereby forming an HSV vaccine.

Embodiment 100

The method of any one of Embodiments 88 to 98, wherein said lipopolysaccharide-derived adjuvant is a lipid A adjuvant without a (R)-3-hydroxytetradecanoyl moiety.

Embodiment 101

The method of any one of Embodiments 88 to 98 and 100, wherein said lipopolysaccharide-derived adjuvant is monophosphoryl lipid A.

Embodiment 102

The method of any one of Embodiments 88 to 98 and 100, wherein said lipopolysaccharide-derived adjuvant is a lipid A adjuvant without a 1-phosphate moiety.

Embodiment 103

The method of any one of Embodiments 88 to 98, 100, and 102, wherein said lipopolysaccharide-derived adjuvant is 3-O-desacyl-4'-monophosphoryl lipid A.

Embodiment 104

The method of any one of Embodiments 88 to 98 and 100 to 103, wherein said lipopolysaccharide-derived adjuvant is a synthetic MPL analogue adjuvant.

Embodiment 105

The method of any one of Embodiments 88 to 104, wherein said lipopolysaccharide-derived adjuvant is capable of binding the TLR4 protein.

Embodiment 106

The method of any one of Embodiments 88 to 105, wherein said aluminum-based mineral salt adjuvant is an aluminum hydroxide adjuvant.

Embodiment 107

The method of any one of Embodiments 88 to 105, wherein said aluminum-based mineral salt adjuvant is an aluminum phosphate adjuvant.

Embodiment 108

The method of any one of Embodiments 88 to 105, wherein said aluminum-based mineral salt adjuvant includes crystalline aluminum hydroxide and not amorphous aluminum hydroxide or aluminum hydroxycarbonate or magnesium hydroxide.

Embodiment 109

The method of any one of Embodiments 88 to 105, wherein said aluminum-based mineral salt adjuvant includes aluminum phosphate gel in the form of a white gelatinous precipitate.

Embodiment 110

The method of any one of Embodiments 88 to 105, wherein said aluminum-based mineral salt adjuvant includes aluminum hydroxide gel in the form of a white gelatinous precipitate.

Embodiment 111

The method of any one of Embodiments 88 to 105, wherein said aluminum-based mineral salt adjuvant is a potassium aluminum sulfate adjuvant.

Embodiment 112

The method of any one of Embodiments 88 to 111, wherein said inactivating comprises contacting said HSV with one or more agents selected from a cross-linking agent, oxidizing agent, reducing agent, heat, radiation, detergent, a pH changing agent, and a chemical agent selected from a furocoumarin, aziridine, ethylenimine, binary ethylenimine, and beta-propiolactone.

Embodiment 113

The method of Embodiment 112, wherein said chemical agent is aziridine.

Embodiment 114

The method of Embodiment 112, wherein said chemical agent is ethylenimine.

Embodiment 115

The method of Embodiment 112, wherein said chemical agent is binary ethylenimine.

Embodiment 116

The method of Embodiment 112, wherein said chemical agent is beta-propiolactone.

Embodiment 117

The method of any one of Embodiments 112 to 116, wherein said radiation is UV radiation.

Embodiment 118

The method of any one of Embodiments 112 to 116, wherein said radiation is electron beam radiation.

Embodiment 119

The method of any one of Embodiments 112 to 116, wherein said radiation is infrared radiation.

Embodiment 120

The method of any one of Embodiments 112 to 116, wherein said radiation is gamma radiation.

Embodiment 121

The method of any one of Embodiments 112 to 120, wherein said cross-linking agent is an aldehyde cross-linking agent.

Embodiment 122

The method of any one of Embodiments 112 to 120, wherein said cross-linking agent is formaldehyde.

Embodiment 123

The method of any one of Embodiments 112 to 120, wherein said cross-linking agent is formalin.

Embodiment 124

The method of any one of Embodiments 112 to 123, wherein said oxidizing agent is sodium periodate.

Embodiment 125

The method of any one of Embodiments 112 to 123, wherein said oxidizing agent is hydrogen peroxide.

Embodiment 126

The method of any one of Embodiments 112 to 125, wherein said reducing agent is aldrithiol-2.

Embodiment 127

The method of any one of Embodiments 112 to 126, wherein said detergent is Triton-X-100.

Embodiment 128

The method of any one of Embodiments 112 to 126, wherein said detergent is NP-40.

Embodiment 129

The method of any one of Embodiments 112 to 126, wherein said detergent is Tween-20.

Embodiment 130

The method of any one of Embodiments 112 to 129, wherein said inactivating comprises contacting said HSV with one or more agents comprising UV radiation and a furocoumarin.

Embodiment 131

The method of any one of Embodiments 112 to 130, wherein said furocoumarin is psoralen.

Embodiment 132

The method of any one of Embodiments 112 to 130, wherein said furocoumarin is 4'-aminomethyl-4,5',8-trimethylpsoralen.

Embodiment 133

The method of any one of Embodiments 112 to 130, wherein said furocoumarin is angelicin.

Embodiment 134

The method of any one of Embodiments 112 to 130, wherein said furocoumarin is xanthotoxin.

Embodiment 135

The method of any one of Embodiments 112 to 130, wherein said furocoumarin is bergapten.

Embodiment 136

The method of any one of Embodiments 112 to 130, wherein said furocoumarin is nodakenetin.

Embodiment 137

A method of preventing or treating a Herpes Simplex Virus (HSV) infection in a subject, comprising administering to a subject in need thereof a DNA vaccine, said DNA vaccine comprising a DNA sequence encoding a portion of at least one conserved HSV gene required for virus replication.

Embodiment 138

The method of Embodiment 137, wherein said HSV is HSV1.

Embodiment 139

The method of Embodiment 137, wherein said HSV is HSV2.

Embodiment 140

The method of any one of Embodiments 137 to 139, said DNA vaccine further comprising a monophosphoryl lipid A (MPL) adjuvant.

Embodiment 141

The method of any one of Embodiments 137 to 140, said DNA vaccine further comprising an alum adjuvant.

Embodiment 142

The method of any one of Embodiments 137 to 141, said DNA vaccine comprising whole, inactivated HSV-2.

Embodiment 143

The method of any one of Embodiments 137 to 141, said DNA vaccine comprising formalin-inactivated HSV-2 (Fl-HSV-2).

Embodiment 144

The method of any one of Embodiments 137 to 141, said DNA sequence encoding at least a portion of a DNA polymerase from HSV-2.

Embodiment 145

The method of Embodiment 144, wherein said DNA polymerase is HSV-2 UL30 DNA polymerase.

Embodiment 146

The method of Embodiment 144, said DNA vaccine further comprising a DNA molecule encoding at least a portion of HSV-2 secreted glycoprotein D2 (gD2t).

Embodiment 147

The method of any one of Embodiments 137 to 146, said DNA sequence encoding at least a portion of a helicase from HSV-2.

Embodiment 148

The method of Embodiment 147, wherein said helicase is HSV-2 UL5 helicase.

Embodiment 149

The method of any one of Embodiments 137 to 148, wherein said administration is prime-boost immunization.

Embodiment 150

A DNA vaccine, comprising a DNA sequence encoding a portion of at least one conserved HSV gene required for virus replication.

Embodiment 151

The DNA vaccine of Embodiment 150, wherein said HSV is HSV1.

Embodiment 152

The DNA vaccine of Embodiment 150, wherein said HSV is HSV2.

Embodiment 153

The DNA vaccine of any one of Embodiments 150 to 152, further comprising a monophosphoryl lipid A (MPL) adjuvant.

Embodiment 154

The DNA vaccine of any one of Embodiments 150 to 153, further comprising an alum adjuvant.

Embodiment 155

The DNA vaccine of any one of Embodiments 150 to 154, comprising whole, inactivated HSV-2.

Embodiment 156

The DNA vaccine of any one of Embodiments 150 to 154, comprising formalin-inactivated HSV-2 (Fl-HSV-2).

Embodiment 157

The DNA vaccine of any one of Embodiments 150 to 154, said DNA sequence encoding at least a portion of a DNA polymerase from HSV-2.

Embodiment 158

The DNA vaccine of Embodiment 157, wherein said DNA sequence is HSV-2 UL30 DNA polymerase.

Embodiment 159

The DNA vaccine of Embodiment 157, said DNA vaccine further comprising a DNA molecule encoding at least a portion of HSV-2 secreted glycoprotein D2 (gD2t).

Embodiment 160

The DNA vaccine of any one of Embodiments 150 to 159, said DNA sequence encoding at least a portion of a helicase from HSV-2.

Embodiment 161

The DNA vaccine of Embodiment 160, wherein said helicase is HSV-2 UL5 helicase.

Embodiment 162

A method of treating or preventing a disease in a patient in need of such treatment or prevention, said method comprising administering a therapeutically or prophylactically effective amount of the HSV vaccine of any one of Embodiments 1 to 66.

Embodiment 163

The method of Embodiment 162, wherein said HSV is HSV1.

Embodiment 164

The method of Embodiment 162, wherein said HSV is HSV2.

Embodiment 165

The method of Embodiment 162, wherein said HSV is HSV1 and HSV2.

Embodiment 166

The method of any one of Embodiments 162 to 165, wherein said disease is selected from the group consisting of herpetic gingivostomatitis, herpes labialis, herpes genitalis, herpetic whitlow, herpes gladiatorum, herpesviral encephalitis, herpesviral meningitis, herpes esophagitis, herpes keratitis, Bell's palsy, Mollaret's meningitis, herpes rugbeiorum, eczema herpeticum, herpetic neuralgia, and post-herpetic neuralgia.

Embodiment 167

The method of Embodiment 166, wherein said disease is herpetic gingivostomatitis.

Embodiment 168

The method of Embodiment 166, wherein said disease is herpes labialis.

Embodiment 169

The method of Embodiment 166, wherein said disease is herpes genitalis.

Embodiment 170

The method of Embodiment 166, wherein said disease is herpetic whitlow.

Embodiment 171

The method of Embodiment 166, wherein said disease is herpes gladiatorum.

Embodiment 172

The method of Embodiment 166, wherein said disease is herpesviral encephalitis.

Embodiment 173

The method of Embodiment 166, wherein said disease is herpesviral meningitis.

Embodiment 174

The method of Embodiment 166, wherein said disease is herpes esophagitis.

Embodiment 175

The method of Embodiment 166, wherein said disease is herpes keratitis.

Embodiment 176

The method of Embodiment 166, wherein said disease is Bell's palsy.

Embodiment 177

The method of Embodiment 166, wherein said disease is Mollaret's meningitis.

Embodiment 178

The method of Embodiment 166, wherein said disease is herpes rugbeiorum.

Embodiment 179

The method of Embodiment 166, wherein said disease is eczema herpeticum.

Embodiment 180

The method of Embodiment 166, wherein said disease is herpetic neuralgia.

Embodiment 181

The method of Embodiment 166, wherein said disease is post-herpetic neuralgia.

Embodiment 182

The method of Embodiment 166, wherein said disease is Alzheimer's disease.

Embodiment 183

The method of any one of Embodiments 162 to 182, comprising a therapeutically effective amount of the HSV vaccine.

Embodiment 184

The method of any one of Embodiments 162 to 182, comprising a prophylactically effective amount of the HSV vaccine.

Embodiment 185

The method of any one of Embodiments 162 to 183, comprising treating said disease

Embodiment 186

The method of any one of Embodiments 162 to 184, comprising preventing said disease.

Embodiment 187

The method of any one of Embodiments 162 to 186, comprising a reduction in viral shedding.

Embodiment 188

The method of any one of Embodiments 162 to 187, comprising a reduction in the frequency of lesion occurrence.

Embodiment 189

The method of any one of Embodiments 162 to 188, comprising a reduction in the duration of lesion occurrence.

Embodiment 190

The method of any one of Embodiments 162 to 189, comprising intramuscular administration.

Embodiment 191

The method of any one of Embodiments 162 to 189, comprising intradermal administration.

Embodiment 192

The method of any one of Embodiments 162 to 189, comprising mucosal administration.

Embodiment 193

The method of any one of Embodiments 162 to 189, comprising intranasal administration.

Embodiment 194

The method of any one of Embodiments 162 to 189, comprising intrarectal administration.

Embodiment 195

The method of any one of Embodiments 162 to 189, comprising intravaginal administration.

Embodiment 196

The method of any one of Embodiments 162 to 189, comprising topical administration.

Embodiment 197

The method of any one of Embodiments 162 to 189, comprising transcutaneous administration.

Embodiment 198

The method of any one of Embodiments 162 to 189, comprising subcutaneous administration.

Embodiment 199

The method of any one of Embodiments 162 to 198, wherein said method does not comprise administration of a prime HSV DNA vaccine.

Embodiment 200

The method of any one of Embodiments 162 to 199, wherein said method does not comprise administration of an HSV DNA vaccine.

Embodiment 201

The method of any one of Embodiments 162 to 198, wherein said method does not comprise administration of a DNA vaccine comprising a gene selected from UL30, UL5, D2, gD2t, or portions thereof.

Embodiment 202

A Herpesvirus (HV) vaccine comprising inactivated HV, a lipopolysaccharide (LPS)-derived adjuvant and an aluminum-based mineral salt adjuvant.

Embodiment 203

The vaccine of Embodiment 202,
wherein said LPS-derived adjuvant is MPL;
said aluminum-based mineral salt adjuvant is aluminum hydroxide adjuvant or aluminum phosphate adjuvant; and
said vaccine does not comprise an isolated nucleic acid sequence formulation.

Embodiment 204

The vaccine of any one of Embodiments 202 to 203, wherein said HV is HHV-3.

Embodiment 205

The vaccine of any one of Embodiments 202 to 203, wherein said HV is HHV-4.

Embodiment 206

The vaccine of any one of Embodiments 202 to 203, wherein said HV is HHV-5.

Embodiment 207

The vaccine of any one of Embodiments 202 to 203, wherein said HV is HHV-6.

Embodiment 208

The vaccine of any one of Embodiments 202 to 203, wherein said HV is HHV-7.

Embodiment 209

The vaccine of any one of Embodiments 202 to 203, wherein said HV is HHV-8.

Embodiment 210

The vaccine of any one of Embodiments 202 to 203, wherein said HV is a Herpes Simplex Virus (HSV).

Embodiment 211

The vaccine of Embodiment 210, wherein said HSV is HSV1.

Embodiment 212

The vaccine of Embodiment 210, wherein said HSV is HSV2.

Embodiment 213

The vaccine of Embodiment 210, wherein said HSV is HSV1 and HSV2.

Embodiment 214

The vaccine of any one of Embodiments 202 to 213, wherein said lipopolysaccharide-derived adjuvant is derived from the *Salmonella minnesota* LPS.

Embodiment 215

The vaccine of any one of Embodiments 202 to 213, wherein said lipopolysaccharide-derived adjuvant is derived from the *Salmonella minnesota* Re595 LPS.

Embodiment 216

The vaccine of any one of Embodiments 202 to 213, wherein said lipopolysaccharide-derived adjuvant is derived from the R595 LPS.

Embodiment 217

The vaccine of any one of Embodiments 202 to 216, wherein said lipopolysaccharide-derived adjuvant is a lipid A adjuvant.

Embodiment 218

The vaccine of any one of Embodiments 202 to 216, wherein said lipopolysaccharide-derived adjuvant is a lipid A adjuvant without an (R)-3-hydroxytetradecanoyl moiety.

Embodiment 219

The vaccine of any one of Embodiments 202 to 216, wherein said lipopolysaccharide-derived adjuvant is monophosphoryl lipid A.

Embodiment 220

The vaccine of any one of Embodiments 202 to 216 and 218, wherein said lipopolysaccharide-derived adjuvant is a lipid A adjuvant without a 1-phosphate moiety

Embodiment 221

The vaccine of any one of Embodiments 202 to 216 and 218 to 220, wherein said lipopolysaccharide-derived adjuvant is 3-O-desacyl-4'-monophosphoryl lipid A.

Embodiment 222

The vaccine of any one of Embodiments 202 to 221, wherein said lipopolysaccharide-derived adjuvant is capable of binding the TLR4 protein.

Embodiment 223

The vaccine of any one of Embodiments 202 to 222, wherein said lipopolysaccharide-derived adjuvant is a synthetic MPL analogue adjuvant.

Embodiment 224

The vaccine of any one of Embodiments 202 to 223, wherein said aluminum-based mineral salt adjuvant is aluminum hydroxide adjuvant.

Embodiment 225

The vaccine of any one of Embodiments 202 to 223, wherein said aluminum-based mineral salt adjuvant is aluminum phosphate adjuvant.

Embodiment 226

The vaccine of any one of Embodiments 202 to 223, wherein said aluminum-based mineral salt adjuvant is adjuphos.

Embodiment 227

The vaccine of any one of Embodiments 202 to 223, wherein said aluminum-based mineral salt adjuvant is alhydrogel.

Embodiment 228

The vaccine of any one of Embodiments 202 to 223, wherein said aluminum-based mineral salt adjuvant is a potassium aluminum sulfate adjuvant.

Embodiment 229

The vaccine of any one of Embodiments 202 to 223, wherein said aluminum-based mineral salt adjuvant includes crystalline aluminum hydroxide and not amorphous aluminum hydroxide or aluminum hydroxycarbonate or magnesium hydroxide.

Embodiment 230

The vaccine of any one of Embodiments 202 to 223, wherein said aluminum-based mineral salt adjuvant includes aluminum phosphate gel in the form of a white gelatinous precipitate.

Embodiment 231

The vaccine of any one of Embodiments 202 to 223, wherein said aluminum-based mineral salt adjuvant includes aluminum hydroxide gel in the form of a white gelatinous precipitate.

Embodiment 232

The vaccine of any one of Embodiments 202 to 231, wherein said inactivated HV comprises a replication decreasing DNA mutation.

Embodiment 233

The vaccine of any one of Embodiments 202 to 231, wherein said inactivated HV is formed by chemical inactivation.

Embodiment 234

The vaccine of any one of Embodiments 202 to 231, wherein said inactivated HV is formed by contacting said HV with one or more agents selected from a cross-linking agent, oxidizing agent, reducing agent, heat, radiation, detergent, a pH changing agent, and a chemical agent selected from a furocoumarin, aziridine, ethylenimine, binary ethylenimine, and beta-propiolactone.

Embodiment 235

The vaccine of Embodiment 234, wherein said chemical agent is aziridine.

Embodiment 236

The vaccine of Embodiment 234, wherein said chemical agent is ethylenimine.

Embodiment 237

The vaccine of Embodiment 234, wherein said chemical agent is binary ethylenimine.

Embodiment 238

The vaccine of Embodiment 234, wherein said chemical agent is beta-propiolactone.

Embodiment 239

The vaccine of any one of Embodiments 234 to 238, wherein said radiation is UV radiation.

Embodiment 240

The vaccine of any one of Embodiments 234 to 238, wherein said radiation is electron beam radiation.

Embodiment 241

The vaccine of any one of Embodiments 234 to 238, wherein said radiation is infrared radiation.

Embodiment 242

The vaccine of any one of Embodiments 234 to 238, wherein said radiation is gamma radiation.

Embodiment 243

The vaccine of any one of Embodiments 234 to 242, wherein said cross-linking agent is an aldehyde cross-linking agent.

Embodiment 244

The vaccine of any one of Embodiments 234 to 242, wherein said cross-linking agent is formaldehyde.

Embodiment 245

The vaccine of any one of Embodiments 234 to 242, wherein said cross-linking agent is formalin.

Embodiment 246

The vaccine of any one of Embodiments 234 to 245, wherein said oxidizing agent is sodium periodate.

Embodiment 247

The vaccine of any one of Embodiments 234 to 245, wherein said oxidizing agent is hydrogen peroxide.

Embodiment 248

The vaccine of any one of Embodiments 234 to 245, wherein said reducing agent is aldrithiol-2.

Embodiment 249

The vaccine of any one of Embodiments 234 to 246, wherein said detergent is Triton-X-100.

Embodiment 250

The vaccine of any one of Embodiments 234 to 246, wherein said detergent is NP-40.

Embodiment 251

The vaccine of any one of Embodiments 234 to 246, wherein said detergent is Tween-20.

Embodiment 252

The vaccine of any one of Embodiments 234 to 251, wherein said inactivated HV is formed by contacting said HV with one or more agents comprising UV radiation and a furocoumarin.

Embodiment 253

The vaccine of any one of Embodiments 234 to 252, wherein said furocoumarin is psoralen.

Embodiment 254

The vaccine of any one of Embodiments 234 to 252, wherein said furocoumarin is 4'-aminomethyl-4,5',8-trimethylpsoralen.

Embodiment 255

The vaccine of any one of Embodiments 234 to 252, wherein said furocoumarin is angelicin.

Embodiment 256

The vaccine of any one of Embodiments 234 to 252, wherein said furocoumarin is xanthotoxin.

Embodiment 257

The vaccine of any one of Embodiments 234 to 252, wherein said furocoumarin is bergapten.

Embodiment 258

The vaccine of any one of Embodiments 234 to 252, wherein said furocoumarin is nodakenetin.

Embodiment 259

The vaccine of any one of Embodiments 202 to 258, wherein said inactivated HV is an inactivated single strain of the HV.

Embodiment 260

The vaccine of any one of Embodiments 202 to 258, wherein said inactivated HV is a combination of two or more inactivated strains of the HV.

Embodiment 261

The vaccine of Embodiment 259, wherein said inactivated HV is an inactivated single strain of HSV1.

Embodiment 262

The vaccine of Embodiment 259, wherein said inactivated HV is an inactivated single strain of HSV2.

Embodiment 263

The vaccine of Embodiment 260, wherein said inactivated HV is a combination of two or more inactivated strains of HSV1.

Embodiment 264

The vaccine of Embodiment 260, wherein said inactivated HV is a combination of two or more inactivated strains of HSV2.

Embodiment 265

The vaccine of any one of Embodiments 202 to 258, wherein said inactivated HV is a combination of one or more inactivated strains or HSV1 and one or more inactivated strains of HSV2.

Embodiment 266

The vaccine of any one of Embodiments 202 to 265, formulated for intramuscular administration.

Embodiment 267

The vaccine of any one of Embodiments 202 to 265, formulated for intradermal administration.

Embodiment 268

The vaccine of any one of Embodiments 202 to 265, formulated for mucosal administration.

Embodiment 269

The vaccine of any one of Embodiments 202 to 265, formulated for intranasal administration.

Embodiment 270

The vaccine of any one of Embodiments 202 to 265, formulated for intrarectal administration.

Embodiment 271

The vaccine of any one of Embodiments 202 to 265, formulated for intravaginal administration.

Embodiment 272

The vaccine of any one of Embodiments 202 to 265, formulated for topical administration.

Embodiment 273

The vaccine of any one of Embodiments 202 to 265, formulated for transcutaneous administration.

Embodiment 274

The vaccine of any one of Embodiments 202 to 265, formulated for subcutaneous administration.

Embodiment 275

The vaccine of any one of Embodiments 203 to 274, wherein said isolated nucleic acid sequence formulation is an antigenic isolated nucleic acid sequence formulation.

Embodiment 276

The HV vaccine of any one of Embodiments 203 to 275, wherein said isolated nucleic acid sequence formulation is a DNA vaccine.

Embodiment 277

The HV vaccine of Embodiment 276, wherein said DNA vaccine is an antigenic isolated nucleic acid sequence formulation.

Embodiment 278

The HV vaccine of any one of Embodiments 202 to 277, wherein said vaccine vaccinates a recipient of said vaccine against HV infection for up to 1, 2, 3, 4, 5, 6, 7, 8, 9, 10, 11, 12, 13, 14, 15, 16, 17, 18, 19, 20, or more years.

Embodiment 279

A method of preparing a Herpesvirus (HV) vaccine, said method comprising:
contacting an HV-cell mixture with a sulfated or sulfonated polysaccharide, wherein said HV-cell mixture comprises HV particles, cells and portions of cells;

separating said HV particles from said cells thereby forming isolated HV particles;
inactivating said isolated HV particles thereby forming inactivated HV particles;
combining said inactivated HV particles with a lipopolysaccharide-derived adjuvant and an aluminum-based mineral salt adjuvant thereby forming an HV vaccine.

Embodiment 280

The method of Embodiment 279, wherein said HV is HHV-1.

Embodiment 281

The method of Embodiment 279, wherein said HV is HHV-2.

Embodiment 282

The method of Embodiment 279, wherein said HV is HHV-3.

Embodiment 283

The method of Embodiment 279, wherein said HV is HHV-4.

Embodiment 284

The method of Embodiment 279, wherein said HV is HHV-5.

Embodiment 285

The method of Embodiment 279, wherein said HV is HHV-6.

Embodiment 286

The method of Embodiment 279, wherein said HV is HHV-7.

Embodiment 287

The method of Embodiment 279, wherein said HV is HHV-8.

Embodiment 288

The method of Embodiment 279, wherein said HV is an HSV.

Embodiment 289

The method of Embodiment 288, wherein said HSV is HSV1.

Embodiment 290

The method of Embodiment 288, wherein said HSV is HSV2.

Embodiment 291

The method of Embodiment 288, wherein said HSV is HSV1 and HSV2.

Embodiment 292

The method of any one of Embodiments 279 to 291, wherein said sulfated or sulfonated polysaccharide is selected from dextran sulfate, heparin, and heparan sulfate.

Embodiment 293

The method of any one of Embodiments 279 to 292, wherein said HV particles are isolated at a concentration of $10^7$ to $10^{10}$ (pfu/microgram protein).

Embodiment 294

The method of any one of Embodiments 279 to 293, wherein said HV vaccine comprises $10^7$ to $10^{10}$ (pfu equivalents/microgram protein) of inactivated HV.

Embodiment 295

The method of any one of Embodiments 279 to 294, wherein said separating comprises centrifugation, polyethylene glycol precipitation, filtration, gel filtration, ultra-filtration, tangential flow ultra-filtration, or affinity chromatography.

Embodiment 296

The method of any one of Embodiments 279 to 295, wherein said lipopolysaccharide-derived adjuvant is derived from the *Salmonella minnesota* LPS.

Embodiment 297

The method of any one of Embodiments 279 to 295, wherein said lipopolysaccharide-derived adjuvant is derived from the *Salmonella minnesota* Re595 LPS.

Embodiment 298

The method of any one of Embodiments 279 to 295, wherein said lipopolysaccharide-derived adjuvant is derived from the R595 LPS.

Embodiment 299

The method of any one of Embodiments 279 to 298, wherein said lipopolysaccharide-derived adjuvant is a lipid A adjuvant.

Embodiment 300

The method of any one of Embodiments 279 to 298, wherein said lipopolysaccharide-derived adjuvant is a lipid A adjuvant without a (R)-3-hydroxytetradecanoyl moiety.

Embodiment 301

The method of any one of Embodiments 279 to 298 and 300, wherein said lipopolysaccharide-derived adjuvant is monophosphoryl lipid A.

Embodiment 302

The method of any one of Embodiments 279 to 298 and 300, wherein said lipopolysaccharide-derived adjuvant is a lipid A adjuvant without a 1-phosphate moiety.

Embodiment 303

The method of any one of Embodiments 279 to 298 and 300 to 302, wherein said lipopolysaccharide-derived adjuvant is 3-O-desacyl-4'-monophosphoryl lipid A.

Embodiment 304

The method of any one of Embodiments 279 to 298 and 300 to 303, wherein said lipopolysaccharide-derived adjuvant is a synthetic MPL analogue adjuvant.

Embodiment 305

The method of any one of Embodiments 279 to 304, wherein said lipopolysaccharide-derived adjuvant is capable of binding the TLR4 protein.

Embodiment 306

The method of any one of Embodiments 279 to 305, wherein said aluminum-based mineral salt adjuvant is an aluminum hydroxide adjuvant.

Embodiment 307

The method of any one of Embodiments 279 to 305, wherein said aluminum-based mineral salt adjuvant is an aluminum phosphate adjuvant.

Embodiment 308

The method of any one of Embodiments 279 to 305, wherein said aluminum-based mineral salt adjuvant includes crystalline aluminum hydroxide and not amorphous aluminum hydroxide or aluminum hydroxycarbonate or magnesium hydroxide.

Embodiment 309

The method of any one of Embodiments 279 to 305, wherein said aluminum-based mineral salt adjuvant includes aluminum phosphate gel in the form of a white gelatinous precipitate.

Embodiment 310

The method of any one of Embodiments 279 to 305, wherein said aluminum-based mineral salt adjuvant includes aluminum hydroxide gel in the form of a white gelatinous precipitate.

Embodiment 311

The method of any one of Embodiments 279 to 305, wherein said aluminum-based mineral salt adjuvant is a potassium aluminum sulfate adjuvant.

Embodiment 312

The method of any one of Embodiments 279 to 311, wherein said inactivating comprises contacting said HV with one or more agents selected from a cross-linking agent, oxidizing agent, reducing agent, heat, radiation, detergent, a pH changing agent, and a chemical agent selected from a furocoumarin, aziridine, ethylenimine, binary ethylenimine, and beta-propiolactone.

Embodiment 313

The method of Embodiment 312, wherein said chemical agent is aziridine.

Embodiment 314

The method of Embodiment 312, wherein said chemical agent is ethylenimine.

Embodiment 315

The method of Embodiment 312, wherein said chemical agent is binary ethylenimine.

Embodiment 316

The method of Embodiment 312, wherein said chemical agent is beta-propiolactone.

Embodiment 317

The method of any one of Embodiments 312 to 316, wherein said radiation is UV radiation.

Embodiment 318

The method of any one of Embodiments 312 to 316, wherein said radiation is electron beam radiation.

Embodiment 319

The method of any one of Embodiments 312 to 316, wherein said radiation is infrared radiation.

Embodiment 320

The method of any one of Embodiments 312 to 316, wherein said radiation is gamma radiation.

Embodiment 321

The method of any one of Embodiments 312 to 320, wherein said cross-linking agent is an aldehyde cross-linking agent.

Embodiment 322

The method of any one of Embodiments 312 to 320, wherein said cross-linking agent is formaldehyde.

Embodiment 323

The method of any one of Embodiments 312 to 320, wherein said cross-linking agent is formalin.

Embodiment 324

The method of any one of Embodiments 312 to 323, wherein said oxidizing agent is sodium periodate.

Embodiment 325

The method of any one of Embodiments 312 to 323, wherein said oxidizing agent is hydrogen peroxide.

Embodiment 326

The method of any one of Embodiments 312 to 325, wherein said reducing agent is aldrithiol-2.

Embodiment 327

The method of any one of Embodiments 312 to 326, wherein said detergent is Triton-X-100.

Embodiment 328

The method of any one of Embodiments 312 to 326, wherein said detergent is NP-40.

Embodiment 329

The method of any one of Embodiments 312 to 326, wherein said detergent is Tween-20.

Embodiment 330

The method of any one of Embodiments 312 to 329, wherein said inactivating comprises contacting said HV with one or more agents comprising UV radiation and a furocoumarin.

Embodiment 331

The method of any one of Embodiments 312 to 330, wherein said furocoumarin is psoralen.

Embodiment 332

The method of any one of Embodiments 312 to 330, wherein said furocoumarin is 4'-aminomethyl-4,5',8-trimethylpsoralen.

Embodiment 333

The method of any one of Embodiments 312 to 330, wherein said furocoumarin is angelicin.

Embodiment 334

The method of any one of Embodiments 312 to 330, wherein said furocoumarin is xanthotoxin.

Embodiment 335

The method of any one of Embodiments 312 to 330, wherein said furocoumarin is bergapten.

Embodiment 336

The method of any one of Embodiments 312 to 330, wherein said furocoumarin is nodakenetin.

Embodiment 337

A method of treating or preventing HV infection in a patient in need of such treatment or prevention, said method comprising administering a therapeutically or prophylactically effective amount of the HV vaccine of any one of Embodiments 202 to 278.

Embodiment 338

The method of Embodiment 337, wherein said HV is HHV-1.

Embodiment 339

The method of Embodiment 337, wherein said HV is HHV-2.

Embodiment 340

The method of Embodiment 337, wherein said HV is HHV-3.

Embodiment 341

The method of Embodiment 337, wherein said HV is HHV-4.

Embodiment 342

The method of Embodiment 337, wherein said HV is HHV-5.

Embodiment 343

The method of Embodiment 337, wherein said HV is HHV-6.

Embodiment 344

The method of Embodiment 337, wherein said HV is HHV-7.

Embodiment 345

The method of Embodiment 337, wherein said HV is HHV-8.

Embodiment 346

The method of Embodiment 337, wherein said HV is an HSV.

Embodiment 347

The method of Embodiment 346, wherein said HSV is HSV1.

Embodiment 348

The method of Embodiment 346, wherein said HSV is HSV2.

Embodiment 349

The method of Embodiment 346, wherein said HSV is HSV1 and HSV2.

Embodiment 350

The method of any one of Embodiments 337 to 349, wherein said HV infection causes a disease selected from herpetic gingivostomatitis, herpes labialis, herpes genitalis, herpetic whitlow, herpes gladiatorum, herpesviral encephalitis, herpesviral meningitis, herpes esophagitis, herpes keratitis, Bell's palsy, Mollaret's meningitis, herpes rugbeiorum, eczema herpeticum, herpetic neuralgia, and post-herpetic neuralgia.

Embodiment 351

A method of treating or preventing a disease in a patient in need of such treatment or prevention, said method comprising administering a therapeutically or prophylactically effective amount of the HV vaccine of any one of Embodiments 202 to 278.

Embodiment 352

The method of Embodiment 351, wherein said disease is an HV associated disease.

Embodiment 353

The method any one of Embodiments 351 to 352, wherein said HV is an HSV.

Embodiment 354

The method of Embodiment 353, wherein said HSV is HSV1.

Embodiment 355

The method of Embodiment 353, wherein said HSV is HSV2.

Embodiment 356

The method of Embodiment 353, wherein said HSV is HSV1 and HSV2.

Embodiment 357

The method of any one of Embodiments 351 to 356, wherein said disease is selected from the group consisting of herpetic gingivostomatitis, herpes labialis, herpes genitalis, herpetic whitlow, herpes gladiatorum, herpesviral encephalitis, herpesviral meningitis, herpes esophagitis, herpes keratitis, Bell's palsy, Mollaret's meningitis, herpes rugbeiorum, eczema herpeticum, herpetic neuralgia, and post-herpetic neuralgia.

Embodiment 358

The method of any one of Embodiments 350 or 357, wherein said disease is herpetic gingivostomatitis.

Embodiment 359

The method of any one of Embodiments 350 or 357, wherein said disease is herpes labialis.

Embodiment 360

The method of any one of Embodiments 350 or 357, wherein said disease is herpes genitalis.

Embodiment 361

The method of any one of Embodiments 350 or 357, wherein said disease is herpetic whitlow.

Embodiment 362

The method of any one of Embodiments 350 or 357, wherein said disease is herpes gladiatorum.

Embodiment 363

The method of any one of Embodiments 350 or 357, wherein said disease is herpesviral encephalitis.

Embodiment 364

The method of any one of Embodiments 350 or 357, wherein said disease is herpesviral meningitis.

Embodiment 365

The method of any one of Embodiments 350 or 357, wherein said disease is herpes esophagitis.

Embodiment 366

The method of any one of Embodiments 350 or 357, wherein said disease is herpes keratitis.

Embodiment 367

The method of any one of Embodiments 350 or 357, wherein said disease is Bell's palsy.

Embodiment 368

The method of any one of Embodiments 350 or 357, wherein said disease is Mollaret's meningitis.

Embodiment 369

The method of any one of Embodiments 350 or 357, wherein said disease is herpes rugbeiorum.

Embodiment 370

The method of any one of Embodiments 350 or 357, wherein said disease is eczema herpeticum.

Embodiment 371

The method of any one of Embodiments 350 or 357, wherein said disease is herpetic neuralgia.

Embodiment 372

The method of any one of Embodiments 350 or 357, wherein said disease is post-herpetic neuralgia.

Embodiment 373

The method of any one of Embodiments 350 or 357, wherein said disease is Alzheimer's disease.

Embodiment 374

The method of any one of Embodiments 337 to 373, wherein said method is a method of treating.

Embodiment 375

The method of any one of Embodiments 337 to 373, wherein said method is a method of preventing.

Embodiment 376

The method of any one of Embodiments 337 to 375, wherein said method includes a therapeutically effective amount of the HV vaccine.

Embodiment 377

The method of any one of Embodiments 337 to 375, wherein said method includes a prophylactically effective amount of the HV vaccine.

Embodiment 378

The method of any one of Embodiments 337 to 377, comprising a reduction in viral shedding.

Embodiment 379

The method of any one of Embodiments 337 to 378, comprising a reduction in the frequency of lesion occurrence.

Embodiment 380

The method of any one of Embodiments 337 to 379, comprising a reduction in the duration of lesion occurrence.

Embodiment 381

The method of any one of Embodiments 337 to 380, comprising intramuscular administration.

Embodiment 382

The method of any one of Embodiments 337 to 380, comprising intradermal administration.

Embodiment 383

The method of any one of Embodiments 337 to 380, comprising mucosal administration.

Embodiment 384

The method of any one of Embodiments 337 to 380, comprising intranasal administration.

Embodiment 385

The method of any one of Embodiments 337 to 380, comprising intrarectal administration.

Embodiment 386

The method of any one of Embodiments 337 to 380, comprising intravaginal administration.

Embodiment 387

The method of any one of Embodiments 337 to 380, comprising topical administration.

Embodiment 388

The method of any one of Embodiments 337 to 380, comprising transcutaneous administration.

Embodiment 389

The method of any one of Embodiments 337 to 380, comprising subcutaneous administration.

Embodiment 390

The method of any one of Embodiments 337 to 389, wherein an isolated nucleic acid sequence formulation is not administered to said patient.

Embodiment 391

The method of Embodiment 390, wherein said isolated nucleic acid sequence formulation is a DNA sequence.

Embodiment 392

The method of Embodiment 390, wherein said isolated nucleic acid sequence formulation is a nucleic acid vaccine.

Embodiment 393

The method of Embodiment 390, wherein said isolated nucleic acid sequence formulation is a DNA vaccine.

Embodiment 394

The method of any one of Embodiments 337 to 389, wherein said method does not comprise administration of a prime HV DNA vaccine.

Embodiment 395

The method of any one of Embodiments 337 to 389, wherein said method does not comprise administration of an HV DNA vaccine.

Embodiment 396

The method of any one of Embodiments 337 to 389, wherein said method does not comprise administration of a DNA vaccine comprising a gene selected from an HSV UL30, UL5, gD2, gD2t, or portions thereof.

Embodiment 397

The method of any one of Embodiments 337 to 396, consisting of a single administration of said HV vaccine.

Embodiment 398

The method of any one of Embodiments 337 to 396, consisting of a prime-boost administration of said HV vaccine.

Embodiment 399

The method of any one of Embodiments 337 to 396, consisting of a prime-boost-boost administration of said HV vaccine.

Embodiment 400

A kit comprising the HV vaccine of any one of Embodiments 202 to 278 and instructions for administering said HV vaccine to a patient.

Embodiment 401

The kit of Embodiment 400, wherein said HV vaccine is administered in a prime-boost administration.

Embodiment 402

The HV vaccine of any one of Embodiments 1 to 66, 150 to 161, and 202 to 278, wherein said HV vaccine protects a subject administered said HV vaccine from multiple strains of said HV.

Embodiment 403

The HV vaccine of any one of Embodiments 1 to 66, 150 to 161, and 202 to 278, wherein said HV vaccine vaccinates a subject administered said HV vaccine from multiple strains of said HV.

Embodiment 404

The HV vaccine of any one of Embodiments 1 to 66, 150 to 161, and 202 to 278, wherein said HV vaccine treats a subject administered said HV vaccine for multiple strains of said HV.

Embodiment 405

The method of any one of Embodiments 67 to 87, 137 to 149, 162 to 201, and 337 to 399, wherein said patient is vaccinated against one or more strains of said HV following said administration.

Embodiment 406

The method of any one of Embodiments 67 to 87, 137 to 149, 162 to 201, and 337 to 399, wherein said patient is protected against one or more strains of said HV following said administration.

Embodiment 407

The method of any one of Embodiments 67 to 87, 137 to 149, 162 to 201, and 337 to 399, wherein said patient is treated for one or more strains of said HV following said administration.

Embodiment 408

The kit of any one of Embodiments 400 to 401, wherein said HV vaccine vaccinates a subject administered said HV vaccine from multiple strains of said HV.

Embodiment 409

The kit of any one of Embodiments 400 to 401, wherein said HV vaccine protects a subject administered said HV vaccine from multiple strains of said HV.

Embodiment 410

The kit of any one of Embodiments 400 to 401, wherein said HV vaccine treats a subject administered said HV vaccine for multiple strains of said HV.

VI. Examples

There are provided, inter alia, methods of use of DNA vaccines encoding conserved HSV-2 genes that are necessary for virus replication as well as a vaccine consisting of whole, inactivated HSV-2 together with monophosphoryl lipid A (MPL) and aluminum-based mineral salt adjuvants. Immunization with the DNA polymerase (UL30) or helicase (UL5) genes of HSV-2 was found to elicit CD8+ T cell responses and coimmunization of UL30 with a DNA encoding secreted glycoprotein D2 (gD2t) resulted in slightly increased protection against disease after lethal, intravaginal (i.vag.) challenge when compared to immunization with gD2t DNA alone. Protection against disease, death, and virus shedding was greater in mice immunized with whole, formalin-inactivated HSV-2 (FI-HSV2) when compared to a gD2t protein subunit vaccine. Prime-boost immunization with UL5, UL30, gD2t DNAs and FI-HSV2 resulted in nearly complete protection against vaginal disease. Single formulation immunization with DNA vaccines, FI-HSV2, and MPL in an aluminum phosphate (Adju-Phos) adjuvant did not give an enhancement in protection relative to FI-HSV2/MPL/Adju-Phos alone. Most strikingly, intramuscular immunization with FI-HSV2 together with MPL and Alhydrogel adjuvants resulted in undetectable levels of HSV-2 shedding (<10 PFU) in the majority of mice after both a challenge and a subsequent long-term (17 weeks) re-challenge.

Without wishing to be bound by any theory, it is believed that genes that are expressed early in the viral life cycle, essential for viral replication, and evolutionarily conserved may be useful vaccine targets for a cellular immune response. Using another herpesvirus challenge model, murine cytomegalovirus (MCMV), we demonstrated that the CD8+ T cell responses generated against DNA vaccines encoding the conserved, essential genes DNA polymerase and helicase were protective (Morello, C. S. et al., J. Virol., 81:7766-7775 (2007)). When DNA immunization was combined with an inactivated virus plus adjuvant boost, mice were completely protected against virus replication in the target organs following systemic challenge (Morello, C. S. et al., J. Virol., 79:159-175 (2005); Morello, C. S., M. Ye, and D. H. Spector., J. Virol., 76:4822-4835 (2002)). Importantly, mice were almost completely protected against a mucosal challenge after the systemic prime-boost immunization (Morello, C. S. et al., J. Virol., 79:159-175 (2005)).

Based on the above studies, we tested whether homologous HSV-2 vaccine targets as well as a similar prime-boost strategy could be efficacious against an i.vag. HSV-2 challenge in mice. DNA vaccines encoding genes required for viral DNA replication, UL30 (HSV-2 DNA polymerase) and UL5 (helicase), were tested either alone or together with the truncated glycoprotein D2 (gD2t) plasmid. The DNA primed animals were subsequently boosted with either gD2t protein with MPL/Alum or formalin inactivated HSV-2 (FI-HSV2)

together with MPL/Alum. For comparison, an additional group received a vaccine similar to that of the one administered in the GSK trials, a purified gD2t protein formulated with MPL/alum alone. We also tested single formulation vaccines consisting of adjuvant plus FI-HSV2 in the presence or absence of DNA. Following i.vag. HSV-2 challenge, the protective efficacies of the vaccines were compared with respect to outcomes of acute disease and virus shedding, and protection against a subsequent challenge.

Our results revealed the following: 1) When DNA encoding HSV-2 genes was solely used as the vaccine, the inclusion of the gD2t plasmid in the mix was critical for providing protection against lethality and disease as well as reduction in viral shedding resulting from HSV-2 challenge. 2) Mice immunized with gD2t protein with MPL/alum had more deaths, higher disease scores, and increased levels of viral shedding compared to mice that received FI-HSV-2 plus MPL/alum. 3) When mice were first immunized with a DNA vaccine containing gD2t, UL5 and UL30 DNA, a boost of FI-HSV-2 in MPL/Alum provided greater protection against disease and viral shedding following an i.vag. HSV-2 challenge than did a boost of gD2t protein in MPL/alum. 4) An optimized vaccine containing only FI-HSV-2 in MPL/Alum provided nearly complete protection against HSV-2 viral shedding after a lethal mucosal (i.vag.) short term challenge and long-term re-challenge. And 5) addition of either empty vector DNA or DNA encoding HSV-2 genes to FI-HSV-2 in MPL/Alum reduced the efficacy of a single formulation vaccine.

Initial work focused on developing a vaccine against cytomegalovirus using the mouse model. We began to explore the possibility that increased protection against mouse cytomegalovirus (MCMV) replication could be achieved by expanding the CD8+-T-cell-mediated immune responses and protective antibody responses against multiple epitopes with a vaccine that included killed whole virus (formalin-inactivated) in a strong adjuvant, such as Alum. Our results showed that prior vaccination with formalin-inactivated murine cytomegalovirus (FI-MCMV) in alum provided greater reduction in titers of virus in the spleen and particularly in the salivary glands than did a comparative vaccination with various DNAs encoding MCMV genes when the mice were challenged with a high dose of virulent virus (Morello et al., 2002; Morello et al. 2005)

Herpes Simplex Virus Type 2 (HSV-2) infection can result in life-long recurrent genital disease, asymptomatic virus shedding, and transmission. No vaccine to date has shown significant protection clinically. Here, we used a mouse model of genital HSV-2 infection to test the efficacy of a vaccine consisting of whole, formalin-inactivated HSV-2 (FI-HSV2) formulated with monophosphoryl lipid A (MPL) and alum adjuvants. Vaccine components were administered alone or as a prime-boost immunization together with DNA vaccines encoding a truncated glycoprotein D2 (gD2t) and two conserved HSV-2 genes necessary for virus replication, UL5 (DNA helicase) and UL30 (DNA polymerase). Our results show: 1) Compared with mock immunized controls, mice immunized with FI-HSV2 plus MPL/Alum consistently showed protection against disease burden and total viral shedding while the mice immunized with gD2t protein with MPL/alum did not; 2) Protection against genital disease and viral replication correlated with the type of boost in a prime-boost immunization with little advantage afforded by a DNA prime; 3) Intramuscular (i.m.) immunization with FI-HSV2 in MPL/Alhydrogel adjuvant provided nearly complete protection against vaginal HSV-2 shedding after a lethal intravaginal (i.vag.) short-term challenge and long-term rechallenge; 4) Single formulation immunization with DNA vaccines, FI-HSV2, and MPL in an aluminum phosphate (Adju-Phos) adjuvant did not increase protection relative to FI-HSV2/MPL/Adju-Phos alone; and 5) addition of MPL/Alum to the FI-HSV2 was required for optimal protection against disease, viral replication, and latent virus load in the dorsal root ganglia (DRG). Most notably, an optimized vaccine formulation of FI-HSV2MPL/Alhydrogel given i.m. completely protected against detectable vaginal HSV-2 shedding in the majority of animals and HSV-2 latent DNA in the DRG of all animals.

A. Materials and Methods

Cells and Viruses.

Vero cells (ATCC CLL-81) were purchased from ATCC and propagated in Dulbecco's Modified Eagle Medium (DMEM) supplemented with 5% heat-inactivated fetal bovine serum (HI-FBS), 5% heat-inactivated newborn calf serum (HI-NCS), 100 U penicillin and 100 µg streptomycin per ml, and 2 mM additional L-glutamine. 293FT cells (Invitrogen) were propagated in DMEM (4.5 g glucose per liter) supplemented with 10% HI-FBS, 1×MEM nonessential amino acids, and penicillin, streptomycin, and additional glutamine as above. Sera and supplements were from Invitrogen Life Technologies.

HSV-2 strain G (Ejercito, P. M. et al., *J. Gen. Virol.*, 2:357-364 (1968)) was a gift from David M. Knipe and was propagated by infection of confluent Vero monolayers at an MOI of 0.1, incubation at 33° C. for 72 h, and then harvest of the cell-associated virus as previously described (Dudek, T. et al., *Virology*, 372:165-175 (2008)). This HSV-2 stock had a titer on Vero cells of $2.08 \times 10^8$ PFU per ml and an approximate $LD_{50}$ of $5 \times 10^3$ PFU in medroxyprogesterone acetate-treated (see below) BALB/c mice following i.vag. infection.

FI-HSV2 that was prepared from cell associated and extracellular virus was obtained following the infection of confluent Vero cell monolayers at an MOI of 0.05 to 0.1 and incubation at 33° C. for 3 days. Cells were shaken off flasks, pelleted, resuspended in $1/17^{th}$ of the volume of infected culture media, and sonicated in a Misonix cuphorn sonicator. The sonicate was clarified by centrifugation at 500×g for 5 min. The resulting pellet was resuspended in Tris-buffered saline (TBS) and homogenized in a Tenbroeck homogenizer. The homogenate was clarified by centrifugation as above and the resulting supernatant combined with the first supernatant. The combined supernatants were clarified again at 4000×g for 15 min and the virus in the supernatant was concentrated by ultracentrifugation through a cushion of 25% (w/v) sorbitol in Tris-buffered saline (TBS) in an SW-27 rotor at 25,000 RPM for 1 h. Pellets were resuspended overnight in TBS, the virus was repelleted by ultracentrifugation as above, and the pellets were resuspended in TBS. The resulting preparation was analyzed for infectious virus by plaque assay on Vero cells and for protein content by Bradford protein assay (Bio-Rad) with BSA (Pierce) standard. For inactivation, a 37% (w/v) formaldehyde stock solution was diluted 2000-fold in Dulbecco's phosphate buffered saline (DPBS, Invitrogen) and an equal volume was added to the virus (final formaldehyde dilution of 1:4000 or 0.009%). After 72 h incubation at 37° C. with end-over-end mixing, equimolar sodium bisulfite was added to quench residual formaldehyde and 0.1 ml of the formalin-treated virus was used to infect Vero cells to confirm the absence of detectable infectivity. Inactivated virus was stored at −80° C. in aliquots. The preparation had a titer of $7 \times 10^7$ PFU equivalents per ml and a pre-inactivation protein content of $4 \times 10^4$ PFU per µg of protein. FI-Mock was prepared in parallel from mock infected Vero cells and media as described above.

FI-HSV2 was prepared from the virus-containing media of Vero cells that were infected and incubated as for the FI-HSV2 above except that media was harvested on day 5 postinfection. Media was twice clarified by centrifugation, first at 500×g for 5 min and subsequently at 4000×g for 15 min. The virus in the resultant supernatant was concentrated by ultracentrifugation as above except through a cushion of 25% (w/v) sucrose in DPBS. Virus pellets were resuspended in DPBS on ice overnight and the combined virus was titered, analyzed for protein content, inactivated, quenched, confirmed for lack of infectivity, and stored in aliquots as above. The extracellular FI-HSV2 had a final titer of $3 \times 10^8$ PFU equivalents per ml, and prior to inactivation, a protein content of $10^5$ PFU per µg of protein. FI-Mock was prepared in parallel from the media of mock infected Vero cells as described above.

FI-HSV2 was also prepared by releasing virus from infected Vero cells by washing them with dextran sulfate, clarifying the wash by low-speed centrifugation, and pelleting the virus through a cushion by ultracentrifugation as previously described (Morello, C. S. et al., 2011, Id.).

Plasmid Construction and Expression.

Genomic DNA was prepared from HSV-2 strain G-infected Vero cells using the DNeasy Blood and Tissue Kit (Qiagen) and used as a template in PCR reactions using KOD Hot-Start DNA Polymerase (Novagen/CN Biosciences). The following ORFs were amplified: DNA polymerase (UL30), helicase-primase (UL5), truncated gD2 (gD2t) corresponding to the extracellular portion of the US6 gene (aa 1-327), and ICP27 (UL54) (see Table 1 for complete list). HSV-2-specific primers were designed based on the strain HG52 genome sequence (Genbank accession no. Z86099.2) and sense primers were designed to introduce a Kozak consensus sequence (GCC ACC) proximal to the initiating AUG (see Table 2 for the sequences of all primers used in the study).

TABLE 1

HSV-2 genes used for DNA immunization or intracellular cytokine staining

| HSV-2 ORF[a] | Gene Product | HCMV Homolog | FastA Identity (%) | Overlap (aa[b]) |
|---|---|---|---|---|
| UL5 | Helicase-primase subunit | UL105 | 39 | 753 |
| UL30 | DNA polymerase catalytic subunit | UL54 | 38 | 955 |
| US6 | glycoprotein D2t (aa 1-327) | — | — | — |
| UL54 | ICP27, gene regulator | UL69 | 37 | 52 |

[a]ORF, open reading frame,
[b]aa, amino acids,
[c]ssDNA, single-stranded DNA

TABLE 2

Primers used for construction of vaccine plasmids Sequence (5'-3')

| HSV-2 ORF Cloned or pVAX Mutagenesis | Forward Primer | Reverse Primer |
|---|---|---|
| UL5 | GCCACCATGGCGGC GTCCGGCGGGGAG (SEQ ID NO: 1) | ATAGACAATGACCACAT TCGGATCGCGTAGAGC (SEQ ID NO: 2) |
| UL30 | GCCACCATGTTTTG TGCCGCGGGCGGC (SEQ ID NO: 3) | TGCTAGAGTATCAAAGG CTCTATGCAACATTCGA CG (SEQ ID NO: 4) |
| US6 (gD2t) | GCCACCATGGGGCG TTTGACCTCC (SEQ ID NO: 5) | GACGTCCTGGATCGACG G (SEQ ID NO: 6) |
| UL54 (ICP27) | GCCACCATGGCTAC CGACATTGATATG (SEQ ID NO: 7) | AAATAGGGAGTTGCAGT AGAAGTATTTGCCGTG (SEQ ID NO: 8) |
| HincII site deletion in pVAX1 | GCCAGATATACGCCA TGACATTGATTATTG (SEQ ID NO: 9) | CAATAATCAATGTCATG GCGTATATCTGGC (SEQ ID NO: 10) |
| HincII site + FLAG tag addition in pVAX1.1 | GGTACCGAGCTCGGA TCCACGTCGACTACA AGGATGACGATGACA AGTGATAATAGTCCA GTGTGGTGGAATTC (SEQ ID NO: 11) | GAATTCCACCACACTGG ACTATTATCACTTGTCA TCGTCATCCTTGTAGTC GACGTGGATCCGAGCTC GGTACC (SEQ ID NO: 12) |

The pVAX1 plasmid vector that was designed for DNA vaccine development in accordance with FDA guidelines was purchased from Invitrogen. Expression of the ORFs in this is driven by the strong, constitutive HCMV major IE promoter/enhancer. This vector was modified by the QuikChange mutagenesis technique (Stratagene) in 2 steps. First, a point mutation was created to remove the single HincII restriction site in the vector (to yield intermediate vector pVAX1.1). Second, the multicloning site was modified to contain a unique HincII site followed by a FLAG tag coding sequence and 3 in-frame stop codons (see Table 2 for mutagenesis primer sequences used). The final vector, designated pVAX1.2 and abbreviated below as pVAX, was the basis for the cloning and expression of carboxyterminally FLAG-tagged HSV-2 ORFs.

PCR products were ligated to HincII-digested pVAX1.2 vector, and resulting clones were screened by restriction digestion and sequencing of the HSV-2 ORFs (Eton Biosciences, San Diego, Calif.). For purification of gD2 protein subunit vaccine, the gD2t-FLAG ORF was subcloned into the pcDNA3-based vector pc3Δneo (Ye, M., C. S. Morello, and D. H. Spector., J. Virol., 76:2100-2112 (2002)). The UL5, UL30, and ICP27 ORFs were also subcloned into pc3Δneo for use in the cell-based CD8+ T cell assay below.

Compared to the HSV-2 HG52 reference sequence, the cloned UL5 (helicase-primase) from strain G contained 3 silent mutations, and the cloned gD2t contained a single silent mutation. The cloned UL30 sequence contained 3 base differences from the reference strain with the resultant putative amino acid changes, G25-A (Ala-Thr), C43-A (Pro-Ser), and T179-C (Leu-Pro). To distinguish between HSV-2 strain polymorphisms and PCR cloning artifacts, 1.4 kb of the 5' end of the UL30 ORF was amplified from the HSV-2 strain G infected Vero cell DNA and the PCR product was directly sequenced. All 3 differences in the UL30 clone were found in the strain G PCR product, indicating that these are present in HSV-2 strain G. The ICP27 clone contained one strain difference, A492-C (Lys-Asn).

Plasmids were purified by Qiagen Endo-Free Mega or Giga anion exchange columns. DNAs were resuspended to ~2.5-3 mg per ml of endotoxin-free Tris-HCl (pH 8), and stored at −20° C. in aliquots. Immediately prior to injections, DNAs are thawed and diluted in endotoxin-free Tris buffered saline, pH 8.

Expression of full-length ORF-FLAG fusion proteins was confirmed by transient transfection into 293FT cells (Invitrogen) using Lipofectamine-2000 (Invitrogen) followed by Western blot. Blots were probed with anti-FLAG mouse monoclonal antibody (M2, Sigma) that was directed against the carboxy-terminal FLAG tag fused onto each HSV-2 ORF. Blots containing lysates from pVAX1.2-gD2t-transfected cells or media were probed with anti-FLAG or anti-gD mouse monoclonal antibody DL6 (Santa Cruz Biotechnology, Inc.). DL6 binds an HSV-1/2 common, conserved linear epitope of gD (aa 272-279.) FIG. 1A shows that the resultant specific protein band for each HSV-2 ORF migrated to the expected position, with expected molecular masses as follows: UL5, 99 kDa; UL30, 137 kDa; gD2t, 45 kDa; and ICP27, 55.9 kDa.

Preparation of gD2 Protein.

Figure 1B:
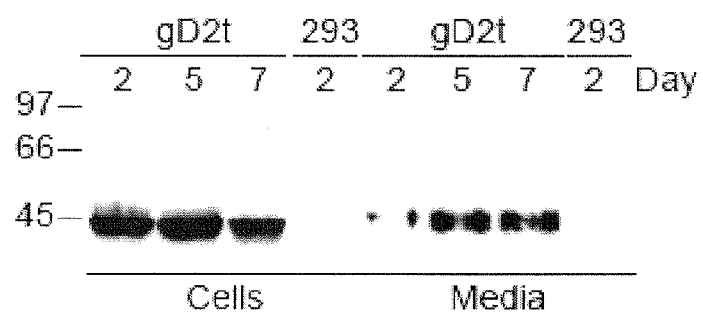

293FT cells in 10 cm tissue culture dishes were transiently transfected as above. The next day, cells were fed with media containing 0.4% (v/v) of mammalian protease inhibitor cocktail (Sigma P1860), and on d 3 posttransfection, the media was collected, a protease inhibitor cocktail (Sigma P8340) was added to a 1% final concentration, and the media was clarified by centrifugation. A time course of expression of the pVAX-gD2t vector was performed in order to characterize the secretory efficiency of the gD2t ORF, and both whole cell lysates and anti-FLAG immunoaffinity purified media were subjected to Western blot analysis (FIG. 1B). Using the gD-specific monoclonal antibody DL6, we found that the gD2t protein was detectable in the media as early as day 2 posttransfection, with peak levels in the media occurring after day 2.

Figure 1C:
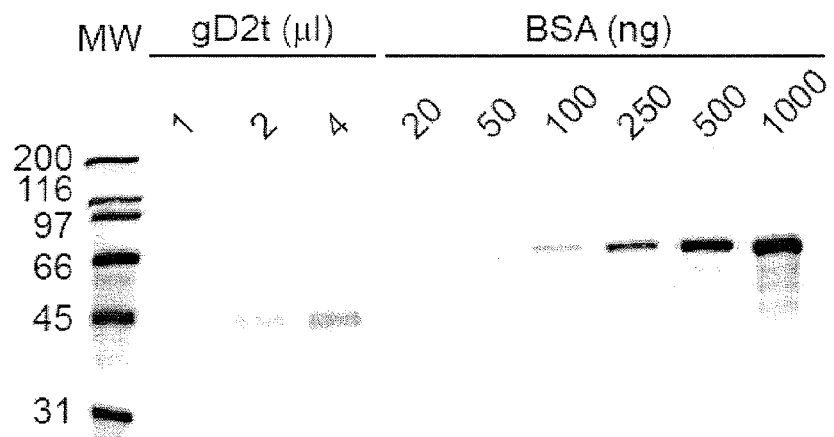

For preparation of a gD2t protein subunit vaccine, we subsequently performed large-scale transfections of 293FT cells with the SV40 ori-containing vector pc3Δneo-gD2t and then subjected the gD2t-containing media to anti-FLAG immunoaffinity chromatography. After clarification of the media containing secreted, truncated gD2, binding buffer was added such that the following concentrations were obtained prior to loading onto a column of anti-FLAG M2 slurry: 50 mM Tris-HCl (pH 7.4), 150 mM NaCl, and 0.1% (v/v) Triton X-100. The column was then washed with 50 mM Tris-buffered saline+0.1% Triton X-100 and then 50 mM Tris-buffered saline prior to elution with 100 μg 3×FLAG peptide (Sigma) per ml of 50 mM Tris-buffered saline following manufacturer's guidelines. The fractions containing truncated gD2 protein were identified by SDS-PAGE and overnight Coomassie blue staining (GelCode Blue, Pierce). After overnight storage on ice, the fractions containing gD2 protein were mixed and stored in aliquots at −80° C. Purity and gD2 protein concentration were determined by SDS-PAGE and staining as above with bovine serum albumin standards run on the same gel for quantification purposes. FIG. 1C shows a representative Coomassie blue stained SDS-PAGE gel of the gD2t-containing eluate and the BSA standard used for quantification purposes. Using Image-J software (NIH), a standard curve of BSA concentrations was generated by optical density and the gD2 protein concentrations were interpolated. Protein yields were approximately 5 μg of gD2t per ml of media. Interestingly, we also found that the majority of the secreted gD2t protein had a carboxy-terminal fragment cleaved off. The resulting protein had lost the FLAG tag but showed no shift in migration on a gel. These findings were similar to those of Murata et al., who showed that the media of Hep2, but not Vero, cells infected with HSV-2 contained a secreted, but fully glycosylated, form of gD2 (Murata, T. et al., J. Gen. Virol., 83:2791-2795 (2002)). For our gD2t protein-based immunizations, only the uncleaved, FLAG-tag purified protein was used.

Immunization and Challenge of Mice.

Specific pathogen free and *Helicobacter* spp. PCR negative BALB/c female mice were purchased from Charles River Laboratories at 3-5 weeks of age and housed in microisolator cages. Mice were allowed to acclimate for at least 2 weeks prior to immunization or infection.

For DNA-based immunizations, mice were intradermally (i.d.) injected into the tail 3 times in 2 weeks with 30 μl of DNA in endotoxin free TBS (see Results for DNA doses). For coimmunization with plasmids, plasmid DNAs were mixed together prior to injection.

For protein-based vaccination, MPL from *Salmonella minnesota* Re 595 (*Salmonella minnesota* Re595) (MPL) was purchased from Sigma, resuspended to 1 mg per ml of 0.5% triethanolamine, emulsified by sonication as previously described (Baldridge, J. R., and R. T. Crane, Methods, 19:103-107 (1999)), and stored at 4° C. until use. FI-HSV2 or purified gD2 subunit stocks were thawed and diluted in either DPBS (protein vaccine only experiment) or endotoxin-free ddH2O (DNA prime-protein vaccine boost experiment) and MPL was added. Imject alum (Pierce) was added dropwise while mixing and then additionally mixed 30 min at room temperature before injection.

For the protein-based vaccine only experiment, mice received 2 subcutaneous (s.c.) injections at approximately mid-back and 3 weeks apart with either 1) $10^7$ PFU equivalents of the cell-associated and extracellular FI-HSV2 (approximately 250 μg protein), 2) an equal volume of FI-Mock, or 3) 5 μg gD2 subunit. Each dose also contained 12.5 μg of MPL and Imject alum (Pierce) equivalent to 725 μg Al. Mice were challenged 4 weeks following the last protein-based vaccination.

For the DNA prime-protein-based vaccine boost experiment, mice were primed by 3 i.d. injections in the tail, 2 weeks apart, with either 1) 50 μg pVAX, 2) 50 μg gD2t DNA, or 3) a cocktail of 20 μg each of the UL5, UL30, and gD2t DNAs. Five weeks after the last DNA injection, mice from each DNA prime group were boosted s.c. with either 1) $10^7$ PFU equivalents of extracellular FI-HSV (containing 8.3 μg protein), 2) an equal volume of FI-Mock, or 3) 5 μg gD2 subunit. Each dose also contained 12.5 μg of MPL and Imject alum equivalent to 125 μg Al(OH)3 and 43.3 μg of Al. Mice received a second boost 3 weeks after the first and then were challenged 4 weeks later.

For the experiment in which DNA vaccines were combined with FI-HSV2 in Adju-Phos adjuvant, mice were given bilateral intramuscular (i.m.) injections of 40 μl into each quadriceps muscles with dextran sulfate wash-derived FI-HSV2 (or dextran sulfate wash-derived FI-Mock) in MPL/Adju-Phos adjuvant as follows. Each immunization contained a total of 12.5 μg of MPL, Adju-Phos (Accurate Chemical & Scientific, Westbury, N.Y.) equivalent to 90 μg Al, and either 1) $10^7$ PFU equivalents of FI-HSV2 (0.34 μg of protein), 2) 60 μg of pVAX DNA plus a volume of FI-Mock equal to that of the FI-HSV2 above, 3) 60 μg of pVAX DNA plus $10^7$ PFU equivalents of FI-HSV2, 4) 20 μg each of UL5, UL30, and gD2t DNAs plus $10^7$ PFU equivalents of FI-HSV2, or 5) 50 μg each of UL5, UL30, and gD2t DNAs plus $10^7$ PFU equivalents FI-HSV2. Adju-Phos was first concentrated 2-fold by centrifugation at 500×g for 5 min followed by the removal of buffer supernatant equivalent to one half the total volume. FI-HSV2 or FI-Mock was adsorbed to the concentrated Adju-Phos for 1 h with mixing prior to the addition of MPL and, if added, the DNA(s). Mice were given an additional injection after 4 weeks. A short-term i.vag. challenge of mice from groups 1, 2, and 5 above was given 3 weeks after the second injection and the remaining mice were given a long-term i.vag. challenge 9 weeks after the second injection.

For the experiment comparing the Alhydrogel or Adju-Phos adjuvants, injection routes, and protection against challenge and re-challenge, $10^7$ PFU equivalents (9.5 or 13.5 µg of protein for the first or second immunizations, respectively) of extracellular FI-HSV2 (or FI-Mock) and 12.5 µg of MPL was given. As above, FI-HSV2 or FI-Mock was first adsorbed to Alhydrogel (Accurate Chemical & Scientific, Westbury, N.Y.) or 2-fold concentrated Adju-Phos equivalent to 54 µg or 450 µg of Al, respectively, prior to addition of MPL and DNA, if used. Groups of mice were immunized with the following components and immunization routes: 1) 60 µg pVAX DNA and FI-Mock in Adju-Phos given i.m., 2) FI-HSV2 in Alhydrogel given s.c., 3) FI-HSV2 in Alhydrogel given i.m., or 4) FI-HSV2 in Adju-Phos given i.m. Mice received an identical immunization after 4 weeks and then i.vag. challenged 3 weeks later. Mice that survived the HSV-2 challenge were medroxyprogesterone treated and re-challenged 17 weeks after the first challenge as above. A group of 8 naïve mice was challenged at the same time to demonstrate the infectivity of the re-challenge virus.

Intravaginal virus challenge, disease scoring, and quantification of viral shedding. On days −7 and −1 relative to challenge, mice received a subcutaneous injection of 3 mg of medroxyprogesterone acetate (Depo-Provera, Sigma M1629) in order to synchronize the estrus cycle and to increase susceptibility to vaginal HSV infection (Parr, M. B. et al., Lab. Invest., 70:369-380 (1994)). Mice were swabbed with a DPBS-moistened polyester tipped swab (MicroPur 1001D, PurFybr Solon, Rhinelander, Wis.) prior to i.vag. challenge with $5×10^4$ PFU of HSV-2 strain G (ca. 10 $LD_{50}$ doses) by micropipette. Mice were scored daily for 21 days for the severity of vaginal inflammation from 0 (no vaginitis), 1 (mild swelling or redness only), 2 (moderate swelling or erosions), 3 (severe genital maceration), or 4 (central nervous system involvement or death), with half scores given to intermediate disease levels. Mice discovered with hind limb paralysis were given a score of 4 and immediately sacrificed.

To measure vaginal virus shedding, intravaginal swab samples were collected on days 1 through 5 (or 6) postchallenge using polyester tipped swabs (above) that were pre-moistened with DPBS+1% HI-NCS+0.1% (w/v) glucose (DNG). Swabs were stored in 1 ml of DNG at −80° C. in until titration by plaque assay on Vero cell monolayers.

For plaque assays, swabs were quickly thawed in a 37° C. water bath and vortex mixed at full-speed for 30 s prior to serial dilution in DNG. Confluent monolayers of Vero cells in 24-well plates were infected for 1 h, 37° C., on a 50-60 RPM orbit shaker with an infection volume of 0.25 ml DNG per well. After adsorption, the inocula were removed and the monolayers were overlaid with 0.5 ml of DMEM with 1% HI-NCS and 0.35% sterile agarose. After 2 d incubation at 37° C. and 7% CO2, formalin in DPBS was added to a 4% formalin final concentration and the plates were fixed at 25° C. for at least 3 h. Agarose overlays were aspirated and monolayers stained with crystal violet. The assay limit of sensitivity of each assay is denoted below, and assays yielding no plaques were assigned a titer of one-half the detection limit for graphing and calculation purposes.

Intracellular Cytokine Staining.

Two weeks following the final injection, levels of antigen specific CD8+ T cells elicited by DNA immunizations were measured as previously described (Morello, C. S. et al., J. Virol., 81:7766-7775 (2007)). BALB SV40 (H-$2^d$) cells were grown in 96-well plates to 80% confluence and transfected with 0.5 µg of plasmid DNA and 1.25 µl of Fugene 6 (Roche) per well.

Forty-eight hours post transfection, splenocytes from immunized mice were harvested and erythrocytes were lysed (BD Pharm Lyse). $8×10^5$ splenocytes were added to duplicate wells of transfected cells in the presence of brefeldin A (GolgiPlug; BD) and stimulated for 8 hours at 37° C. and 7% $CO_2$. As a positive control, $2×10^6$ splenocytes were stimulated with 50 ng PMA and 1 µg ionomycin per ml. Duplicate wells of $2×10^6$ splenocytes were also stimulated with 0.1 µM of a previously published H-$2^d$ CD8+ T cell epitope of ICP27 (HGPSLYRTF (SEQ ID NO:13); GenScript, NJ (Haynes, J. R. et al., Vaccine, 24:5016-5026 (2006)).

For staining, duplicate wells were combined into one well of a 96-well round bottom plate and washed once with PBS. To differentiate live versus dead cells, a viability dye (50 µA per well) was added to cells for 10 minutes at 37° C. (LIVE/DEAD fixable violet; Molecular Probes, Invitrogen). Fc block (CD16/32; BD) was added (2 µg per well), and splenocytes were incubated for 10 min at 4° C. to prevent nonspecific binding to Fc receptors. Splenocytes were stained for surface markers CD8-Ax488 (Clone 53-6.7; BD) and CD4-Ax647 (clone RM4-5; BD) for 30 minutes at 4° C. and then permeabilized and fixed using the BD Cytofix/Cytoperm kit. CD3-PE-Cy5 (Clone 145-2C11; BD) and IFN-γ-PE (Clone XMG1.2; BD) were included in the intracellular stain for 45 minutes at 4° C. Data from 50,000 live CD3+ T cells were collected on a BD FACSCanto flow cytometer and analyzed with BD FACSDiva software at the Research Flow Cytometry Core Facility of the San Diego Center for AIDS Research and the Veterans Medical Research Foundation and VA San Diego Healthcare System, La Jolla, Calif.

B. DNA Immunization with the Conserved, Essential HSV-2 Genes Together with GD2t DNA is Protective Against Lethal Intravaginal. (I.Vag.) Challenge Our previous DNA immunization studies using the MCMV model showed that vaccination with plasmids expressing two essential genes that are conserved among herpesviruses, DNA polymerase (MCMV M54) and a helicase/primase subunit (MCMV M105), elicited protection against virus replication in the spleen. This protection was as high as that afforded by the immunodominant gene IE1-pp 89 (Morello, C. S. et al., J. Virol., 81:7766-7775 (2007)). DNA immunization with these two MCMV genes also resulted in primary and postchallenge CD8+ T cell levels that were higher than those elicited by MCMV infection (Morello, C. S. et al., J. Virol., 81:7766-7775 (2007)). We also showed that mice immunized with a mixture of plasmids encoding MCMV glycoprotein B and two nonstructural proteins followed by a boost with formalin-inactivated MCMV in alum showed long-term complete protection against a systemic challenge with MCMV and almost complete protection against a mucosal challenge (Morello, C. S. et al., J. Virol., 79:159-175 (2005)).

Because protective effects have been described for the truncated, secreted gD2 DNA in both the mouse and guinea pig models (Bernstein, D. I. et al., *Vaccine,* 17:1964-1969 (1999); Fotouhi, F. et al., *Fems Immunol. Med. Microbiol.,* 54:18-26 (2008); Higgins, T. J. et al., *J. Infect. Dis.,* 182: 1311-1320 (2000); Hoshino, Y. et al., *J. Virol.,* 79:410-418 (2005); Strasser, J. E. et al., *J. Infect. Dis.,* 182:1304-1310 (2000)), we were interested in determining whether conserved, essential HSV-2 genes could be used together with the gD2t DNA to augment the level of protection. In view of the limited success of DNA only vaccines in the human trials to date, we additionally sought to assess whether DNA immunization could augment the protection and immune responses elicited by a whole, killed HSV-2 vaccine together with MPL and alum adjuvants.

In our initial experiment we examined the protective efficacy of the corresponding conserved HSV-2 genes for the DNA polymerase (UL30) and helicase/primase (UL5) in the presence and absence of the DNA encoding the truncated HSV-2 glycoprotein D (gD2t). Eight mice per group were i.d. immunized with either 50 µg of pVAX (pVAX group), 25 µg each of pVAX and gD2t DNA (gD2t group), 25 µg of pVAX plus 25 µg of UL5 or UL30 DNA (UL5 or UL30 groups, respectively), or 25 µg UL5 or UL30 DNA plus 25 µg gD2t DNA (UL5+gD2t and UL30+gD2t groups, respectively). Mice were treated with medroxyprogesterone acetate to increase susceptibility to i.vag. HSV-2 infection, and 3 weeks after the last DNA immunization, they were given a lethal, i.vag. challenge of 5×10$^4$ PFU (approximately 10×LD$_{50}$) of HSV-2 strain G. Mice were monitored for survival through day 21 postchallenge and scored for disease severity using a previously described severity scale as described in the Materials and Methods through day 12 postchallenge. Intravaginal swabs were collected on days 1-6 postchallenge to measure HSV-2 shedding.

We found that immunization with either UL5 or UL30 DNA alone did not increase 21-day survival relative to the pVAX controls, but these DNAs together with gD2t DNA resulted in protection, as measured by survival, that was similar to that generated by gD2t DNA alone (FIG. 2A). Similarly, anogenital disease severity in the mice immunized with UL5 or UL30 alone were similar to that in the pVAX group. Mean disease severity in the groups receiving gD2t DNA was reduced relative to the pVAX controls, with disease severity peaking at 1.2-1.7 on days 4 or 5 postchallenge and then decreasing to day 11. On day 11, one mouse died in the gD2t group and in the UL5+gD2t group. Of all the vaccine groups, immunization with UL30+gD2t DNAs resulted in the lowest peak disease (mean of 1.2) and total disease burden through day 12, and no deaths.

Vaginal HSV-2 shedding was measured by plaque assay on Vero cell monolayers. On day 1 postchallenge, mice immunized with either pVAX, UL5, or UL30 had mean HSV-2 titers of 10$^{4.4}$ PFU per swab, while the mean titers in the gD2t DNA immunized groups were reduced between 1 to 1.4 Logs. Titers peaked in all of the immunization groups on day 2 postchallenge, with the pVAX immunized group shedding 10$^{5.5}$ PFU and the other immunization groups having titer reductions of 0.5 to 1.5 logs. The UL30+gD2t group had the lowest titers on both days 1 and 2. By day 3 postchallenge, all groups including the pVAX control had similar titers of 10$^4$ PFU. After this time, the shedding in all of the groups receiving gD2t DNA showed increased clearance kinetics relative to the groups not receiving gD2t. Taken together, immunization with UL30+gD2t DNAs resulted in both the lowest disease and the lowest shedding levels early in infection, but shedding from days 3 to 6 was identical to that in mice receiving only gD2t DNA.

A second immunization experiment was performed to test whether enhanced protection against disease or virus shedding could be achieved through coimmunization with UL5 and UL30 DNAs. Groups of 8 mice were immunized with either 50 µg of pVAX (pVAX group) or 25 µg gD2t+25 µg pVAX DNA (gD2t group). For the UL5+UL30 groups, 20 µg each of UL5 and UL30 DNAs were immunized with either 20 µg of pVAX (UL5+UL30 group) or 20 µg of gD2t DNA (UL5+UL30+gD2t group). Immunized mice were treated with medroxyprogesterone acetate and i.vag. challenged 3 weeks after the last immunization as above. Death, disease, and vaginal HSV-2 shedding were assessed.

FIG. 2B illustrates that none of the mice immunized with pVAX survived through 21 days postchallenge. Combining UL5 and UL30 DNA in the vaccine without the addition of gD2t DNA also did not increase protection against death (FIG. 2B), disease, or reduce HSV-2 shedding, relative to that observed in groups immunized with pVAX, UL5, or UL30 DNA alone. When gD2t DNA was added to the UL5 plus UL30 vaccine, resultant viral titers were similar to that of the group immunized with gD2t DNA alone.

C. DNA Immunization with Conserved Essential Genes Elicits Antigen Specific CD8+ T Cells In view of the lack of protection elicited by the UL5 and UL30 DNAs in the absence of gD2t DNA, it was important to determine whether vaccination elicited CD8+ T cells. Mice were immunized three times in two weeks with the UL5 or UL30 plasmids. Two weeks following the final immunization, mice were sacrificed and their spleens were harvested. Splenocytes were stimulated for 8 hours in the presence of BALB SV40 stimulator cells that had been transiently transfected with the respective antigen-encoding plasmid or empty pcDNA3 plasmid, and an intracellular cytokine staining assay was performed.

Figure 3A:
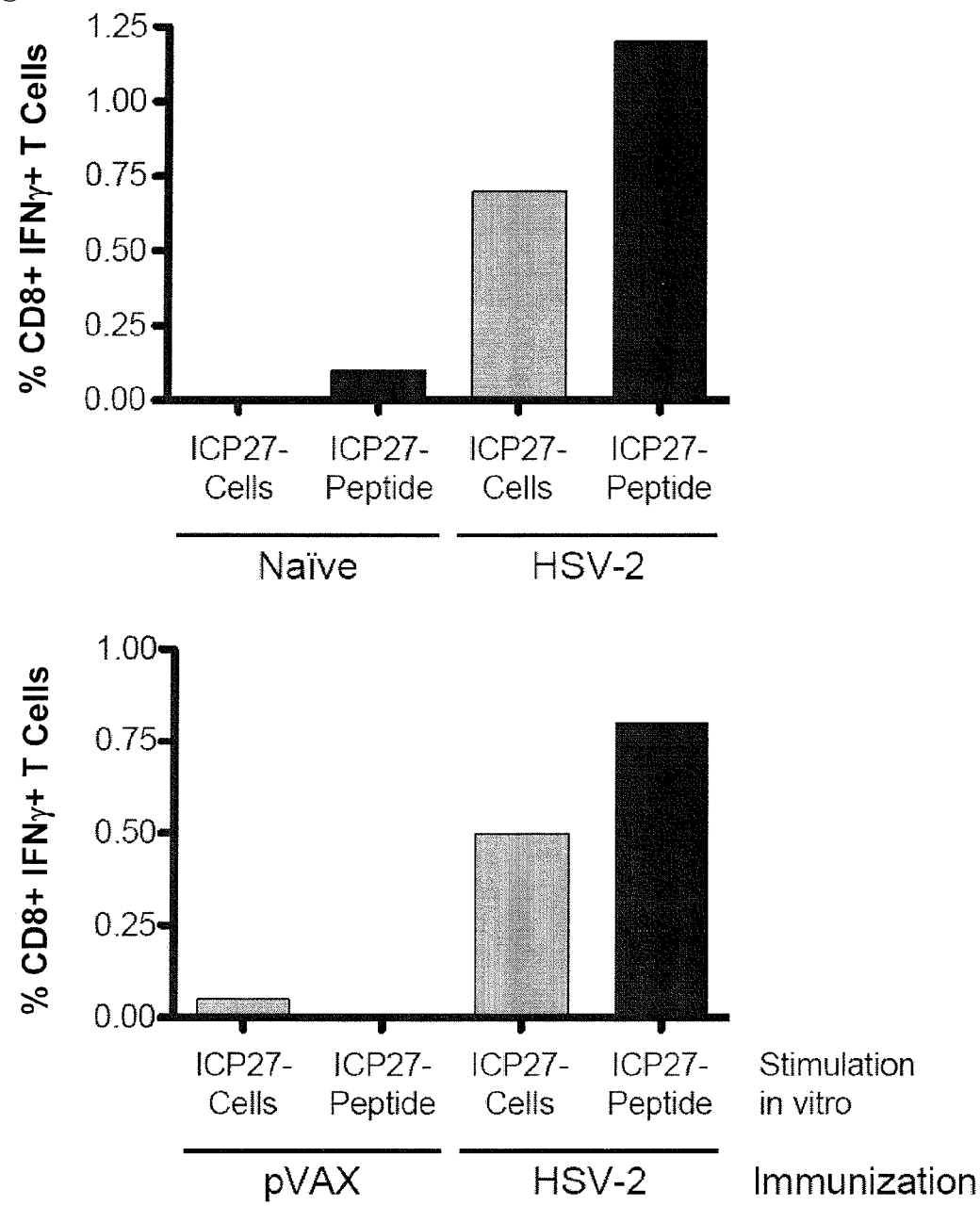
FIG. 3A to FIG. 3C. DNA immunization with conserved essential genes elicits antigen specific CD8+ T cells.

We initially performed two independent experiments to validate the use of antigen-expressing BALB SV40 transfectants to stimulate CD8+ T cells to produce IFN-γ. For these studies, we infected BALB/c mice with 2×10$^6$ PFU of HSV-2 Strain G in the footpad, and 7 days later isolated splenocytes from the infected and control naïve mice. As another control, splenocytes were collected from mice that were immunized intradermally with the backbone vector DNA (pVAX). The splenocytes were stimulated either with BALB SV40 cells transfected with pcDNA3-ICP27 (ICP27 cells) or an ICP27 peptide corresponding to a known CD8+ T cell epitope in BALB/c mice (Haynes, J. R. et al., *Vaccine,* 24:5016-5026 (2006)). FIG. 3A shows that a mean of 0.6% of the CD8+ T cells from HSV-2 infected mice were IFN-γ positive when stimulated with ICP27 cells as compared to a mean of 1.0% of the CD8+ T cells when stimulated with the ICP27 peptide. Only background levels of IFN-γ positive CD8+ T cells were detected in the splenocytes from the control naïve mice or pVAX DNA immunized mice regardless of the type of stimulation.

Figure 3B:
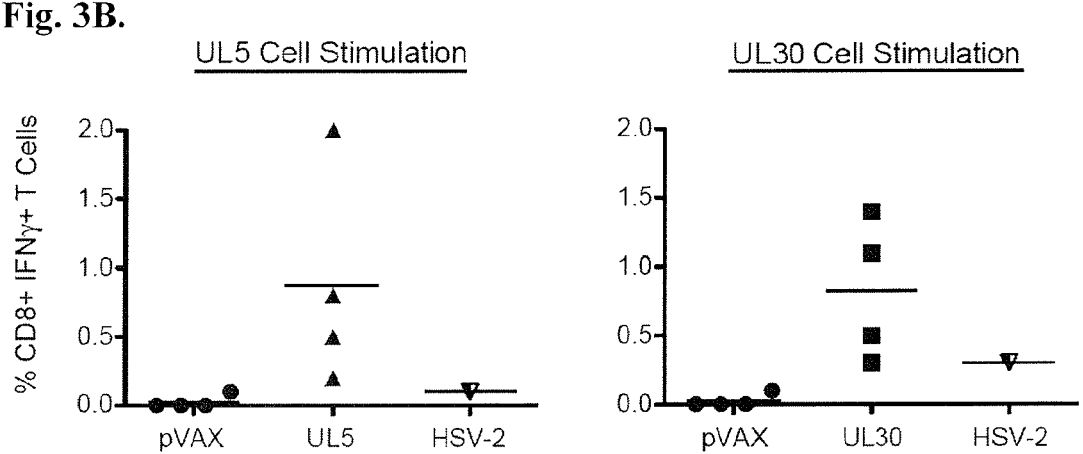

In the next experiment, 2 groups of mice (n=4) were given intradermal injections of 60 µg total plasmid DNA: pVAX, UL5, or UL30. FIG. 3B shows that mice immunized with either UL5 or UL30 had varying levels of CD8+ T cell responses to UL5 (mean=0.875%) or UL30 (mean=0.825%). These numbers are likely an underestimate since a lower frequency of ICP27 specific CD8+ T cells was detected when the splenocytes from HSV-2 infected mice were stimulated with ICP27 cells than with the ICP27 peptide (FIG. 3A). Nevertheless, UL5 and UL30 represent novel vaccine target antigens since IFN-γ+CD8+ T cells specific for either protein were also not observed in HSV-2 infected mice.

Figure 3C:
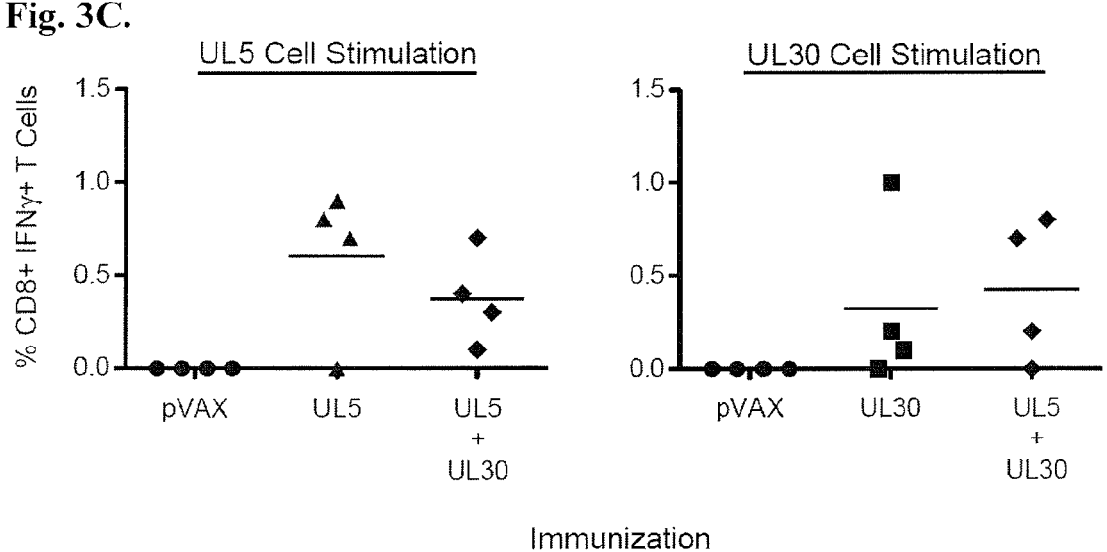

In a repeat experiment, a combination group with 60 μg each of UL5, and UL30 was included (FIG. 3C). The CD8+ T cell responses in mice immunized with UL5 or UL30 alone were lower than the first experiment (mean=0.600% and 0.325%, respectively). The variability between the experiments is likely due to the inconsistent nature of the transfected stimulator cells, since a third experiment resulted in mean UL5 and UL30 responses of 0.875% and 0.750%, respectively. When mice were co-immunized with UL5 plus UL30 DNA, CD8+ T cell responses to both UL5 and UL30 were detectable (mean=0.375% and 0.425%, respectively). In summary, the conserved, essential HSV-2 gene plasmids UL5 and UL30, elicit modest CD8+ T cell responses, as measured by IFN-γ production.

D. Immunization with FI-HSV2 Together with MPL/Alum is Highly Protective Against HSV-2 Disease and Shedding Because subunit vaccination with HSV-2 envelope glycoproteins, including the GSK gD2 vaccine containing an MPL/Alum adjuvant, has not shown consistent levels of protection in clinical trials, we asked whether a multivalent vaccine consisting of FI-HSV2 together with MPL/Alum could be more protective than gD2 protein subunit/MPL/Alum vaccination. For the FI-HSV2 vaccine, HSV-2 was harvested from infected Vero cells and extracellular supernatants, pelleted through a sorbitol cushion, washed with DPBS, and inactivated with formalin as described in Materials and Methods. In addition, an FI-Mock virion preparation was made in parallel using mock-infected Vero cells. Secreted gD2t protein was prepared using anti-FLAG immunoaffinity chromatography on the extracellular supernatants of 293FT cells that were transiently transfected with pc3Δneo-gD2t vector.

Mice (n=8) were subcutaneously (s.c.) immunized and then boosted 3 weeks later with one of the following: $10^7$ PFU equivalents of FI-HSV2, a volume of FI-Mock equal to the FI-HSV2 above, or 5 μg of gD2t protein, with each vaccine including MPL/Alum. Mice were challenged as above 4 weeks following the last vaccination.

We found that by 21 days postchallenge, all 8 of the FI-Mock immunized mice had died, whereas all 8 of the FI-HSV2 immunized mice survived (FIG. 4A). In the gD2t protein immunized group, 5 mice survived. Peak mean disease score in the mice immunized with the gD2t protein was approximately 1.0 until day 12 postchallenge, and then rose slightly (FIG. 4B). In contrast, the peak mean disease score in the FI-HSV2 immunized group was 0.5 on day 5 postchallenge, and there were only 2 additional days of 0.3 to 0.4 mean scores. The maximum disease score for individual mice in this group was 0.5, except for one mouse with a score of 1.0 for one day only. Thus, only a transient, low-level inflammation in the anogenital region after lethal HSV-2 challenge occurred in FI-HSV2 immunization animals.

Levels of vaginal virus shedding on days 1 through 6 postchallenge are shown in FIG. 4C. Peak mean virus titers were observed on day 2 postchallenge for the FI-Mock group and day 3 for the gD2t protein group. Mean virus titers in the FI-HSV2 group were reduced 2.1 to 3.7 Logs compared with the FI-Mock group. Although on day 1 postchallenge, the gD2t protein group had a mean titer reduction of 27-fold relative to the FI-Mock group, by day 3 postchallenge, these groups showed similar levels of virus shedding (FIG. 4C).

Compared with the peak mean virus titers of $10^{5.7}$ and $10^5$ PFU observed in the FI-Mock group and the gD2t protein group, respectively, mean titers in the FI-HSV2 immunized mice ranged between $10^{1.5}$ and $10^{2.2}$ PFU throughout the observation period. On day 2 postchallenge, the mean level of viral shedding in the FI-HSV2 immunized mice was 3600-fold lower than that in the FI-Mock group. However, as shown in FIG. 4D, protection against vaginal HSV-2 shedding in individual mice in the gD2t protein and FI-HSV2 groups did show considerable variability. Viral titers in individual FI-HSV2 immunized mice ranged from approximately $10^4$ PFU to below the limit of assay protection (2 PFU per swab). Two of the FI-HSV2 immunized mice had no detectable virus on any day through day 6 postchallenge, although they did show low-level inflammation (severity scores of 0.5) between days 3 and 6 postchallenge. Taken together, immunization with FI-HSV2/MPL/Alum provided high levels of protection against both disease and virus shedding compared with gD2t protein immunization.

E. Prime-Boost Immunization with UL5, UL30, and GD2T DNAs-FI-HSV2 Provides Nearly Complete Protection Against HSV-2 Genital Disease We had successfully used a DNA prime-inactivated whole virus boost strategy against systemic or mucosal MCMV challenge in mice, with undetectable levels of virus in the target organs after challenge (Morello, C. S. et al., J. Virol., 79:159-175 (2005); Morello, C. S., M. Ye, and D. H. Spector., J. Virol., 76:4822-4835 (2002)). We therefore proceeded to test whether this strategy would also provide high-level protection and to compare the various efficacies of immunization with DNA, protein subunit, or FI-HSV2 alone or in combination.

Figures 5A, 5B:
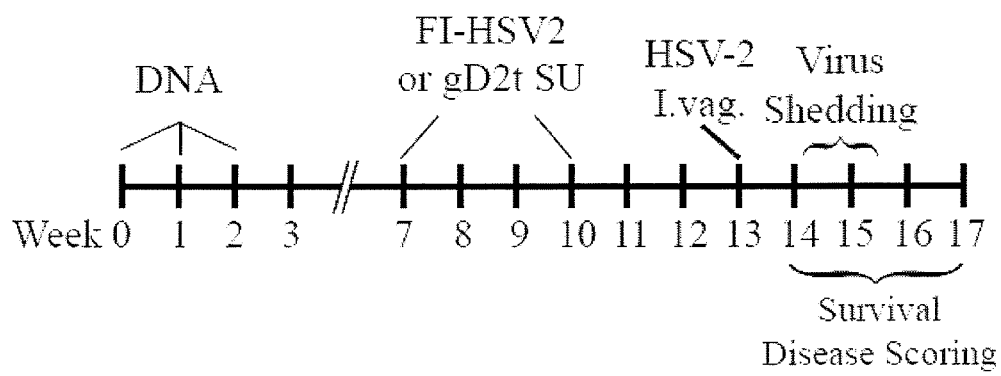
FIG. 5A to FIG. 5D. Protection against HSV-2 after prime-boost immunization.

Mice (n=8) were DNA primed with one of the following: 1) 50 μg of pVAX, 2) 50 μg of gD2t DNA, or 3) a cocktail of 20 μg each of the UL5, UL30, and gD2t DNAs using the schedule shown in FIG. 5A. Five weeks after the last DNA injection, mice from each DNA prime group were s.c. boosted with one the following formulated with MPL/Alum 1) $10^7$ PFU equivalents of FI-HSV2, 2) an equal volume of FI-Mock, or 3) 5 μg gD2 subunit. Mice received a second boost 3 weeks after the first and then were lethally i.vag. challenged 4 weeks later as above.

Survival to 21 days postchallenge is summarized in FIG. 5B. In the mice primed with pVAX, boosting with the FI-Mock preparation gave no protection against death. In the FI-Mock boosted mice, prior immunization with gD2t DNA resulted in 5 of 8 mice surviving, and the addition of UL5 and UL30 DNAs to the gD2t DNA prime resulted in fewer survivors (3 of 8). Boosting with gD2t protein was completely protective against death in the pVAX and gD2t DNA primed groups. One mouse in the UL5, UL30, gD2t DNA primed group that was boosted with gD2t protein died postchallenge (and one died of an ear infection before challenge), leaving only 6 survivors. Boosting with FI-HSV2 gave similar protection against death when compared with the gD2t protein, with one mouse in each of the pVAX and UL5, UL30, and gD2t DNAs groups succumbing to challenge.

The severity of disease in the mice with each prime-boost combination was scored through day 12 postchallenge (FIG.

Figure 5C:
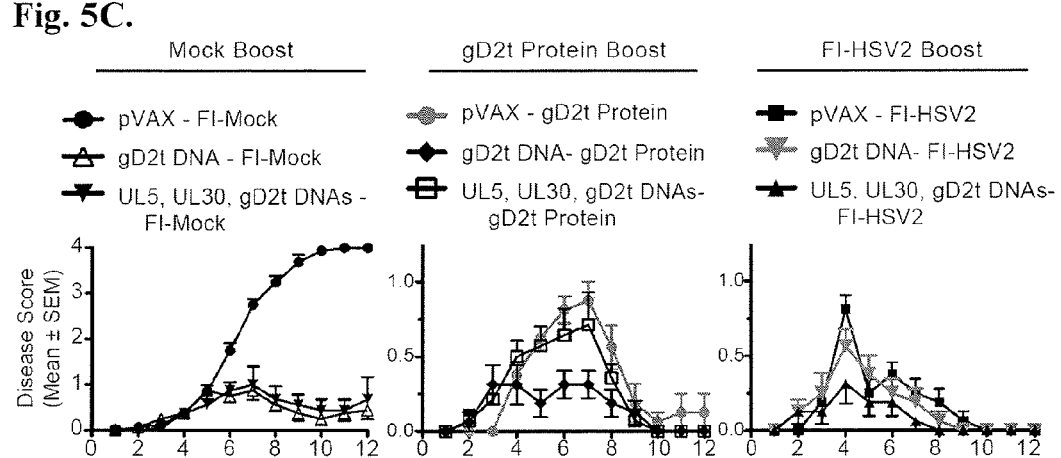

5C). Of the mice boosted with FI-Mock, all of the pVAX primed mice were dead by day 11 postchallenge, while priming with gD2t DNA or a combination of UL5, UL30, and gD2t DNAs gave similar peak mean disease scores of 0.9-1 on day 7 postchallenge and then near resolution to below a mean of 0.25-0.5 by day 10 (FIG. 5C, left). However, late deaths in the gD2t DNA (3 mice) and UL5, UL30, and gD2t DNAs (5 mice) resulted in the increasing mean scores shown.

Peak mean disease scores in the mice boosted with gD2t protein were lowest in the gD2t DNA primed mice (0.3), with disease at this level lasting between days 3 to 7 postchallenge (FIG. 5C, middle). The peak disease in the groups primed with pVAX or a combination of UL5, UL30, and gD2t DNAs and then boosted with gD2t protein had similar levels of 0.9 and 0.7.

The groups boosted with FI-HSV2 all showed a peak in disease at day 4 postchallenge, with the lowest peak of 0.3 in the UL5, UL30, gD2t DNAs-FI-HSV2 group (FIG. 5C, right). The highest level of disease observed in the mice in this latter group was a score of 1 for one day. The remaining mice had disease scores of 0 or 0.5 until disease was completely resolved by day 8 postchallenge. However, one mouse in this group that had no observable vaginal disease except for a single 0.5 score on day 2 postchallenge died on day 20.

In general, protection against vaginal disease seemed to be most closely related to the type of boost. Groups that were boosted with gD2t protein showed more protection than the groups that received HSV-2 DNA and the FI-Mock boost, and groups receiving the FI-HSV-2 boost showed the highest level of protection. The best protection was afforded in the prime boost groups given gD2t DNA-gD2t protein or UL5, UL30, gD2t DNAs-FI-HSV2, with similar peak levels of disease but lower total disease burden in the latter group.

Figure 5D:
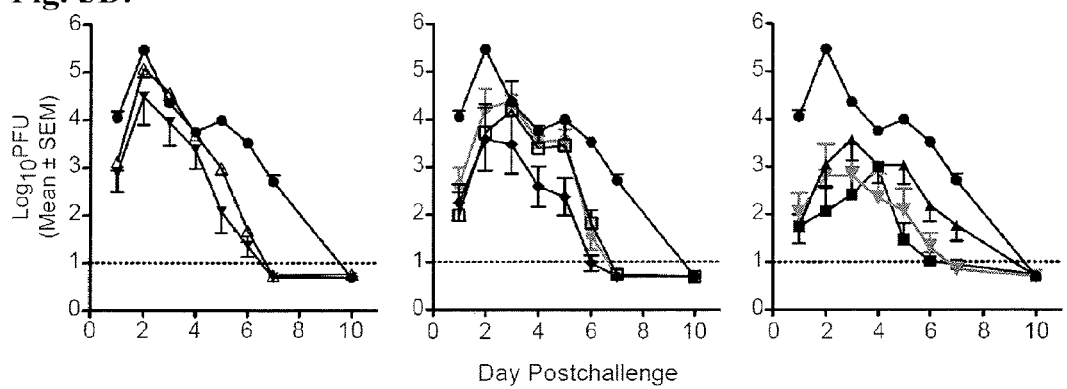

Vaginal HSV-2 shedding was measured from intravaginal swabs on days 1 through 10 postchallenge by plaque assay. Viral shedding in the pVAX primed-Mock boosted groups peaked at $10^{5.5}$ PFU on day 2 postchallenge, with virus still detectable in all of these mice on day 7 postchallenge (FIG. 5D, left). Mock boosted mice that were primed with gD2t DNA or a combination of UL5, UL30, and gD2t DNAs initially had approximately 10-fold lower titer on day 1 postchallenge, but only the latter group showed this decrease on day 2. Decreases in vaginal virus shedding relative to pVAX primed mice were more evident by day 5 postchallenge, and by day 7, virus was detectable in only 1 of the gD2t DNA primed mice and in none of the UL5, UL30, gD2t DNAs primed mice.

Boosting with gD2t protein resulted in greater initial decreases in HSV-2 shedding of 1.5 to 2 Logs relative to the pVAX–FI-Mock group, while only the gD2t DNA-gD2t protein group maintained decreased levels of virus shedding on days 3 through 5 postchallenge. In the latter group, viral infection was more rapidly cleared, and virus levels were at or below the limit of detection in 7 of 8 mice by day 6 postchallenge (FIG. 5D, middle). Of note, 2 of the 8 mice in this group had no detectable virus in any of the swabs (<10 PFU per swab).

Boosting with FI-HSV2 was found to result in the greatest initial decreases of virus shedding, from 2-2.25 Logs on day 1 postchallenge in each of the DNA primed groups relative to the pVAX–FI-Mock controls (FIG. 5D, right). On day 2 postchallenge, mean HSV-2 shedding levels in the pVAX–FI-HSV2 group were approximately 3.5 Logs lower than controls, and virus was rapidly cleared in this group to a mean level at the detection limit by day 6. Peak HSV-2 shedding was similar in the gD2t DNA-FI-HSV2 group, although the peak occurred earlier in the infection and viral shedding persisting one additional day. However, 3 of 8 mice in gD2t DNA-FI-HSV2 group had no detectable shedding throughout the entire time course. Finally, a peak titer of $10^{3.6}$ PFU on day 3 in the UL5, UL30, gD2t DNAs-FI-HSV2 group was slightly higher than in the other FI-HSV2 groups, and virus in this group persisted at a level of approximately $10^2$ PFU until days 6-7 postchallenge.

F. Co-Immunization with Plasmid DNA and FI-HSV2 IN Adju-Phos as a Single Formulation is Less Effective than FI-HSV2 in Adju-Phos Alone While the prime-boost strategy proved highly protective, co-injection of the DNA and FI-HSV2 in a single formulation would be highly advantageous for both manufacturing vaccine and for clinical application. In addition, combination of the two platforms may result in cooperative protective responses to the vaccine components. Adju-Phos is a clinically approved aluminum phosphate adjuvant that when delivered together with a hepatitis B viral antigen encoding plasmid DNA and protein, elicited both a Th1 and Th2 type immune response against the DNA and protein, respectively (Kwissa, M. et al., *J. Mol. Med.*, 81:502-510 (2003)). Accordingly, groups of mice (n=8) were given intramuscular injections with MPL/Adju-Phos formulated with $10^7$ PFU equivalents FI-HSV2+/–DNA plasmids encoding UL5, UL30, and gD2t (50 μg each). The negative control group received MPL/Adju-Phos formulated pVAX and FI-Mock. Mice were given a second injection 4 weeks after the first and then medroxyprogesterone treated and challenged as previously described.

Figure 6A:
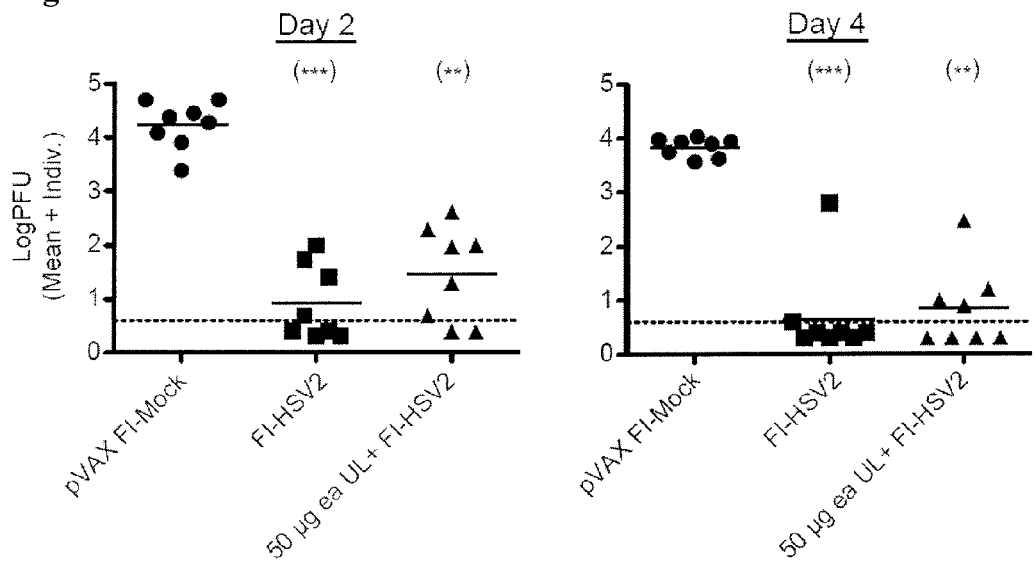
FIG. 6A to FIG. 6D. Protection against HSV-2 shedding after a single formulation of FI-HSV2 and DNA plasmids in MPL plus Adju-Phos.

On day 2 postchallenge, all of the negative control mice (pVAX+FI-Mock) were shedding HSV-2 and the mean titer was $10^{4.2}$ PFU (FIG. 6A, left panel). The groups of mice that received the FI-HSV2 had significantly reduced mean titers (approximately 3 Logs, P<0.001 and P<0.01, Kruskal-Wallis, plus Dunn's Multiple Comparisons Test). In addition half of the mice in the group that received FI-HSV2 (no DNA) had levels of HSV-2 shedding that were below the detection limit. By Day 4, 7 out of 8 of these animals, and half of the UL5, UL30, gD2t+FI-HSV2 immunized group had levels of shedding that were at or below the limit of detection (FIG. 6A, right panel). In contrast, the mean titers of the pVAX+FI-Mock immunized animals remained elevated at $10^{3.8}$ PFU. Immunization with UL5, UL30, gD2t DNA and FI-HSV2MPL/Adju-Phos was not significantly better than FI-HSV2MPL/Adju-Phos alone.

Figure 6B:
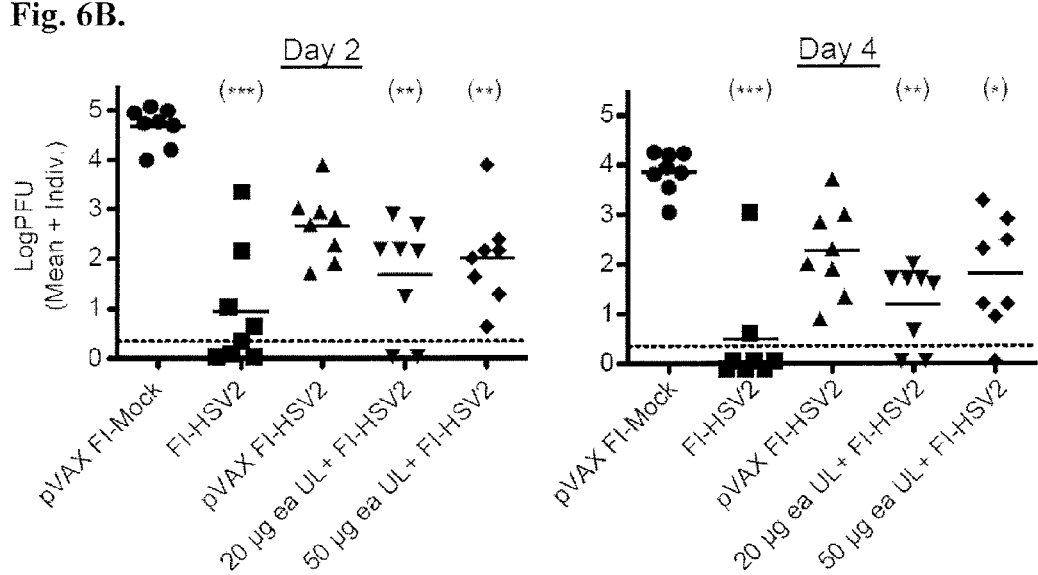

In another experiment, the durability of the immune response elicited by the single formulation was examined by waiting 9 weeks after the second immunization before challenge. In addition to the previous 3 groups included in the short-term challenge (pVAX+FI-Mock, FI-HSV2, and FI-HSV2+50 μg each UL5, UL30, gD2t), 2 more groups formulated in MPL/Adju-Phos were added. 1) FI-HSV2+20 μg each UL5, UL30, gD2t DNA plasmids in order to test the dose used in the earlier DNA experiments and 2) FI-HSV2+60 μg pVAX DNA plasmid to serve as a control. Two days postchallenge, the pVAX+FI-Mock group had mean titers of $10^{4.7}$ PFU whereas the group that received FI-HSV2 alone (no DNA) had almost a 4 Log reduction in titer, $10^{0.96}$ PFU (FIG. 6B. left panel). Compared to the negative control animals, the groups that received UL5, UL30, gD2t DNA, either 20 or 50 μg, had a similar approximate 3 Log reduction, $10^{1.7}$ and $10^{2.0}$, respectively. By Day 4, 6 out of 8 mice in the FI-HSV2 only group had virus titers that were below the limit of detection, whereas only 1 or 2 out of 8 animals in the 20 μg and 50 μg UL5, UL30, gD2t DNA+ FI-HSV2 groups, respectively, were shedding virus below the limit of detection (FIG. 6B, right panel). The reduction in virus shedding on Days 2 and 4 for each of the groups that received antigenic DNA+FI-HSV2 were statistically significant compared to the pVAX FI-Mock group ($P<0.001$ to $P<0.05$, Kruskal-Wallis plus Dunn's Multiple Comparison Tests). However, the group that received the pVAX+FI-HSV2, did not have a statistically significant reduction in virus shedding on either day, with mean titers of $10^{2.7}$ and $10^{2.3}$, respectively.

Taken together, these data suggest that the combination of FI-HSV2 and plasmid DNA into a single formulation with MPL/Adju-Phos is not as efficacious in preventing HSV-2 shedding as FI-HSV2 alone. These results were also observed in the HSV-2 disease scores in the animals that received the same type of immunization and the long-term challenge. Of greater significance, the FI-HSV2 immunized animals had the best protection against both viral shedding and disease in both a short- and long-term challenge, suggesting that FI-HSV2 elicits a durable and highly protective immune response.

G. Immunization With FI-HSV2 in Alhydrogel or Adju-Phos Adjuvants is Highly Protective Against HSV-2 Replication Following Challenge and Re-Challenge In the experiment above, we found that the best protection against virus shedding tested was provided by immunization with FI-HSV2 alone. We next sought to confirm these results and to determine whether the FI-HSV2 immunization could be improved. One of the first considerations was that Imject alum consists of both crystalline and amorphous aluminum phases and is not a well-defined form of alum suitable for clinical translation. Since both aluminum hydroxide and aluminum phosphate adjuvants have been licensed for use in vaccines, it was important to test the more clinically relevant forms of alum, such as Alhydrogel or Adju-Phos, to eliminate the possibility that an undefined aspect of the Imject alum contributed to the protection. We also sought to test whether the route of immunization could affect the resultant protection.

To this end, groups of 8 mice were immunized with $10^7$ PFU equivalents of FI-HSV2 and MPL as above, except that the types of alum and the injection routes were as follows: 1) FI-HSV2/MPL/Alhydrogel given s.c.; 2) FI-HSV2/MPL/Alhydrogel given i.m.; or 3) FI-HSV2/MPL/Adju-Phos given i.m. A control group received FI-Mock/MPL/Adju-Phos given i.m. Mice were given a second injection 4 weeks after the first and then medroxyprogesterone treated and challenged as above.

Two mice in the pVAX FI-Mock group died prior to challenge, and the remaining mice in this group succumbed to HSV-2 disease by day 12 postchallenge. No deaths occurred in any of the FI-HSV2 immunized groups. For the few animals in this group that showed signs of infection, only mild erythema or swelling was observed. Mean disease scores in the FI-HSV2 groups peaked on day 7 postchallenge to similar levels of 0.2-0.25, and complete resolution of disease was observed in 7 of 8 mice in each group by day 11.

Figure 7A:
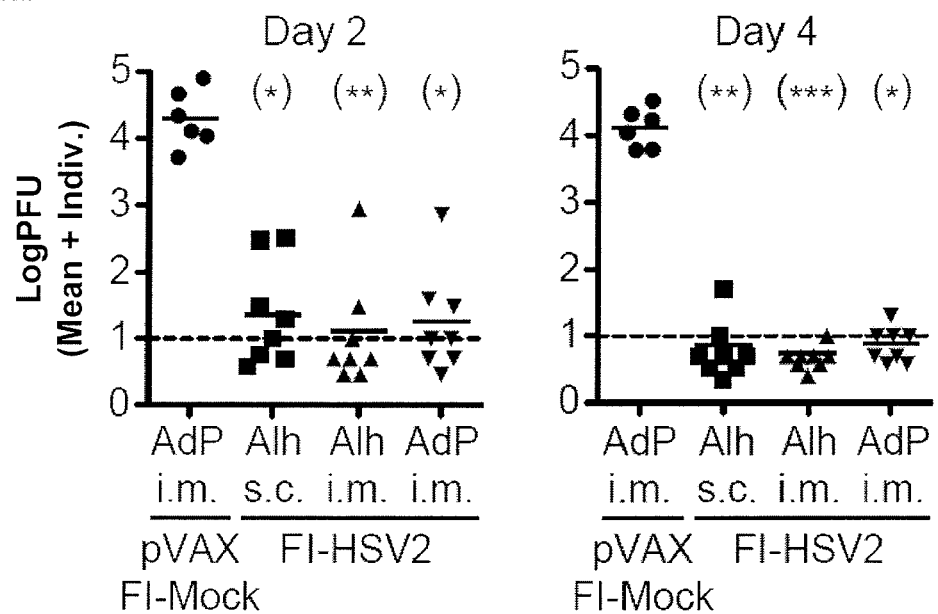
FIG. 7A to FIG. 7C. Protection against HSV-2 challenge and re-challenge after immunization with FI-HSV2 in MPL plus Alhydrogel or Adju-Phos. Groups of mice were i.m. or s.c. immunized as indicated with $10^7$ PFU equivalents of FI-HSV2, 12.5 µg of MPL, and either 54 µg of Alhydrogel (Alh) or 450 µg of Adju-Phos (AdP). In addition, a negative control group received 60 µg of pVAX DNA mixed with MPL, Adju-Phos, and a volume of FI-Mock equal to the FI-HSV2 used in the other groups. Four weeks later, mice were given an additional immunization, rested for 3 weeks, and then i.vag. challenged with HSV-2 as above. A. Vaginal virus shedding on day 2 (Left panel) or day 4 (Right panel) postchallenge as in FIG. 4C except that the limit of assay sensitivity was 10 PFU per swab. Data points below the sensitivity limit(s) were staggered for increased visibility in the panels for both FIG. 7A and FIG. 7C.

On day 2 postchallenge, the mean HSV-2 titer in the pVAX FI-Mock control group was $10^{4.3}$ PFU, and the mean titers in the groups receiving FI-HSV2 were reduced by 3 Logs (FIG. 7A, left panel). In addition, half or more of the mice in each FI-HSV2 groups had reductions in virus shedding to levels at or below the detection limit. While HSV-2 titers in the pVAX FI-Mock control group remained at the $10^4$ PFU level on day 4 postchallenge, no or only very low levels of virus was detectable in any of the FI-HSV2 immunized mice (FIG. 7A, right panel). The reduction in virus shedding for each of the FI-HSV2 groups, relative to the pVAX FI-Mock group, was statistical significant on each day postchallenge ($P<0.05$ to $P<0.001$, Kruskal-Wallis plus Dunn's Multiple Comparison Tests). No significant differences, however, were seen between the protected groups (FIG. 7A). Taken together, immunization with FI-HSV2 and MPL together with the aluminum containing adjuvants Alhydrogel or Adju-Phos resulted in protection against HSV-2 disease and shedding that was at least as robust as that afforded by Imject alum.

In this experiment, several of the FI-HSV2 immunized mice in each group had no detectable shedding (<10 PFU) on either day tested. An important question was whether the high level protection against challenge that was provided by the FI-HSV2/MPL/Alum would also be effective against a long-term re-challenge. To this end, the FI-HSV2 immunized mice were medroxyprogesterone treated as before and then re-challenged 17 weeks after the first challenge with the same $10 \times LD_{50}$ dose of HSV-2. As a control for the re-challenge, a naïve group of 8 mice was infected concurrently with the same HSV-2 inoculum as the rest of the mice.

One of the FI-HSV2/Alhydrogel/s.c. mice died after the first medroxyprogesterone treatment, and thus there were 7 mice remaining in this group for re-challenge. All of the naïve mice died by day 14 postchallenge, and one of the 7 mice of the FI-HSV2/Alhydrogel/s.c. mice died on day 21 after the re-challenge. None of the other mice showed HSV-2 disease beyond mild erythema or swelling through day 21 postchallenge.

Figure 7B:
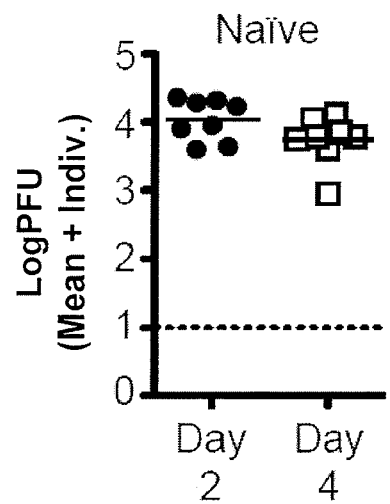
Figure 7C:
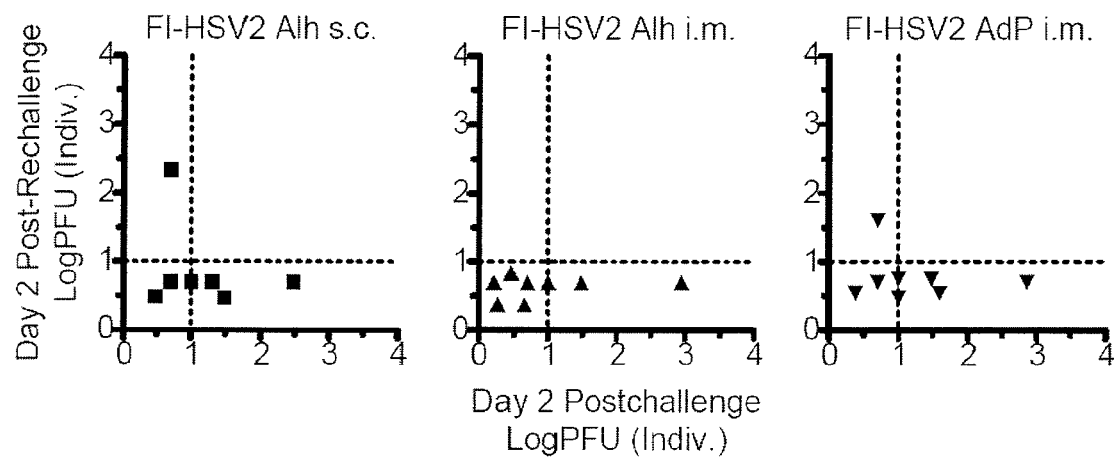

The re-challenge dose of HSV-2 given to the naïve group resulted in virus shedding levels of approximately $10^4$ PFU on both days 2 and 4 postchallenge (FIG. 7B), which were similar to those in the pVAX FI-Mock group on the respective days postchallenge (FIG. 7A left and right). Strikingly, only 2 of the re-challenged mice in the FI-HSV2 groups (n=23) had a detectable, low level of virus. The mouse in the FI-HSV2/Alhydrogel/s.c. group that died on day 21 had detectable virus on day 2 (see e.g., FIG. 7C). It is particularly notable that in the FI-HSV2/Alhydrogel/i.m. group, 5 of the 8 mice had no detectable virus on day 2 postchallenge or post re-challenge, and 2 additional mice in this group had very low level shedding postchallenge ($10^1$-$10^{1.5}$ PFU) and no detectable virus post re-challenge (FIG. 7C, middle). No virus was detectable in any of the FI-HSV2 groups on day 4 post re-challenge. Taken together, we found that immunization with FI-HSV2 that was formulated with MPL and any of a variety of alum adjuvants elicits nearly complete protection against HSV-2 disease. Moreover, these vaccines provide strong and durable protection against vaginal HSV-2 shedding, with some animals showing sterilizing immunity, following challenge or long-term re-challenge.

H. Analysis

In this study, we tested the protective properties of two vaccine components against HSV-2 genital infection when each component was given either alone or as a prime-boost vaccine. The prime component consisted of DNA encoding the immunogenic gD2t protein, which has been shown to provide protective effects in both the mouse and guinea pig models (Bourne, N. et al., *Vaccine*, 14:1230-1234 (1996);

Bourne, N. et al., *J. Infect. Dis.*, 173:800-807 (1996); Higgins, T. J. et al., *J. Infect. Dis.*, 182:1311-1320 (2000); Strasser, J. E. et al., *J. Infect. Dis.*, 182:1304-1310 (2000)). We also tested DNA encoding the conserved essential proteins HSV-2 DNA polymerase (UL30) and helicase/primase (UL5), as previous studies had shown that their counterparts encoded by MCMV were individually protective against a systemic challenge of MCMV in mice (Morello, C. S. et al., *J. Virol.*, 81:7766-7775 (2007)). The boost component contained either formalin-inactivated HSV-2 (FI-HSV-2) formulated with one of several alum compounds and MPL or gD2t protein plus MPL and alum.

Although DNA immunization with both the UL5 and UL30 genes elicited a CD8+ T-cell response as measured by IFN-γ production, neither gene was protective against disease or viral shedding unless the DNA encoding gD2t was also included. Since we and others have shown that gD2t DNA immunization generates a high level of neutralizing antibody specific for gD2 (Flo, J., *Vaccine*, 21:1239-1245 (2003); Hoshino, Y. et al., *J. Virol.*, 79:410-418 (2005)), it may be that this antibody was more protective against the genital challenge, at least locally, than CD8 T cells directed against UL5 or UL30. However, relative to mice immunized with gD2t DNA alone or gD2t plus UL5, the group immunized with gD2t DNA plus UL30 had the lowest peak disease (mean of 1.2) and disease burden through day 12 and the greatest reduction in viral shedding on days 1 and 2. The combination of UL5 and UL30 DNAs did not appear to further augment the protection elicited by either plasmid alone or when given with or without gD2t DNA co-administration.

In the mice receiving prime-boost immunizations, protection against HSV-2 vaginal disease was most closely related to the type of boost, with groups receiving the FI-HSV-2/MPL/Alum boost showing a higher level of protection than groups that received gD2t protein in MPL/Alum, and both boosts providing more protection than immunization with HSV-2 DNA alone. Boosting with FI-HSV-2/MPL/Alum also provided the greatest decreases of peak virus shedding. The mean virus titer in the FI-HSV2 group was 3.5-4.2 Logs lower than mock group and 2.8-3.5 Logs lower than gD2t protein-immunized mice during the first week post-challenge. When we combined the DNA prime with the FI-HSV2 or gD2t protein boost, we found that the combination of the UL5, UL30, gD2t DNA prime and FI-HSV2 boost gave nearly complete protection against HSV-2 genital disease.

The high level of protection observed in the group that was primed with empty vector and then boosted with FI-HSV-2/MPL/Alum prompted us to determine whether modification of the composition of the inactivated virus vaccine could improve its efficacy as a single vaccine. After completion of the prime-boost studies, we learned that that Imject alum consists of both crystalline and amorphous aluminum phases and is not a well-defined form of alum suitable for clinical translation (Hem, S. L. et al., *Vaccine*, 25:4985-4986 (2007)). This raised the concern that an undefined aspect of the Imject alum contributed to the protection, and thus it was essential that we test the more well-defined alum adjuvants, Alhydrogel and Adju-Phos, that are used in clinical vaccines.

Adju-Phos has been previously shown to be a successful formulation for the co-delivery of DNA plasmid and protein antigens in that immune responses were elicited to both vaccine components (Kwissa, M. et al., *J. Mol. Med.*, 81:502-510 (2003)). We found that when we combined plasmid DNAs encoding UL5, UL30, and gD2t with the FI-HSV2 in Adju-Phos in a single injection or gave FI-HSV2 in Adju-Phos alone, mice were significantly protected from HSV-2 shedding after a short-term challenge (3 weeks following the last immunization). The addition of the DNAs did not further enhance the protection relative to that elicited by FI-HSV2 alone and surprisingly may have decreased it. This effect was more apparent following a long-term challenge (9 weeks post boost), regardless of whether the DNA was empty vector or encoded viral antigen. Kwissa, et al. showed that although an aluminum phosphate adjuvant formulated with a plasmid DNA that expresses the hepatitis B virus surface antigen (HBsAg) can elicit both HBsAg-specific IFN-γ secreting and cytotoxic CD8+ T cells, coadministration of this formulation with either of 2 heterologous proteins abrogated the CD8+ T cytolytic activity without affecting the levels of IFN-γ positive cells (Kwissa, M. et al., *J. Mol. Med.*, 81:502-510 (2003)). While addition of pVAX DNA to the FI-HSV2/MPL/Adju-Phos vaccine resulted in decreased protective efficacy, total IgG, IgG1, and IgG2a levels were not affected. This suggests that a different immune correlate of protection elicited by the FI-HSV2 may have been decreased by pVAX DNA addition and it is possible that coadministration of the HSV-2 antigen expressing plasmids (UL5, UL30, and gD2t) may have compensated partially for the decrease in protection. In any event, the FI-HSV2MPL/Adju-Phos formulation alone provided impressive levels of protection, with 4 out of the 8 animals at day 2 and 6 out of the 8 animals at day 4 shedding virus at or below the limit of detection.

Accordingly, we compared the efficacy of vaccines containing FI-HSV2 formulated with MPL and Adju-Phos that was given intramuscularly with FI-HSV-2 formulated with MPL and Alhydrogel that was given either intramuscularly or subcutaneously. No deaths occurred in any of the FI-HSV2 groups and genital disease was minimal following challenge with HSV-2. In fact, the mild erythema and swelling seen in a few mice may have been due to the inflammatory response, since half or more of the mice in each group had reductions in virus shedding to levels at or below the detection limit, suggesting that these animals may have sterilizing immunity. To determine if the protection was durable and mice were resistant to a second challenge, they were re-challenged 17 weeks after the first challenge with the same 10×$LD_{50}$ dose of HSV-2 given for the first challenge. It was particularly noteworthy that only 2 of the re-challenged mice in the FI-HSV2 groups had a detectable, low level of virus. Overall, the best protection was seen in the FI-HSV2/Alhydrogel/i.m. group, where 5 of the 8 mice had no detectable virus after the first challenge or after the re-challenge given over 4 months later, and 2 additional mice in this group had very low level shedding after the first challenge and no detectable virus after the re-challenge. These results are also in sharp contrast with our results in mice that were immunized with gD2t DNA or protein in which the mice that were most protected from virus shedding after the first challenge subsequently showed the highest shedding levels after the re-challenge. These exciting results force further consideration of an inactivated virus vaccine that is formulated with appropriate adjuvants.

Recently, we reported the results of experiments in which we evaluated a similar prime-boost strategy for its protective efficacy against i.vag. HSV-2 challenge in guinea pigs, a model in which both acute and recurrent disease could be studied (Morello, C. S. et al., *J. Virol.,* 85:3461-3472 (2011)). Guinea pigs were primed with 3 plasmid DNAs: the gD2t DNA plus UL5 and UL30 or two additional conserved, essential genes of HSV-2 (UL29 and UL52). Both of these groups were subsequently boosted with formalin-inactivated HSV-2 (FI-HSV2) in MPL/Alhydrogel. As a control for the contribution of the FI-HSV2/MPL/alum alone to the protection, a third group was primed with plasmid backbone DNA (pVAX) and boosted with FI-HSV-2. For comparative purposes, a fourth vaccine group received purified gD2t protein plus MPL/Alhydrogel. The UL5, UL30, gD2t DNA-FI-HSV2 group showed a 97% reduction in recurrent lesion days compared with the mock controls. Relative to the other immunized groups, this group also had the highest reduction in days with recurrent disease, and contained the lowest mean HSV-2 DNA load in the dorsal root ganglia. We noted, however, that when the FI-HSV2-MPL-Alhydrogel vaccine was given to the pVAX-primed guinea pigs, with the exception of one "nonresponder" animal in the group, there was complete protection against both acute and recurrent lesion development. This group also had undetectable levels of HSV-2 DNA in the DRG, lower cumulative acute disease scores, and lower numbers of recurrent disease days that were comparable to those for the UL5, UL30, gD2t DNA-FI-HSV2 group. Based upon the success of the FI-HSV2/MPL/Alhydrogel in protecting against virus shedding in mice after challenge and long-term re-challenge and against acute and recurrent disease in the guinea pig, it is possible that this vaccination strategy could provide broad and durable immunity against HSV-2 that is at least as effective as that engendered by attenuated or replication-defective HSV-2 vaccines in animal models. The use of inactivated HSV-2 also eliminates the safety concerns of a attenuated virus vaccine that has the potential for the establishment of latency or recombination with a wild-type virus.

We recently evaluated a DNA prime-inactivated virus boost strategy for its efficacy against intravaginal (i.vag.) HSV-2 challenge in guinea pigs, a model for studying both acute and recurrent disease [19]. Guinea pigs were primed with plasmids encoding gD2t, UL5, and UL30, and then boosted with formalin-inactivated HSV-2 (FI-HSV2) in MPL/Alhydrogel. After i.vag. challenge, this group showed a 97% reduction in recurrent lesion days compared with the mock controls, had the highest reduction in days with recurrent disease, and contained the lowest mean HSV-2 DNA load in the dorsal root ganglia. However, the FI-HSV2/MPL/Alhydrogel component alone (the pVAX empty vector DNA-FI-HSV2 group), with the exception of one "nonresponder" animal, elicited complete protection against both acute and recurrent lesions and detectable HSV-2 DNA in the DRG. Cumulative acute disease scores and numbers of recurrent disease days were also comparable to the UL5, UL30, gD2t DNA-FI-HSV2 group.

Disclosed herein is use of the mouse model to further characterize the immunity and protection afforded by the DNA, FI-HSV2, and adjuvant. We also tested single formulation vaccines in order to simplify and expedite administration and to increase protective responses.

I. Materials and Methods

Vaccines

FI-HSV2 and a formalin inactivated mock preparation (FI-Mock) were prepared from HSV-2 infected or uninfected cells, respectively. Extracellular virus was purified and inactivated as described above [19], and dextran sulfate wash-derived virus was purified as described above for ELISA antigen [19] and then formalin inactivated. Cell associated virus was obtained from the clarified supernatant of HSV-2 infected Vero cells that were sonicated in virus containing extracellular media. The virus was subsequently pelleted and inactivated as described above [19]. No infectious virus was detected after inactivation of any preparation. The preparation used for each experiment is denoted in each figure legend. All FI-HSV2 immunizations contained $10^7$ PFU equivalents and 12.5 µg of MPL (Sigma L6895). Alum was purchased from Thermo Pierce (Imject alum) or Accurate Chemical & Scientific (Adju-Phos and Alhydrogel), with Al doses described in figure legends. Plasmids expressing HSV-2 strain G UL5, UL30, and gD2t (aa 1-327) and the gD2t protein subunit vaccine were constructed and prepared as described above [19].

Mice and Ethics Statement

Female BALB/c mice were purchased from Charles River Laboratories, housed in microisolator cages, and acclimated for at least 2 weeks prior to use. Studies were carried out in strict accordance with the recommendations in the Guide for the Care and Use of Laboratory Animals of the National Institutes of Health. All use of vertebrate animals was approved by the Institutional Animal Care and Use Committee, University of California, San Diego.

Intravaginal HSV-2 Challenge Model

Mice were treated with medroxyprogesterone acetate (Depo-Provera, Sigma M1629) [20] and i.vag. swabbed with a DPBS-moistened polyester tipped swab (MicroPur 1001D, PurFybr Solon, Rhinelander, Wis.) immediately prior to instillation of $5 \times 10^4$ PFU of HSV-2 strain G (ca. 10 $LD_{50}$ doses) by micropipette. The HSV-2 preparation used for challenge was described above [19].

Anogenital disease was scored as described in the FIG. 4A to FIG. 4C legend. Vaginal virus shedding of infectious virus was measured by plaque assay [19], and the limit of sensitivity of each assay is denoted in each figure.

Antibody Quantification: HSV-2 Virion Specific IgG

ELISAs were as described above [19] except that alkaline phosphatase goat anti-mouse conjugates specific for IgG (Sigma), IgG1 or IgG2a (SouthernBiotech) were used, and endpoint titers were Fit Spline interpolated (GraphPad Prism 5.0d).

Neutralizing Antibody Assay

Complement-dependent HSV-2 neutralizing antibodies were measured by plaque reduction assay as described previously [21].

Intracellular Cytokine Staining

Eleven days following the second injection, mice were in vivo restimulated by HSV-2 injection in the footpad. Four days later, splenocytes were stimulated in vitro with 10 PFU per cell of HSV-2 (or an equivalent volume of a mock preparation) for 2 hours. Brefeldin A was added for an additional 8 hours.

For staining, a viability dye (LIVE/DEAD fixable violet; Molecular Probes, Invitrogen) and Fc block (CD16/32; BD) was added for 30 minutes at 4° C. Surface markers CD8-Ax488 (Clone 53-6.7; BD) and CD4-Ax647 (clone RM4-5; BD) were added for 30 minutes at 4° C. and then cells permeabilized and fixed using the BD Cytofix/Cytoperm kit. CD3-PE-Cy5 (Clone 145-2C11; BD) and IFN-γ-PE (Clone XMG1.2; BD) were included in the intracellular stain for 45 minutes at 4° C. Data from 50,000-100,000 live CD3+ T cells were collected on a BD FACSCanto flow cytometer and analyzed with BD FACSDiva software at the Research Flow Cytometry Core Facility of the San Diego Center for AIDS Research and the Veterans Medical Research Foundation and VA San Diego Healthcare System, La Jolla, Calif.

Statistical Analysis

Kruskal-Wallis analysis determined statistical significance for all data groups and Dunn's multiple comparison tests (GraphPad Prism 5.0d) compared all pairs of vaccine groups. Significance scores, (*)P<0.05; ()P<0.01; (*)P<0.001; and (ns), not significant.

J. FI-HSV2 Provides More Consistent Protection Against HSV-2 Genital Disease and Shedding Than gD2 Subunit To examine the protective efficacy of the protein-based "boost" vaccine components, mice were immunized twice with FI-HSV2, FI-Mock, or gD2t protein (each plus MPL/Imject Alum), and i.vag. challenged. FI-HSV2 was completely protective against death (FIG. 4A), with both anogenital disease (FIG. 4B) and vaginal virus shedding (FIG. 4C) significantly reduced below FI-Mock controls (P<0.001). On day 2, vaginal virus titer reductions in the FI-HSV2 mice were reduced 3.6 Logs compared with FI-Mock (P<0.001), although FI-HSV2 and gD2t-mediated protection were variable (FIG. 4C).

Next, we examined the protective efficacy of DNA priming (gD2t DNA alone or with UL5 and UL30 DNAs) followed by the above boost types in MPL/Alum (see FIG. 5A for timeline). Boosting with gD2t or FI-HSV2 gave similar protection against death (FIG. 5B), and compared with pVAX–FI-Mock, all 3 of the FI-HSV2 boosted groups had significant reductions in total disease burden (P<0.01 for the pVAX primed group and P<0.001 for the others) (FIG. 5C) and total virus shedding (P<0.001 for pVAX, P<0.01 for gD2t DNA, and P<0.05 for UL5, UL30, and gD2t DNAs) (FIG. 5D). The gD2t DNA-gD2t protein group also showed significantly reduced disease burden and total virus shedding (P<0.001). Total shedding was lower in FI-HSV2 boosted mice compared to gD2t protein, but the differences were not statistically significant.

K. Co-Immunization with Tested Plasmid DNA and FI-HSV2 in MPL/Adju-Phos as a Single Formulation did not Enhance FI-HSV2 Mediated Protection We next tested whether the vaccine components could be combined into a single formulation, as immune responses were shown to be elicited against both plasmid DNA and protein following codelivery in aluminum phosphate (Adju-Phos) [22]. Mice were injected with FI-HSV2 and MPL/Adju-Phos with or without the UL5, UL30, and gD2t DNAs. Two days post short-term challenge, both vaccinated groups had significantly reduced titers compared to the negative control group (P<0.01 and P<0.001, respectively) (FIG. 6A, left). In the FI-HSV2 alone group, no virus was detected in 4 of the animals on day 2 and in 6 animals on day 4 (FIG. 6A, right).

We next tested the durability of responses, and 2 days post long-term challenge, the FI-HSV2 alone group had a significant 4 Log reduction in titers relative to Mock (P<0.001), with rates of undetectable virus similar to those following short-term challenge (FIG. 6B). On day 4, all of the pVAX FI-HSV2 mice had detectable virus.

Figure 6C:
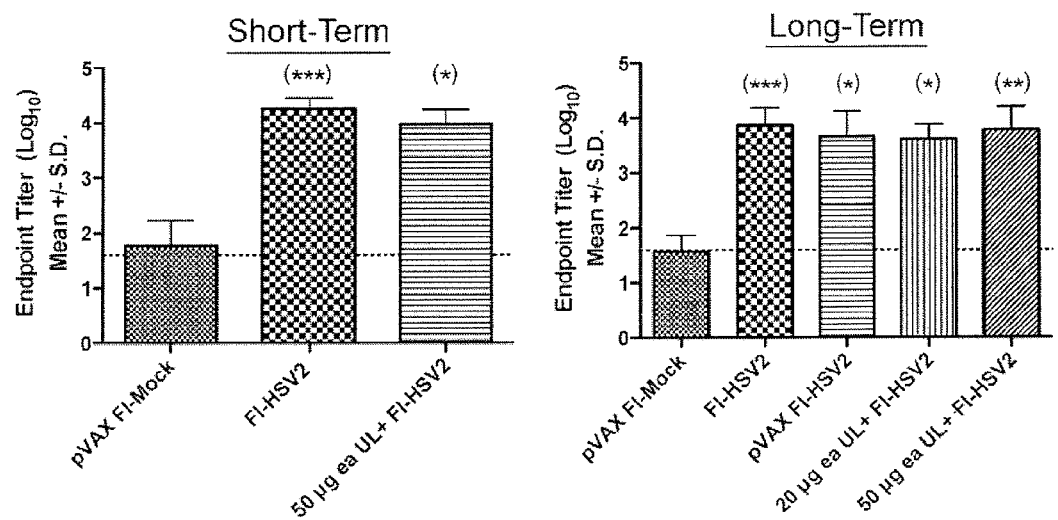
Figure 6D:
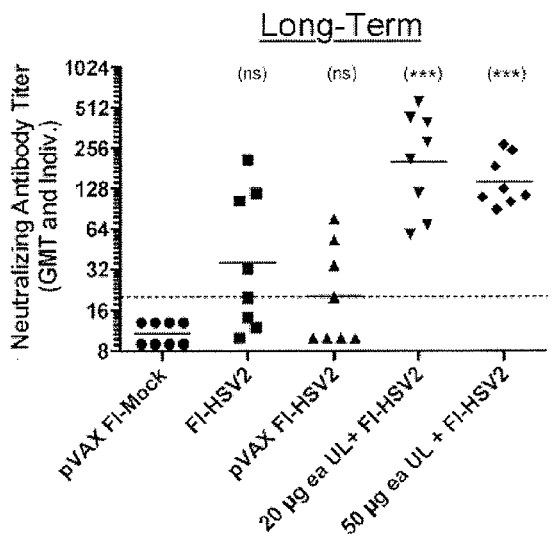

Levels of HSV-2 specific IgG prior to short-term challenge were similarly high in both vaccinated groups, and decreased by 1.5-2.5-fold in the long-term challenge animals (FIG. 6C left versus right). Surprisingly, neutralizing antibody titers prior to long-term challenge were only significantly above Mock in animals that received antigenic DNA (P<0.001 compared to pVAX FI-Mock) (FIG. 6C).

L. Immunization With FI-HSV2 in Alhydrogel or Adju-Phos Adjuvants is Highly Protective Against HSV-2 Replication Following Challenge and Rechallenge The best protection against virus shedding was observed in FI-HSV2MPL/Adju-Phos immunized mice. We next compared two immunization routes, intramuscular (i.m.) and subcutaneous (s.c.), in addition to the adjuvants Adju-Phos and Alhydrogel (a well-defined aluminum hydroxide compared to Imject), and assessed the subsequent protection against a second challenge.

On day 2 postchallenge, virus shedding in all the FI-HSV2 groups was significantly reduced by 3 Logs compared to mock controls (P<0.01 or P<0.05) (FIG. 7A, left). Half or more of the mice in each FI-HSV2 group had shedding levels at or below the detection limit. By day 4 postchallenge, no or very low level virus was detectable in any of the FI-HSV2 immunized mice (FIG. 7A, right).

Figure 11:
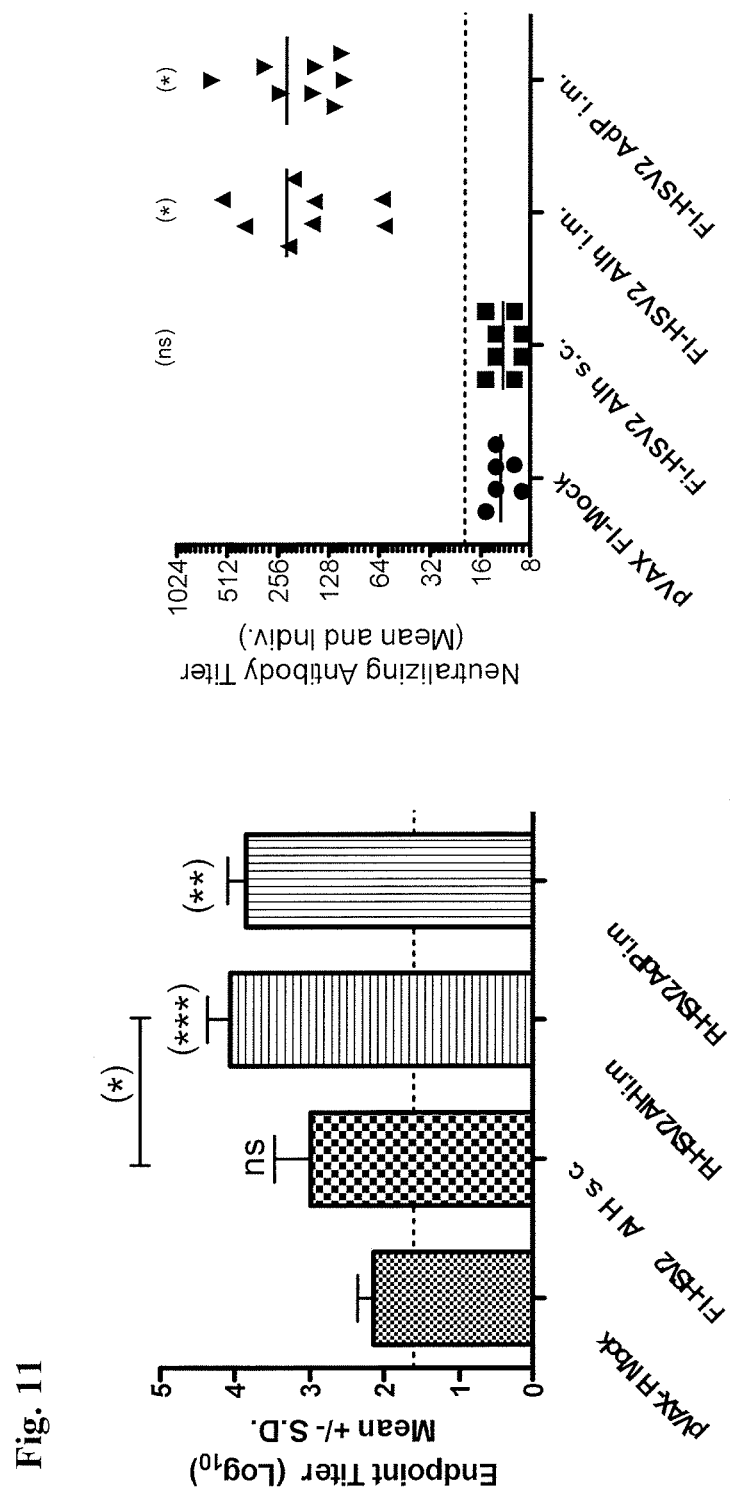
FIG. 11. Total virion-specific IgG, and neutralization titers.
Figure 12:
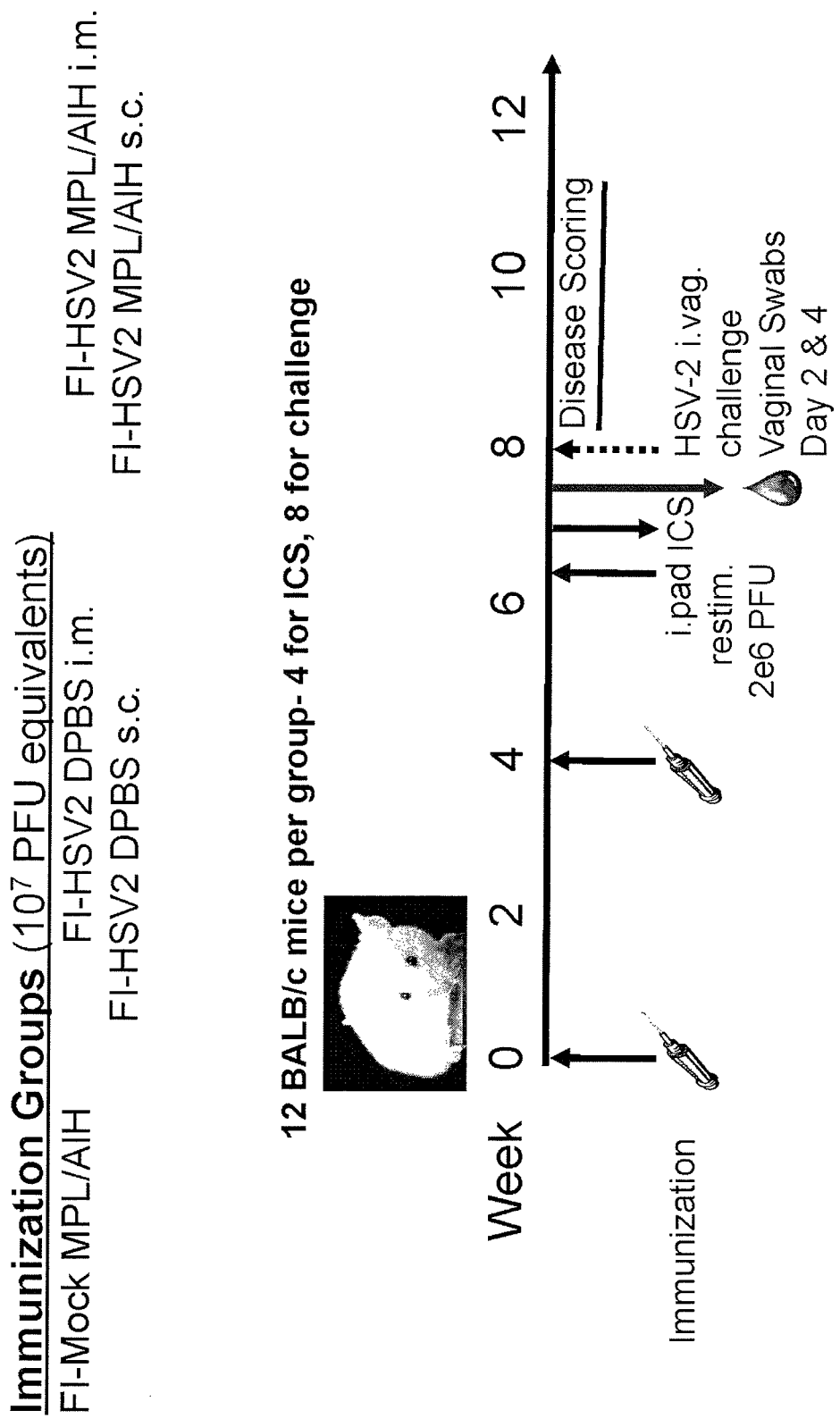
FIG. 12. Immunization groups and timeline for mouse experiment evaluating the adjuvant effect of monophosphoryl lipid A (MPL) together with Alhydrogel Alum (AlH) for intramuscular (i.m.) or subcutaneous (s.c.) immunization when formulated with formalin inactivated HSV-2 (FI-HSV2). Syringes indicate weeks of vaccination, the blood drop indicates the week of blood sampling, blue arrows indicate weeks of in vivo restimulation (Week 6.5) or harvest (Week 7) for intracellular cytokine staining (ICS) assay, and the dotted arrow indicate the week of lethal HSV-2 challenge. DPBS, Dulbecco's phosphate buffered saline. Resulting data are represented by FIG. 8A to FIG. 8C and FIG. 9A to FIG. 9C.
Figure 13:
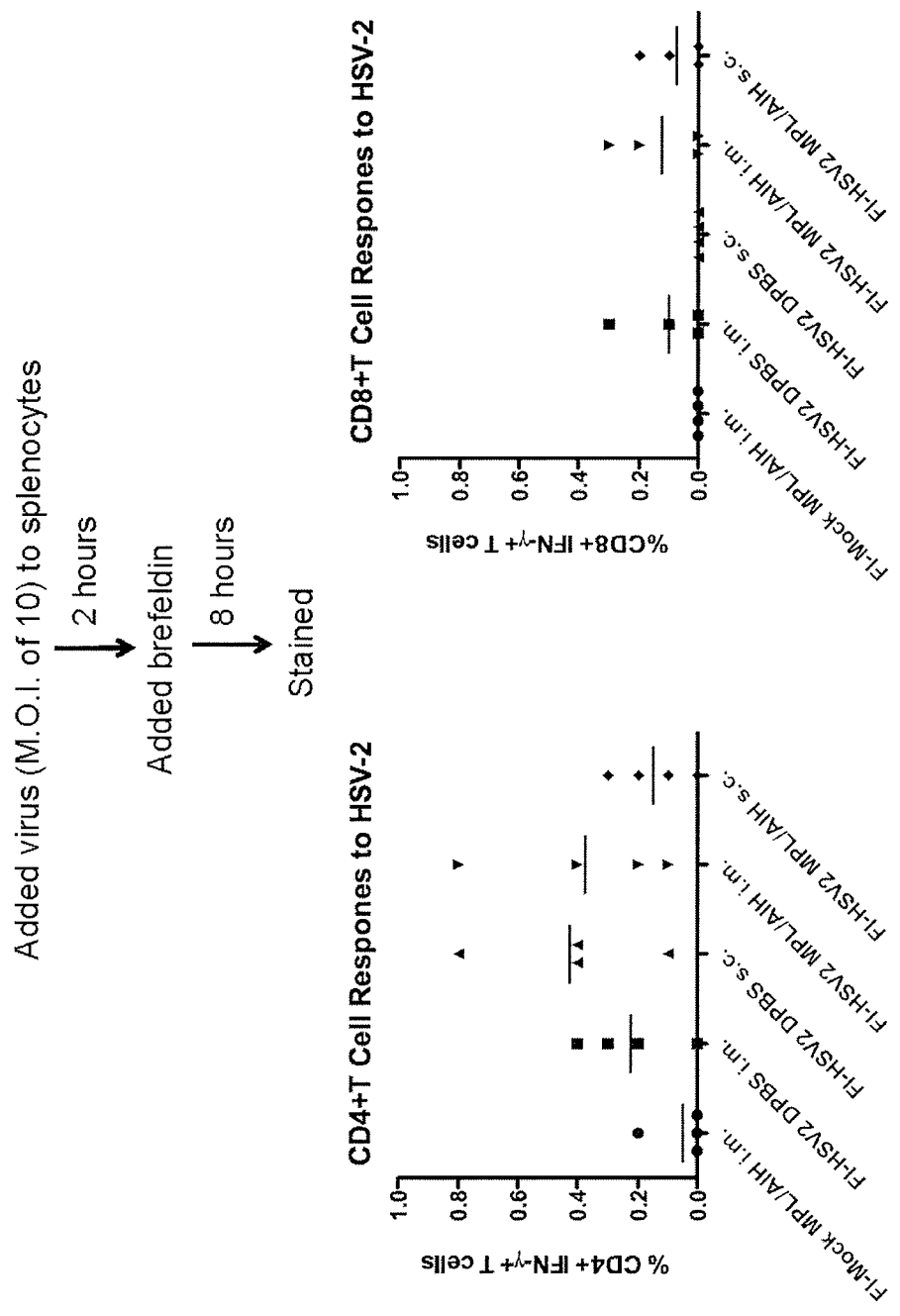
FIG. 13. Experimental method for intracellular cytokine staining assay. Data shown corresponds to FIG. 9C, with the figure also showing the background staining levels.
Figure 14:
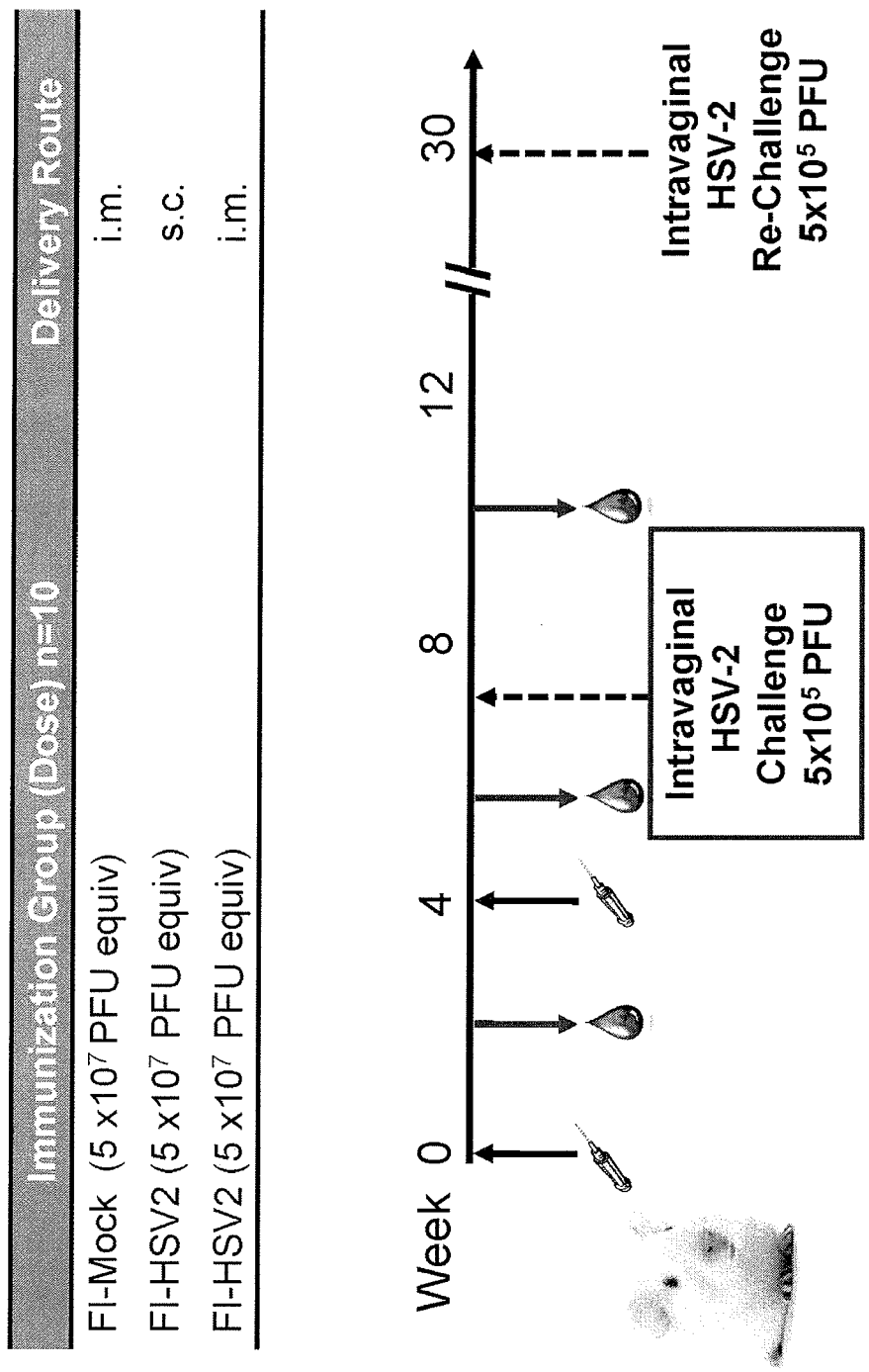
FIG. 14. Immunization groups and timeline for guinea pig experiment evaluating protective efficacy against challenge or rechallenge with HSV-2. Formalin inactivated (FI−) HSV-2 or Mock virion (FI-Mock) were formulated with monophosphoryl lipid A and Alhydrogel and then administered by intramuscular (i.m.) or subcutaneous (s.c.) routes. Syringes indicate weeks of vaccination, blood drops indicate weeks of blood sampling, and dotted arrows indicate weeks of sublethal HSV-2 challenge. PFU equiv, PFU equivalents.
Figure 15:
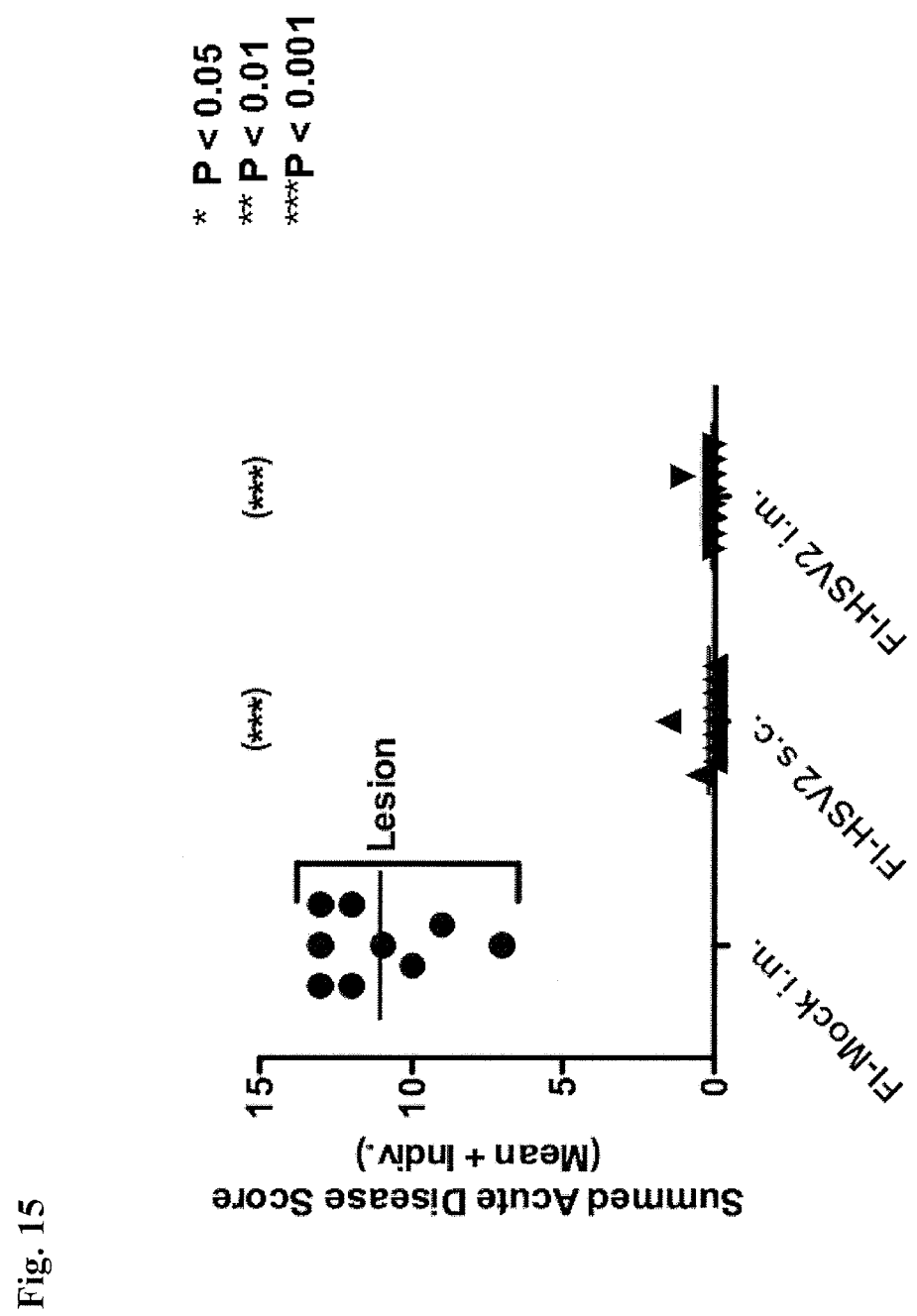
FIG. 15. Protection against anogenital disease of immunized guinea pigs during primary (acute phase) HSV-2 infection. Each symbol represents the summed disease score of an individual (Indiv.) guinea pig from days 0 through 14 post intravaginal challenge and bars represent group means. Symbols for the guinea pigs that showed at least one lesion day are bracketed. Statistical significances by Kruskal-Wallis and Dunn's multiple comparison tests are indicated by asterisks with significance levels shown in the legend.
Figure 16:
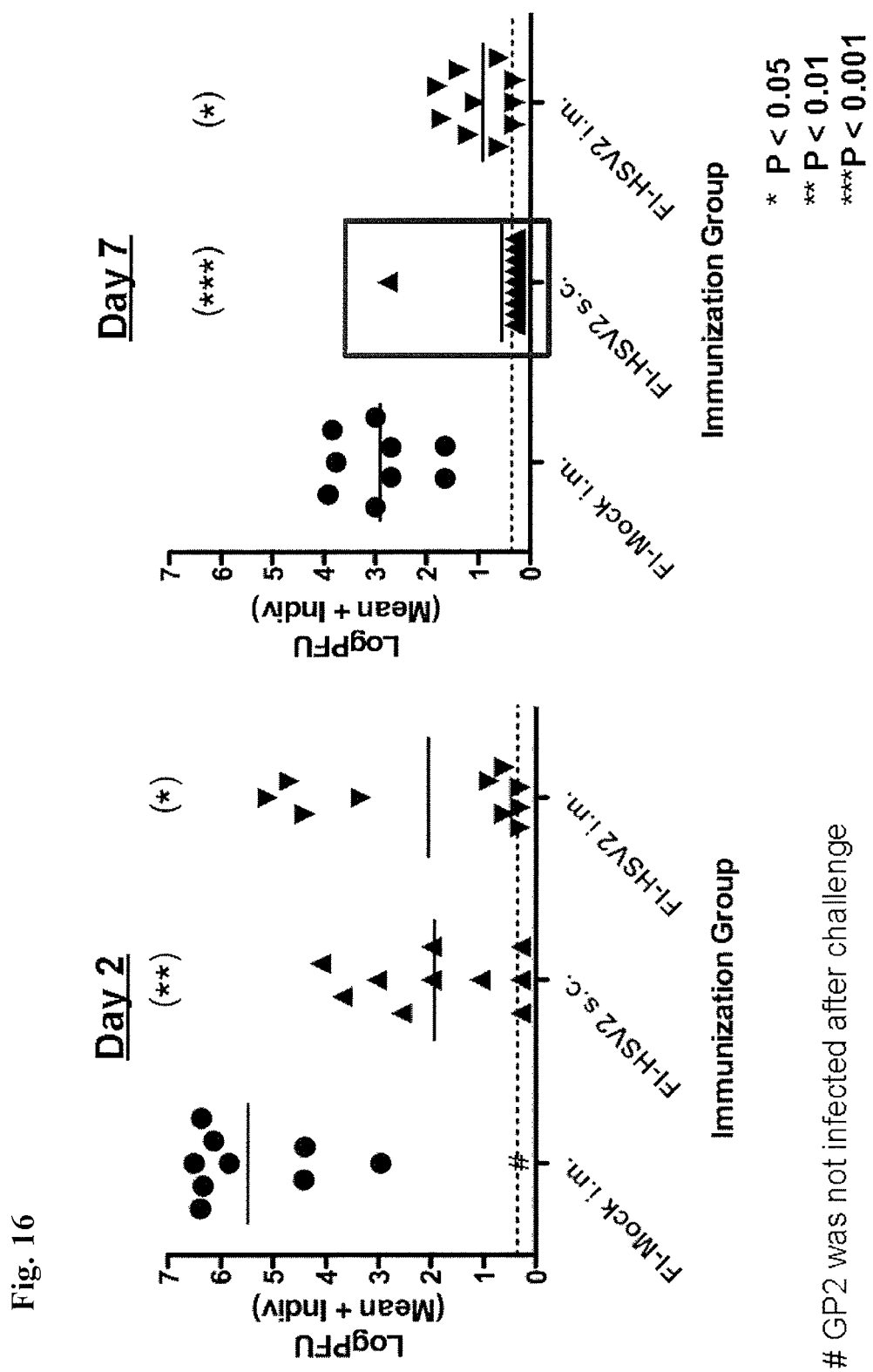
FIG. 16. Vaginal HSV-2 shedding levels on days 2 and 7 postchallenge. Intravaginal swabs were performed and stored for quantification of infectious virus by plaque assay. Each symbol represents the Log PFU/swab of an individual (Indiv.) guinea pig and bars represent group means. Statistical significances by Kruskal-Wallis and Dunn's multiple comparison tests are indicated by asterisks with significance levels shown in the legend. Dotted lines indicate the assay limit of detection, and the box indicates nearly complete clearance of virus in this immunization group on day 7.
Figure 17:
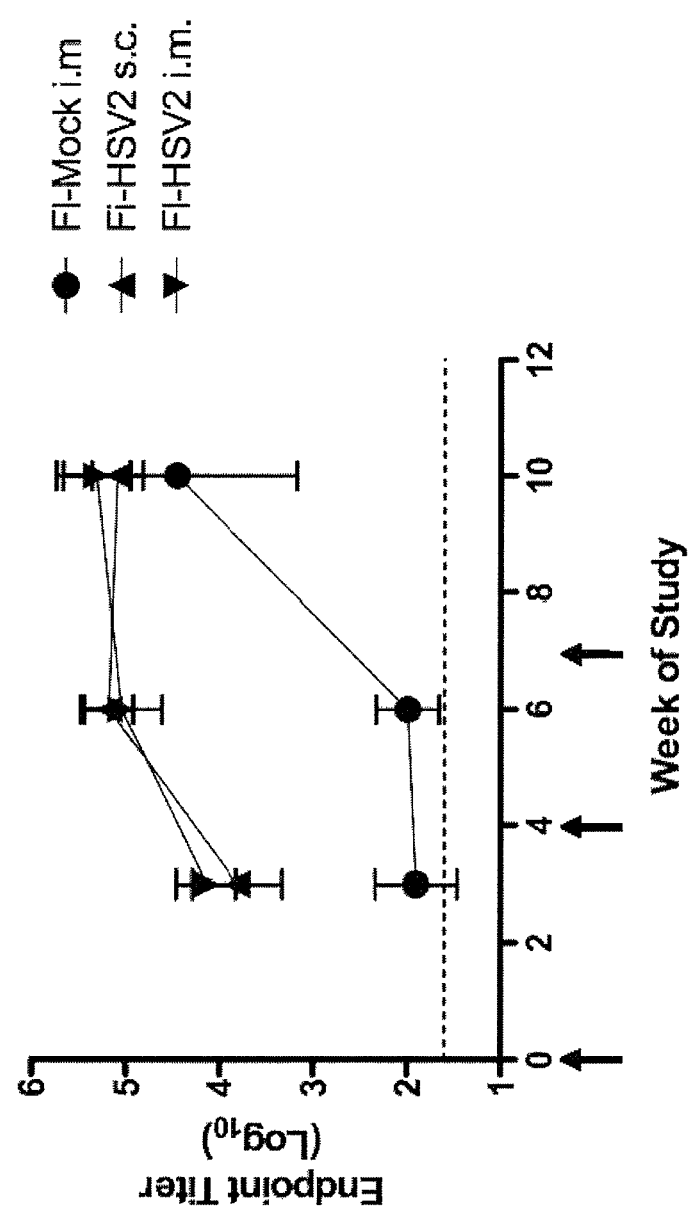
FIG. 17. HSV-2 virion specific IgG as measured by ELISA using dextran sulfate wash derived HSV-2. Each symbol represents the group mean Log 10 Endpoint titer and bars indicate SEM. Arrows show weeks of immunization (Weeks 0 and 4) or week of challenge (Week 7).
Figure 18:
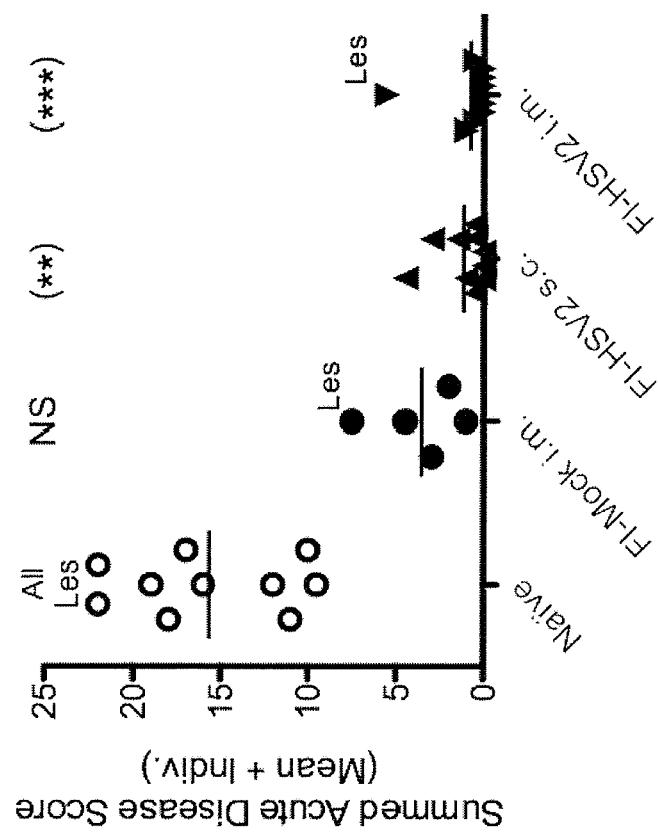
FIG. 18. Protection against anogenital disease of immunized guinea pigs following re-challenge with HSV-2. Each symbol represents the summed disease score of an individual (Indiv.) guinea pig from days 0 through 14 post intravaginal re-challenge (given 18 weeks following the first challenge) and bars represent group means. Symbols of guinea pigs that showed at least one lesion day are indicated (Les), with all of the animals in the Naïve group showing lesions (All Les). Statistical significances by Kruskal-Wallis and Dunn's multiple comparison tests are indicated by asterisks with significance levels as follows: *$P<0.05$; $P<0.01$; *$P<0.001$; NS, not significant.
Figure 19:
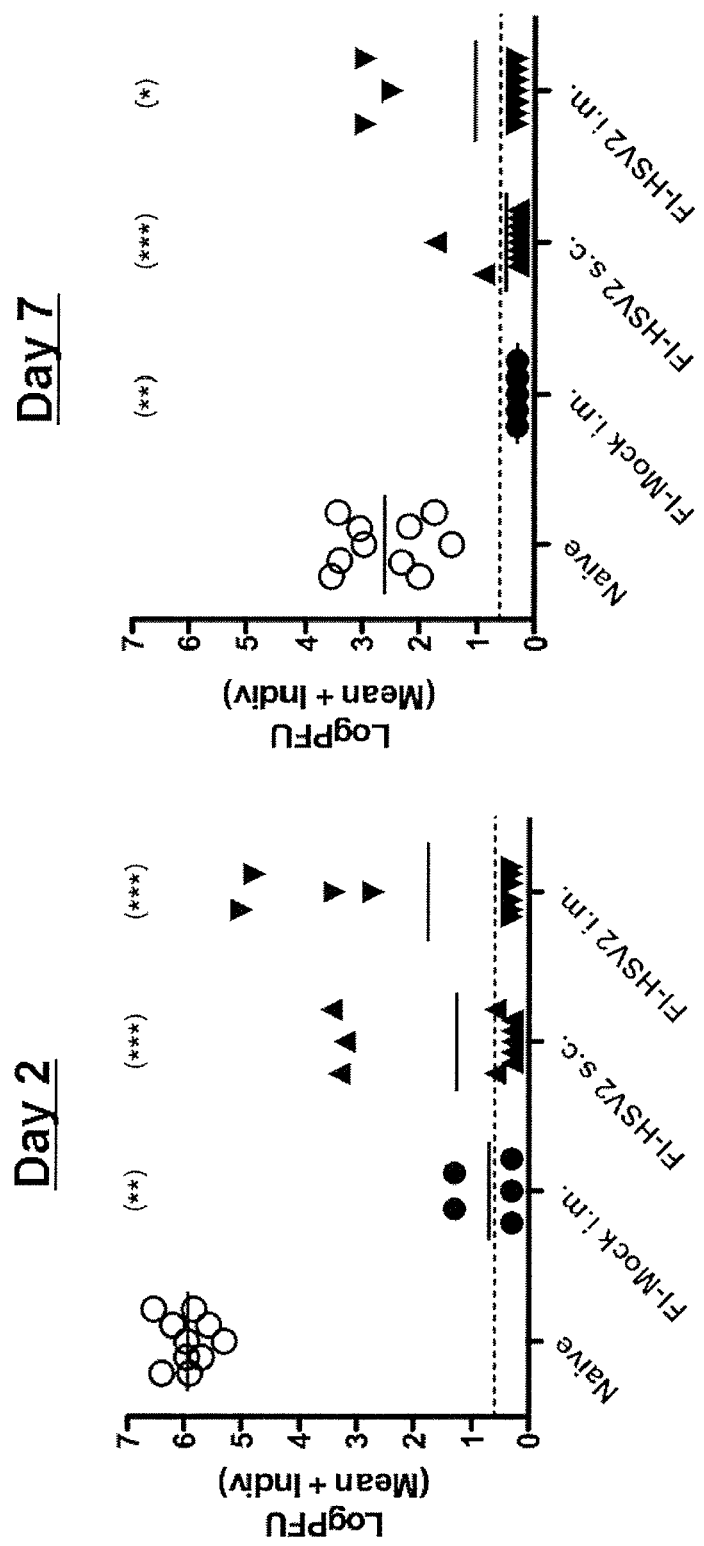
FIG. 19. Vaginal HSV-2 shedding levels on days 2 and 7 post re-challenge. Intravaginal swabs were performed and stored for quantification of infectious virus by plaque assay. Each symbol represents the Log PFU/swab of an individual (Indiv.) guinea pig and bars represent group means. Dotted lines represent the assay limit of detection. Statistical significances by Kruskal-Wallis and Dunn's multiple comparison tests are indicated by asterisks with significance levels as follows *$P<0.05$; $P<0.01$; *$P<0.001$.
Figure 20:
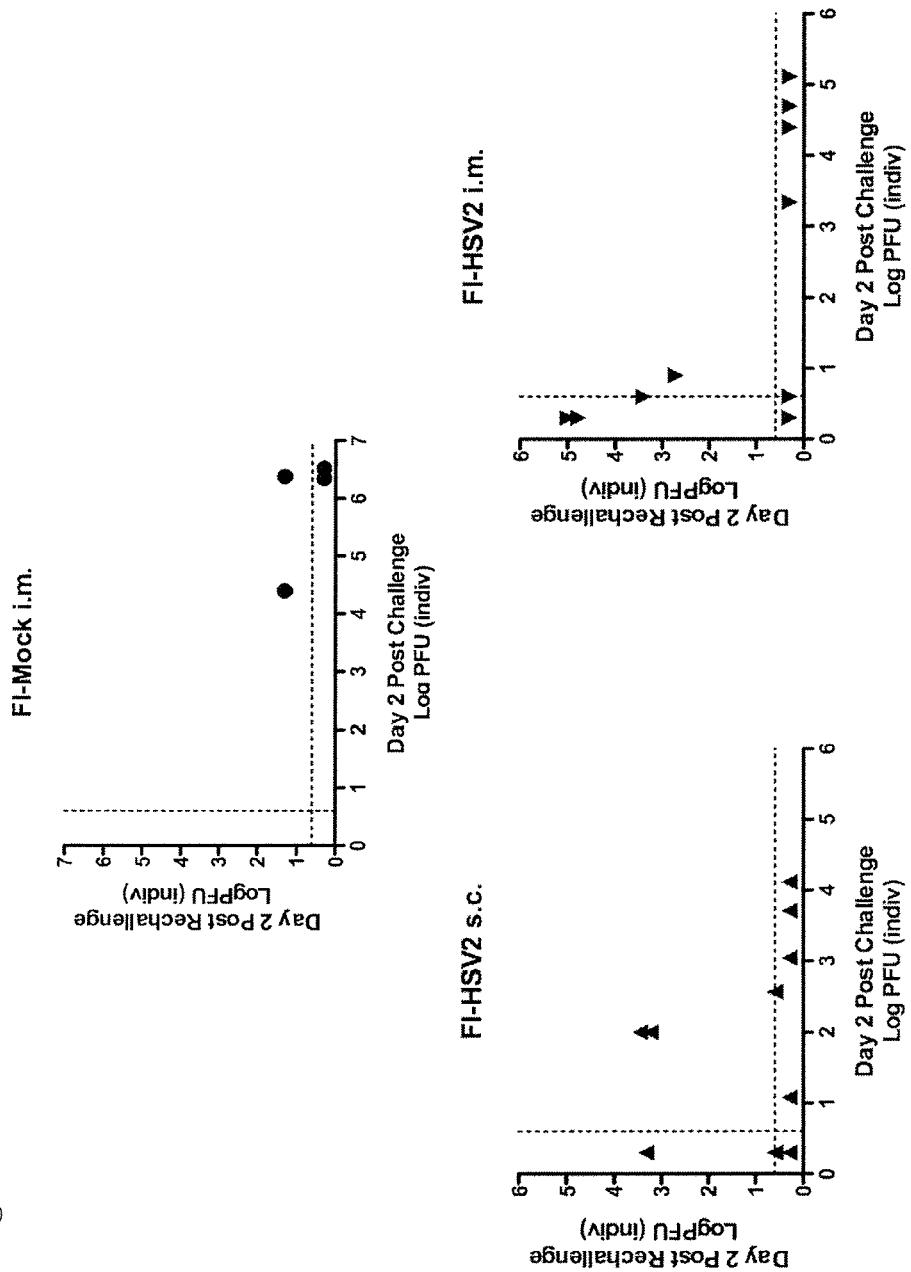
FIG. 20. XY plot of the vaginal HSV-2 shedding for individual (Indiv.) guinea pigs on day 2 post challenge (x-axis) and day 2 post re-challenge (y-axis), with values calculated as the Log 10 PFU per swab. Dotted lines indicate assay limits of sensitivity.
Figure 21:
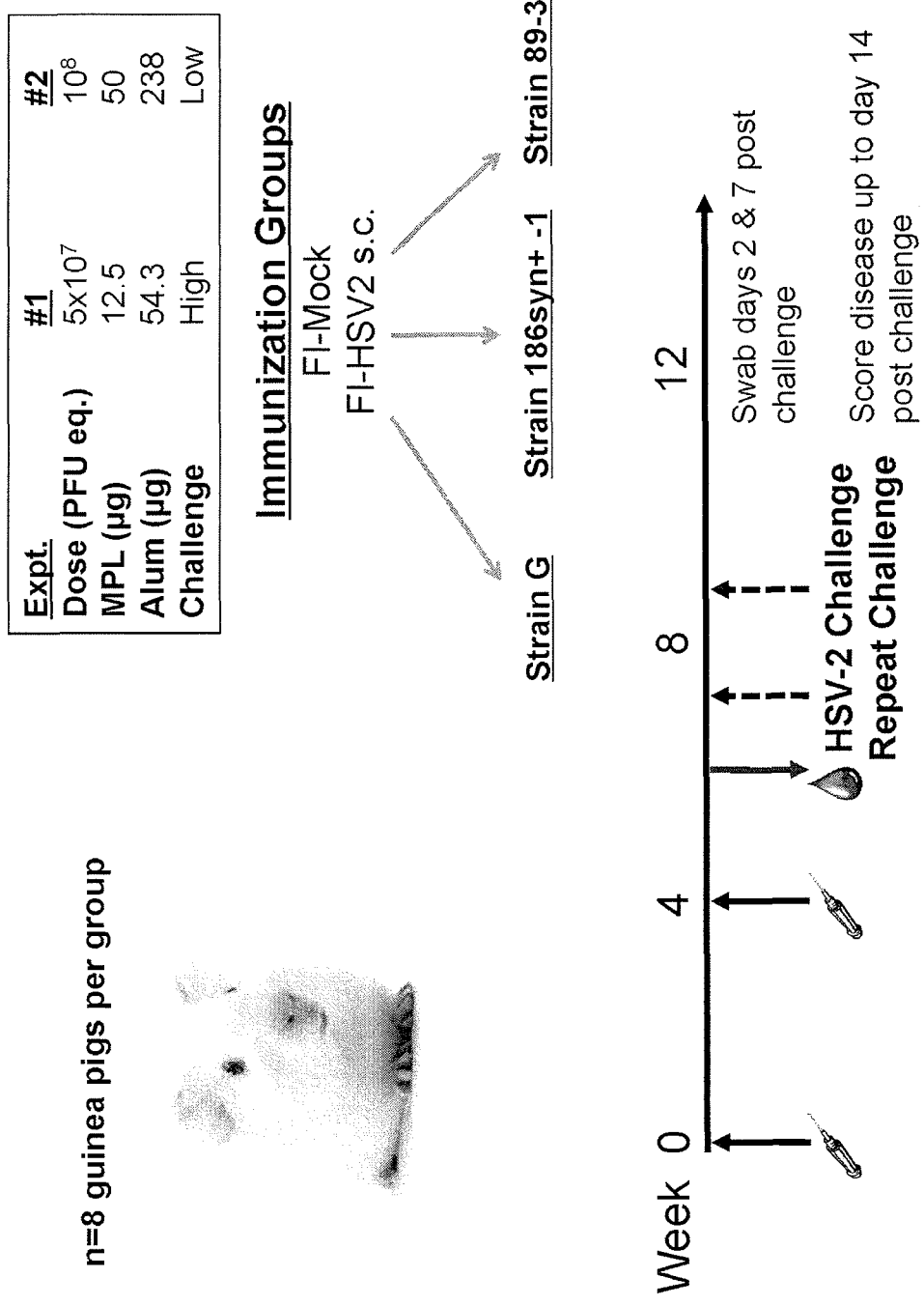
FIG. 21. Experimental scheme and timeline for testing the efficacy of formalin inactivated HSV-2 (FI-HSV2) to protect against the homologous (Strain G) or heterologous (Strain 186syn+−1 and Strain 89-390) HSV-2 strains isolated from the U.S. Syringes indicate weeks of vaccination, the blood drop indicate the week of blood sampling, and dotted arrows indicate weeks of sublethal HSV-2 challenge (Week 7) or repeat (Week 9). Note that repeat challenge was performed only on animals that had no detectable HSV-2 from intravaginal swabs on day 2 postchallenge. PFU eq., PFU equivalents; MPL, monophosphoryl lipid A; Alum, Alhydrogel; High, $5\times10^5$ PFU challenge; Low, $2.5\times10^4$ PFU challenge; FI-Mock, formalin inactivated mock virion preparation; s.c., subcutaneous FIG. 22. Protection against anogenital disease of immunized guinea pigs, with challenge and repeat challenge data combined. Each symbol represents the summed disease score of an individual (Indiv.) guinea pig from days 0 through 14 post intravaginal challenge and bars represent group means. Disease scoring criteria are listed in the legend. Symbols of guinea pigs that showed at least one lesion day are bracketed. Statistical significances by Kruskal-Wallis and Dunn's multiple comparison tests are indicated by asterisks with significance levels indicated in the legend. No FI-HSV2 immunized animals developed lesions.
Figure 22:
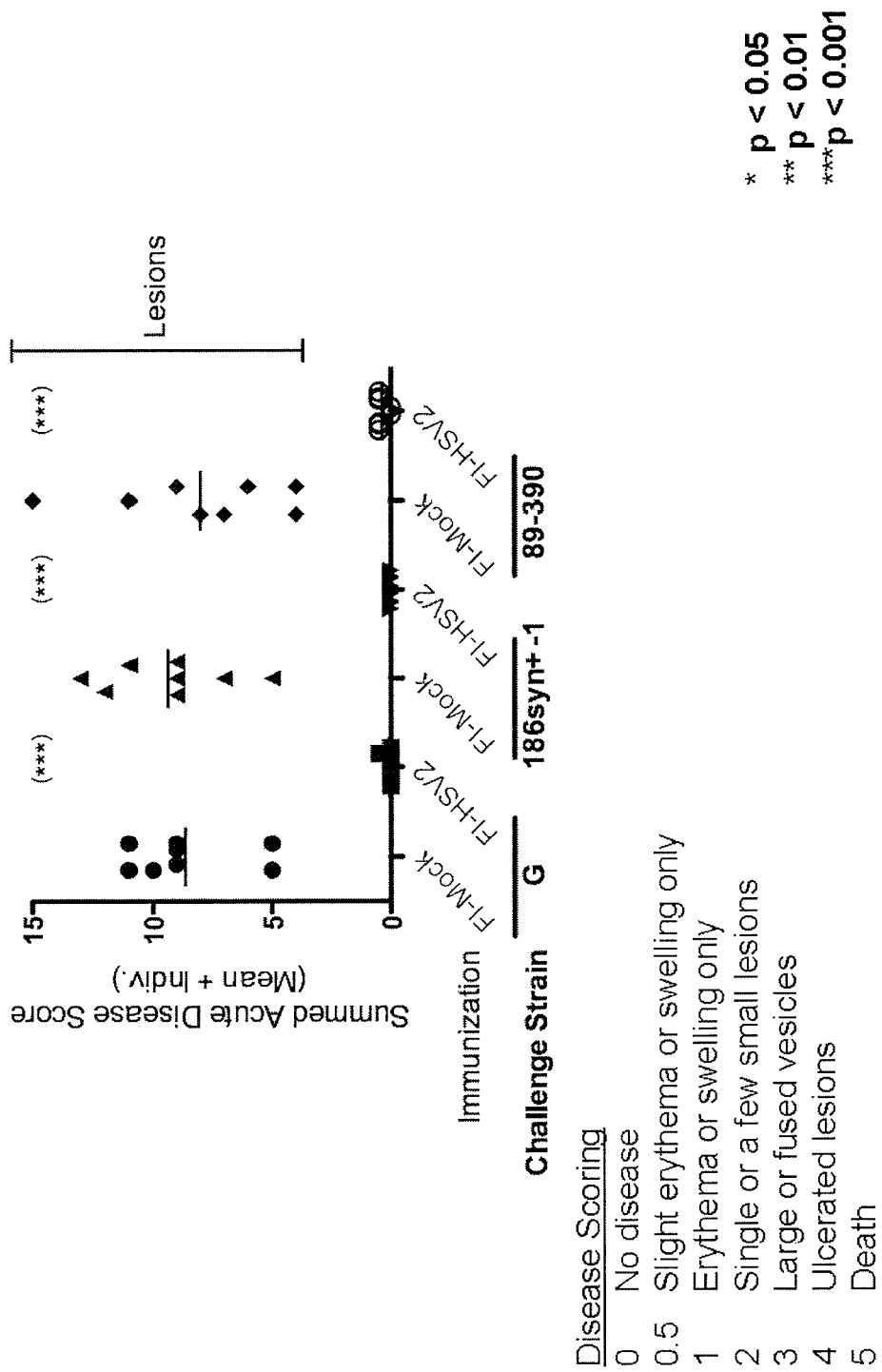
Figure 23:
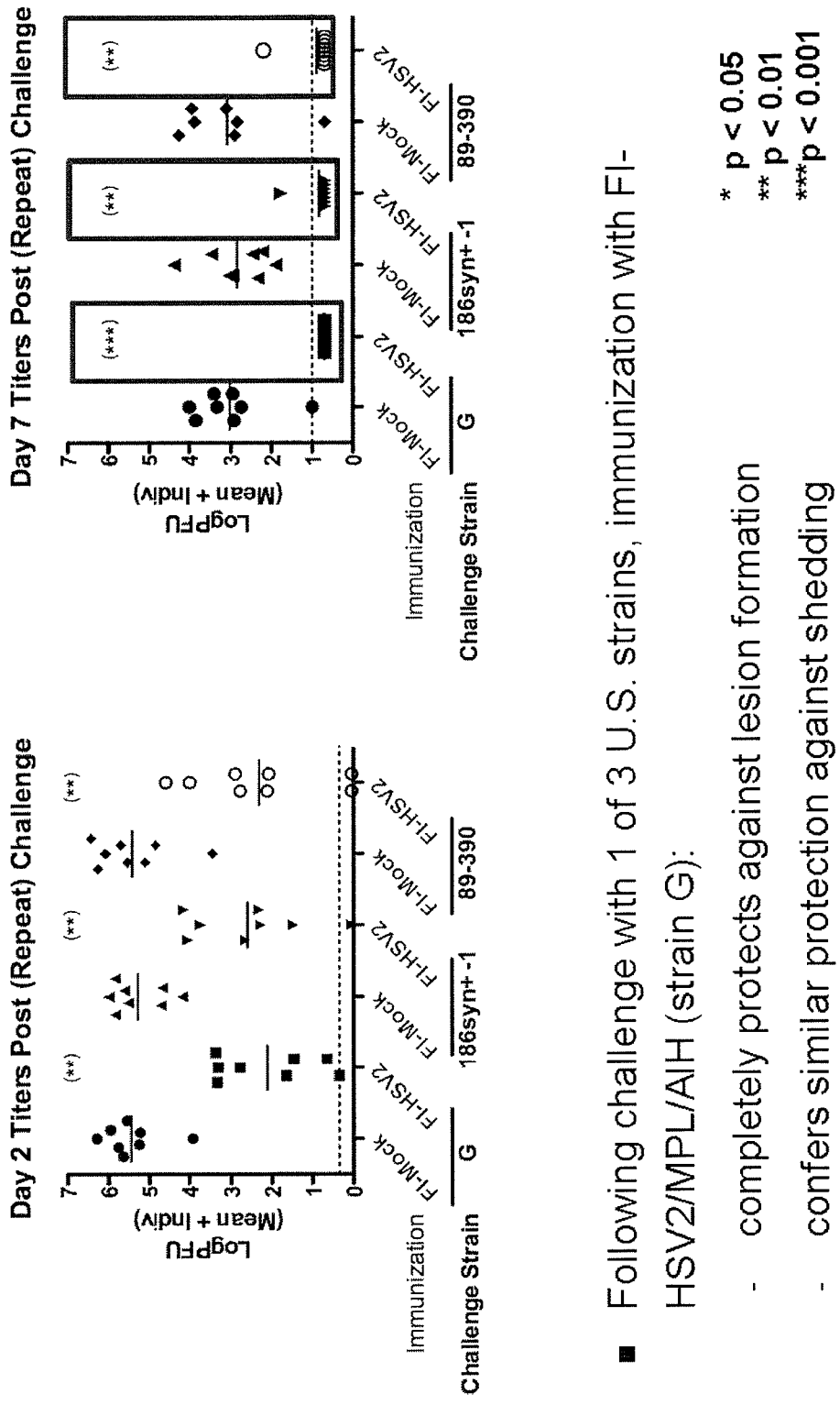
FIG. 23. Vaginal HSV-2 shedding levels on days 2 and 7 post challenge with the homologous (Strain G) or with heterologous (186syn+−1 and 89-390) strains of HSV-2. Intravaginal swabs were performed and stored for quantification of infectious virus by plaque assay. Each symbol represents the Log PFU/swab of an individual (Indiv.) guinea pig and bars represent group means. Dotted lines represent the assay limit of detection. Boxes indicate nearly complete virus clearance by day 7. Statistical significances by Kruskal-Wallis and Dunn's multiple comparison tests with significance levels indicated in the legend.

Mice immunized i.m. with FI-HSV2 in Alhydrogel or Adju-Phos had similar high levels of virus-specific IgG that were statistically greater than Mock (P<0.001 and P<0.01, respectively) (FIG. 11, left). FI-HSV2 in Alhydrogel i.m. elicited significantly higher IgG compared to s.c. (P<0.05). Although all groups were significantly protected against shedding, FI-HSV2 given i.m., but not s.c., elicited significant neutralizing antibody titers (P<0.01) (FIG. 11, right).

Nearly half of the animals receiving FI-HSV2 had no detectable shedding, so we next tested whether this high level protection would also be effective against re-challenge. After long-term rechallenge, only 2 of 23 mice immunized with FI-HSV2 had detectable vaginal virus (FIG. 7C y-axis) with levels that were low compared with naïve controls (FIG. 7B). Strikingly, 5 of 8 FI-HSV2/Alhydrogel/i.m. mice had no detectable virus on day 2 postchallenge or post-rechallenge (FIG. 7C, middle).

Figure 8A:
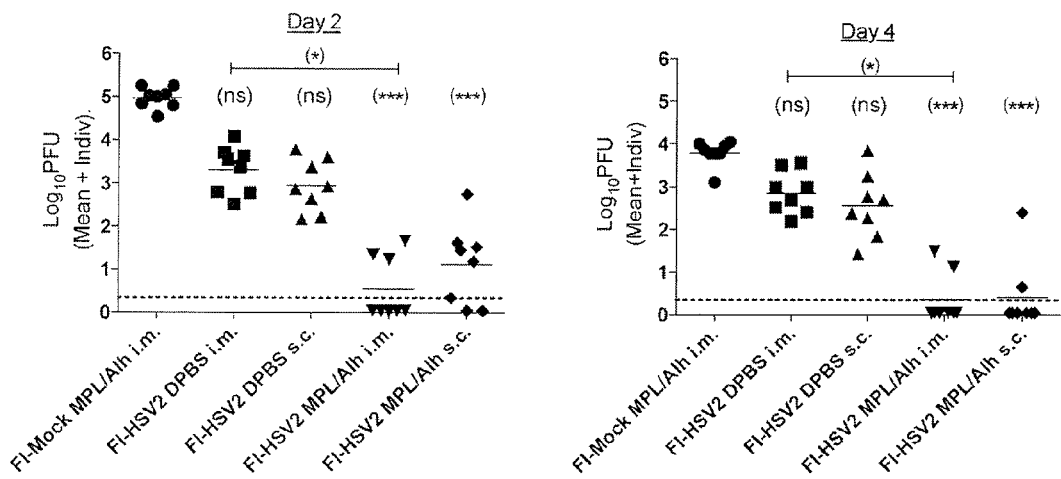
FIG. 8A to FIG. 8C. Immunization with FI-HSV2 formulated in MPL/Alhydrogel is required for protection against HSV-2 replication, disease, and latent viral load in the DRG. Groups of mice (n=8) were immunized s.c. or i.m. with dextran sulfate-derived FI-HSV2 (1 µg of protein) in either MPL and Alhydrogel (equivalent to 54 µg of Al) or DPBS. In addition, a negative control group received a volume of FI-Mock equal to the FI-HSV2 used in the other groups in MPL and Alhydrogel. Two injections were given 4 weeks apart, and mice were challenged 3 weeks later.

M. The Addition of LPS-Derived Adjuvant/Aluminum-Based Mineral Salt Adjuvant (E.G. MPL/Alhydrogel) to the FI-HSV2 Vaccine is Required for Protection Against HSV-2 Replication, Disease, and Latent Viral Load in the DRG We next determined whether formulation of FI-HSV2 in MPL/Alhydrogel was necessary for optimal protection and confirmed the above effect of immunization route on protection. On day 2 postchallenge, mice immunized with FI-HSV2 in MPL/Alhydrogel had statistically significant ca. 4 Log reductions in mean virus titer relative to Mock (P<0.001), with 5 or 2 of 8 animals immunized i.m. or s.c. having no detectable virus, respectively (FIG. 8A, left). By contrast, shedding levels following immunization with FI-HSV2 in DPBS were not significantly different than Mock. In the i.m. injection groups, MPL/Alhydrogel provided significantly lower virus levels than did DPBS (P<0.05). On day 4, the FI-HSV2 MPL/Alhydrogel groups had very similar mean titers and 6 of 8 animals each with no detectable virus (FIG. 8A, right).

Figure 8B:
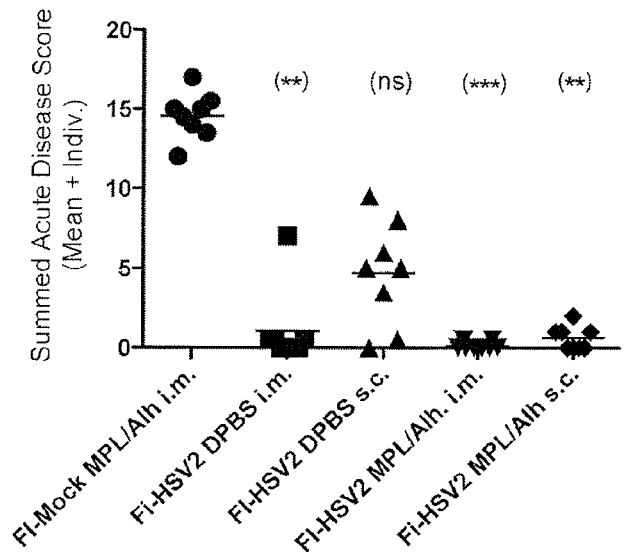

Mice immunized i.m. with FI-HSV2MPL/Alhydrogel were completely protected against any disease beyond very slight erythema (P<0.001) (FIG. 8B). While the FI-HSV2 MPL/Alhydrogel s.c. and DPBS i.m. groups were also significantly protected from disease relative to controls (P<0.01), the DPBS s.c. group was not. Two mice died in each of the DPBS groups.

Figure 8C:
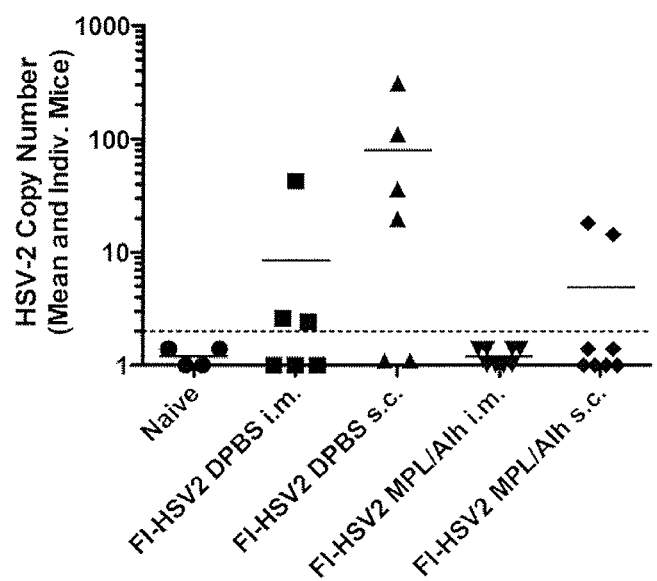

Four weeks postchallenge, DRG from the surviving mice and 4 naïve mice were harvested to quantify latent HSV-2 DNA levels by real-time qPCR (FIG. 8C). Interestingly, animals immunized i.m. with FI-HSV2 in MPL/Alhydrogel had no detectable HSV-2 DNA. Only two mice from the FI-HSV2MPL/Alhydrogel s.c. group had detectable HSV-2 DNA, with the mouse with 14 genome copies having the highest titers on day 2 and the mouse with 18 copies having undetectable virus.

Figure 9A:
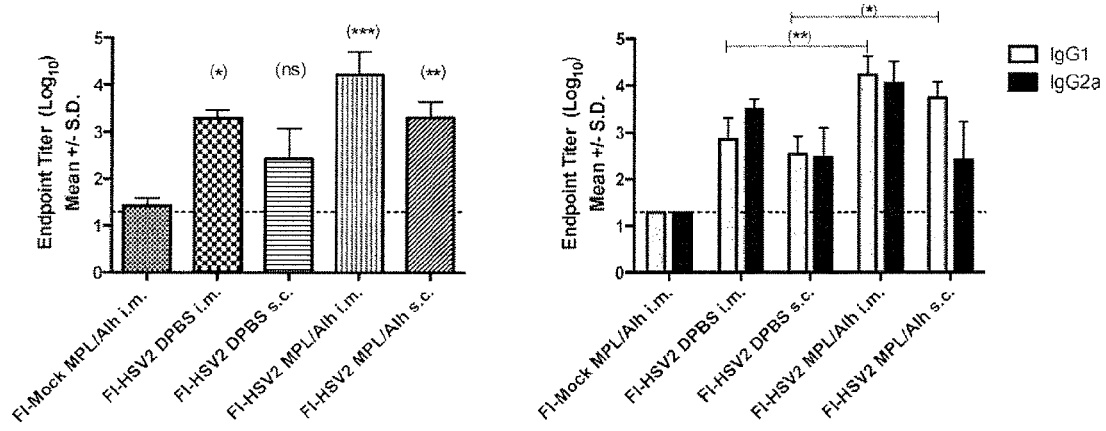
FIG. 9A to FIG. 9C. Virus specific antibody and T cell levels in mice immunized s.c. or i.m. with FI-HSV2 in MPL/Alhydrogel or DPBS.

I.m. immunization with FI-HSV2MPL/Alhydrogel elicited the highest titers of virus specific total IgG (FIG. 9A, left) and neutralizing antibodies (FIG. 9B), with IgG titers approximately 10-fold higher than in the FI-HSV2/DPBS i.m. group (FIG. 9A, left). FI-HSV2 DPBS given i.m., but not s.c., elicited significant IgG levels relative to controls (P<0.05). Addition of MPL/Alhydrogel to the FI-HSV2 s.c. immunization increased IgG levels by 7.6-fold and to a significant level over Mock (P<0.01). We tested whether the injection route or addition of MPL/Alhydrogel biased the HSV-2 specific antibody response toward a Th1 (IgG2a) or Th2 (IgG1) response. Addition of MPL/Alhydrogel to the FI-HSV2 groups gave significantly increased IgG1 responses compared to their respective DPBS groups (i.m.: P<0.01 and s.c.: P<0.05), suggesting a Th2 bias (FIG. 9A, right).

Figure 9B:
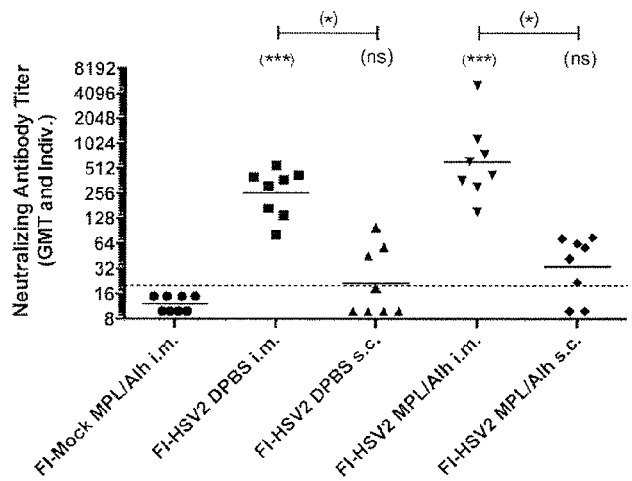

FIG. 9B shows that the highest levels of neutralizing antibody titers resulted from i.m. vaccination with FI-HSV2 (P<0.001 compared to FI-Mock). Addition of MPL/Alhydrogel i.m. gave a 2.4-fold increase (not significant) in neutralization titers compared to the DPBS i.m. group, and neither s.c. group was statistically different than FI-Mock.

Figure 9C:
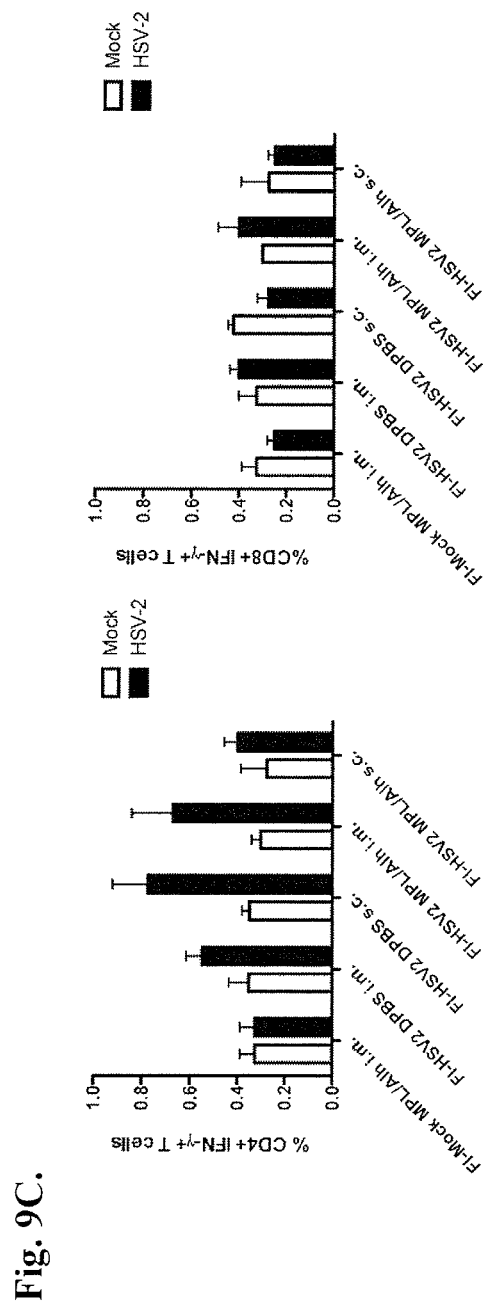
Figure 10:
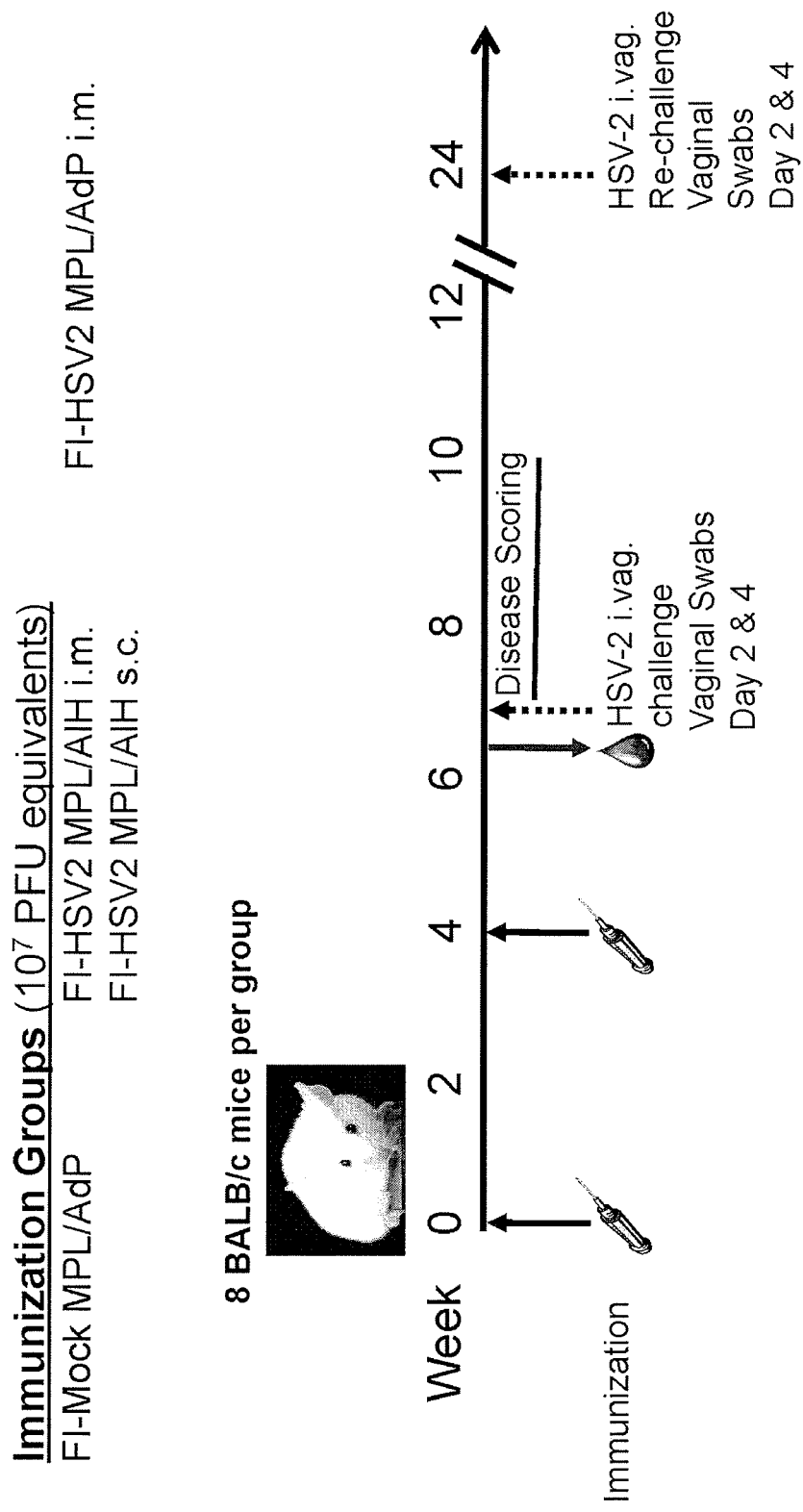
FIG. 10. Immunization groups and timeline for mouse experiment evaluating protective efficacy against HSV-2 challenge or re-challenge. Adjuvants Adju-Phos (AdP) or Alhydrogel (AlH) were each tested in formulations with formalin inactivated HSV-2 (FI-HSV2) and monophosphoryl lipid A. Vaccines were administered by intramuscular (i.m.) or subcutaneous (s.c.) routes in the adjuvants and routes shown. Syringes indicate weeks of vaccination, the blood drop indicates the week of blood sampling, and dotted arrows indicate weeks of lethal HSV-2 challenge. Resulting data are represented by FIG. 7A to FIG. 7C.

Finally, an ICS assay was performed to analyze IFN-γ+ T cell responses to the inactivated virus (FIG. 9C). Low levels of HSV-2 specific CD4+ IFN-γ+ T cells were detected in the splenocytes of vaccinated and in vivo restimulated mice (net mean range from 0.15 to 0.43%), compared to the control group (net mean=0.05%). However, CD8+ T cell responses were undetectable above background. Stimulation of splenocytes with a pool of overlapping peptides spanning gD2 did not result in any CD4+ or CD8+ T cell responses above background.

N. Analysis

In this study, it was determined that the best protection against HSV-2 disease and shedding was obtained by i.m. injection of inactivated HSV2/LPS-derived adjuvant/aluminum-based mineral salt adjuvant (e.g. FI-HSV2/MPL/Alhydrogel). This vaccine prevented HSV-2 disease other than mild inflammation, reduced virus shedding by 3 to 4 Logs, protected the majority of animals from detectable vaginal virus even after two challenges, and provided complete protection against HSV-2 DNA in DRG. The high level efficacy in these experiments was dependent upon formulation with MPL/Alhydrogel or MPL/Adju-Phos. The long-term challenge experiment with FI-HSV2/MPL/Adju-Phos demonstrated that responses were durable, as similar high level protection was observed at 3 and 9 weeks post-boost.

Immunization with FI-HSV2/MPL/Alhydrogel by different routes affected the immune response, but not the resulting high level protection (FIGS. 7-9, 11). In 2 independent experiments, i.m. immunization elicited significantly higher levels of virus neutralizing antibodies compared to the s.c. and mock groups (FIGS. 11 and 9B). Clinical studies of vaccines for influenza [23], diphtheria and tetanus (DT) [24], and others [25, 26] have compared i.m. versus s.c. administration. In general, similar levels of antibody titers were attained with either route, but overall fewer adverse events (local and/or systemic) were observed following i.m. injection.

Similar to a recent study comparing HSV-2 subunit vaccines [27], we found that no single measure of immunity correlated with protection, including neutralizing antibody, total IgG, IgG subtypes, or T cell responses. We found that FI-HSV2/MPL/Alhydrogel i.m. elicited levels of virus specific CD4+ IFN-γ+ T cells similar to those observed in BALB/c mice immunized with replication-defective HSV-2 vaccines as measured with a similar assay [21, 28]. In general, FI-HSV2/MPL/Alhydrogel immunization consistently resulted in ca. 4 Log reductions in peak virus replication, reductions similar to the those in mice immunized with replication-defective virus vaccines [28], subunit vaccines with experimental adjuvants [29], and live attenuated vaccines [30, 31]. Most notably, the majority of FI-HSV2/MPL/Alhydrogel i.m. immunized mice had no detectable virus shedding, suggesting they may have had sterilizing immunity.

Compared with a single glycoprotein subunit, a potential advantage of a whole virus vaccine is that it delivers a broad diversity of antibody targets in the context of the virus particle. We considered the possibility that FI-HSV2 mediated protection was largely due to responses against the FI-HSV2 derived gD2. However, the cell associated FI-HSV2 used in FIG. 4A to FIG. 4C contained 2.9 µg of gD2 compared to 5 µg in the gD2t protein group, indicating that gD2 was not the key to protection. Subsequent FI-HSV2 preparations derived from dextran sulfate washes contained only 20 ng gD2 per dose and elicited the highest protection. Thus, the optimal protection from FI-HSV2 was not likely due to the nanogram quantities of gD2 protein but rather the total response to the virion-associated antigens.

We have now shown that FI-HSV2/MPL/Alhydrogel protects mice against virus shedding after challenge and long-term rechallenge, and guinea pigs against acute and recurrent disease [19]. The protection in animal models appears to be at least as high as that engendered by attenuated or replication-defective HSV-2 vaccines, strategies that have the potential for the establishment of latency or recombination with a wild-type virus. While vaccination with inactivated virus eliminates many safety concerns, a major criticism of the first-generation inactivated HSV-2 vaccines has been the poor durability of elicited responses. However, we show that formulation with adjuvants such as MPL/Alhydrogel challenges this dogma. These exciting results demand further consideration of inactivated HSV-2 vaccines formulated with the modern, clinically approved adjuvants.

O. References

[1] Xu F, Sternberg M R, Gottlieb S L, Berman S M, Markowitz L E, Forhan S E, et al. Seroprevalence of Herpes Simplex Virus Type 2 Among Persons Aged 14-49 Years—United States, 2005-2008. Atlanta, Ga.: Centers for Disease Control and Prevention; 2010 Apr. 23, 2010.

[2] Kimberlin D W. Management of HSV encephalitis in adults and neonates: diagnosis, prognosis and treatment. Herpes 2007 June; 14(1):11-6.

[3] Dupuis S, Jouanguy E, Al-Hajjar S, Fieschi C, Al-Mohsen I Z, Al-Jumaah S, et al. Impaired response to interferon-alpha/beta and lethal viral disease in human STAT1 deficiency. Nat Genet. 2003 March; 33(3):388-91.

[4] Freeman E E, Weiss H A, Glynn J R, Cross P L, Whitworth J A, Hayes R J. Herpes simplex virus 2 infection increases HIV acquisition in men and women: systematic review and meta-analysis of longitudinal studies. AIDS 2006 Jan. 2; 20(1):73-83.

[5] Wald A, Link K. Risk of human immunodeficiency virus infection in herpes simplex virus type 2-seropositive persons: a meta-analysis. J Infect Dis 2002 Jan. 1; 185(1):45-52.

[6] Schiffer J T, Wald A, Selke S, Corey L, Magaret A. The kinetics of mucosal herpes simplex virus-2 infection in humans: evidence for rapid viral-host interactions. J Inf Dis 2011 Aug. 15; 204(4):554-61.

[7] Schacker T, Zeh J, Hu H L, Hill E, Corey L. Frequency of symptomatic and asymptomatic herpes simplex virus type 2 reactivations among human immunodeficiency virus-infected men. J Infect Dis 1998 December; 178(6): 1616-22.

[8] Corey L, Langenberg A G, Ashley R, Sekulovich R E, Izu A E, Douglas J M, Jr., et al. Recombinant glycoprotein vaccine for the prevention of genital HSV-2 infection: two randomized controlled trials. Chiron HSV Vaccine Study Group. J Amer Med Assoc 1999 Jul. 28; 282(4):331-40.

[9] Koelle D M, Corey L. Herpes simplex: insights on pathogenesis and possible vaccines. Annu Rev Med 2008; 59:381-95.

[10] Zhu J, Koelle D M, Cao J, Vazquez J, Huang M L, Hladik F, et al. Virus-specific CD8+ T cells accumulate near sensory nerve endings in genital skin during subclinical HSV-2 reactivation. J Exp Med 2007 Mar. 19; 204(3):595-603.

[11] Koelle D M, Posavad C M, Barnum G R, Johnson M L, Frank J M, Corey L. Clearance of HSV-2 from recurrent genital lesions correlates with infiltration of HSV-specific cytotoxic T lymphocytes. J Clin Invest 1998 Apr. 1; 101(7):1500-8.

[12] Belshe R B, Leone P A, Bernstein D I, Wald A, Levin M J, Stapleton J T, et al. Efficacy results of a trial of a herpes simplex vaccine. N Engl J Med 2012 Jan. 5; 366(1):34-43.

[13] Da Costa X, Kramer M F, Zhu J, Brockman M A, Knipe D M. Construction, phenotypic analysis, and immunogenicity of a UL5/UL29 double deletion mutant of herpes simplex virus 2. J Virol 2000 September; 74(17):7963-71.

[14] Da Costa X J, Jones C A, Knipe D M. Immunization against genital herpes with a vaccine virus that has defects in productive and latent infection. Proc Natl Acad Sci USA 1999 Jun. 8; 96(12):6994-8.

[15] Hoshino Y, Dalai S K, Wang K, Pesnicak L, Lau T Y, Knipe D M, et al. Comparative efficacy and immunogenicity of replication-defective, recombinant glycoprotein, and DNA vaccines for herpes simplex virus 2 infections in mice and guinea pigs. J Virol 2005 January; 79(1):410-8.

[16] Hoshino Y, Pesnicak L, Dowdell K C, Burbelo P D, Knipe D M, Straus S E, et al. Protection from herpes simplex virus (HSV)-2 infection with replication-defective HSV-2 or glycoprotein D2 vaccines in HSV-1-seropositive and HSV-1-seronegative guinea pigs. J Infect Dis 2009 Oct. 1; 200(7):1088-95.

[17] Hoshino Y, Pesnicak L, Dowdell K C, Lacayo J, Dudek T, Knipe D M, et al. Comparison of immunogenicity and protective efficacy of genital herpes vaccine candidates herpes simplex virus 2 d15-29 and d15-29-41L in mice and guinea pigs. Vaccine 2008 Jul. 29; 26(32):4034-40.

[18] Roizman B, Knipe D M, Whitley R J. Herpes Simplex Viruses. In: Knipe D M, Howley P M, editors. Fields Virology. 5th ed. Philadelphia: Lippincott Williams & Wilkins, 2007: 2501-601.

[19] Morello C S, Levinson M S, Kraynyak K A, Spector D H. Immunization with Herpes Simplex Virus 2 (HSV-2) genes plus inactivated HSV-2 Is highly protective against acute and recurrent HSV-2 disease. J Virol 2011 April; 85(7):3461-72.

[20] Parr M B, Kepple L, McDermott M R, Drew M D, Bozzola J J, Parr E L. A mouse model for studies of mucosal immunity to vaginal infection by herpes simplex virus type 2. Lab Invest 1994 March; 70(3):369-80.

[21] Dudek T, Mathews L C, Knipe D M. Disruption of the U(L)41 gene in the herpes simplex virus 2 d15-29 mutant increases its immunogenicity and protective capacity in a murine model of genital herpes. Virology 2008 Mar. 1; 372(1):165-75.

[22] Kwissa M, Lindblad E B, Schirmbeck R, Reimann J. Codelivery of a DNA vaccine and a protein vaccine with aluminum phosphate stimulates a potent and multivalent immune response. J Mol Med 2003 August; 81(8):502-10.

[23] Cook I F, Barr I, Hartel G, Pond D, Hampson A W. Reactogenicity and immunogenicity of an inactivated influenza vaccine administered by intramuscular or subcutaneous injection in elderly adults. Vaccine 2006 Mar. 20; 24(13):2395-402.

[24] Mark A, Carlsson R M, Granstrom M. Subcutaneous versus intramuscular injection for booster D T vaccination of adolescents. Vaccine 1999 Apr. 9; 17(15-16):2067-72.

[25] Pittman P R. Aluminum-containing vaccine associated adverse events: role of route of administration and gender. Vaccine 2002 May 31; 20 Suppl 3:S48-50.

[26] Ruben F L, Froeschle J E, Meschievitz C, Chen K, George J, Reeves-Hoche M K, et al. Choosing a route of administration for quadrivalent meningococcal polysaccharide vaccine: intramuscular versus subcutaneous. Clin Infect Dis 2001 January; 32(1):170-2.

[27] Khodai T, Chappell D, Christy C, Cockle P, Eyles J, Hammond D, et al. Single and combination herpes simplex virus type 2 glycoprotein vaccines adjuvanted with CpG oligodeoxynucleotides or monophosphoryl lipid A exhibit differential immunity that is not correlated to protection in animal models. Clin Vaccine 1 mm 2011 October; 18(10): 1702-9.

[28] Dudek T E, Torres-Lopez E, Crumpacker C, Knipe D M. Evidence for differences in immunologic and pathogenesis properties of herpes simplex virus 2 strains from the United States and South Africa. J Inf Dis 2011 May 15; 203(10):1434-41.

[29] Awasthi S, Lubinski J M, Shaw C E, Barrett S M, Cai M, Wang F, et al. Immunization with a vaccine combining herpes simplex virus 2 (HSV-2) glycoprotein C (gC) and gD subunits improves the protection of dorsal root ganglia in mice and reduces the frequency of recurrent vaginal shedding of HSV-2 DNA in guinea pigs compared to immunization with gD alone. J Virol 2011 October; 85(20):10472-86.

[30] Awasthi S, Zumbrun E E, Si H, Wang F, Shaw C E, Cai M, et al. Live attenuated herpes simplex virus 2 glycoprotein E deletion mutant as a vaccine candidate defective in neuronal spread. J Virol 2012 April; 86(8):4586-98.

[31] Halford W P, Puschel R, Gershburg E, Wilber A, Gershburg S, Rakowski B. A live-attenuated HSV-2 ICP0 virus elicits 10 to 100 times greater protection against genital herpes than a glycoprotein D subunit vaccine. PLoS One 2011; 6(3):e17748.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A kit consisting of one or more immunogenic compositions and instructions for use, wherein each of said one or more immunogenic compositions comprise:
   i) an inactivated human herpesvirus (HV);
   ii) monophosphoryl lipid A (MPL); and
   iii) an aluminum hydroxide adjuvant or aluminum phosphate adjuvant;
   wherein
   each of said one or more immunogenic compositions is provided in unit dosage form within a container and does not comprise DNA that is immunogenic; and wherein said inactivated human herpesvirus comprises inactivated genomic DNA that is not immunogenic.

2. The kit of claim 1, wherein said inactivated human herpesvirus is a Herpes Simplex Virus (HSV).

3. The kit of claim 2, wherein said inactivated human herpesvirus is formed by chemical inactivation.

4. The kit of claim 2, wherein said inactivated human herpesvirus is formed by contacting said inactivated human herpesvirus with one or more agents selected from a cross-linking agent, oxidizing agent, reducing agent, heat, radiation, detergent, a pH changing agent, furocoumarin, aziridine, ethylenimine, binary ethylenimine, and beta-propiolactone.

5. The kit of claim 1, wherein said herpesvirus is a Herpes Simplex Virus 2.

* * * * *

```
                           SEQUENCE LISTING

<160> NUMBER OF SEQ ID NOS: 16

<210> SEQ ID NO 1
<211> LENGTH: 27
<212> TYPE: DNA
<213> ORGANISM: Artificial sequence
<220> FEATURE:
<223> OTHER INFORMATION: Synthetic oligonucleotide primer.

<400> SEQUENCE: 1
gccaccatgg cggcgtccgg cggggag                                          27

<210> SEQ ID NO 2
<211> LENGTH: 33
<212> TYPE: DNA
<213> ORGANISM: Artificial sequence
<220> FEATURE:
<223> OTHER INFORMATION: Synthetic oligonucleotide primer.

<400> SEQUENCE: 2
atagacaatg accacattcg gatcgcgtag agc                                   33

<210> SEQ ID NO 3
<211> LENGTH: 27
<212> TYPE: DNA
<213> ORGANISM: Artificial sequence
<220> FEATURE:
<223> OTHER INFORMATION: Synthetic oligonucleotide primer.

<400> SEQUENCE: 3
gccaccatgt tttgtgccgc gggcggc                                          27

<210> SEQ ID NO 4
<211> LENGTH: 36
<212> TYPE: DNA
<213> ORGANISM: Artificial sequence
<220> FEATURE:
<223> OTHER INFORMATION: Synthetic oligonucleotide primer.

<400> SEQUENCE: 4
tgctagagta tcaaaggctc tatgcaacat tcgacg                                36

<210> SEQ ID NO 5
<211> LENGTH: 24
<212> TYPE: DNA
<213> ORGANISM: Artificial sequence
<220> FEATURE:
<223> OTHER INFORMATION: Synthetic oligonucleotide primer.

<400> SEQUENCE: 5
gccaccatgg ggcgtttgac ctcc                                             24

<210> SEQ ID NO 6
<211> LENGTH: 18
<212> TYPE: DNA
<213> ORGANISM: Artificial sequence
<220> FEATURE:
<223> OTHER INFORMATION: Synthetic oligonucleotide primer.

<400> SEQUENCE: 6
gacgtcctgg atcgacgg                                                    18
```

<210> SEQ ID NO 7
<211> LENGTH: 27
<212> TYPE: DNA
<213> ORGANISM: Artificial sequence
<220> FEATURE:
<223> OTHER INFORMATION: Synthetic oligonucleotide primer.

<400> SEQUENCE: 7
gccaccatgg ctaccgacat tgatatg                                          27

<210> SEQ ID NO 8
<211> LENGTH: 33
<212> TYPE: DNA
<213> ORGANISM: Artificial sequence
<220> FEATURE:
<223> OTHER INFORMATION: Synthetic oligonucleotide primer.

<400> SEQUENCE: 8
aaatagggag ttgcagtaga agtatttgcc gtg                                   33

<210> SEQ ID NO 9
<211> LENGTH: 30
<212> TYPE: DNA
<213> ORGANISM: Artificial sequence
<220> FEATURE:
<223> OTHER INFORMATION: Synthetic oligonucleotide primer.

<400> SEQUENCE: 9
gccagatata cgccatgaca ttgattattg                                       30

<210> SEQ ID NO 10
<211> LENGTH: 30
<212> TYPE: DNA
<213> ORGANISM: Artificial sequence
<220> FEATURE:
<223> OTHER INFORMATION: Synthetic oligonucleotide primer.

<400> SEQUENCE: 10
caataatcaa tgtcatggcg tatatctggc                                       30

<210> SEQ ID NO 11
<211> LENGTH: 74
<212> TYPE: DNA
<213> ORGANISM: Artificial sequence
<220> FEATURE:
<223> OTHER INFORMATION: Synthetic oligonucleotide primer.

<400> SEQUENCE: 11
ggtaccgagc tcggatccac gtcgactaca aggatgacga tgacaagtga taatagtcca     60
gtgtggtgga attc                                                        74

<210> SEQ ID NO 12
<211> LENGTH: 74
<212> TYPE: DNA
<213> ORGANISM: Artificial sequence
<220> FEATURE:
<223> OTHER INFORMATION: Synthetic oligonucleotide primer.

<400> SEQUENCE: 12
gaattccacc acactggact attatcactt gtcatcgtca tccttgtagt cgacgtggat     60
ccgagctcgg tacc                                                        74

<210> SEQ ID NO 13

```
<211> LENGTH: 9
<212> TYPE: PRT
<213> ORGANISM: Artificial sequence
<220> FEATURE:
<223> OTHER INFORMATION: Synthetic polypeptide.

<400> SEQUENCE: 13

His Gly Pro Ser Leu Tyr Arg Thr Phe
1               5

<210> SEQ ID NO 14
<211> LENGTH: 19
<212> TYPE: DNA
<213> ORGANISM: Artificial sequence
<220> FEATURE:
<223> OTHER INFORMATION: Synthetic oligonucleotide primer.

<400> SEQUENCE: 14
tgtggcaatg gcaaaaagc                                                19

<210> SEQ ID NO 15
<211> LENGTH: 25
<212> TYPE: DNA
<213> ORGANISM: Artificial sequence
<220> FEATURE:
<223> OTHER INFORMATION: Synthetic oligonucleotide primer.

<400> SEQUENCE: 15
tgttaccatt tgtgatgttt tcgat                                         25

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide primer.
<220> FEATURE:
<221> NAME/KEY: modified_base
<222> LOCATION: (1)..(1)
<223> OTHER INFORMATION: 5' c modified with cgtctatac oligonucleotide
      modified at 5' c with 6-FAM oligonucleotide and linked through
      Zen(TM) linker.
<220> FEATURE:
<221> NAME/KEY: modified_base
<222> LOCATION: (20)..(20)
<223> OTHER INFORMATION: 3' a modified with Iowa Black F Quencher

<400> SEQUENCE: 16
ccgagtgtca tcctaccgga                                               20
```